(12) United States Patent
Gallant et al.

(10) Patent No.: US 10,407,414 B2
(45) Date of Patent: Sep. 10, 2019

(54) MANNOSE DERIVATIVES FOR TREATING BACTERIAL INFECTIONS

(71) Applicant: Vertex Pharmaceuticals Incorporated, Boston, MA (US)

(72) Inventors: Michel Gallant, Pierrefonds (CA); Jean-Francois Truchon, Saint-Laurent (CA); Thumkunta Jagadeeswar Reddy, Pierrefonds (CA); Evelyne Dietrich, Laval (CA); Louis Vaillancourt, Laval (CA); Frederic Vallee, Montreal (CA)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 15/735,412

(22) PCT Filed: Jun. 13, 2016

(86) PCT No.: PCT/IB2016/053469
§ 371 (c)(1),
(2) Date: Dec. 11, 2017

(87) PCT Pub. No.: WO2016/199105
PCT Pub. Date: Dec. 15, 2016

(65) Prior Publication Data
US 2018/0244658 A1  Aug. 30, 2018

Related U.S. Application Data

(60) Provisional application No. 62/174,662, filed on Jun. 12, 2015.

(51) Int. Cl.
*C07D 405/06* (2006.01)
*C07D 405/14* (2006.01)
*C07D 413/14* (2006.01)
*C07D 471/04* (2006.01)
*A61P 31/04* (2006.01)
*C07D 413/06* (2006.01)

(52) U.S. Cl.
CPC ............ *C07D 405/06* (2013.01); *A61P 31/04* (2018.01); *C07D 405/14* (2013.01); *C07D 413/06* (2013.01); *C07D 413/14* (2013.01); *C07D 471/04* (2013.01)

(58) Field of Classification Search
CPC .................................................. C07D 405/06
See application file for complete search history.

(56) References Cited

FOREIGN PATENT DOCUMENTS

WO        2014/100158 A1    6/2014
WO        WO2014100158  *  6/2014  ........... C07D 309/10

OTHER PUBLICATIONS

Man, S.M. et al., The role of bacteria and pattern-recognition receptors in Crohn's disease, Nat Rev Gastroenterol Hepatol, 2011, vol. 8, pp. 152-168.
Peterson, D.A. et al., Metagenomic Approaches for Defining the Pathogenesis of Inflammatory Bowel Diseases, Cell Host Microbe, 2008, vol. 3, pp. 417-427.
Frank, D.N. et al., Molecular-phylogenetic characterization of microbial community imbalances in human inflammatory bowel diseases, Proc. Natl. Acad. Sci., 2007, vol. 104, No. 34, pp. 13780-13785.
Darfeuille-Michaud, A. et al., High Prevalence of Adherent-Invasive *Escherichia coli* Associated with Ileal Mucosa in Chron's Disease, Gastroenterology, 2004, vol. 127, pp. 412-421.
Martinez-Medina, M. et al., Molecular Diversity of *Escherichia coli* in the Human Gut: New Ecological Evidence Supporting the Role of Adherent-Invasive *E. coli* (AIEC) in Crohn's Disease, Inflamm Bowel Dis, 2009, vol. 15, No. 6, pp. 872-882.
Barnich, N. et al., CEACAM6 acts as a receptor for adherent-invasive *E.coli*, supporting ileal mucosa colonization in Crohn disease, The Journal of Clinical Investigation, 2007, vol. 117, No. 6, pp. 1566-1574.
Carvalho, F.A. et al., Crohn's disease adherent-invasive *Escherichia coli* colonize and induce strong gut inflammation in transgenic mice expressing human CEACAM, The Journal of Experimental Medicine, 2009, vol. 206, No. 10, pp. 2179-2189.
Klein, T. et al., FimH Antagonists for the Oral Treatment of Urinary Tract Infections: From Design and Synthesis to in Vitro and in Vivo Evaluation, Journal of Medicinal Chemistry, 2010, vol. 53, No. 24, pp. 8627-8641.
S.L. Harbeson and R.D. Tung, Deuterium in Drug Discovery and Development, Ann. Rep. Med. Chem., 2011, vol. 46, pp. 403-417.
Hanzlik R.P. et al., Active Site Dynamics of Toluene Hydroxylation by Cytochrome P-450, J. Org. Chem., 1990, vol. 55, No. 13, pp. 3992-3997.
Reider, P.J., Synthesis of (R)-Serine-2-d and Its Conversion to the Broad Spectrum Antibiotic Fludalanine, J. Org. Chem., 1987, vol. 52, No. 15, pp. 3326-3334.

(Continued)

*Primary Examiner* — Paul V Ward
(74) *Attorney, Agent, or Firm* — Banner & Witcoff, Ltd.

(57) ABSTRACT

The compounds represented by Formula (I) or pharmaceutically acceptable salts thereof: with U, W, X, Y, Z, p and ring A as defined in claim 1. Those compounds are useful for the treatment or prevention of bacteria infections. The variables of Formula (I) are as described herein. Pharmaceutically acceptable compositions comprise the compounds of Formula (I) or pharmaceutically acceptable salts thereof and pharmaceutically acceptable carriers, adjuvants, or vehicles. Methods of treating bacteria infections employ such compounds or pharmaceutically acceptable salts thereof.

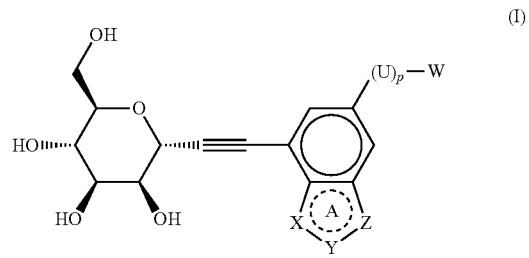

19 Claims, 1 Drawing Sheet

(56) References Cited

OTHER PUBLICATIONS

Foster, A.B., Deuterium Isotope Effects in the Metabolism of Drugs and Xenobiotics: Implications for Drug Design, Advances in Drug Research, 1985, vol. 14, pp. 1-40.

Gillette, J.R., Theory for the Observed Isotope Effects on the Formation of Multiple Products by Different Kinetic Mechanisms of Cythochrome P450 Enzymes, Biochemistry, 1994, vol. 33, pp. 2927-2937.

Jarman, M. et al., The deuterium isotope effect for the alpha-hydroxlation of tamoxifen by rat liver microsomes accounts for the reduced genotoxicity of (D5-ethyl)tamoxifen, Carcinogenesis, 1995, vol. 16, No. 4, pp. 683-688.

Greene, T.W. and Wuts, P.G., (1999), "Protection for the Amino Group", Protective Groups in Organic Synthesis (3rd ed.), pp. 494-653, New York: John Wiley & Sons, Inc.

Berge, S.M. et al., Pharmaceutical Salts, Journal of Pharmaceutrical Sciences, 1977, vol. 66, No. 1, pp. 1-19.

Holford, N.H.G. et al., Understanding the Dose-Effect Relationship: Clinical Application of Pharmacokinetic-Pharmacodynamic Models, Clinical Pharmacokiinetics, 1981, vol. 6, pp. 429-453.

Loewe, S. and Muischnek, H., Arch. Exp. Pathol Pharmacol. 114: 313-326 (1926).

Chou, T.C. et al., Quantitative Analysis of Dose-Effect Relationships: The Combined Effects of Multiple Drugs or Enzyme Inhibitors, Adv. Enzyme Regul., 1984, vol. 22, pp. 27-55.

Stichler-Bonaparte, J. et al., Oligosasccharide Analogues of Polysaccharides Part 23. Synthesis of a Dimeric Acetyleno Cyclodextrin from a Mannopyranose-Derived Dialkyne, Helvetica Chimica Acta, 2001, vol. 84, No. 8, pp. 2355-2367.

Boudeau, J. et al., Invasive Ability of an *Escherichia coli* Strain Isolated from the Ileal Mucosa of a Patient with Crohn's Disease, Infection and Immunity, 1999, vol. 67, No. 9, pp. 4499-4509.

Brument, S. et al., Thiazolylaminomannosides as Potent Antiadhesives of Type 1 Piliated *Escherichia coli* Isolated from Crohn's Disease Patients, Journal of Medicinal Chemistry, 2013, vol. 56, pp. 5395-5406.

* cited by examiner

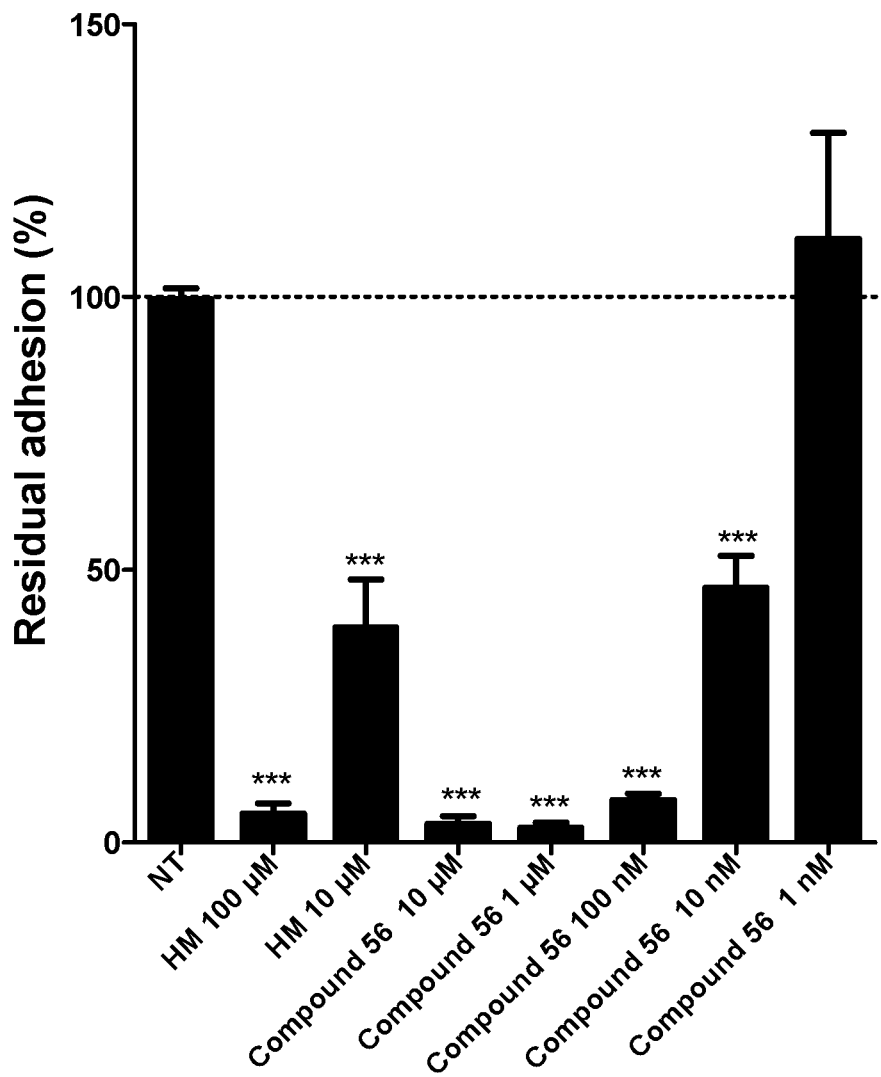

MANNOSE DERIVATIVES FOR TREATING BACTERIAL INFECTIONS

RELATED APPLICATION DATA

This application is a National Stage Application under 35 U.S.C. 371 of co-pending PCT application number PCT/IB2016/053469 designating the United States and filed Jun. 13, 2016; which claims the benefit of U.S. provisional application No. 62/174,662 and filed Jun. 12, 2015 each of which are hereby incorporated by reference in their entireties.

TECHNICAL FIELD OF INVENTION

The present invention relates to compounds useful for treating Inflammatory bowel disease (IBD) and pharmaceutical compositions thereof and methods of using such compounds and compositions in the treatment of IBD.

BACKGROUND OF THE INVENTION

Inflammatory bowel disease (IBD) is a complex chronic inflammatory disorder, with the two more common forms being ulcerative colitis (UC) and Crohn's disease (CD). IBD is a multifactorial disease that results from a combination of predisposing genetic factors, environmental triggers, dysbiosis of the gastrointestinal microbiota and an inappropriate inflammatory response (Man et al., 2011, Nat Rev Gastroenterol Hepatol, March, 8(3):152-68).

Several studies on fecal and mucosa-associated bacterial communities have shown that the microbiota of patients with Crohn's disease (CD) differ from those of healthy controls, as well as those of patients with ulcerative colitis (UC). Although the reported changes are not always consistent, numbers of *Escherichia coil* are generally increased, whereas *Firmicutes* are scarcer in CD patients (Peterson et al., 2008, Cell Host Microbe, 3: 17-27; Frank et al., 2007, Proc. Natl. Acad. Sci., 104:13780-13785). Whether these changes are causative factors or consequences of inflammation, it remains controversial. To date, several pathogens have been proposed as causative agents. In particular, adherent-invasive *E. coli* (AIEC) has been reported to be more prevalent in CD patients than in controls in several countries (United Kingdom, France and the USA) (Darfeuille-Michaud et al., 2004, Gastroenterology, 127:412-421; Martinez-Medina et al., 2009, Inflamm Bowel Dis., 15:872-882). AIEC strains have been isolated from ileal lesions in ~35% of CD patients compared to ~5% of healthy subjects. One of the features of AIEC is their ability to adhere and invade epithelial cells. It is known from various models that the binding of adhesins expressed on the bacterial cell surface to defined glycosylated receptors on the host tissue surface is considered to be an initial and critical step in pathogenesis, then opening a new avenue for therapy such as blocking the interaction between type 1 pili and CEACAM6, a known host receptor for FimH (Barnich et al., 2007, J. Clin. Invest., 117:1566-1574; Carvalho et al., 2009, *JEM*, vol. 206, no. 10, 2179-2189). Therefore, inhibition of adhesion, and consequently intracellular replication of ALEC in epithelial cells, may prevent establishment of a sub-mucosal infection leading to mucosal inflammation and epithelial barrier disruption.

It has also been demonstrated recently that FimH antagonists are potentially effective in treating urinary tract infections (J. Med. Chem. 2010, 53, 8627-8641).

SUMMARY OF THE INVENTION

The present invention provides compounds of Formula (I) or pharmaceutically acceptable salts thereof; pharmaceutical formulations comprising the compounds of Formula (I) or pharmaceutically acceptable salts thereof; methods of the treatment or prevention of bacteria infections, such as urinary tract infection (UTI) and inflammatory bowel diseases (IBD), with the compounds of Formula (I) or pharmaceutically acceptable salts thereof; and processes to make the compounds of Formula (I) or pharmaceutically acceptable salts thereof.

In one aspect, the present invention is directed to a compound of Formula (I), or a pharmaceutically acceptable salt thereof:

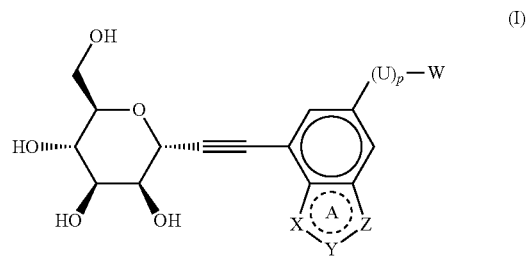

wherein:
X—Y—Z is —NR—N=CH—, =N—NR—CH—, —CH=N—NR—, —NH—CH=CH—, —NH—CH=N—, —NH—N=N—, —NH—CH$_2$—CH$_2$—, —O—CH=N—, —NH—C(=O)—CH$_2$—, or —NH—C(=O)—NH—;

R is —H, C$_{1-4}$alkyl, C$_{1-4}$haloalkyl or —(C$_{1-4}$alkyl)-Ph, wherein Ph is phenyl optionally substituted with 1-3 occurrences of J$^{Ph}$;

U is —CH=CH—, —C≡C—, or phenylene;

p is 0 or 1;

W is —H; halogen; —CN; —C(=O)NR$^1$R$^2$; —C(=O)OR$^3$; C$_{1-6}$alkyl; a 3-8 membered saturated, partially unsaturated, or aromatic monocyclic ring having 0-4 heteroatoms selected from oxygen, nitrogen, or sulfur; or an 8-10 membered saturated, partially unsaturated, or aromatic bicyclic ring having 0-4 heteroatoms selected from oxygen, nitrogen, or sulfur; wherein said C$_{1-6}$alkyl is optionally substituted with 1-4 occurrences of J$^{W1}$, and wherein each of said monocyclic and bicyclic rings independently and optionally is substituted with 1-4 occurrences of J$^{W2}$;

each of R$^1$, R$^3$, R$^4$, R$^5$, and R$^6$ independently is —H; C$_{1-6}$alkyl optionally substituted with 1-3 occurrences of J$^A$; C$_{3-6}$cycloalkyl optionally substituted with 1-3 occurrences of J$^B$; or —(C$_{1-4}$alkyl)-Ph wherein Ph is phenyl optionally substituted with 1-3 occurrences of J$^{Ph}$;

R$^2$ is C$_{1-6}$alkyl optionally substituted with 1-3 occurrences of J$^A$; C$_{3-6}$cycloalkyl optionally substituted with 1-3 occurrences of J$^B$; or —(C$_{1-4}$alkyl)-Ph wherein Ph is phenyl optionally substituted with 1-3 occurrences of J$^{Ph}$; or optionally R$^1$ and R$^2$ together with the nitrogen atom to which they are attached form a 4-6 membered, non-aromatic, monocyclic ring wherein up to one methylene unit of the ring is optionally replaced with O, NH, N(C$_{1-4}$alkyl), S, C(O), S(O), or S(O)$_2$; or optionally R$^4$ and R$^5$ together with the nitrogen atom to which they are attached form a 4-6 membered, non-aromatic, monocyclic ring wherein up to one methylene unit of the ring is optionally replaced with O, NH, N(C$_{1-4}$alkyl), S, C(O), S(O), or S(O)$_2$; and each J$^A$ independently is halogen, CN, —OH, —O(C$_{1-4}$ alkyl), or —O(C$_{1-4}$haloalkyl);

each J$^B$ independently is halogen, —CN, —OH, —O(C$_{1-4}$ alkyl), —O(C$_{1-4}$haloalkyl), C$_{1-4}$alkyl, or C$_{1-4}$haloalkyl;

each J$^{Ph}$ independently is halogen, —CN, —OH, —O(C$_{1-4}$ alkyl), —O(C$_{1-4}$haloalkyl), C$_{1-4}$alkyl, or C$_{1-4}$haloalkyl;

J$^{W1}$ is halogen, —CN, —OR$^6$, —NR$^4$R$^5$, —NR$^4$COR$^5$, —C(=O)NR$^4$R$^5$, —C(=O)OR$^6$, —S(O)$_2$NR$^4$R$^5$—, S(O)$_2$R$^6$—, or Ph, wherein said Ph is phenyl optionally substituted with 1-3 occurrences of J$^{Ph}$; and J$^{W2}$ is oxo, —NO$_2$, halogen, —CN, —OR$^6$, —O(CH$_2$) O—, —O(CH$_2$)$_2$O—, —NR$^4$R$^5$, —NR$^4$COR$^5$, —C(=O) NR$^4$R$^5$, —C(=O)OR$^6$, —S(O)$_2$NR$^4$R$^5$—, S(O)$_2$R$^6$—, —C$_{1-6}$alkyl, Ph, —(C$_{1-4}$alkyl)Ph, or —O(C$_{1-4}$alkyl)Ph, wherein said —C$_{1-6}$alkyl is optionally substituted with 1-3 occurrences of J$^A$, and wherein said Ph is phenyl optionally substituted with 1-3 occurrences of J$^{Ph}$.

Another aspect of the present invention is directed to a composition comprising a compound of Formula (I) or a pharmaceutically acceptable salt thereof, and a pharmaceutically acceptable carrier, adjuvant, or vehicle.

The present invention also provides a method of preparing a compound represented by Formula (I) or a pharmaceutically acceptable salt thereof. In one embodiment, the method comprises reacting Compound (A1) with Compound (M1) in the presence of a Pd or Pd/Cu catalyst, wherein U, X, Y, Z, and p of Compound (A1) and Formula (I) are each independently as defined in claim 1; W of Compound (A1) and Formula (I) are each independently —H, halogen, —CN, —C(=O)OR$^3$ or C$_{1-6}$alkyl, wherein R$^3$ is as defined in claim 1; and L$^1$ of Compound (A1) is —Cl or —Br:

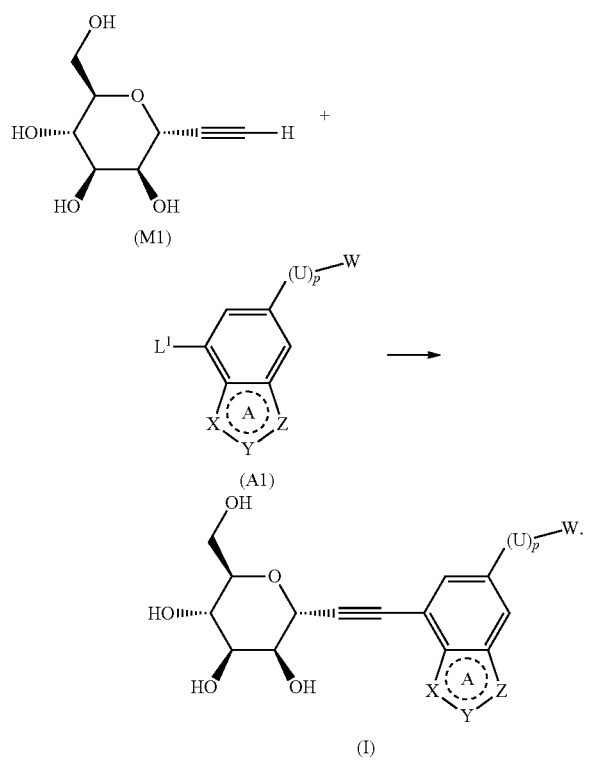

In another embodiment, the method comprises reacting Compound (X-1) with Compound (Y-1) or (Y-2) in the presence of a Pd catalyst, wherein X, Y, and Z of Compound (X-1) and Formula (I) are each and independently as defined herein; p of Formula (I) is 0; W of Formula (I) is Ring B; and Ring B of Compounds (Y-1) and (Y-2) are each independently a 3-8 membered saturated, partially unsaturated, or aromatic monocyclic ring having 0-4 heteroatoms selected from oxygen, nitrogen, or sulfur; or an 8-10 membered saturated, partially unsaturated, or aromatic bicyclic ring having 0-4 heteroatoms selected from oxygen, nitrogen, or sulfur; wherein said C$_{1-6}$alkyl is optionally substituted with 1-4 occurrences of J$^{W1}$, and wherein each of said monocyclic and bicyclic rings independently and optionally is substituted with 1-4 occurrences of J$^{W2}$:

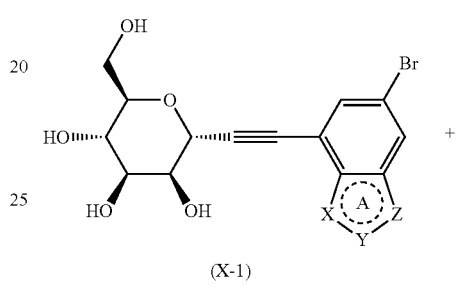

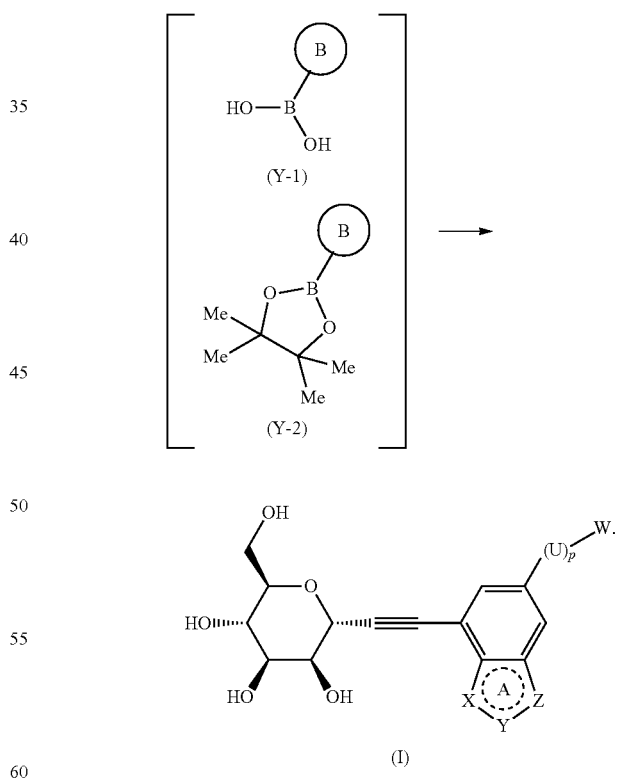

In yet another embodiment, the method comprises reacting Compound (X-1) with Compound (Y-3) in the presence of Pd or Pd/Cu catalyst, wherein p of Formula (I) is 1; and the other variables of Formula (I) and the variables of Compounds (X-1) and (Y-3) are each and independently as defined herein:

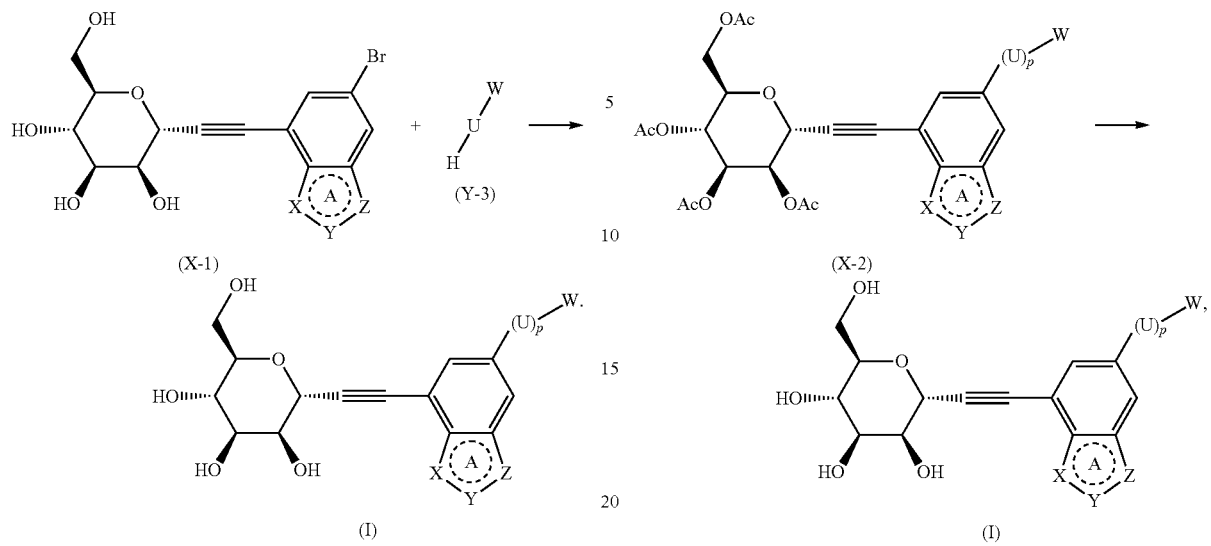

In yet another embodiment, the method comprises:

coupling between Compound (M3) and Compound (Y-4) to generate Compound (X-2):

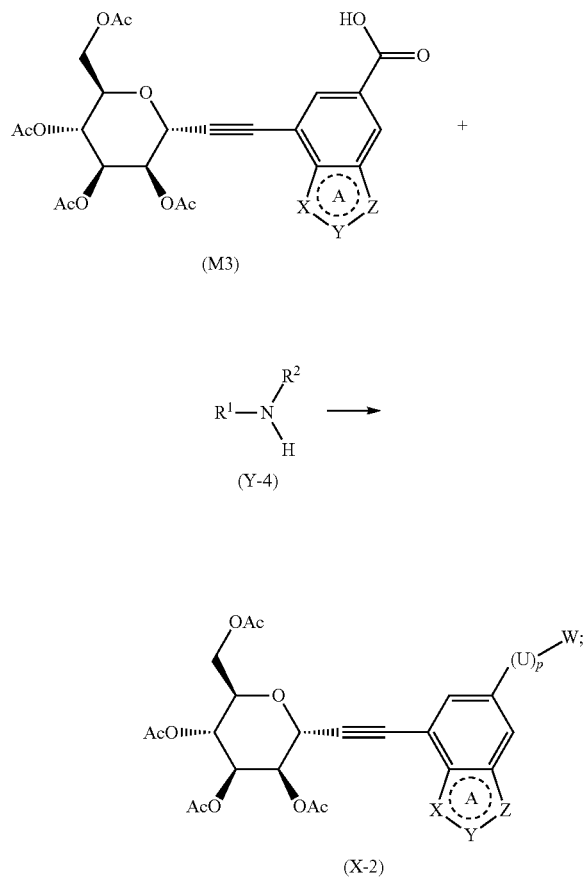

and deprotecting -OAc groups of Compound (X-2) to generate a compound of Formula (I) or a pharmaceutically acceptable salt thereof:

wherein the variables of Compounds (M3), (Y-4), and (X-2), and Formula (I) are each independently as defined herein; and OAc of Compound (X-2) is acetate.

The present invention also provides a method of treating or preventing bacteria infection in a subject, comprising administering to the subject an effective amount of the compound or the composition described herein.

DETAILED DESCRIPTION OF THE INVENTION

In one aspect, the present invention relates to compounds useful for the treatment or prevention of bacteria infections, such as urinary tract infection (UTI) and inflammatory bowel diseases (IBD).

In one embodiment, the invention provides compounds of Formula (I) or pharmaceutically acceptable salts thereof:

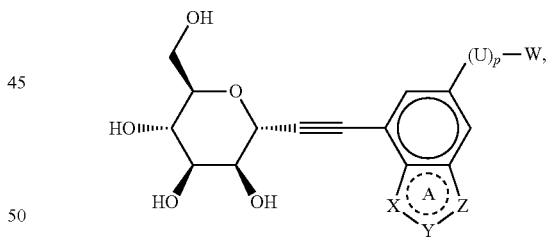

wherein the variables are described herein.

In first set of variables of Formula (I), X—Y—Z is —NR—N=CH—, =N—NR—CH—, —CH=N—NR—, —NH—CH=CH—, —NH—CH=N—, —NH—N=N—, —NH—CH$_2$—CH$_2$—, —O—CH=N—, —NH—C(=O)—CH$_2$—, or —NH—C(=O)—NH—. In a specific embodiment, X—Y—Z is —NR—N=CH—, —NH—C(=O)—NH—; —NH—CH=N—, =NH—N=N—, —CH=N—NR—, or —N—NR—CH—. In another specific embodiment, X—Y—Z is —NR—N=CH—.

R is —H, C$_{1-4}$alkyl, C$_{1-4}$haloalkyl or —(C$_{1-4}$alkyl)-Ph, wherein Ph is phenyl optionally substituted with 1-3 occurrences of J$^{Ph}$. In a specific embodiment, R is H, C$_{1-4}$alkyl, or —(C$_{1-4}$alkyl)-Ph, wherein Ph is phenyl optionally substituted with 1-2 occurrences of halogen, CN, —OH, —O(C$_{1-4}$alkyl), —O(C$_{1-4}$haloalkyl), C$_{1-4}$alkyl, or C$_{1-4}$haloalkyl. In another specific embodiment, R is —H or C$_{1-4}$alkyl. In another specific embodiment, R is —H or —CH$_3$. In yet another specific embodiment, R is —H.

U is —CH=CH—, —C≡C—, or phenylene. In a specific embodiment, U is —C≡C—.

p is 0 or 1. In a specific embodiment, p is 0.

W is —H; halogen; —CN; —C(=O)NR$^1$R$^2$; —C(=O)OR$^3$; C$_{1-6}$alkyl; a 3-8 membered saturated, partially unsaturated, or aromatic monocyclic ring having 0-4 heteroatoms selected from oxygen, nitrogen, or sulfur; or an 8-10 membered saturated, partially unsaturated, or aromatic bicyclic ring having 0-4 heteroatoms selected from oxygen, nitrogen, or sulfur; wherein said C$_{1-6}$alkyl is optionally substituted with 1-4 occurrences of J$^{W1}$, and wherein each of said monocyclic and bicyclic rings independently and optionally is substituted with 1-4 occurrences of J$^{W2}$. In a specific embodiment, W is —C(=O)NR$^1$R$^2$; C$_{1-6}$alkyl optionally substituted with 1-4 occurrences of J$^{W1}$; a 3-8 membered saturated, partially unsaturated, or aromatic monocyclic ring having 0-4 heteroatoms selected from oxygen, nitrogen, or sulfur; or an 8-10 membered saturated, partially unsaturated, or aromatic bicyclic ring having 0-4 heteroatoms selected from oxygen, nitrogen, or sulfur; wherein each of monocyclic and bicyclic rings independently and optionally is substituted with 1-4 occurrences of J$^{W2}$. In another specific embodiment, W is 3,6-dihydro-2H-1λ$^2$-pyridine, 3,6-dihydro-2H-pyran, C$_{5-6}$ cycloalkenyl, benzene, pyridine, indole, pyridine-2-one, imidazo[1,2-a]pyridine, benzoimidazole, benzo[d][1,3]dioxole, 1,3,4-oxadiazole, pyrrole, or triazole, each of which independently and optionally is substituted. In yet another embodiment, W is

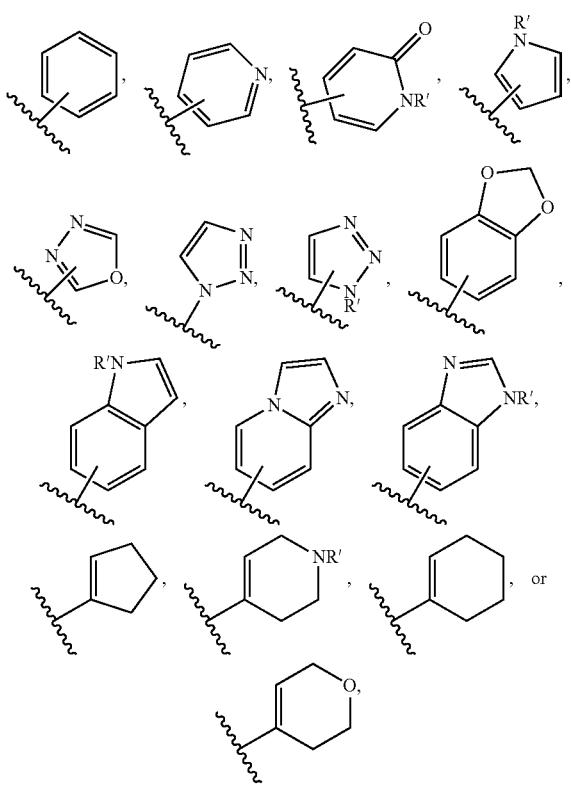

wherein each W is independently and optionally substituted, and each R' independently —H or —C$_{1-4}$alkyl. In yet another specific embodiment, W is optionally substituted C$_{1-6}$alkyl. In yet another specific embodiment, W is C$_{1-6}$alkyl. In yet another specific embodiment, W is a 5-6 membered, optionally substituted, aromatic monocyclic ring; or an 8-10 membered, optionally substituted, aromatic bicyclic ring. Specific examples of the aromatic rings of W include a benzene, pyridine, pyridine-2-one, imidazo[1,2-a] pyridine, benzoimidazole, benzo[d] [1,3]dioxole, indole, 1,3,4-oxadiazole, pyrrole, or triazole, each of which independently and optionally is substituted.

J$^{W1}$ is halogen, —CN, —OR$^6$, —NR$^4$R$^5$, —NR$^4$COR$^5$, —C(=O)NR$^4$R$^5$, —C(=O)OR$^6$, —S(O)$_2$NR$^4$R$^5$—, S(O)$_2$R$^6$—, or Ph, wherein said Ph is phenyl optionally substituted with 1-3 occurrences of J$^{Ph}$. In a specific embodiment, wherein J$^{W1}$ is selected from the group consisting of halogen, CN, —OH, —O(C$_{1-4}$alkyl), —O(C$_{1-4}$haloalkyl), —O(C$_{1-4}$alkyl)-Ph, —NH$_2$, —NH(C$_{1-4}$alkyl), and —N(C$_{1-4}$alkyl)$_2$. In a specific embodiment, J$^{W1}$ is halogen, CN, —OH, —O(C$_{1-4}$alkyl), —O(C$_{1-4}$haloalkyl), —O(C$_{1-4}$alkyl)-Ph, —NH$_2$, —NH(C$_{1-4}$alkyl), or —N(C$_{1-4}$alkyl)$_2$. In another specific embodiment, J$^{W1}$ is —F, —Cl, —CN, —OH, —O(C$_{1-2}$alkyl), —O(C$_{1-2}$haloalkyl), —O(C$_{1-2}$alkyl)-Ph, —NH$_2$, —NH(C$_{1-2}$alkyl), or —N(C$_{1-2}$alkyl)$_2$.

J$^{W2}$ is oxo, —NO$_2$, halogen, —CN, —OR$^6$, —O(CH$_2$)O—, —O(CH$_2$)$_2$O—, —NR$^4$R$^5$, —NR$^4$COR$^5$, —C(=O)NR$^4$R$^5$, —C(=O)OR$^6$, —S(O)$_2$NR$^4$R$^5$—, S(O)$_2$R$^6$—, —C$_{1-6}$alkyl, Ph, —(C$_{1-4}$alkyl)Ph, or —O(C$_{1-4}$alkyl)Ph, wherein said —C$_{1-6}$alkyl is optionally substituted with 1-3 occurrences of J$^A$, and wherein said Ph is phenyl optionally substituted with 1-3 occurrences of J$^{Ph}$. In a specific embodiment, J$^{W2}$ is halogen, CN, oxo, NO$_2$, C$_{1-4}$alkyl, C$_{1-4}$haloalkyl, —NH$_2$, —NH(C$_{1-4}$alkyl), —N(C$_{1-4}$alkyl)$_2$, —C(=O)OH, —C(=O)O(C$_{1-4}$alkyl), —OH, —O(C$_{1-4}$alkyl), —O(C$_{1-4}$haloalkyl), —O(C$_{1-4}$alkyl)-Ph, —O(CH$_2$)O—, —O(CH$_2$)$_2$O—, —C(=O)NH$_2$, —C(=O)NH(C$_{1-4}$alkyl), —C(=O)N(C$_{1-4}$alkyl)$_2$, —SO$_2$(C$_{1-4}$alkyl), —NHCO(C$_{1-4}$alkyl), —SO$_2$NH$_2$, —SO$_2$NH(C$_{1-4}$alkyl), or —SO$_2$N(C$_{1-4}$alkyl)$_2$. In another specific embodiment, J$^{W2}$ is —F, —Cl, —CN, NO$_2$, C$_{1-2}$alkyl, C$_{1-2}$haloalkyl, —NH$_2$, —NH(C$_{1-2}$alkyl), —N(C$_{1-2}$alkyl)$_2$, —C(=O)O(C$_{1-2}$alkyl), —OH, —O(C$_{1-2}$alkyl), —O(C$_{1-2}$haloalkyl), —O(C$_{1-2}$alkyl)-Ph, —C(=O)NH$_2$, —C(=O)NH(C$_{1-2}$alkyl), —C(=O)N(C$_{1-2}$alkyl)$_2$, —SO$_2$(C$_{1-2}$alkyl), —NHCO(C$_{1-2}$alkyl), —SO$_2$NH$_2$, —SO$_2$NH(C$_{1-2}$alkyl), or —SO$_2$N(C$_{1-2}$alkyl)$_2$. In yet another specific embodiment, J$^{W2}$ selected from —F, —Cl, —CN, NO$_2$, —CH$_3$, —C$_2$H$_5$, NH(CH$_3$), —N(CH$_3$)$_2$, —C(=O)OH, —C(=O)O(CH$_3$), —C(=O)O(C$_2$H$_5$), —OH, —O(CH$_3$), —O(C$_2$H$_5$), —OCH$_2$Ph, —C(=O)NH$_2$, —C(=O)NH(CH$_3$), —C(=O)N(CH$_3$)$_2$, —SO$_2$(CH$_3$), —NHCO(CH$_3$), —SO$_2$NH$_2$, —SO$_2$NH (CH$_3$), —SO$_2$N(CH$_3$)$_2$, or —SO$_2$N(C$_2$H$_5$)$_2$. In yet another specific embodiment, J$^{W2}$ selected from —F, —Cl, —CN, NO$_2$, —CH$_3$, —C$_2$H$_5$, —N(CH$_3$)$_2$, —OH, —O(CH$_3$), —O(C$_2$H$_5$), —OCH$_2$Ph, —C(=O)NH$_2$, —C(=O)NH (CH$_3$), —C(=O)N(CH$_3$)$_2$, —SO$_2$(CH$_3$), —NHCO(CH$_3$), —SO$_2$NH$_2$, —SO$_2$NH(CH$_3$), —SO$_2$N(CH$_3$)$_2$, or —SO$_2$N (C$_2$H$_2$.

Each of R$^1$, R$^3$, R$^4$, R$^5$, and R$^6$ independently is —H, C$_{1-6}$alkyl optionally substituted with 1-3 occurrences of J$^A$, C$_{3-6}$cycloalkyl optionally substituted with 1-3 occurrences of J$^B$, or —(C$_{1-4}$alkyl)-Ph wherein Ph is phenyl optionally substituted with 1-3 occurrences of J$^{Ph}$. R$^2$ is C$_{1-6}$alkyl optionally substituted with 1-3 occurrences of J$^A$, C$_{3-6}$cycloalkyl optionally substituted with 1-3 occurrences of J$^B$, or —(C$_{1-4}$alkyl)-Ph wherein Ph is phenyl optionally substituted with 1-3 occurrences of J$^{Ph}$; or optionally R$^4$ and R$^5$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$; or optionally $R^1$ and $R^2$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$. In a specific embodiment, each of $R^1$, $R^3$, $R^4$, $R^5$, and $R^6$ independently is —H, $C_{1-4}$alkyl, $C_{1-4}$haloalkyl, or $C_{3-6}$cycloalkyl; $R^2$ independently is $C_{1-4}$alkyl, $C_{1-4}$haloalkyl, or $C_{3-6}$cycloalkyl; or optionally $R^1$ and $R^2$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$; or optionally $R^4$ and $R^5$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$. In another specific embodiment, each of $R^1$ and $R^2$ independently is an optionally substituted, $C_{1-4}$alkyl or $C_{3-6}$cycloalkyl group; or optionally $R^1$ and $R^2$ together with the nitrogen atom to which they are attached form a 5-6 membered, non-aromatic, monocyclic ring wherein up to one methylene unit of the ring is optionally replaced with O, NH, N($C_{1-4}$alkyl), S, C(O), S(O), or S(O)$_2$. In yet another specific embodiment, each of $R^1$ and $R^2$ independently is $C_{1-4}$alkyl, cyclopentyl or cyclohexyl, or $R^1$ and $R^2$ together with the nitrogen atom to which they are attached form a morpholine ring.

Each $J^A$ independently is halogen, CN, —OH, —O($C_{1-4}$alkyl), or —O($C_{1-4}$haloalkyl).

Each $J^B$ independently is halogen, —CN, —OH, —O($C_{1-4}$ alkyl), —O($C_{1-4}$haloalkyl), $C_{1-4}$alkyl, or $C_{1-4}$haloalkyl.

Each $J^{Ph}$ independently is halogen, —CN, —OH, —O($C_{1-4}$alkyl), —O($C_{1-4}$haloalkyl), $C_{1-4}$alkyl, or $C_{1-4}$haloalkyl.

In the second set of variables of Formula (I), R is H, $C_{1-4}$alkyl, or —($C_{1-4}$alkyl)-Ph, wherein Ph is phenyl optionally substituted with 1-2 occurrences of halogen, CN, —OH, —O($C_{1-4}$alkyl), —O($C_{1-4}$haloalkyl), $C_{1-4}$alkyl, or $C_{1-4}$haloalkyl; and the other variables of Formula (I) are each and independently as described in the first set of variables of Formula (I).

In the third set of variables of Formula (I), R is —H or $C_{1-4}$alkyl; and the other variables of Formula (I) are each and independently as described in the first set of variables of Formula (I).

In the fourth set of variables of Formula (I), X—Y—Z is —NR—N=CH—, —NH—C(=O)—NH—; —NH—CH=N—, —NH—N=N—, —CH=N—NR—, or =N—NR—CH—; and the other variables of Formula (I) are each and independently as described in the first set of variables of Formula (I).

In the fifth set of variables of Formula (I), X—Y—Z is —NR—N=CH—, —NH—C(=O)—NH—; —NH—CH=N—, —NH—N=N—, —CH=N—NR—, or =N—NR—CH—; R is H, $C_{1-4}$alkyl, or —($C_{1-4}$alkyl)-Ph, wherein Ph is phenyl optionally substituted with 1-2 occurrences of halogen, CN, —OH, —O($C_{1-4}$alkyl), —O($C_{1-4}$haloalkyl), $C_{1-4}$alkyl, or $C_{1-4}$haloalkyl; and the other variables of Formula (I) are each and independently as described in the first set of variables of Formula (I).

In the sisth set of variables of Formula (I), X—Y—Z is —NR—N=CH—, —NH—C(=O)—NH—; —NH—CH=N—, —NH—N=N—, —CH=N—NR—, or =N—NR—CH—; R is —H or $C_{1-4}$alkyl; and the other variables of Formula (I) are each and independently as described in the first set of variables of Formula (I).

In the seventh set of variables of Formula (I), each of $R^1$, $R^3$, $R^4$, $R^5$, and $R^6$ independently is —H, $C_{1-4}$alkyl, $C_{1-4}$haloalkyl, or $C_{3-6}$cycloalkyl; and $R^2$ is $C_{1-4}$alkyl, $C_{1-4}$haloalkyl, or $C_{3-6}$cycloalkyl; or optionally $R^1$ and $R^2$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$; or optionally $R^4$ and $R^5$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$. The other variables of Formula (I) are each and independently as described in the first set of variables of Formula (I).

In the eighth set of variables of Formula (I), R is H, $C_{1-4}$alkyl, or —($C_{1-4}$alkyl)-Ph, wherein Ph is phenyl optionally substituted with 1-2 occurrences of halogen, CN, —OH, —O($C_{1-4}$alkyl), —O($C_{1-4}$haloalkyl), $C_{1-4}$alkyl, or $C_{1-4}$haloalkyl; each of $R^1$, $R^3$, $R^4$, $R^5$, and $R^6$ independently is —H, $C_{1-4}$alkyl, $C_{1-4}$haloalkyl, or $C_{3-6}$cycloalkyl; and $R^2$ is $C_{1-4}$alkyl, $C_{1-4}$haloalkyl, or $C_{3-6}$cycloalkyl; or optionally $R^1$ and $R^2$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$; or optionally $R^4$ and $R^5$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$. The other variables of Formula (I) are each and independently as described in the first set of variables of Formula (I).

In the ninth set of variables of Formula (I), R is —H or $C_{1-4}$alkyl; each of $R^1$, $R^3$, $R^4$, $R^5$, and $R^6$ independently is —H, $C_{1-4}$alkyl, $C_{1-4}$haloalkyl, or $C_{3-6}$cycloalkyl; and $R^2$ is $C_{1-4}$alkyl, $C_{1-4}$haloalkyl, or $C_{3-6}$cycloalkyl; or optionally $R^1$ and $R^2$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$; or optionally $R^4$ and $R^5$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$. The other variables of Formula (I) are each and independently as described in the first set of variables of Formula (I).

In the tenth set of variables of Formula (I), X—Y—Z is —NR—N=CH—, —NH—C(=O)—NH—; —NH—CH=N—, —NH—N=N—, —CH=N—NR—, or =N—NR—CH—; each of $R^1$, $R^3$, $R^4$, $R^5$, and $R^6$ independently is —H, $C_{1-4}$alkyl, $C_{1-4}$haloalkyl, or $C_{3-6}$cycloalkyl; and $R^2$ is $C_{1-4}$alkyl, ($C_{1-4}$haloalkyl, or $C_{3-6}$cycloalkyl; or optionally $R^1$ and $R^2$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$; or optionally $R^4$ and $R^5$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$. The other variables of Formula (I) are each and independently as described in the first set of variables of Formula (I).

In the eleventh set of variables of Formula (I), X—Y—Z is —NR—N=CH—, —NH—C(=O)—NH—; —NH—CH=N—, —NH—N=N—, —CH=N—NR—, or =N—NR—CH—; R is H, $C_{1-4}$alkyl, or —($C_{1-4}$alkyl)-Ph, wherein Ph is phenyl optionally substituted with 1-2 occurrences of halogen, CN, —OH, —O($C_{1-4}$alkyl), —O($C_{1-4}$haloalkyl), $C_{1-4}$alkyl, or $C_{1-4}$haloalkyl; each of $R^1$, $R^3$, $R^4$, $R^5$, and $R^6$ independently is —H, $C_{1-4}$alkyl, $C_{1-4}$haloalkyl, or $C_{3-6}$cycloalkyl; and $R^2$ is $C_{1-4}$alkyl, ($C_{1-4}$haloalkyl, or $C_{3-6}$cycloalkyl; or optionally $R^1$ and $R^2$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$; or optionally $R^4$ and $R^5$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$. The other variables of Formula (I) are each and independently as described in the first set of variables of Formula (I).

In the thirteenth set of variables of Formula (I), X—Y—Z is —NR—N=CH—, —NH—C(=O)—NH—; —NH—CH=N—, —NH—N=N—, —CH=N—NR—, or =N—NR—CH—; R is —H or $C_{1-4}$alkyl; each of $R^1$, $R^3$, $R^4$, $R^5$, and $R^6$ independently is —H, $C_{1-4}$alkyl, $C_{1-4}$haloalkyl, or $C_{3-6}$cycloalkyl; and $R^2$ is $C_{1-4}$alkyl, $C_{1-4}$haloalkyl, or $C_{3-6}$cycloalkyl; or optionally $R^1$ and $R^2$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$; or optionally $R^4$ and $R^5$ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)$_2$. The other variables of Formula (I) are each and independently as described in the first set of variables of Formula (I).

In the fourteenth set of variables of Formula (I), p is 0; and the other variables of Formula (I) are each and independently as described in any of the first set through thirteenth set of variables of Formula (I).

In another embodiment, the invention is directed to compounds represented by any of Formulae (II), (III), (IV), (V), (VI), or (VII), or pharmaceutically acceptable salts thereof:

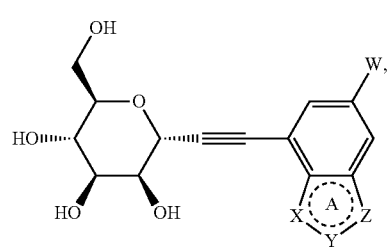

(II)

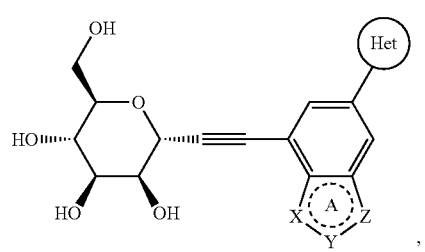

(III)

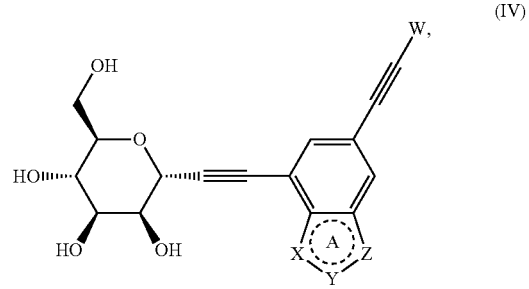

(IV)

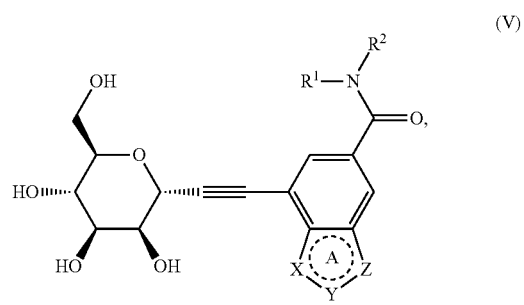

(V)

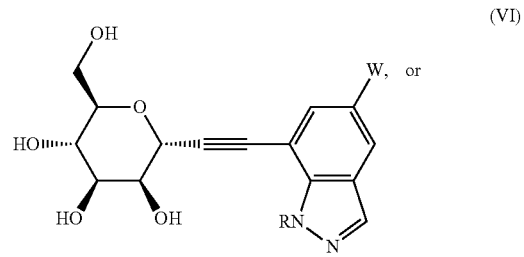

(VI)

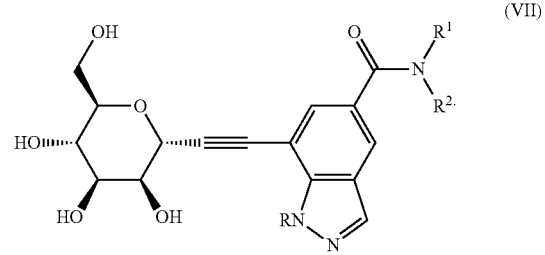

(VII)

Het of Formula (III) is a 3-8 membered saturated, partially unsaturated, or aromatic monocyclic ring having 1-4 heteroatoms selected from oxygen, nitrogen, or sulfur; or an 8-10 membered saturated, partially unsaturated, or aromatic bicyclic ring having 1-4 heteroatoms selected from oxygen, nitrogen, or sulfur; wherein each of said monocyclic and bicyclic rings independently and optionally is substituted with 1-4 occurrences of $JW^2$. The other variables of Formulae (II), (III), (IV), (V), (VI), and (VII) are each and independently as described in any one of the first set through fourteenth set of variables of Formula (I).

In yet another embodiment, the invention is directed to compounds represented by Formula (VI) or pharmaceutically acceptable salts thereof:

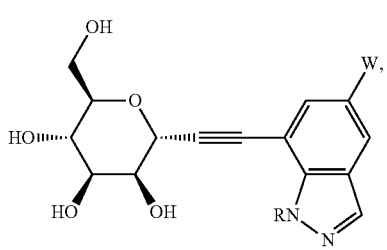

(VI)

wherein the variables of Formula (VI) are each and independently as described herein.

In the first set of variables of Formula (VI), R is —H or —CH$_3$; and the other variables of Formula (VI) are each and independently as described in the first set of variables of Formula (I).

In the second set of variables of Formula (VI), R is —H; and the other variables of Formula (VI) are each and independently as described in the first set of variables of Formula (I).

In the third set of variables of Formula (VI), R is —H or —CH$_3$; and W is —C(=O)NR$^1$R$^2$; C$_{1-6}$alkyl optionally substituted with 1-4 occurrences of J$^{W1}$; a 3-8 membered saturated, partially unsaturated, or aromatic monocyclic ring having 0-4 heteroatoms selected from oxygen, nitrogen, or sulfur; or an 8-10 membered saturated, partially unsaturated, or aromatic bicyclic ring having 0-4 heteroatoms selected from oxygen, nitrogen, or sulfur; wherein each of monocyclic and bicyclic rings independently and optionally is substituted with 1-4 occurrences of J$^{W2}$. The other variables of Formula (VI) are each and independently as described in the first set of variables of Formula (I).

In the fourth set of variables of Formula (VI), R is —H; and W is —C(=O)NR$^1$R$^2$; C$_{1-6}$alkyl optionally substituted with 1-4 occurrences of J$^{W1}$; a 3-8 membered saturated, partially unsaturated, or aromatic monocyclic ring having 0-4 heteroatoms selected from oxygen, nitrogen, or sulfur; or an 8-10 membered saturated, partially unsaturated, or aromatic bicyclic ring having 0-4 heteroatoms selected from oxygen, nitrogen, or sulfur; wherein each of monocyclic and bicyclic rings independently and optionally is substituted with 1-4 occurrences of J$^{W2}$. The other variables of Formula (VI) are each and independently as described in the first set of variables of Formula (I).

In the fifth set of variables of Formula (VI), R is —H or —CH$_3$; and W is a 3,6-dihydro-2H-1λ$^2$-pyridine, 3,6-dihydro-2H-pyran, C$_{5-6}$ cycloalkenyl, benzene, pyridine, indole, pyridine-2-one, imidazo[1,2-a]pyridine, benzoimidazole, benzo[d][1,3]dioxole, 1,3,4-oxadiazole, pyrrole, or triazole, each of which independently and optionally is substituted. The other variables of Formula (VI) are each and independently as described in the first set of variables of Formula (I).

In the sixth set of variables of Formula (VI), R is —H; and W is a 3,6-dihydro-2H-1λ$^2$-pyridine, 3,6-dihydro-2H-pyran, C$_{5-6}$ cycloalkenyl, benzene, pyridine, indole, pyridine-2-one, imidazo[1,2-a]pyridine, benzoimidazole, benzo[d][1,3]dioxole, 1,3,4-oxadiazole, pyrrole, or triazole, each of which independently and optionally is substituted. The other variables of Formula (VI) are each and independently as described in the first set of variables of Formula (I).

In the seventh set of variables of Formula (VI), R is —H or —CH$_3$; and W is

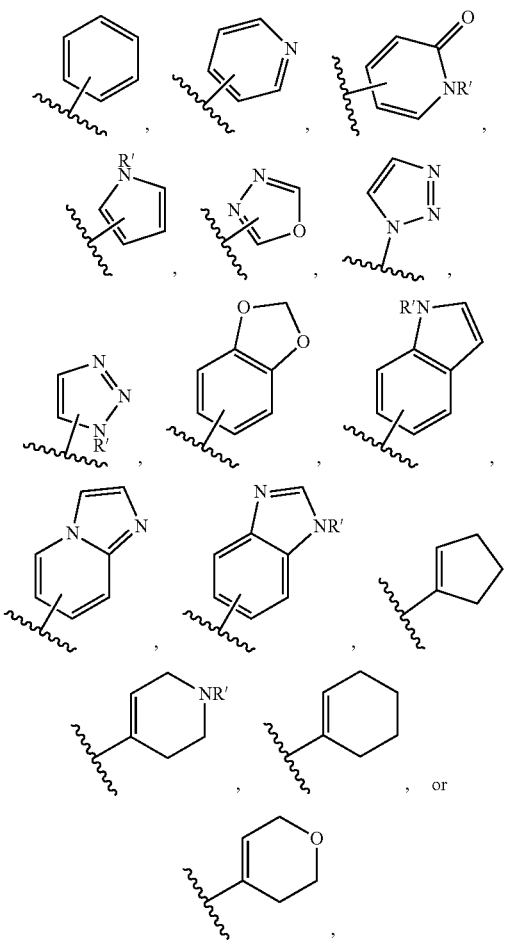

wherein each W is independently and optionally substituted, and each R' independently —H or —C$_{1-4}$alkyl. The other variables of Formula (VI) are each and independently as described in the first set of variables of Formula (I).

In the eighth set of variables of Formula (VI), R is —H; and W is

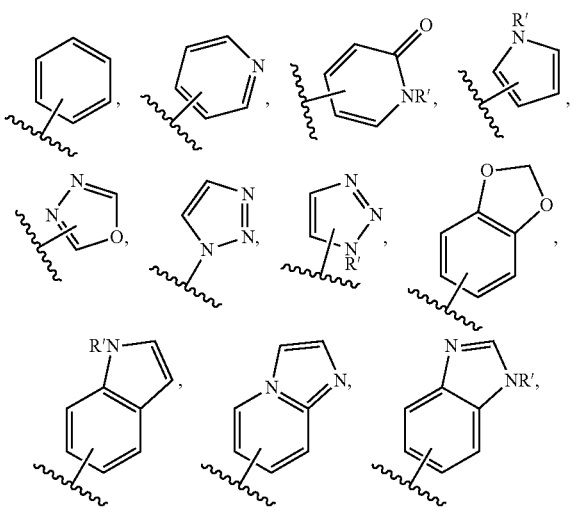

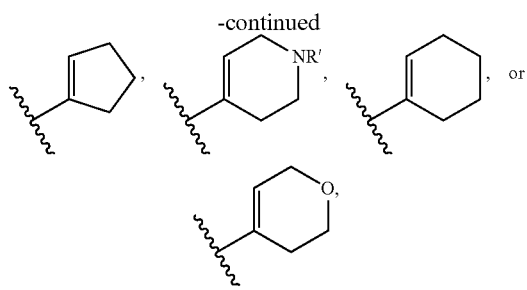

wherein each W is independently and optionally substituted, and each R' independently —H or —C$_{1-4}$alkyl. The other variables of Formula (VI) are each and independently as described in the first set of variables of Formula (I).

In the ninth set of variables of Formula (VI), R is —H or —CH$_3$; and W is optionally substituted C$_{1-6}$alkyl; and the other variables of Formula (VI) are each and independently as described in the first set of variables of Formula (I).

In the tenth set of variables of Formula (VI), R is —H; and W is optionally substituted C$_{1-6}$alkyl; and the other variables of Formula (VI) are each and independently as described in the first set of variables of Formula (I).

In the eleventh set of variables of Formula (VI), R is —H or —CH$_3$; and W is a 5-6 membered, optionally substituted, aromatic monocyclic ring; or an 8-10 membered, optionally substituted, aromatic bicyclic ring. Specific examples of W include a benzene, pyridine, pyridine-2-one, imidazo[1,2-a]pyridine, benzoimidazole, indole, benzo[d][1,3]dioxole, 1,3,4-oxadiazole, pyrrole, or triazole, each of which independently and optionally is substituted. The other variables of Formula (VI) are each and independently as described in the first set of variables of Formula (I).

In the twelfth set of variables of Formula (VI), R is —H; and W is a 5-6 membered, optionally substituted, aromatic monocyclic ring; or an 8-10 membered, optionally substituted, aromatic bicyclic ring. Specific examples of W include a benzene, pyridine, pyridine-2-one, imidazo[1,2-a]pyridine, benzoimidazole, indole, benzo[d][1,3]dioxole, 1,3,4-oxadiazole, pyrrole, or triazole, each of which independently and optionally is substituted. The other variables of Formula (VI) are each and independently as described in the first set of variables of Formula (I).

In the thirteenth set of variables of Formula (VI), R is —H or —CH$_3$; and W is a 3,6-dihydro-2H-1λ$^2$-pyridine, 3,6-dihydro-2H-pyran, C$_{5-6}$ cycloalkenyl, benzene, pyridine, indole, pyridine-2-one, imidazo[1,2-a]pyridine, benzoimidazole, benzo[d][1,3]dioxole, 1,3,4-oxadiazole, pyrrole, or triazole, each of which independently and optionally is substituted. The other variables of Formula (VI) are each and independently as described in the first set of variables of Formula (I).

In the fourteenth set of variables of Formula (VI), R is —H; and W is a 3,6-dihydro-2H-1λ$^2$-pyridine, 3,6-dihydro-2H-pyran, C$_{5-6}$ cycloalkenyl, benzene, pyridine, indole, pyridine-2-one, imidazo[1,2-a]pyridine, benzoimidazole, benzo[d][1,3]dioxole, 1,3,4-oxadiazole, pyrrole, or triazole, each of which independently and optionally is substituted. The other variables of Formula (VI) are each and independently as described in the first set of variables of Formula (I).

In the fifteenth set of variables of Formula (VI), J$^{W1}$ is selected from the group consisting of halogen, CN, —OH, —O(C$_{1-4}$alkyl), —O(C$_{1-4}$haloalkyl), —O(C$_{1-4}$alkyl)-Ph, —NH$_2$, —NH(C$_{1-4}$alkyl), and —N(C$_{1-4}$alkyl)$_2$; and J$^{W2}$ is selected from the group consisting of halogen, CN, oxo, NO$_2$, C$_{1-4}$alkyl, C$_{1-4}$haloalkyl, —NH$_2$, —NH(C$_{1-4}$alkyl), —N(C$_{1-4}$alkyl)$_2$, —C(=O)OH, —C(=O)O(C$_{1-4}$alkyl), —OH, —O(C$_{1-4}$alkyl), —O(C$_{1-4}$haloalkyl), —O(C$_{1-4}$alkyl)-Ph, —O(CH$_2$)O—, —O(CH$_2$)$_2$O—, —C(=O)NH$_2$, —C(=O)NH(C$_{1-4}$alkyl), —C(=O)N(C$_{1-4}$alkyl)$_2$, —SO$_2$(C$_{1-4}$alkyl), —NHCO(C$_{1-4}$alkyl), —SO$_2$NH$_2$, —SO$_2$NH(C$_{1-4}$alkyl), and —SO$_2$N(C$_{1-4}$alkyl)$_2$. The other variables of Formula (VI) are each and independently as described in any of the first set through fourteenth set of variables of Formula (I).

In yet another embodiment, the invention is directed to compounds represented by any of Formulae (VIa), (VIb), (VIc), (VId), (VIe), (VIf), (VIg), (VIh), (VIi), (VIj), (VIk), and (VIm), or pharmaceutically acceptable salts thereof:

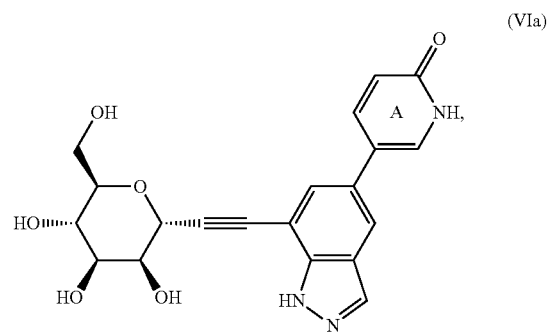

(VIa)

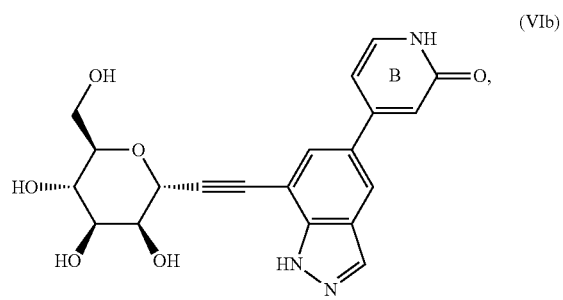

(VIb)

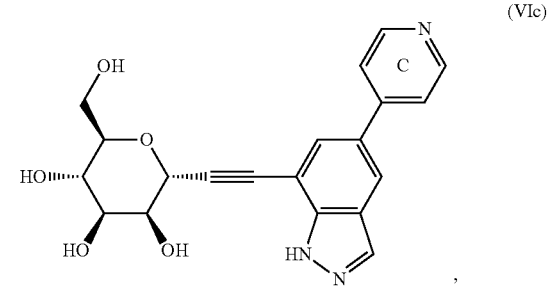

(VIc)

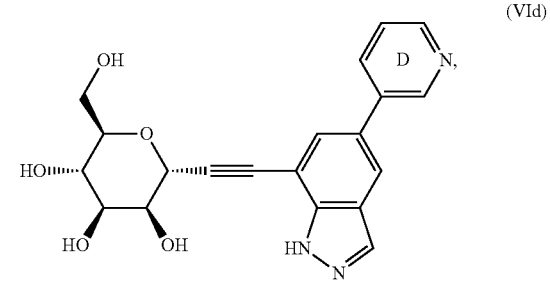

(VId)

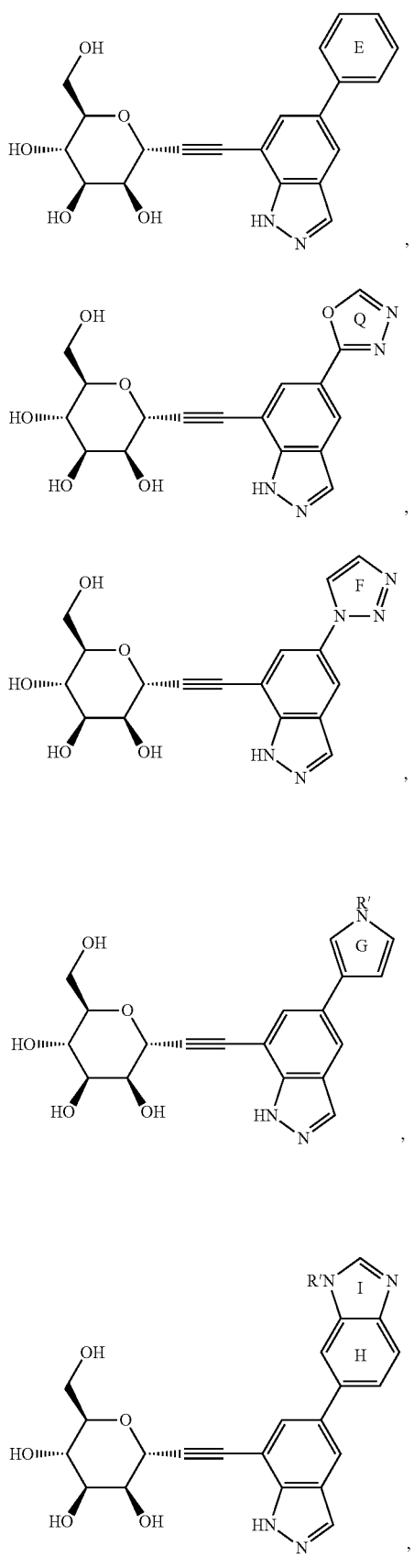
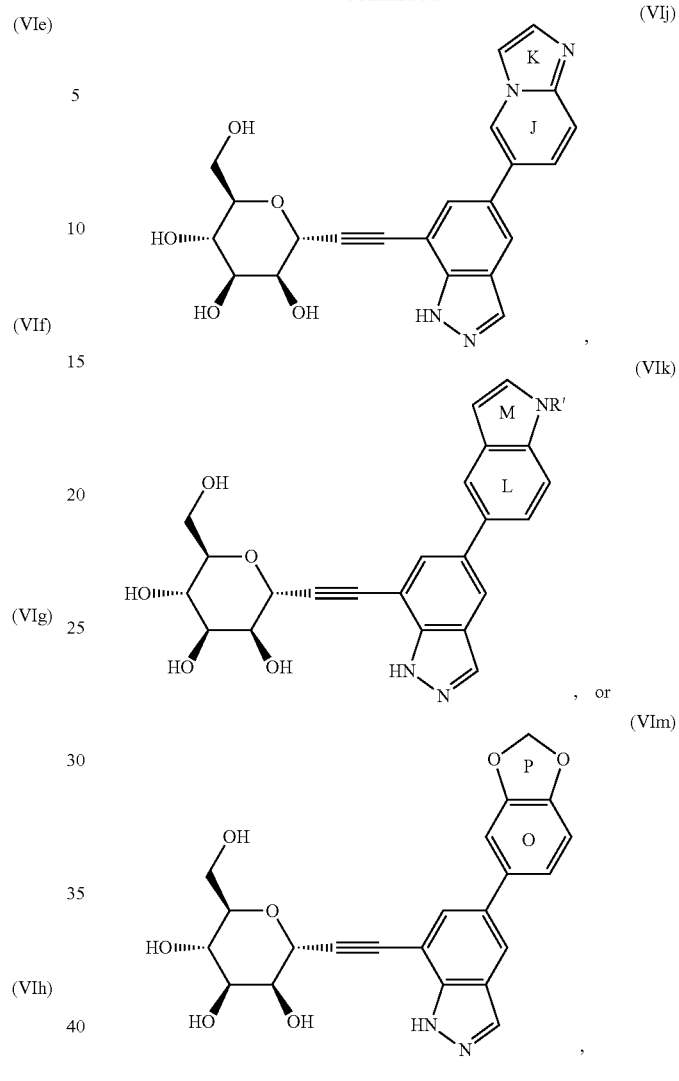

wherein each of Rings A-Q independently and optionally is substituted, and each R' is —H or methyl. The substituents for Rings A-Q are as described for $J^{W2}$ for Formula (I). In certain embodiments, the compound is a compound of Formula (VIa) or pharmaceutically acceptable salt of Formula (VIa), wherein Ring A optionally is substituted, and each R' is —H or methyl. In certain embodiments, the compound is a compound of Formula (VId) or pharmaceutically acceptable salt of Formula (VIa), wherein Ring D optionally is substituted, and each R' is —H or methyl.

In a specific embodiment, each of Rings A-Q is independently and optionally substituted with 1-3 occurrences of $J^{W2}$ selected from —F, —Cl, —CN, $NO_2$, $C_{1-2}$alkyl, —NH($C_{1-2}$alkyl), —N($C_{1-2}$alkyl)$_2$, —C(=O)O($C_{1-2}$alkyl), —OH, —O($C_{1-2}$alkyl), —O($C_{1-2}$haloalkyl), —O($C_{1-2}$ alkyl)-Ph, —C(=O)NH$_2$, —C(=O)NH($C_{1-2}$alkyl), —C(=O)N($C_{1-2}$alkyl)$_2$, —SO$_2$($C_{1-2}$alkyl), —NHCO($C_{1-2}$ alkyl), —SO$_2$NH$_2$, —SO$_2$NH($C_{1-2}$alkyl), or —SO$_2$N($C_{1-2}$ alkyl)$_2$.

In another specific embodiment, each of Rings A-Q is independently and optionally substituted with 1-3 occurrences of $J^{W2}$ selected from —F, —Cl, —CN, $NO_2$, —CH$_3$, —C$_2$H$_5$, NH(CH$_3$), —N(CH$_3$)$_2$, —C(=O)OH, —C(=O)O (CH$_3$), —C(=O)O(C$_2$H$_5$), —OH, —O(CH$_3$), —O(C$_2$H$_5$), —OCH$_2$Ph, —C(=O)NH$_2$, —C(=O)NH(CH$_3$), —C(=O)N(CH$_3$)$_2$, —SO$_2$(CH$_3$), —NHCO(CH$_3$), —SO$_2$NH$_2$, —SO$_2$NH(CH$_3$), —SO$_2$N(CH$_3$)$_2$, or —SO$_2$N(C$_2$H$_5$)$_2$.

In yet another embodiment, the invention is directed to compounds represented by any of Formula (VII) or pharmaceutically acceptable salts thereof:

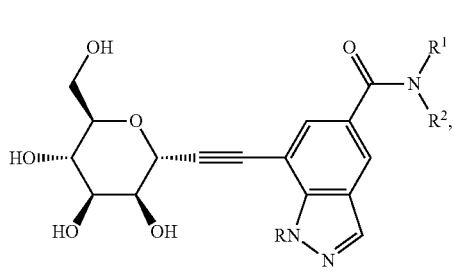

(VII)

wherein the variables of Formula (VII) are each and independently as described herein.

In the first set of variables of Formula (VII), R is H or CH$_3$; and each of R$^1$ and R$^2$ is independently as described in the first set of variables of Formula (I).

In the second set of variables of Formula (VII), R is H or CH$_3$; and each of R$^1$ and R$^2$ independently is C$_{1-4}$alkyl optionally substituted with 1-3 occurrences of J$^A$; or C$_{3-6}$cycloalkyl optionally substituted with 1-3 occurrences of J$^B$; or optionally R$^1$ and R$^2$ together with the nitrogen atom to which they are attached form a 5-6 membered, non-aromatic, monocyclic ring wherein up to one methylene unit of the ring is optionally replaced with O, NH, N(C$_{1-4}$alkyl), S, C(O), S(O), or S(O)$_2$. In a further specific embodiment, each J$^A$ independently is halogen, CN, —OH, —OCH$_3$, or —OCF$_3$; and each J$^B$ independently is halogen, —CN, —OH, —OCH$_3$, —OCF$_3$, —CH$_3$, or —CF$_3$.

In the third set of variables of Formula (VII), R is H; and each of R$^1$ and R$^2$ independently is C$_{1-4}$alkyl optionally substituted with 1-3 occurrences of J$^A$; or C$_{3-6}$cycloalkyl optionally substituted with 1-3 occurrences of J$^B$; or optionally R$^1$ and R$^2$ together with the nitrogen atom to which they are attached form a 5-6 membered, non-aromatic, monocyclic ring wherein up to one methylene unit of the ring is optionally replaced with O, NH, N(C$_{1-4}$alkyl), S, C(O), S(O), or S(O)$_2$. In a further specific embodiment, each J$^A$ independently is halogen, CN, —OH, —OCH$_3$, or —OCF$_3$; and each J$^B$ independently is halogen, —CN, —OH, —OCH$_3$, —OCF$_3$, —CH$_3$, or —CF$_3$.

In the fourth set of variables of Formula (VII), R is H or CH$_3$; and each of R$^1$ and R$^2$ independently is C$_{1-4}$alkyl, C$_{1-4}$haloalkyl, or C$_{3-6}$cycloalkyl, or R$^1$ and R$^2$ together with the nitrogen atom to which they are attached form a morpholine ring.

In the fifth set of variables of Formula (VII), R is H or CH$_3$; and each of R$^1$ and R$^2$ independently is C$_{1-4}$alkyl, cyclopentyl or cyclohexyl, or R$^1$ and R$^2$ together with the nitrogen atom to which they are attached form a morpholine ring.

In the sixth set of variables of Formula (VII), R is H or CH$_3$; and each of R$^1$ and R$^2$ independently is C$_{1-4}$alkyl, C$_{1-4}$haloalkyl, or C$_{3-6}$cycloalkyl, or R$^1$ and R$^2$ together with the nitrogen atom to which they are attached form a morpholine ring.

In the seventh set of variables of Formula (VII), R is H or CH$_3$; and each of R$^1$ and R$^2$ independently is C$_{1-4}$alkyl, cyclopentyl or cyclohexyl, or R$^1$ and R$^2$ together with the nitrogen atom to which they are attached form a morpholine ring.

In yet another embodiment, the invention is directed to compounds represented by any one of Formulae (II) (III), (IV) (V), (VI), (VIa), (VIb), (VIc), (VId), (VIe), (VIf), (VIg), (VIi), (VIj), (VIk), (VIm), (VI) and (VII), or pharmaceutically acceptable salts thereof, wherein the variables are each and independently as described in any one of the first set through the fourteenth set of variables of Formula (I).

In yet another embodiment, the invention is directed to compounds represented by any one of the following structural formulae or pharmaceutically acceptable salts thereof:

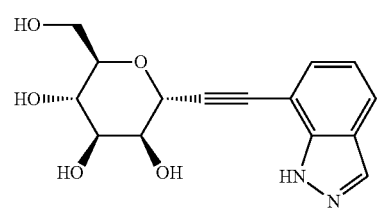

1

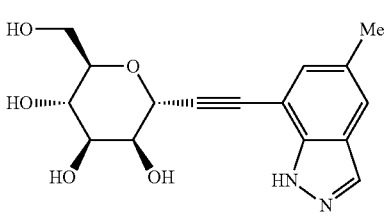

2

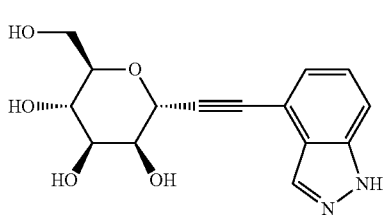

3

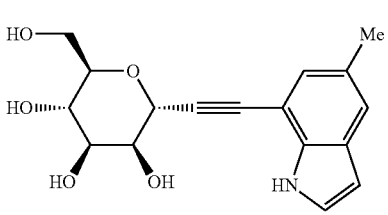

4

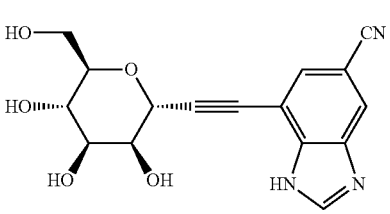

5

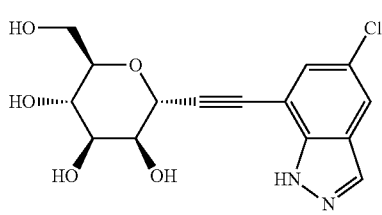

6

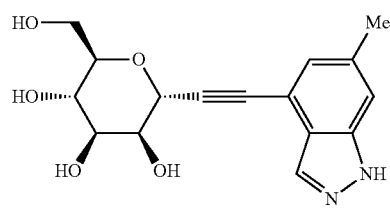
7
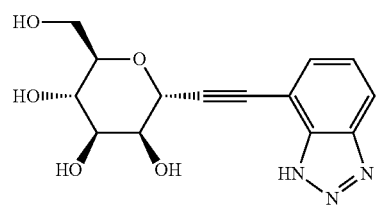
8
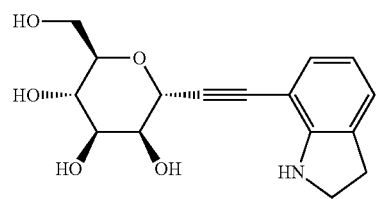
9
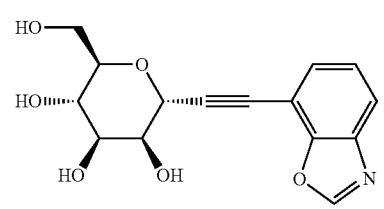
10
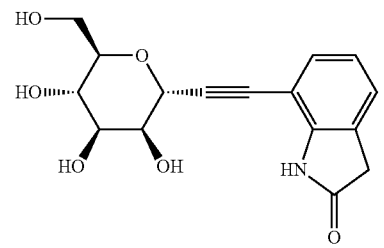
11
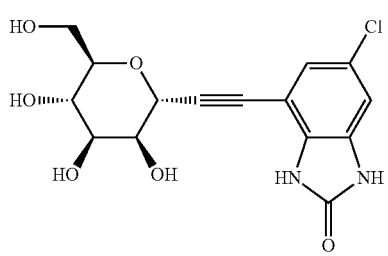
12
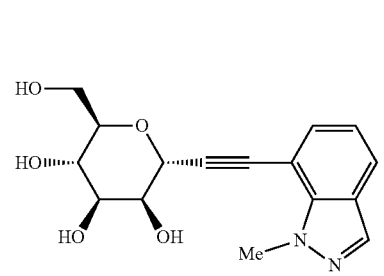
13
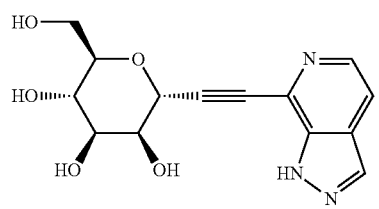
14
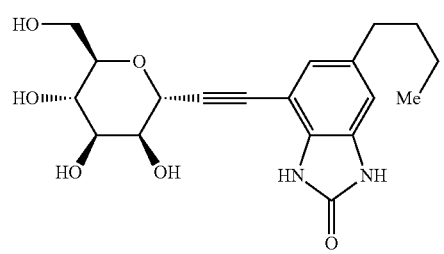
15
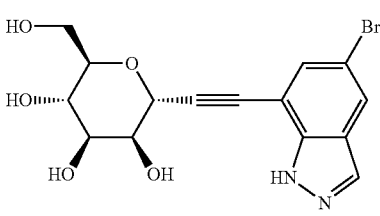
16
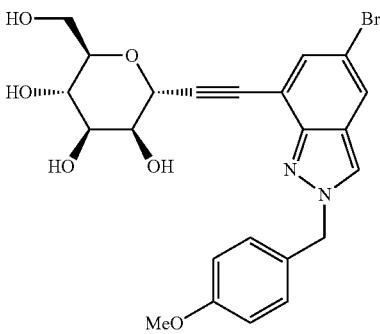
17
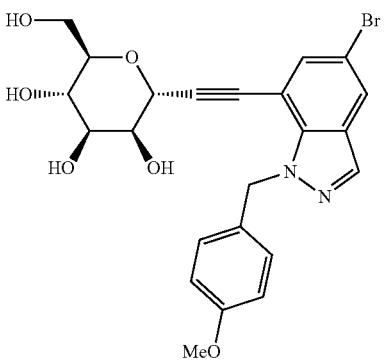
18
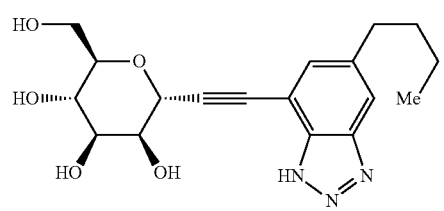
19

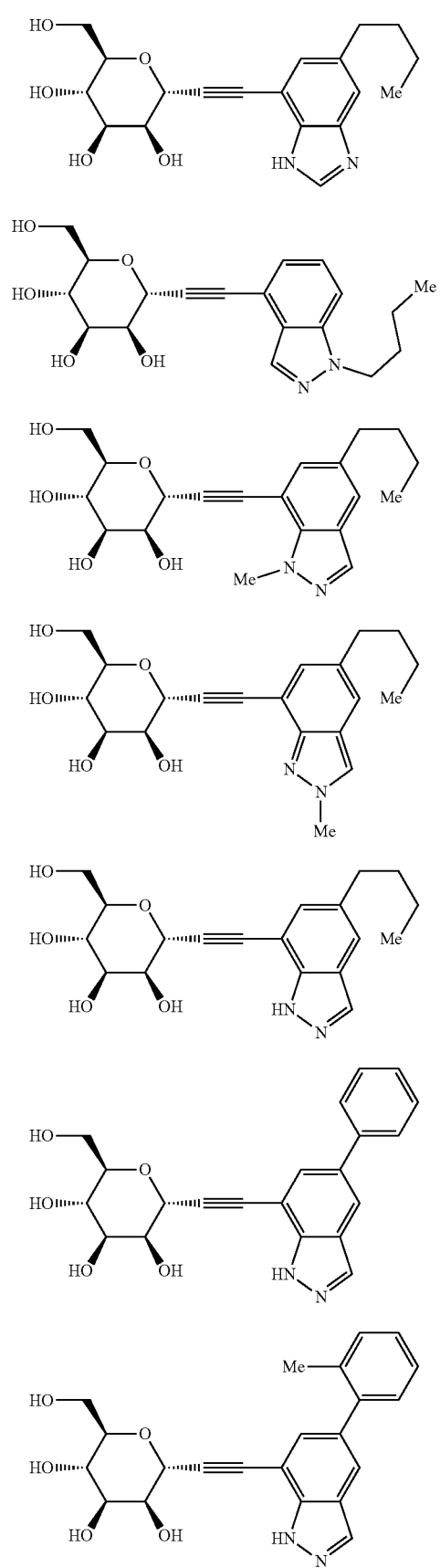
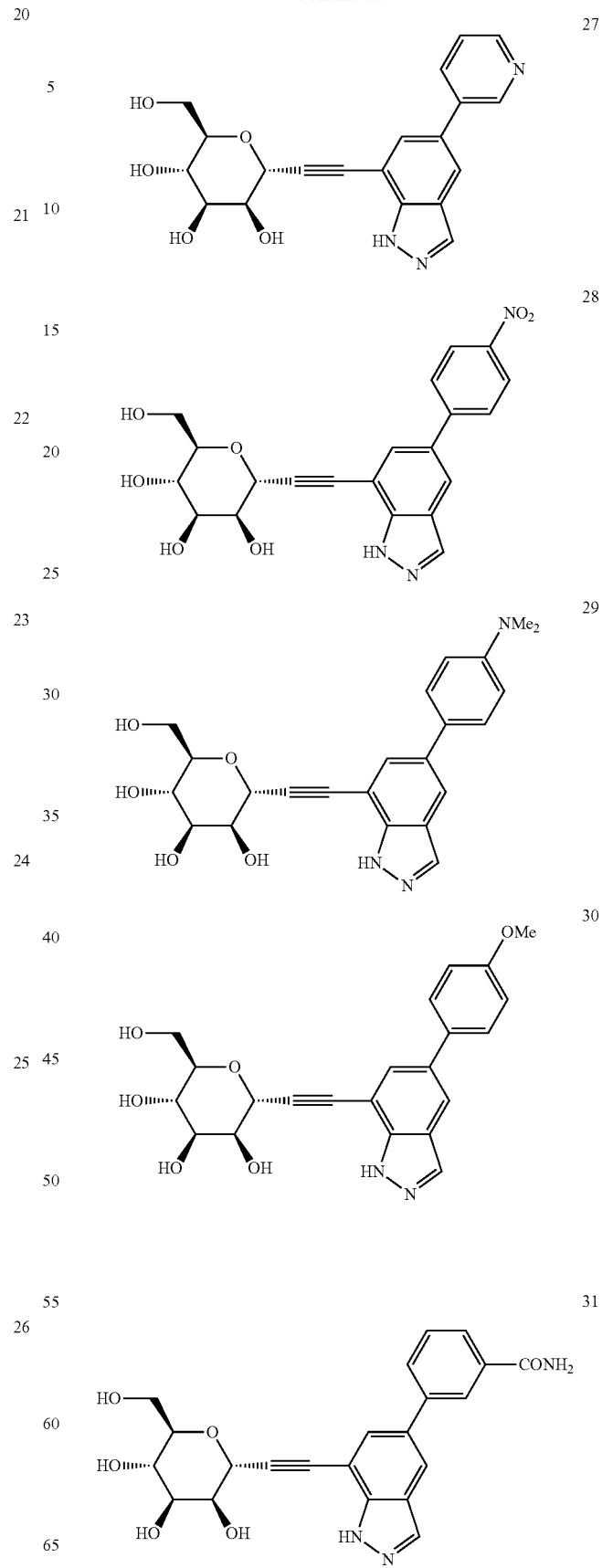

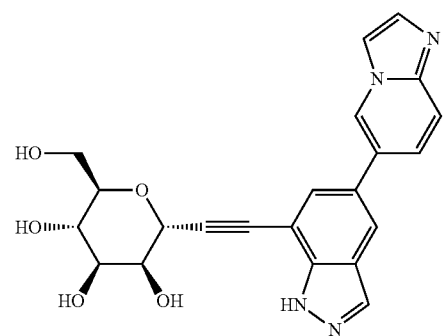
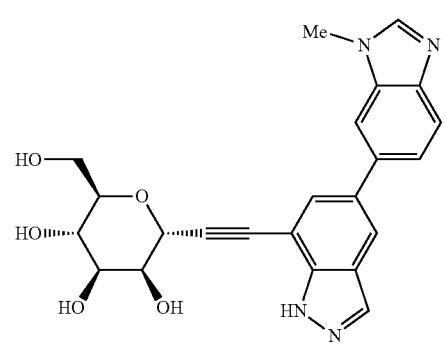
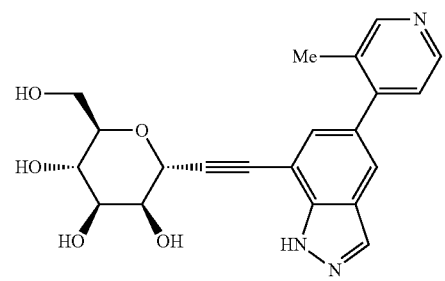
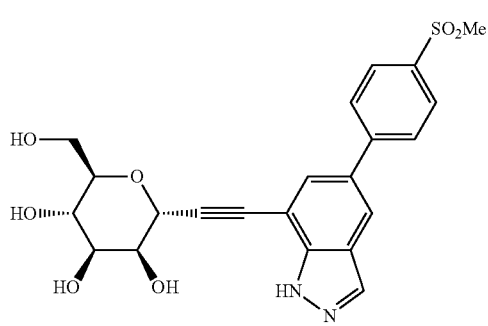
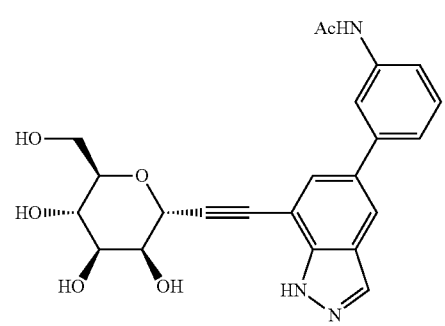
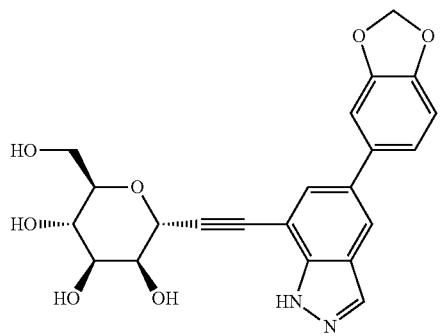
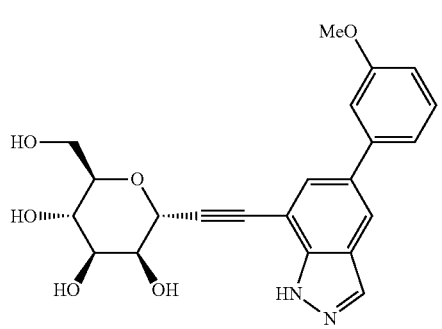
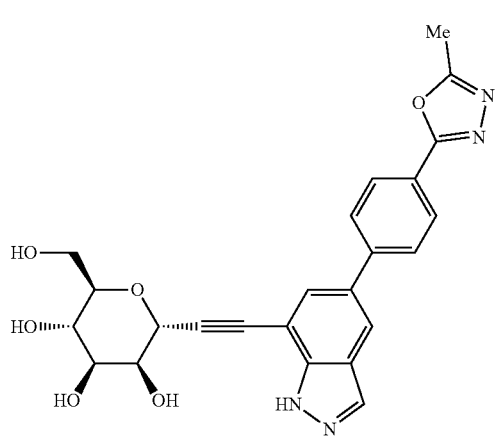
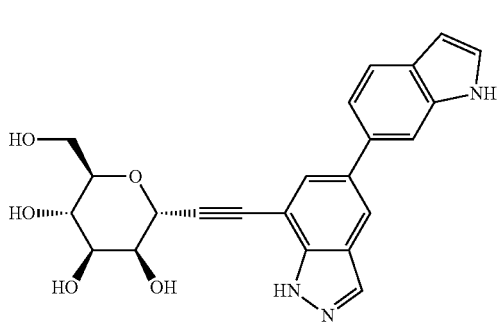

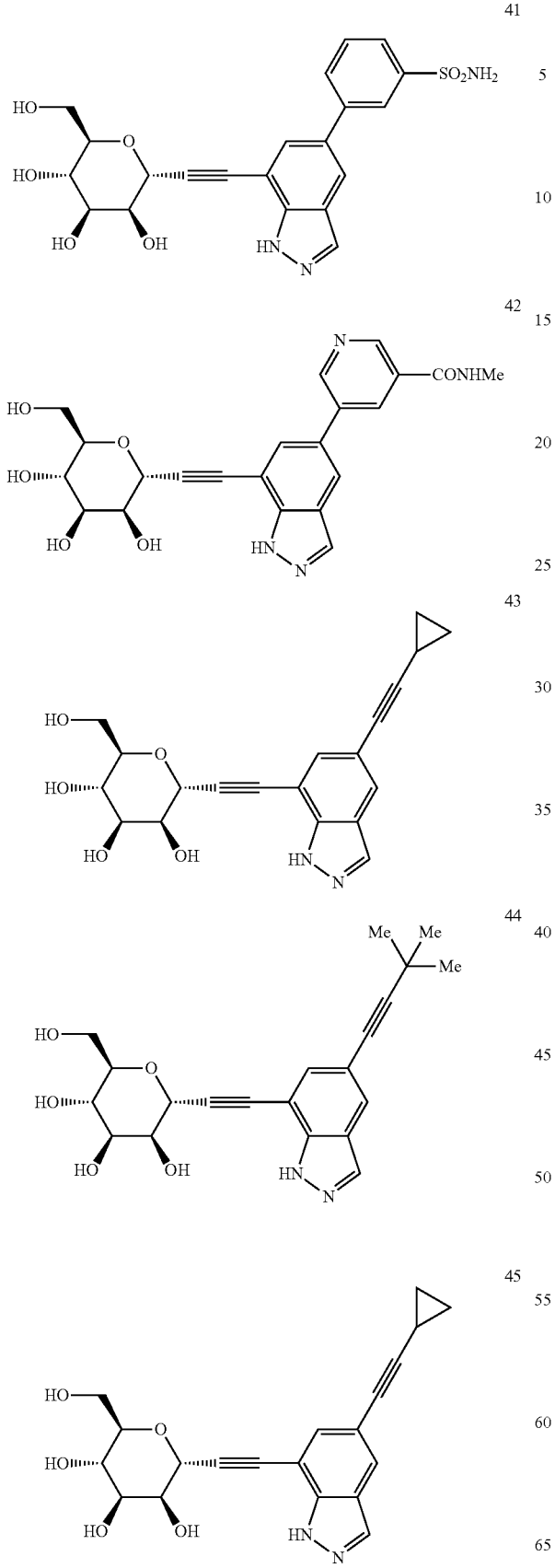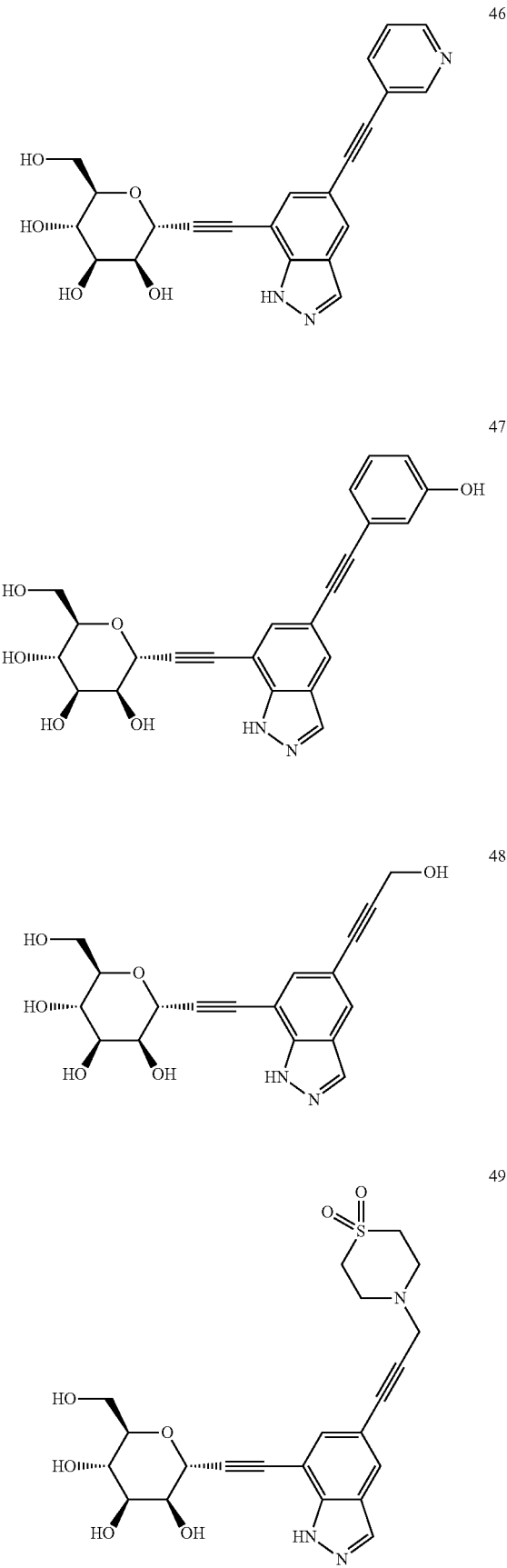

50
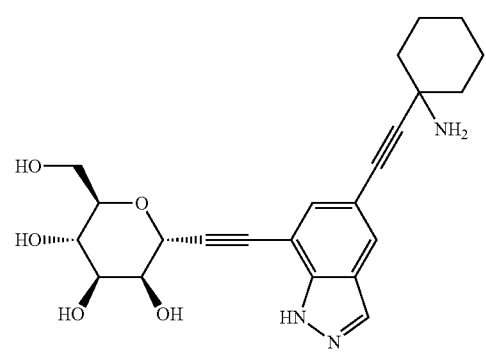
51
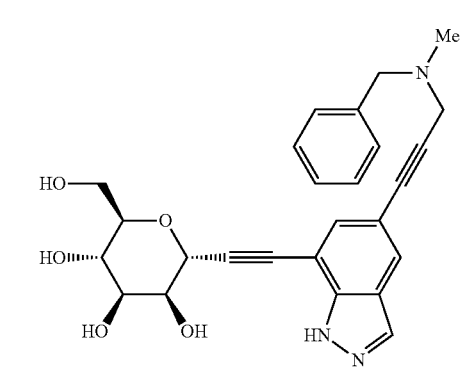
52
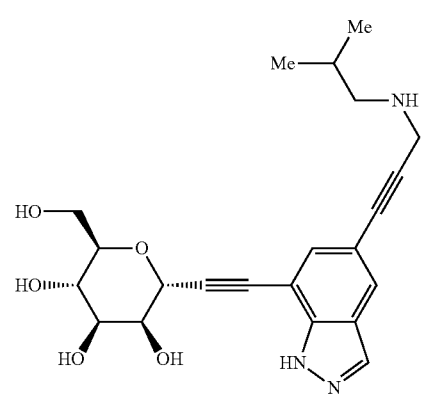
53
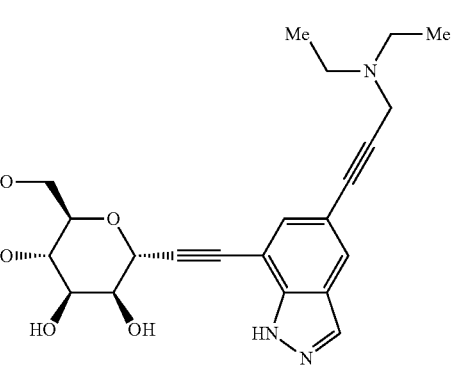
54
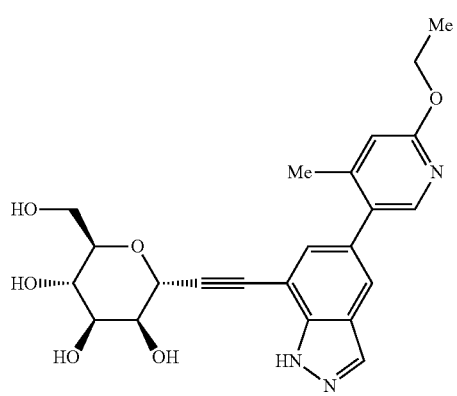
55
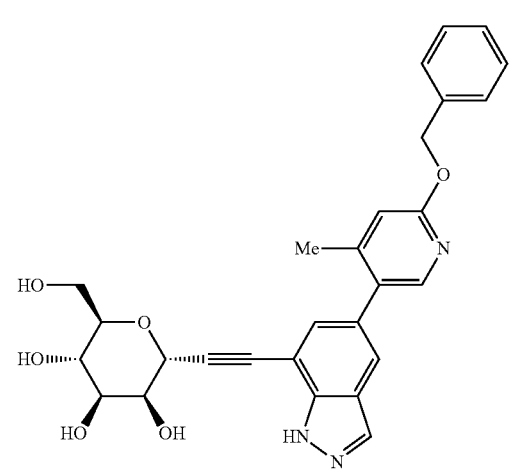
56
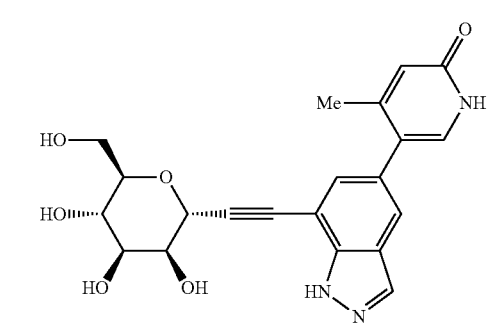
57
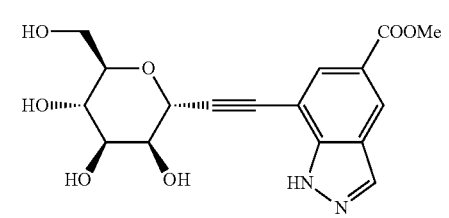
58
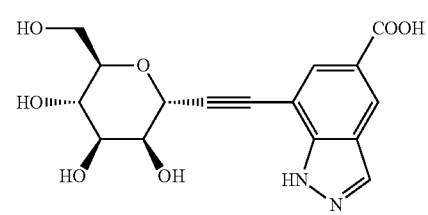

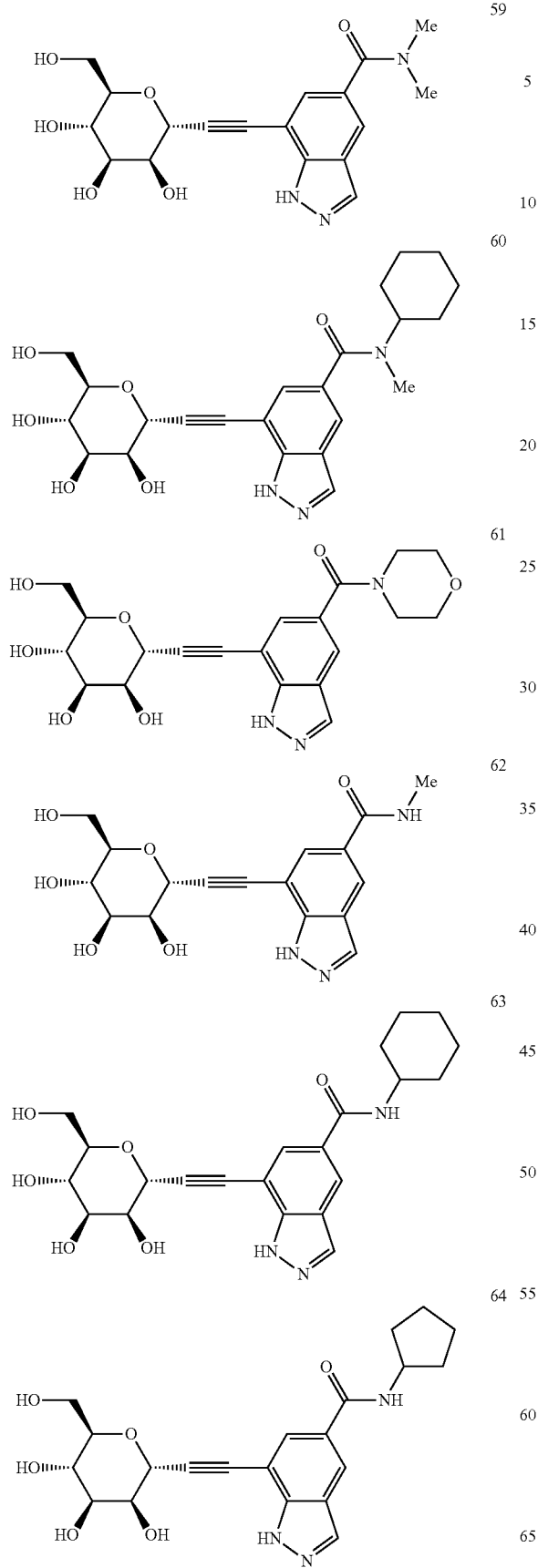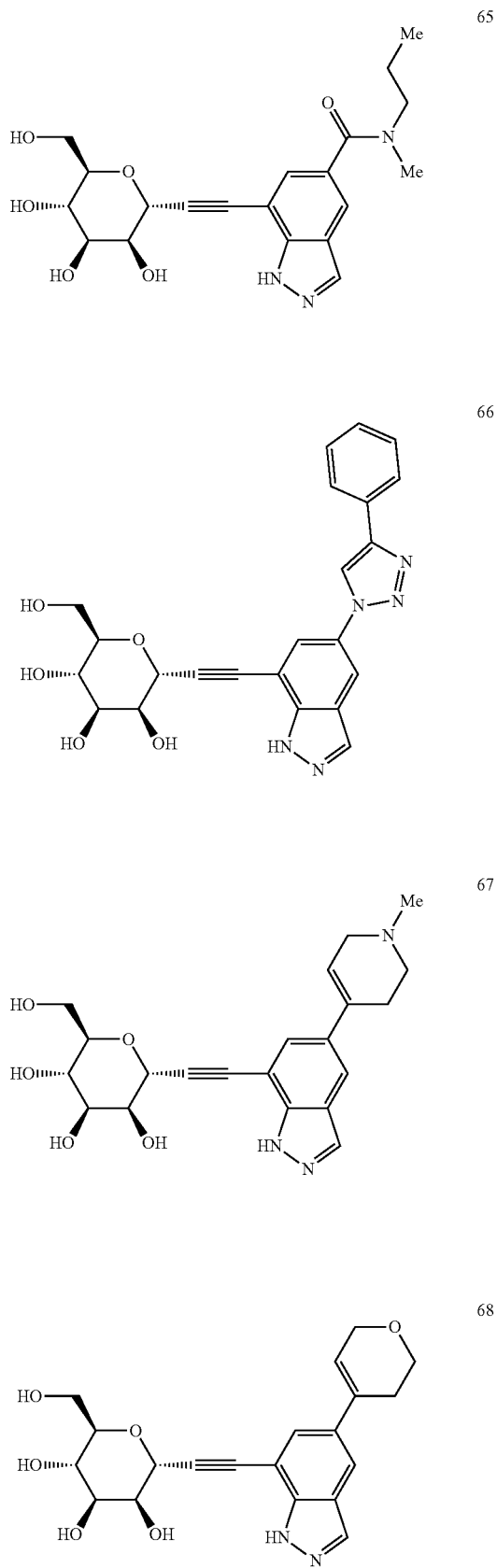

33 34
-continued -continued
69 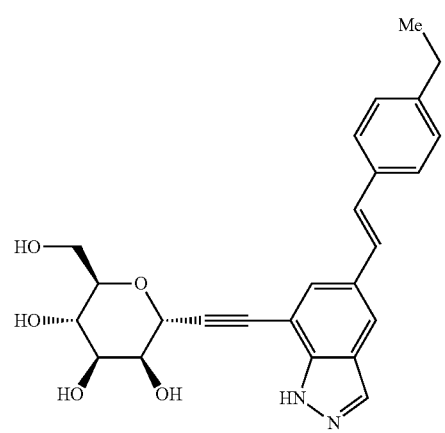
73 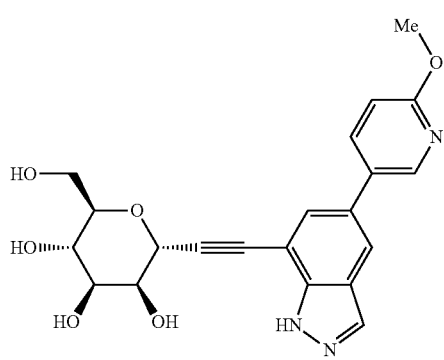
70 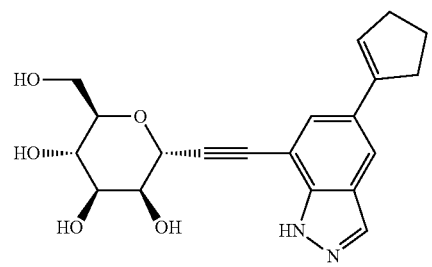
74 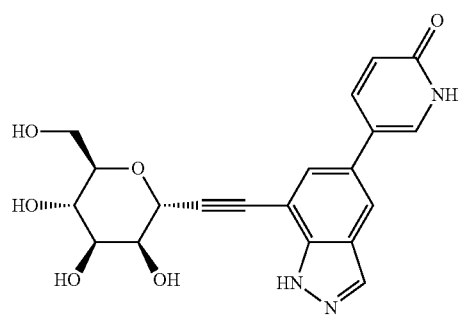
71 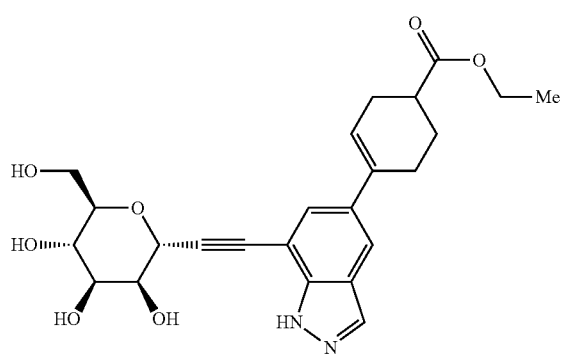
75 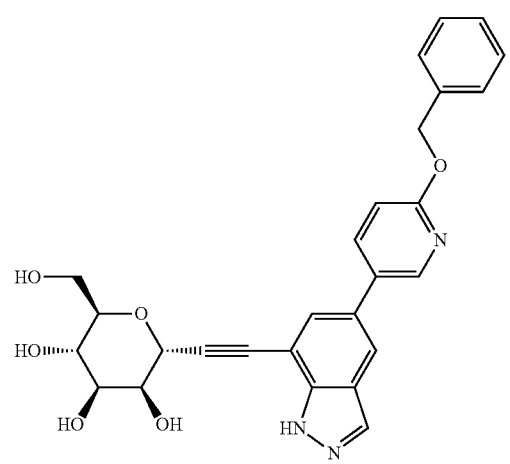
72 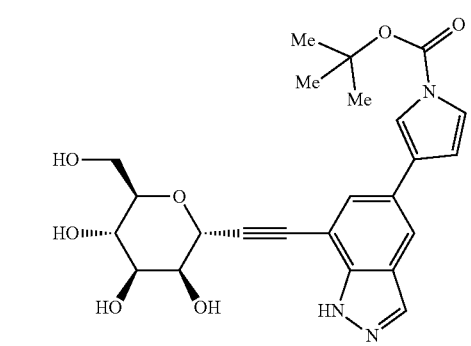
76 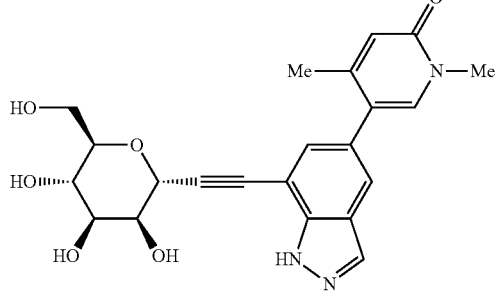

77
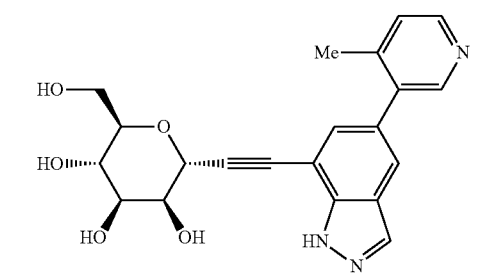
78
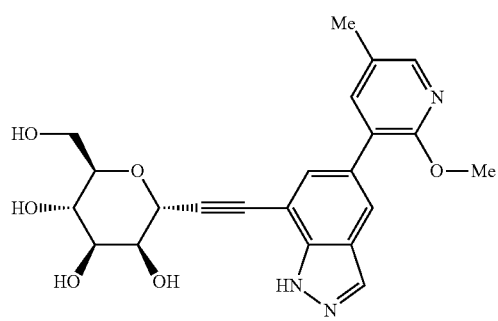
79
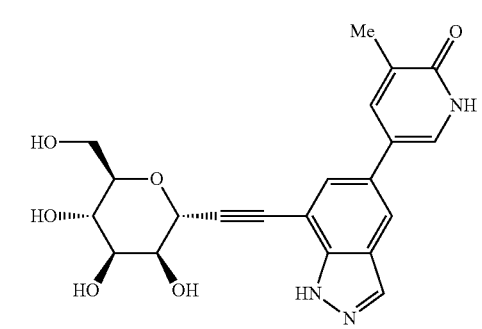
80
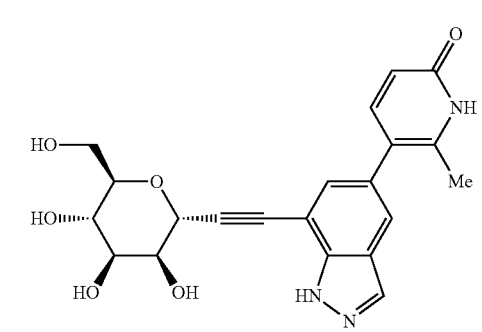
81
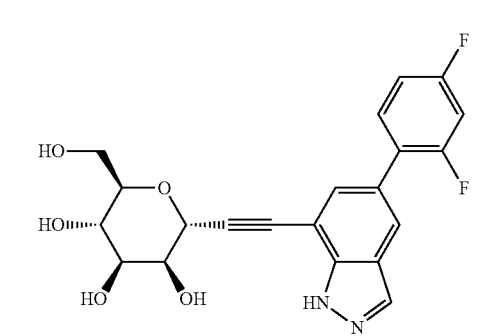
82
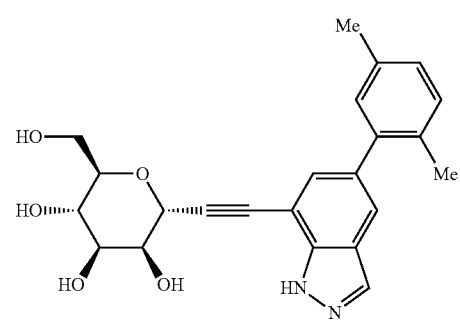
83
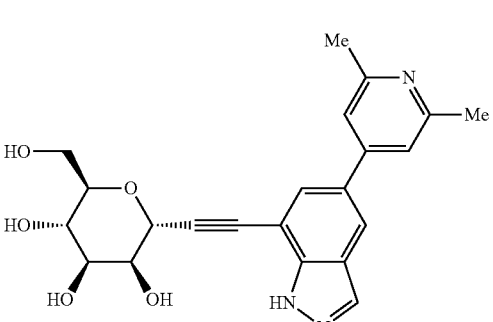
84
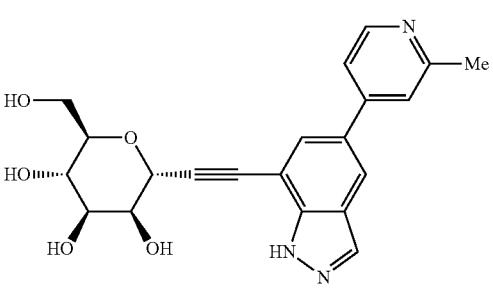
85
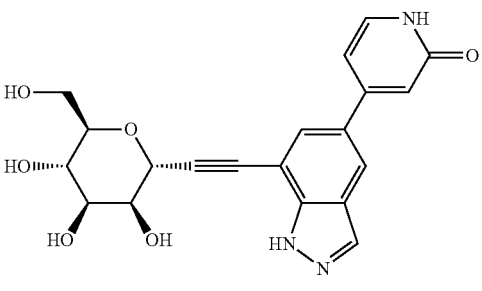
86
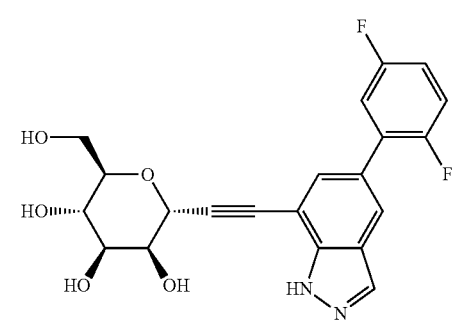

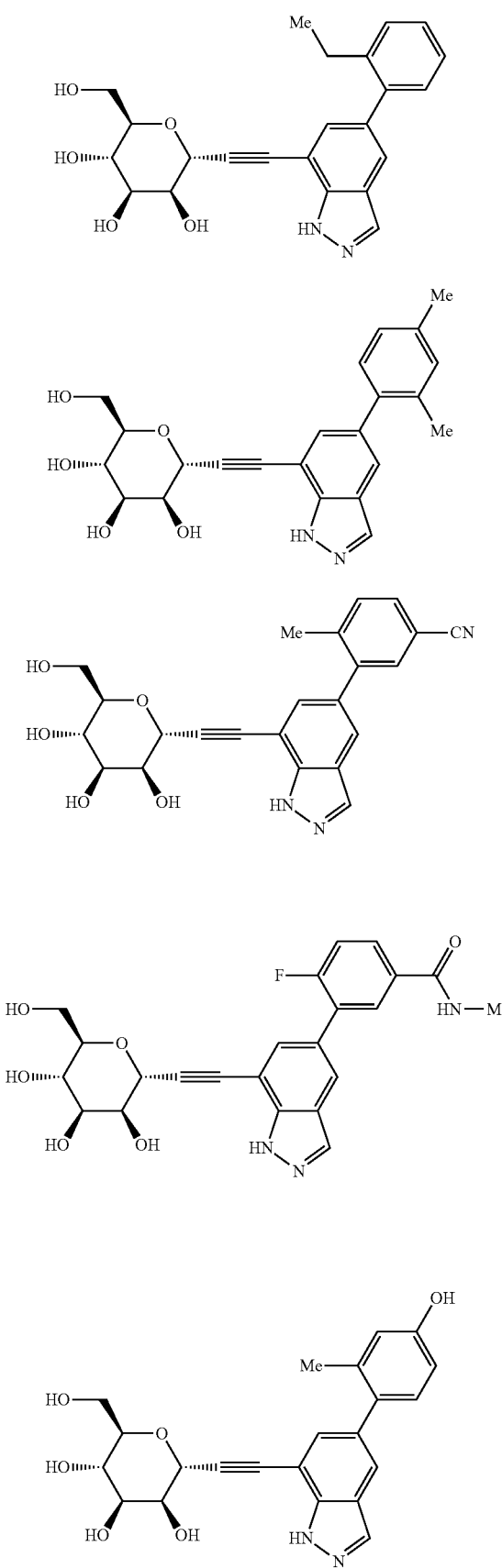

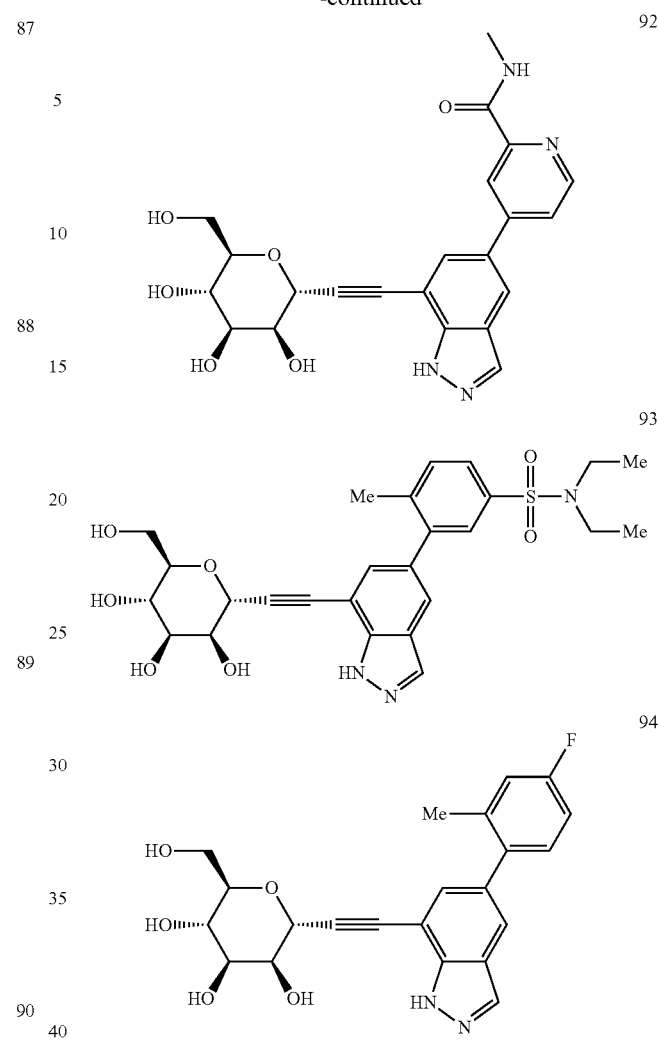

In some embodiments, the invention is directed to compounds represented by any one of Formulae (I), (II) (III), (IV) (V), (VI), (VIa), (VIb), (VIc), (VId), (VIe), (VIf), (VIg), (VIi), (VIj), (VIk), (VIm), and (VII), or pharmaceutically acceptable salts thereof, wherein the variables are each and independently as depicted in the compounds of the disclosure, including the specific compounds depicted in the preceding paragraph. In certain embodiments, the invention is directed to a compound, wherein the compound is compound 27, 39, 56, 70, 77, 80, or a pharmaceutically acceptable salt thereof. In certain embodiments, the invention is directed to compound 56, or a pharmaceutically acceptable salt thereof. In certain embodiments, the invention is directed to compound 56. In certain embodiments, the invention is directed to compound 77, or a pharmaceutically acceptable salt thereof. In certain embodiments, the invention is directed to compound 77. In certain embodiments, the invention is directed to compound 80, or a pharmaceutically acceptable salt thereof. In certain embodiments, the invention is directed to compound 80.

In general, the compounds of the invention can be prepared by methods described herein or by other methods known to those skilled in the art. Specific exemplary preparations of the compounds of the invention are described in the Exemplification section below.

In one embodiment, the methods of preparing compounds represented by Formula (I) or pharmaceutically acceptable salts thereof employ the step of reacting Compound (A1) with Compound (M1) in the presence of a Pd or Pd/Cu catalyst (e.g., Sonogashira coupling), wherein U, X, Y, Z, and p of Compound (A1) and Formula (I) are each independently as defined in claim 1; W of Compound (A1) and Formula (I) are each independently —H, halogen, —CN, —C(=O)OR³ or $C_{1-6}$alkyl, wherein $R^3$ is as defined in claim 1; and $L^1$ of Compound (A1) is —Cl or —Br:

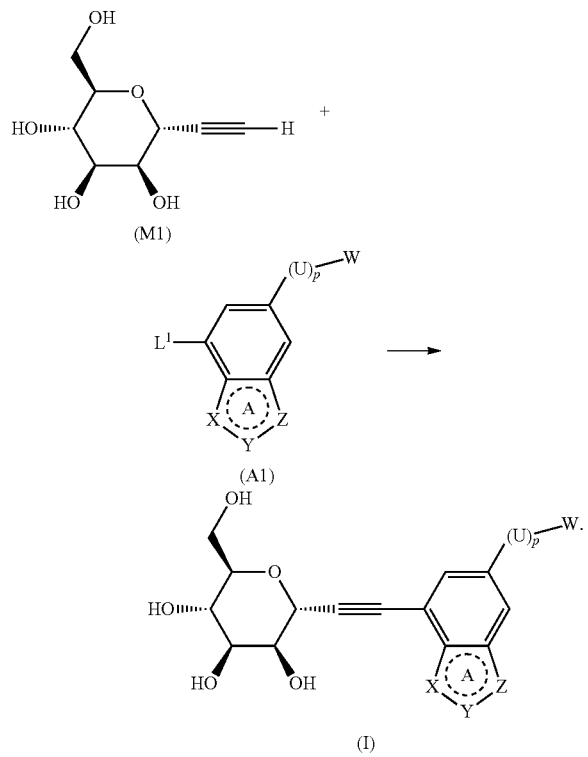

Any suitable conditions known in the art for, for example, Sonogashira coupling can be employed. Some suitable examples of Pd and Pd/Cu catalysts include $Pd(PPh_3)_4$ and $CuI/PdCl_2(dppf)$. $PdCl_2(dppf)$ is 1,1'-Bis-(diphenylphosphino)-ferrocene)palladium (II) dichloride. In a specific embodiment, the coupling occurs in the presence of a base, such as a $C_{1-6}$alkyl amine (e.g., DIPEA). In a specific embodiment, the base includes DIPEA (N-ethyl-N-isopropyl-propan-2-amine).

In another embodiment, the method comprises reacting Compound (X-1) with Compound (Y-1) or (Y-2) in the presence of a Pd catalyst (e.g., Suzuki coupling), wherein X, Y, and Z of Compound (X-1) and Formula (I) are each and independently as defined herein; p of Formula (I) is 0; W of Formula (I) is Ring B; and Ring B of Compounds (Y-1) and (Y-2) are each independently a 3-8 membered saturated, partially unsaturated, or aromatic monocyclic ring having 0-4 heteroatoms selected from oxygen, nitrogen, or sulfur; or an 8-10 membered saturated, partially unsaturated, or aromatic bicyclic ring having 0-4 heteroatoms selected from oxygen, nitrogen, or sulfur; wherein said $C_{1-6}$alkyl is optionally substituted with 1-4 occurrences of $J^{W1}$, and wherein each of said monocyclic and bicyclic rings independently and optionally is substituted with 1-4 occurrences of $J^{W2}$:

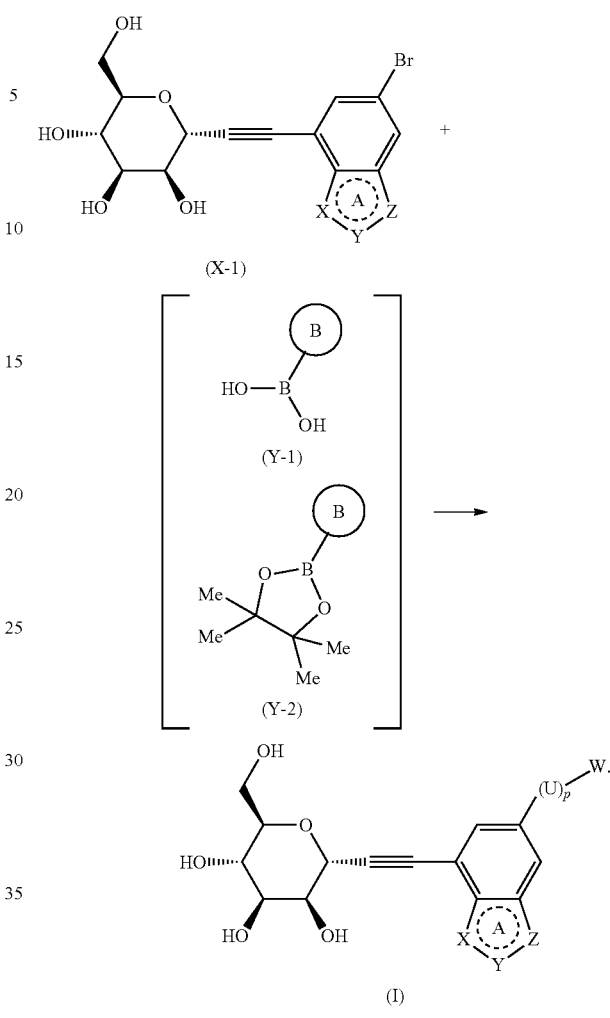

Any suitable conditions known in the art for, for example, Suzuki coupling can be employed. Suitable examples of the Pd catalyst include $PdCl_2(dppf)$ and $PdCl_2(dppf)$.DCM (1,1'-Bis-(diphenylphosphino)-ferrocene)palladium (II) dichloride dichloromethane complex).

In yet another embodiment, the method comprises reacting Compound (X-1) with Compound (Y-3) in the presence of Pd or Pd/Cu catalyst (e.g., Sonogashira coupling), wherein p of Formula (I) is 1; and the other variables of Formula (I) and the variables of Compounds (X-1) and (Y-3) are each and independently as defined herein:

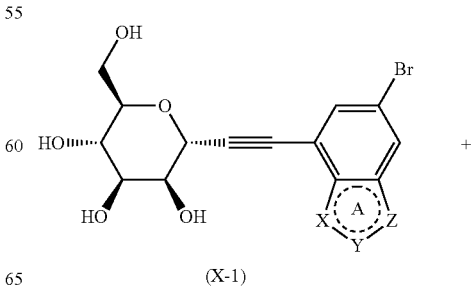

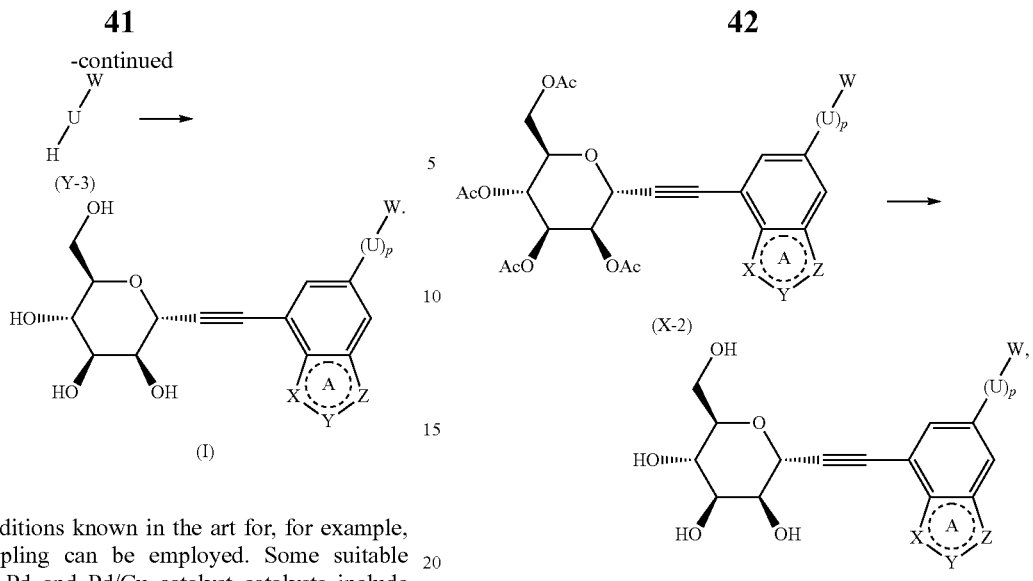

Any suitable conditions known in the art for, for example, Sonogashira coupling can be employed. Some suitable examples of the Pd and Pd/Cu catalyst catalysts include Pd(PPh$_3$)$_4$ and CuI/PdCl$_2$(dppf). In a specific embodiment, the coupling occurs in the presence of a base, such as a C$_{1-6}$alkyl amine (e.g., DIPEA). In a specific embodiment, the base includes DIPEA.

In yet another embodiment, the method comprises:

coupling between Compound (M3) and Compound (Y-4) to generate Compound (X-2); and

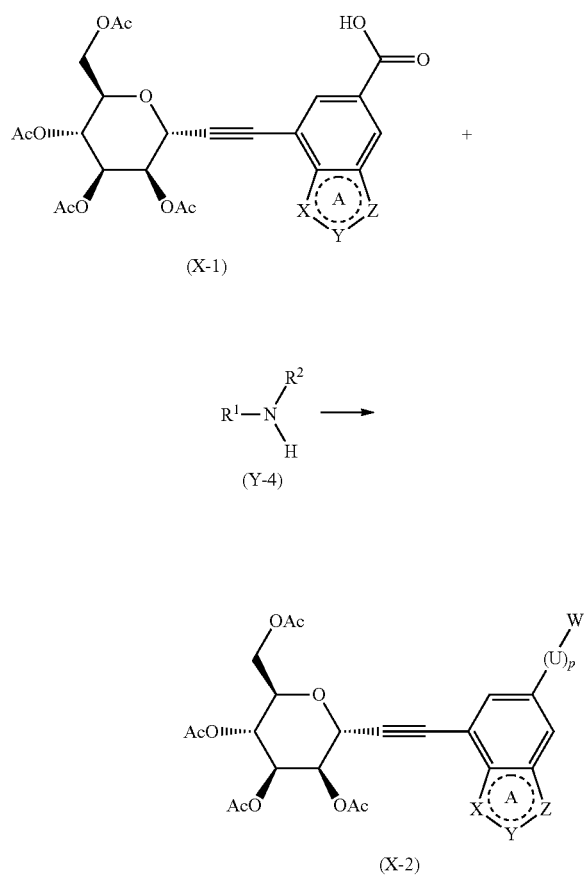

deprotecting -OAc groups of Compound (X-2) to generate a compound of Formula (I)

wherein the variables of Compounds (M3), (Y-4), and (X-2), and Formula (I) are each independently as defined herein; and OAc of Compound (X-2) is acetate. Any suitable conditions known in the art for amide coupling and de-protecting the ester protective groups can be employed. In a specific embodiment, the amide coupling employs HATU (O-(7-azabenzotriazol-1-yl),N,N,N'',N'''-tetramethyluroni-umhexafluorophosphate).

In some embodiments, the invention is directed to isotope-labelled compounds of Formula (I') or pharmaceutically acceptable salts thereof, wherein the formula and variables of Formula (I') are each and independently as described above for Formula (I) or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the invention include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively.

The isotope-labelled compounds of the invention, including pharmaceutically acceptable salts thereof, can be used in a number of beneficial ways. They can be suitable for medicaments and/or various types of assays, such as substrate tissue distribution assays. For example, tritium ($^3$H)— and/or carbon-14 ($^{14}$C)-labelled compounds are particularly useful for various types of assays, such as substrate tissue distribution assays, due to relatively simple preparation and excellent detectability. For example, deuterium ($^2$H)-labelled compounds are therapeutically useful with potential therapeutic advantages over the non-$^2$H-labelled compounds. In general, deuterium ($^2$H)-labelled compounds can have higher metabolic stability as compared to those compounds that are not isotope-labelled owing to the kinetic isotope effect described below. Higher metabolic stability translates directly into an increased in vivo half-life or lower dosages, which under most circumstances would represent a preferred embodiment of the present invention. The isotope-labelled compounds of the invention can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds of the invention are deuterium ($^2$H)-labelled compounds. In some specific embodiments, the isotope-labelled compounds of Formula (I') or pharmaceutically acceptable salts thereof are deuterium ($^2$H)-labelled, wherein one or more hydrogen atoms therein have been replaced by deuterium.

Deuterium ($^2$H)-labelled compounds of the invention can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to, for example, a compound of Formula (I'), the profile of this compound in vivo can be drastically modified and result in improved pharmacokinetic properties. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of the isotope(s) (e.g., deuterium) incorporated into the isotope-labelled compounds of the invention may be defined by the isotopic enrichment factor. The term "isotopic enrichment factor" as used herein means the ratio between the isotopic abundance and the natural abundance of a specified isotope. In some embodiments, if a substituent in a compound of the invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimise pharmacokinetic parameters while retaining desirable in vitro properties. It may be reasonable to assume that many compounds with poor pharmacokinetic profiles are susceptible to oxidative metabolism. In vitro liver microsomal assays currently available provide valuable information on the course of oxidative metabolism of this type, which in turn permits the rational design of the deuterium ($^2$H)-labelled compounds of the invention which can have improved stability through resistance to such oxidative metabolism. Significant improvements in the pharmacokinetic profiles of such compounds can thereby be obtained, and can be expressed quantitatively in terms of increases in the in vivo half-life ($t_{1/2}$), concentration at maximum therapeutic effect ($C_{max}$), area under the dose response curve (AUC), and bioavailability; and in terms of reduced clearance, dose and materials costs.

The following is intended to illustrate the above: a deuterium ($^2$H)-labelled compound of the invention, which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a deuterium ($^2$H)-labelled compound of the invention can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

The term "stable", as used herein, refers to compounds that are not substantially altered when subjected to conditions to allow for their production, detection, recovery, storage, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), or branched, hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is $C_1$-$C_6$ alkyl or $C_1$-$C_4$ alkyl. In some embodiments, the "alkenyl" is $C_2$-$C_6$ alkenyl or $C_2$-$C_4$ alkenyl. In some embodiments, the "alkynyl" is $C_2$-$C_6$ alkynyl or $C_2$-$C_4$ alkynyl.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more carbocyclic non-aromatic or aromatic rings, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic") as used herein means refers to a non-aromatic monocyclic ring which can be saturated or contain one or more units of unsaturation, having three to fourteen ring atoms in which one or more ring carbons is replaced by a heteroatom such as, N, S, or O. The term includes polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, thienothienyl, thienothiazolyl, benzothiolanyl, benzodithianyl, 3-(1-alkyl)-benzimidazol-2-onyl, and 1,3-dihydro-imidazol-2-onyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the molecule through an oxygen ("alkoxy" e.g., —O-alkyl) or sulfur ("thioalkyl" e.g., —S-alkyl) atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —$CF_3$ and —$CF_2CF_3$.

The terms "halogen", "halo", and "hal" mean F, Cl, Br, or I.

The term "aryl" used alone or as part of a larger moiety as in "aralkyl", "aralkoxy", or "aryloxyalkyl", refers to carbon only containing aromatic ring systems. The term "aryl" may be used interchangeably with the term "aryl ring".

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is fused to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, where indicated a methylene unit of an aliphatic chain is optionally replaced with another atom or group. Examples of such atoms or groups include, but are not limited to, —NR—, —O—, —C(O)—, —C(=N—CN)—, —C(=NR)—, —C(=NOR)—, —S—, —S(O)—, and —S(O)$_2$—. These atoms or groups can be combined to form larger groups. Examples of such larger groups include, but are not limited to, —OC(O)—, —C(O) CO—, —CO$_2$—, —C(O)NR—, —C(=N—CN), —NRC (O)—, —NRC(O)O—, —S(O)$_2$NR—, —NRSO$_2$—, —NRC(O)NR—, —OC(O)NR—, and —NRSO$_2$NR—, wherein R is defined herein.

Only those replacement and combinations of groups that result in a stable structure are contemplated. Optional replacements can occur both within the chain and/or at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain. For example, a C$_3$ aliphatic can be optionally replaced by —NR—, —C(O)—, and —NR-to form —NRC(O)NR— (a urea). Unless otherwise indicated, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

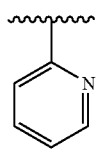

also represents

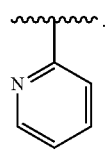

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

As described herein, where indicated compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

Only those choices and combinations of substituents that result in a stable structure are contemplated. Such choices and combinations will be apparent to those of ordinary skill in the art and may be determined without undue experimentation.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

An aryl group as defined herein may contain one or more substitutable ring atoms, which may be bonded to a suitable substituent. Examples of suitable substituents on a substitutable ring carbon atom of an aryl group include R'. R' is —Ra, —Br, —Cl, —I, —F, —ORa, —SRa, —O—CORa, —CORa, —CSRa, —CN, —NO$_2$, —NCS, —SO$_3$H, —N(RaRb), —COORa, —NRcNRcCORa, —NRcNRcCO$_2$Ra, —CHO, —CON(RaRb), —OC(O)N (RaRb), —CSN(RaRb), —NRcCORa, —NRcCOORa, —NRcCSRa, —NRcCON(RaRb), —NRcNRcC(O)N(RaRb), —NRcCSN(RaRb), —C(=NRc)-N(RaRb), —C(=S)N(RaRb), —NRd-C(=NRc)-N(RaRb), —NRcN-RaRb, —S(O)$_p$NRaRb, —NRcSO$_2$N(RaRb), —NRcS(O)$_p$Ra, —S(O)$_p$Ra, —OS(O)$_p$NRaRb or —OS(O)$_p$Ra; wherein p is 1 or 2.

Ra-Rd are each independently —H, an aliphatic group, aromatic group, non-aromatic carbocyclic or heterocyclic group or —N(RaRb), taken together, form a non-aromatic heterocyclic group. The aliphatic, aromatic and non-aromatic heterocyclic group represented by Ra-Rd and the non-aromatic heterocyclic group represented by —N(RaRb) are each optionally and independently substituted with one or more groups represented by R$^\#$. Preferably Ra-Rd are unsubstituted.

R$^\#$ is halogen, R$^+$, —OR$^+$, —SR$^+$, —NO$_2$, —CN, —N(R$^+$)$_2$, —COOR$^+$, —NHCO$_2$R$^+$, —NHC(O)R$^+$, —NHNHC(O)R$^+$, —NHC(O)N(R$^+$)$_2$, —NHNHC(O)N(R$^+$)$_2$, —NHNHCO$_2$R$^+$, —C(O)N(R$^+$)$_2$, —OC(O)R$^+$, —OC(O)N(R$^+$)$_2$, —S(O)$_2$R$^+$, —SO$_2$N(R$^+$)$_2$, —S(O)R$^+$, —NHSO$_2$N(R$^+$)$_2$, —NHSO$_2$R$^+$, —C(=S)N(R$^+$)$_2$, or —C(=NH)—N(R$^+$)$_2$.

R$^+$ is —H, a C1-C4 alkyl group, a monocyclic aryl group, a non-aromatic carbocyclic or heterocyclic group each optionally substituted with alkyl, haloalkyl, alkoxy, haloalkoxy, halo, —CN, —NO$_2$, amine, alkylamine or dialkylamine. Preferably R+ is unsubstituted.

An aliphatic or a non-aromatic heterocyclic or carbocyclic group as used herein may contain one or more substituents. Examples of suitable substituents for an aliphatic group or a ring carbon of a non-aromatic heterocyclic group is R". R" include those substituents listed above for R' and =O, =S, =NNHR, =NN(R)$_2$, =NNHC(O)R, =NNHCO$_2$(alkyl), =NNHSO$_2$(alkyl), =NR, spiro cycloalkyl group or fused cycloalkyl group. Each R is independently selected from hydrogen, an unsubstituted alkyl group or a substituted alkyl group. Examples of substituents on the alkyl group represented by R include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

A preferred position for substitution of a non-aromatic nitrogen-containing heterocyclic group is the nitrogen ring atom. Suitable substituents on the nitrogen of a non-aromatic heterocyclic group or heteroaryl group include —R^, —N(R^)$_2$, C(O)R^, CO$_2$R^, —C(O)C(O)R^, —SO$_2$R^, SO$_2$N(R^)$_2$, C(=S)N(R^)$_2$, C(=NH)—N(R^)$_2$, and —NR^SO$_2$R^; wherein R^ is hydrogen, an aliphatic group, a substituted aliphatic group, aryl, substituted aryl, heterocyclic or carbocyclic ring or a substituted heterocyclic or carbocyclic ring. Examples of substituents on the group represented by R^ include alkyl, haloalkoxy, haloalkyl, alkoxyalkyl, sulfonyl, alkylsulfonyl, halogen, nitro, cyano, hydroxy, aryl, carbocyclic or heterocyclic ring, oxo, amino, alkylamino, dialkylamino, aminocarbonyl, alkylaminocarbonyl, dialkylaminocarbonyloxy, alkoxy, carboxy, alkoxycarbonyl, or alkylcarbonyl. Preferably R^ is not substituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

As used herein an optionally substituted aralkyl can be substituted on both the alkyl and the aryl portion. Unless otherwise indicated as used herein optionally substituted aralkyl is optionally substituted on the aryl portion.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds of this invention, pharmaceutically acceptable derivatives or prodrugs of the compounds of this invention may also be employed in compositions to treat or prevent the herein identified disorders.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" includes any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

In one embodiment the present invention is a pharmaceutical composition comprising a compound of the present invention and a pharmaceutically acceptable carrier, diluent, adjuvant or vehicle. In one embodiment the present invention is a pharmaceutical composition comprising an effective amount of compound of the present invention and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds of present invention or pharmaceutical salts thereof may be formulated into pharmaceutical compositions for administration to a subject as defined herein. These pharmaceutical compositions, which comprise an amount of the compounds effective to treat or prevent a bacteria infection, such as IBD, and a pharmaceutically acceptable carrier, are another embodiment of the present invention.

In one embodiment the present invention is a method of treating or preventing a bacteria infection, such as IBD, in a subject in need thereof, comprising administering to the subject an effective amount of a compound or composition of the present invention. In one embodiment, the method comprises administering an effective amount of a compound or composition comprising same, wherein the compound is compound 27, 39, 56, 70, 77, 80, or a pharmaceutically acceptable salt thereof. In one embodiment, the method comprises administering an effective amount of compound 56 or a pharmaceutically acceptable salt thereof or a composition of the invention comprising same. In one embodiment, the method comprises administering an effective amount of compound 56 or a composition of the invention comprising same. In one embodiment, the method comprises administering an effective amount of compound 77 or a pharmaceutically acceptable salt thereof or a composition of the invention comprising same. In one embodiment, the method comprises administering an effective amount of compound 77 or a composition of the invention comprising same. In one embodiment, the method comprises administering an effective amount of compound 80 or a pharmaceutically acceptable salt thereof or a composition of the invention comprising same. In one embodiment, the method comprises administering an effective amount of compound 80 or a composition of the invention comprising same.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, an "effective amount" refers to an amount sufficient to elicit the desired biological response. In the present invention the desired biological response is to reduce or ameliorate the severity, duration, progression, or onset of a bateria infection, prevent the advancement of a bateria infection, cause the regression of a bateria infection, prevent the recurrence, development, onset or progression of a symptom associated with a bateria infection, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of bateria infection, and the mode of administration. The skilled artisan will be able to determine appropriate dosages depending on these and other factors. When co-administered with other agents, e.g., when co-administered with a bateria infection agent, an "effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a bateria infection, or the amelioration of one or more symptoms (preferably, one or more discernible symptoms) of a bateria infection resulting from the administration of one or more therapies (e.g., one or more therapeutic agents such as a compound of the invention). In specific embodiments, the terms "treat", "treatment" and "treating" refer to the amelioration of at least one measurable physical parameter of a bacteria infection. In other embodiments the terms "treat", "treatment" and "treating" refer to the inhibition of the progression of a bateria infection, either physically by, e.g., stabilization of a discernible symptom, physiologically by, e.g., stabilization of a physical parameter, or both. In other embodiments the terms "treat", "treatment" and "treating" refer to the reduction or stabilization of a bateria infection.

As used herein, the terms "prevent", "prevention" and "preventing" refer to the reduction in the risk of acquiring or developing a given bateria infection, or the reduction or inhibition of the recurrence or a bateria infection. In one embodiment, a compound of the invention is administered as a preventative measure to a patient, preferably a human, having a genetic predisposition to any of the conditions, diseases or disorders described herein.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The dosage regimen utilizing the compounds of present invention can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compound of present invention required to treat, for example, to prevent, inhibit (fully or partially) or arrest the progress of the disease.

Dosages of the compounds of present invention can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosings such as twice, three or four times per day.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

An effective amount can be achieved in the method or pharmaceutical composition of the invention employing a compound of present invention or a pharmaceutically acceptable salt thereof alone or in combination with an additional suitable therapeutic agent, for example, a cancer-therapeutic agent. When combination therapy is employed, an effective amount can be achieved using a first amount of a compound of present invention or a pharmaceutically acceptable salt thereof and a second amount of an additional suitable therapeutic agent.

In one embodiment, the compound of present invention and the additional therapeutic agent, are each administered in an effective amount (i.e., each in an amount which would be therapeutically effective if administered alone). In another embodiment, the compound of present invention and the additional therapeutic agent are each administered in an amount which alone does not provide a therapeutic effect (a sub-therapeutic dose). In yet another embodiment, the compound of present invention can be administered in an effective amount, while the additional therapeutic agent is administered in a sub-therapeutic dose. In still another embodiment, the compound of present invention can be administered in a sub-therapeutic dose, while the additional therapeutic agent, for example, a suitable cancer-therapeutic agent is administered in an effective amount.

As used herein, the terms "in combination" or "coadministration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

When coadministration involves the separate administration of the first amount of a compound of present invention and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of present invention and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of coadministration of a first amount of a compound of present invention and a second amount of an additional therapeutic agent can result in an enhanced or synergistic therapeutic effect, wherein the combined effect is greater than the additive effect that would result from separate administration of the first amount of the compound of present invention and the second amount of the additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

The activity of the compounds as inhibitors of bacteria infection may be assayed in vitro or in vivo. In vitro assays include assays that determine inhibition of the FimH activity. Alternate in vitro assays quantitate the ability of the inhibitor to bind to the FimH and may be measured either by radiolabelling the inhibitor prior to binding, isolating the inhibitor complex and determining the amount of radiolabel bound, or by running a competition experiment where new inhibitors are incubated with the FimH bound to known radioligands. Detailed conditions for assaying a compound utilized in this invention are set forth in the Examples below.

FIGURES

FIG. 1 shows the residual adhesion of the LF82 AIEC on T84 colonocytes culture after incubation with the reference compound heptylmannose (HM), and compound 56. Residual adhesion is the ratio of level of colonization/decolonization of AIEC measured on cells, and is expressed in percentage. 100% corresponds to the control experiment (NT).

EXEMPLIFICATION

The following abbreviations are used in the examples below:

| | |
|---|---|
| Ac | acetyl |
| AcOH | acetic acid |
| Ac2O | acetic anhydride |
| BF3•OEt$_2$ | diethyloxonio-trifluoro-boron |
| Bn | benzyl |
| CH$_3$CN | acetonitrile |
| CD$_3$OD | methanol-D4 |
| CDCl$_3$ | chloroform-D |
| CH$_2$Cl$_2$ | methylene chloride or dichloromethane |

-continued

| | |
|---|---|
| conc | concentrate |
| Cs$_2$CO$_3$ | cesium carbonate |
| CuI | copper (I) iodide |
| CuSO$_4$ | copper (II) sulfate |
| CV | column volume |
| DBU | 1,8-diazabicyclo[5.4.0]undec-7-ene |
| DIPEA | N-ethyl-N-isopropyl-propan-2-amine |
| DMAP | 4-dimethylaminopyridine |
| DMF | dimethylformamide |
| DMSO | dimethylsulfoxide |
| eq. | equivalent |
| EtOAc | ethyl acetate |
| HATU | O-(7-azabenzotriazol-1-y1),N,N,N'',N''-tetramethyluroniumhexafluorophosphate |
| h | hour(s) |
| Hex | hexanes |
| M | molar |
| MeOH | methanol |
| MeONa | sodium methoxide |
| min | minute(s) |
| MTBE | methyl tert-butyl ether |
| NaIO$_4$ | sodium periodate |
| Na$_2$SO$_4$ | sodium sulfate |
| NMO | N-methylmorpholine-N-oxide |
| Pd(PPh$_3$)$_4$ | palladium tetrakis triphenylphosphine |
| PdCl$_2$(dppf)•DCM | (1,1'-Bis-(diphenylphosphino)-ferrocene)palladium (II) dichloride dichloromethane complex |
| Piv | trimethylacetyl |
| Py | pyridine |
| RT | room temperature |
| TBAF | tetrabutylammonium fluoride |
| TEA | triethylamine |
| Tf | trifluoromethanesulfonyl |
| TFA | trifluoroacetic acid |
| THF | tetrahydrofuran |

The compounds of this invention may be prepared in light of the specification using steps generally known to those of ordinary skill in the art. Those compounds may be analyzed by known methods, including but not limited to LC-MS (liquid chromatography mass spectrometry), HPLC (high performance liquid chromatography) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following Examples are as defined herein.

Mass spec. samples were analyzed on a Waters UPLC Acquity mass spectrometer operated in single MS mode with electrospray ionization. Samples were introduced into the mass spectrometer using chromatography. Mobile phase for the mass spec. analyses consisted of 0.1% formic acid and CH$_3$CN-water mixture. Column gradient conditions were 5%-85% CH$_3$CN-water over 6 minutes run time, Acquity HSS T3 1.8µ 2.1 mm ID×5 0 mm Flow rate was 1.0 mL/min. As used herein, the term "Rt(min)" refers to the LC-MS retention time, in minutes, associated with the compound. Unless otherwise indicated, the LC-MS method utilized to obtain the reported retention time is as detailed above.

Purification by reverse phase HPLC was carried out under standard conditions using either Phenomenex Gemini 21.2 mm ID×250 mm column (5 µm), Gemini 21.2 mm ID×75 mm column, (5 µm), 110 Å or in most cases a Waters XSELECT CSH Prep C18 (5 µm) ODB 19×100 mm column. Elution was performed using a linear gradient CH$_3$CN—H$_2$O (with or without 0.01% TFA buffer or 0.1% HCOH) as mobile phase. Solvent system was tailored according to the polarity of the compound, Flow rate, 20 mL/min Compounds were collected either by UV or Waters 3100 Mass Detector, ESI Positive Mode. Fractions containing the desired compound were combined, concentrated (rotary evaporator) to remove excess CH$_3$CN and the resulting aqueous solution was lyophilized to afford the desired material.

General Method of Synthesis

Compounds described therein are prepared from key intermediates using two reactions: Suzuki and Sonogashira coupling.

Compounds of Formula (II) in which W is H, alkyl, COOMe, halogen, can be prepared by Methods A or B, as exemplified in Scheme 1. In Method A, the Sonogashira coupling between the heterocycle (A1) and the Intermediate M1 is catalyzed by Pd(PPh$_3$)$_4$ while in Method B the catalysts are CuI/PdCl$_2$(dppf), both conducted in presence of a strong base (e.g., DIPEA).

Scheme 1: Method A and B for the preparation of Compounds of Formula (II)

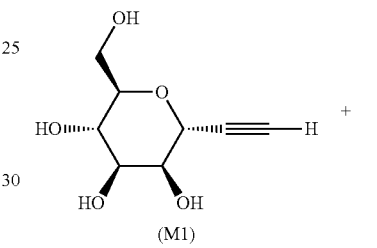

(M1)

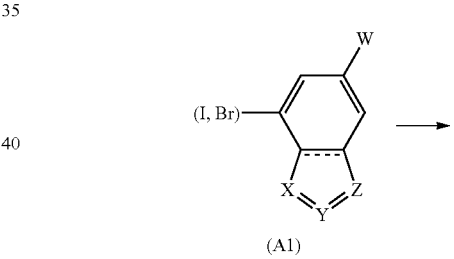

(A1)

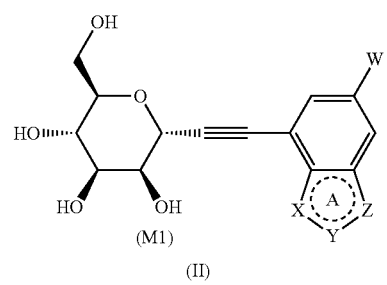

(II)

Compounds of Formula (III), can be prepared by Methods C, as exemplified in Scheme 2. Palladium catalyzed (e.g., PdCl$_2$(dppf).DCM) Suzuki coupling between Compound (X-1), prepared by Method A or B, and either the commercially available and appropriately substituted boronic acid (Y-1) or the pinacole boronate (Y-2) can afford the desired compounds of type (III).

Scheme 2: Method C for the preparation of Compounds of Formula (III)

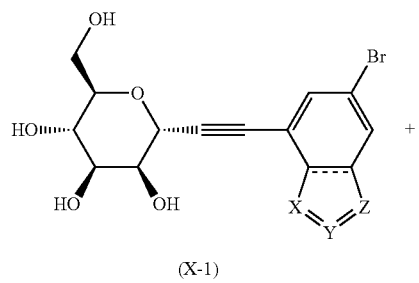

(X-1)

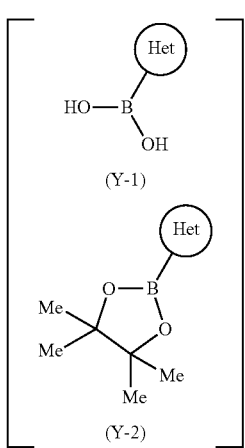

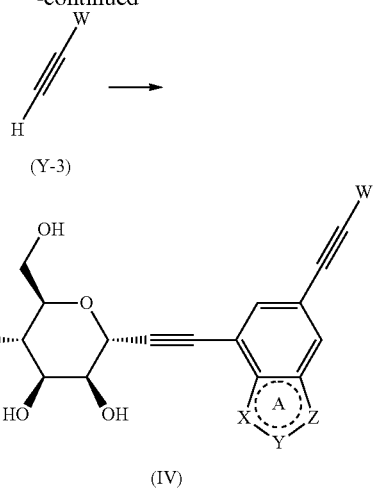

(IV)

Compounds of Formula (V) can be prepared in two steps using Method E as exemplified in Scheme 4. Amide coupling using HATU between Intermediate M3 and commercially available primary or secondary amines (Y-4) followed by removal of the acetate protective groups (MeONa, MeOH) can generate the desired compounds of Formula (V).

Scheme 4: Method E for the preparation of Compounds of Formula (V)

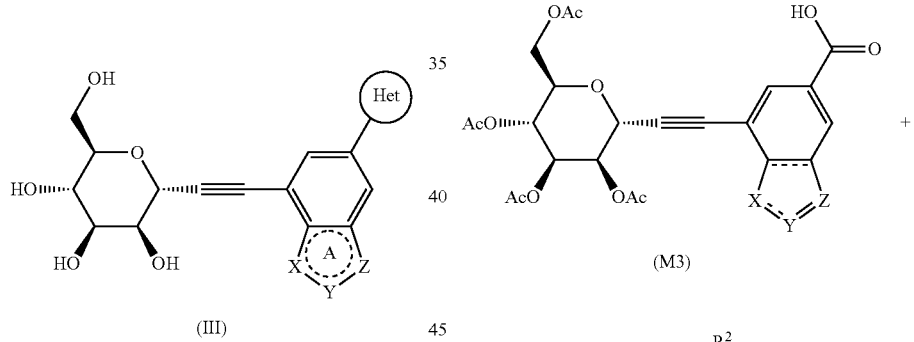

Compounds of Formula (IV), can be prepared by Methods D, as exemplified in Scheme 3. Sonogashira coupling between Compound (X-1) and Compound (Y-3) catalyzed CuI/PdCl$_2$(dppf) in presence of a strong base (i.e. DIPEA) can afford the desired compounds of Formula (IV).

Scheme 3: Method D for the preparation of Compounds of Formula (IV).

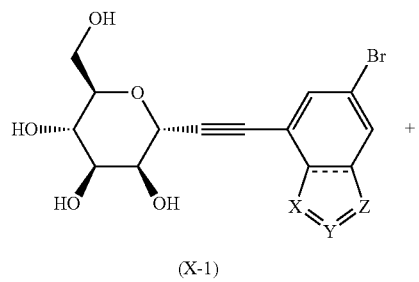

(X-1)

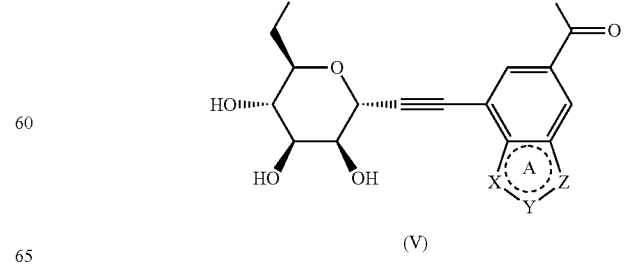

(V)

Certain intermediates which are used in the preparation of Compounds described therein are listed below:
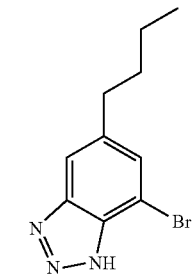 B1
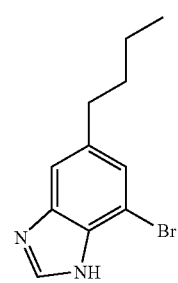 B2
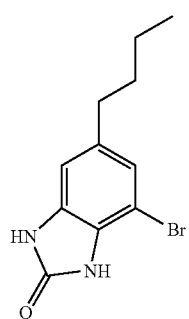 B3
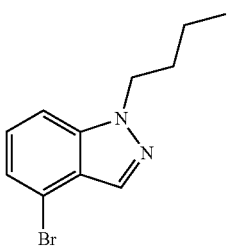 B4
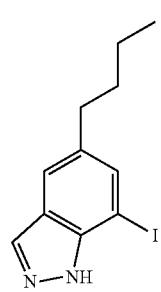 B5
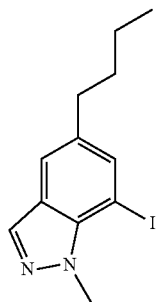 B6
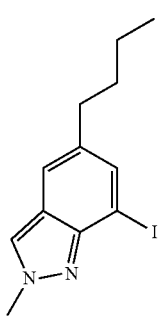 B7
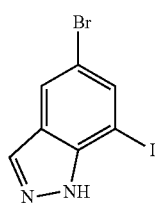 B8
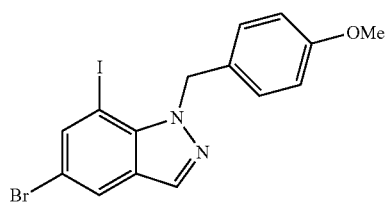 B9
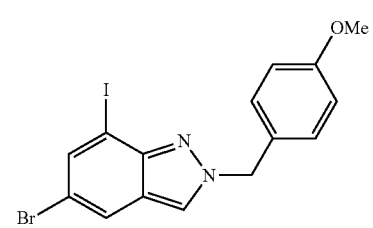 B10
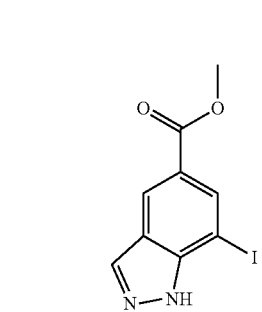 B11

Preparation of Intermediates B1, B2 and B3: 7-bromo-5-butyl-1H-benzotriazole (B1), 7-bromo-5-butyl-1H-benzimidazole (B2), 4-bromo-6-butyl-1,3-dihydrobenzimidazol-2-one (B3)

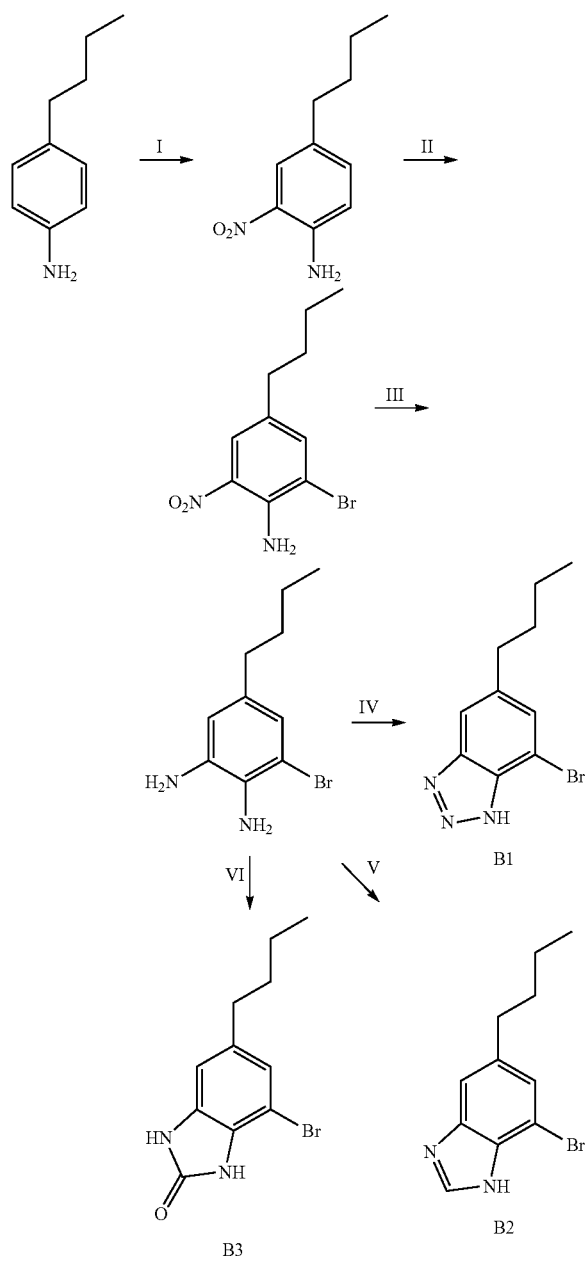

Step I: 4-butyl-2-nitro-aniline

To cold (ice-bath) Ac₂O (27.0 mL, 286 mmol) was added slowly 4-butylaniline (5.08 g, 34.0 mmol). The ice-bath was removed, the resulting thick slurry is stirred for 40 min at RT and cooled again in an ice-bath. HNO₃ (34 mL of 70% w/v, 378 mmol) was slowly added via an addition funnel. After the addition was complete, the reaction mixture was poured into 200 mL mixture of ice and H₂O and extracted twice with EtOAc (200 mL, 100 mL). The combined organic extracts were washed with H₂O (100 mL), saturated aqueous NaHCO₃ (100 mL), brine (100 mL), dried over Na₂SO₄, filtered, concentrated and dried in vacuo to provide 7.38 g dark orange oil, which was redissolved in dioxane (20 mL). HCl aqueous (30.0 mL of 6 M, 180 mmol) was added, the reaction flask was equipped with a condenser and heated to 80° C. for 3 h. The reaction mixture was brought back to RT, diluted with EtOAc (150 mL) and neutralized with 1M NaOH solution (230 mL). The layers were separated. The aqueous layer was back extracted with EtOAc (100 mL). The combined organic extracts were washed with H₂O, brine (150 mL each), dried over Na₂SO₄, filtered and concentrated. The crude product was purified by flash chromatography on a Biotage™ snap 340 g silica cartridge using a gradient of EtOAc in Hex (0-30%) as eluent. The fractions were combined and concentrated, providing the title compound (1.84 g, 28% yield). ¹H NMR (400 MHz, CDCl₃) δ 7.92 (d, J=1.9 Hz, 1H), 7.21 (dd, J=8.5, 2.0 Hz, 1H), 6.74 (d, J=8.5 Hz, 1H), 5.94 (s, 2H), 2.61-2.44 (m, 2H), 1.65-1.49 (m, 2H), 1.34 (h, J=7.3 Hz, 2H), 0.92 (t, J=7.3 Hz, 3H).

Step II: 2-bromo-4-butyl-6-nitro-aniline 4-butyl-2-nitro-aniline (1.84 g, 9.47 mmol) was dissolved in AcOH (15 mL) Br₂ (540 μL, 10.5 mmol) was added slowly while monitoring the internal temperature. After stirring for 30 min, the reaction mixture was quenched with ice water (100 mL) and extracted with EtOAc (3×50 mL) The combined organic extracts were washed with saturated aqueous NaHCO₃ (50 mL) and brine (50 mL), dried over Na₂SO₄, filtered and concentrated. The crude product was purified by flash chromatography on a Biotage™ snap 100 g silica cartridge, using a gradient of EtOAc in Hex (0-20%) as eluent. The fractions were combined and concentrated, providing the title compound (2.19 g, 85% yield). ¹H NMR (400 MHz, CDCl₃) δ 7.94 (d, J=2.0 Hz, 1H), 7.56 (d, J=2.0 Hz, 1H), 6.48 (s, 2H), 2.59-2.42 (m, 2H), 1.64-1.49 (m, 2H), 1.34 (h, J=7.3 Hz, 2H), 0.93 (t, J=7.3 Hz, 3H).

Step III: 3-bromo-5-butyl-benzene-1,2-diamine

To a solution of 2-bromo-4-butyl-6-nitro-aniline (1.0 g, 3.66 mmol) in MeOH (20 mL) was added a saturated aqueous solution of NH₄Cl (6.7 mL) The resulting suspension was cooled to 0° C. and zinc dust (1.21 g, 18.5 mmol) was added in one portion. The reaction mixture was stirred at 0° C. for 30 min then at RT overnight. The reaction mixture was diluted with EtOAc and saturated aqueous NaHCO₃ solution (50 mL each). After stirring vigorously, it was filtered on a Celite™ pad, which was rinsed with portions of EtOAc (3×10 mL). The layers were separated and the organic layer is washed with brine (25 mL), dried over Na₂SO₄, filtered and concentrated. The residue was purified by flash chromatography on a Biotage™ snap 25 g silica cartridge, using a gradient of EtOAc in Hex (5-40%) as eluent. The fractions were combined and concentrated, providing the title compound (605 mg, 68% yield). ¹H NMR (400 MHz, CDCl₃) δ6.80 (d, J=1.6 Hz, 1H), 6.48 (d, J=1.5 Hz, 1H), 3.66 (s, 2H), 3.45 (s, 2H), 2.50-2.33 (m, 2H), 1.57-1.43 (m, 2H), 1.40-1.21 (m, 2H), 0.91 (t, J=7.3 Hz, 3H).

Step IV: Intermediate B1

3-bromo-5-butyl-benzene-1,2-diamine (255 mg, 1.05 mmol) was dissolved in AcOH (1.8 mL) and NaNO2 (76 mg, 1.10 mmol) was added. The reaction mixture was stirred for 1.5 h, then diluted with DCM (5 mL) and H₂O (2 mL). The layers were separated and the aqueous layer was back extracted with DCM (2×5 mL) The combined organic extracts were concentrated and purified on a 5 g bond-elut silica cartridge eluting with DCM, then 2% MeOH in DCM. The fractions were combined and concentrated, affording 7-bromo-5-butyl-1H-benzotriazole (247 mg, 93% yield). $^1$H NMR (400 MHz, CD₃OD) δ 7.57 (s, 1H), 7.52 (s, 1H), 2.87-2.72 (m, 2H), 1.76-1.59 (m, 2H), 1.40 (h, J=7.4 Hz, 2H), 0.97 (t, J=7.4 Hz, 3H).

Step V: Intermediate B2

To a solution of 3-bromo-5-butyl-benzene-1,2-diamine (153 mg, 0.629 mmol) in DMF (900 μL) was added trimethoxymethane (1.7 mL, 15.5 mmol), followed by aqueous HCl (60 μL of 12 M, 0.720 mmol). The reaction mixture was stirred at RT for 25 min, diluted with H₂O (3 mL), quenched with saturated NaHCO₃ solution (3 mL) and extracted with EtOAc (2×5 mL). The combined organic extracts were dried over Na₂SO₄, filtered and concentrated. The crude product was purified on a 5 g bond-elut silica cartridge using DCM, then 5% MeOH in DCM as eluent. The fractions were combined and concentrated to provide the title compound (153 mg, 96% yield). $^1$H NMR (400 MHz, DMSO) δ 12.62 (s, 1H), 8.21 (s, 1H), 7.30 (s, 1H), 7.24 (d, J=1.2 Hz, 1H), 2.66 (t, J=7.6 Hz, 2H), 1.68–1.48 (m, 2H), 1.40–1.18 (m, 2H), 0.89 (t, J=7.3 Hz, 3H).

Step VI: Intermediate B3

To a solution of 3-bromo-5-butyl-benzene-1,2-diamine (176 mg, 0.724 mmol) in dioxane (900 μL) in a pressure vessel was added carbonyldiimidazole (142 mg, 0.876 mmol). The pressure vessel was capped and heated to 40° C. After stirring for 30 min, the reaction mixture was cooled down to RT, Et₂O was added, and the precipitate was collected by filtration and rinsed with small portions of Et₂O. The resulting material obtained was dried under vacuum to provide the title compound (128 mg, 66% yield). $^1$H NMR (400 MHz, DMSO) δ 10.89 (s, 1H), 10.80 (s, 1H), 6.92 (d, J=1.1 Hz, 1H), 6.72 (s, 1H), 2.57-2.44 (m, 2H), 1.55-1.42 (m, 2H), 1.33-1.18 (m, 2H), 0.87 (t, J=7.3 Hz, 3H).

Preparation of Intermediates B4:
4-bromo-1-butyl-1H-indazole

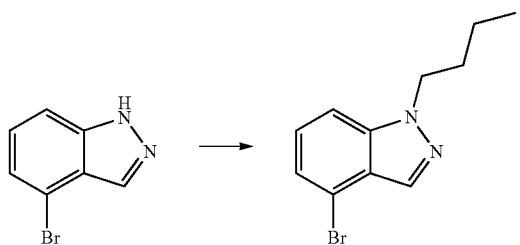

To a cold (0° C.) solution of 4-bromo-1H-indazole (46 mg, 0.234 mmol) in DMF (700 μL) was added NaH (10.0 mg, 0.250 mmol). The resulting dark red solution stirred for 20 min, then 1-bromobutane (25.0 μL, 0.233 mmol) was added and the cold bath was removed. After stirring for another 30 min, a saturated aqueous NH₄Cl solution (3 mL) was added. The mixture was extracted with EtOAc (3×3 mL). The combined organic extracts were washed with brine (3 mL), dried over Na₂SO₄, filtered and concentrated. The crude residue was purified by flash chromatography on a Biotage™ snap 10 g silica cartridge, using a gradient of EtOAc in Hex (0-20%) as eluent. The fractions were combined and concentrated, to provide the title compound (28 mg, 47% yield). $^1$H NMR (400 MHz, CDCl₃) δ 8.00 (d, J=0.9 Hz, 1H), 7.36 (dt, J=8.3, 0.8 Hz, 1H), 7.29 (dd, J=7.3, 0.8 Hz, 1H), 7.22 (dd, J=8.3, 7.4 Hz, 1H), 4.37 (t, J=7.1 Hz, 2H), 1.98-1.83 (m, 2H), 1.33 (h, J=7.4 Hz, 2H), 0.94 (t, J=7.4 Hz, 3H).

Preparation of Intermediates B4:
5-butyl-7-iodo-1H-indazole

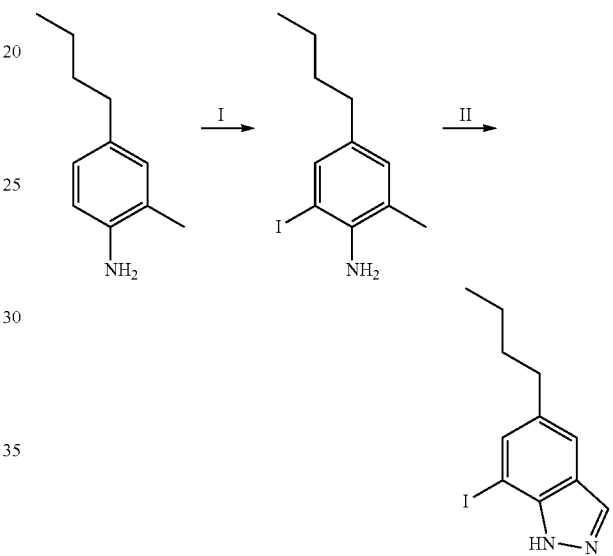

Step I: 4-butyl-2-iodo-6-methyl-aniline

To a stirred solution of 4-butyl-2-methyl-aniline (19.40 g, 119 mmol) in DCM (230 mL) was added 1-pyridin-1-ium-1-yliodanuidylpyridin-1-ium (Boron Tetrafluoride Ion) (48.62 g, 131 mmol) in one portion via a funnel, rinsed with DCM (20 mL) After stirring for 100 min, the reaction mixture was quenched with saturated NaHCO₃ (200 mL) and diluted with DCM (100 mL). The layers were separated. The aqueous layer was diluted with H₂O (100 mL) and was back extracted with DCM (2×150 mL) The combined organic extracts were washed with aqueous 1M Na₂S₂O₃ solution (150 mL), dried over Na₂SO₄, filtered and concentrated, then co-evaporated with heptane (2×) to afford the crude product, which was purified by flash chromatography on a silica pad (1000 cc) using Hex then 3% EtOAc in Hex as eluent. The fraction containing the desired product was concentrated and purified further by recrystallization from Hex to provide the title compound (12.68 g, 37% yield). A second crop of title compound was obtained by concentrating the mother liquors from the recrystallization and purification by flash chromatography on a Biotage™ snap 340 g silica cartridge, using a gradient of EtOAc in Hex (0-15%) as eluent. The fractions were combined and concentrated. The mix fractions were concentrated and purified again by flash chromatography on a Biotage™ snap Ultra 100 g silica cartridge, using a gradient of DCM in Hex, 0-80% as eluent. The clean fractions from the two columns were combined to provide more of the title compound (15.31 g, 45% yield). ¹H NMR (400 MHz, CDCl₃) δ 7.35 (d, J=1.4 Hz, 1H), 6.84 (s, 1H), 3.93 (broad s, 2H), 2.51-2.38 (m, 2H), 2.20 (s, 3H), 1.57-1.45 (m, 2H), 1.32 (h, J=7.3 Hz, 2H), 0.91 (t, J=7.3 Hz, 3H).

Step II: 5-butyl-7-iodo-1H-indazole

To a stirred solution of 4-butyl-2-iodo-6-methyl-aniline (28.31 g, 97.9 mmol) in AcOH (310 mL) was added a solution of NaNO₂ (7.446 g, 107.9 mmol) in H₂O (20 mL) over 2 min, rinsed with H₂O (8.5 mL), added to the mixture. The reaction mixture was stirred for 1 h, then concentrated on rotavap until a thick paste was obtained. The crude mixture was transferred to an Erlenmeyer flask using DCM (300 mL) and under mechanical stirring, neutralized by adding saturated NaHCO₃ solution carefully. The layers were separated and the aqueous layer was extracted with DCM (2×200 mL). The combined organic extracts were dried over Na₂SO4, filtered and concentrated. The crude product was purified by flash chromatography on a silica pad (2000 cc) eluting with DCM. The desired fractions were concentrated and the resulting material was further purified by recrystallization in heptane (about 26 mL), stirring overnight. The precipitate was cooled down in an ice-bath then filtered and washed with cold heptane, to afford the title product (9.81 g, 33% yield). A second crop of product was obtained by concentrating the mother liquors, purifying the residue by flash chromatography on a Biotage™ snap Ultra100 g silica cartridge, using a gradient of EtOAc (0-20%) in Hex as eluent. The fractions were combined and concentrated then recrystallized in heptane, providing more of the title compound (1.21 g, 4% yield). ¹H NMR (400 MHz, CDCl₃) δ 10.01 (brs, 1H), 8.13 (s, 1H), 7.59 (d, J=1.0 Hz, 1H), 7.47 (d, J=0.6 Hz, 1H), 2.72-2.61 (m, 2H), 1.70-1.55 (m, 2H), 1.43-1.30 (m, 2H), 0.92 (t, J=7.3 Hz, 3H).

Preparation of Intermediates B6 and B7: 5-butyl-7-iodo-1-methyl-1H-indazole (B6), 5-butyl-7-iodo-2-methyl-2H-indazole (B7)

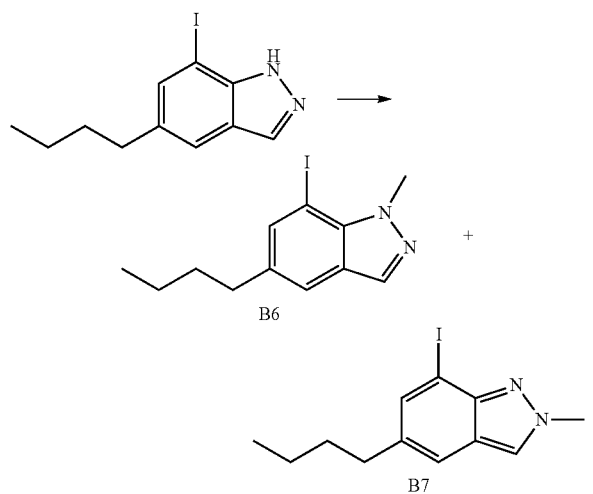

To a cold (0° C.) solution of 5-butyl-7-iodo-1H-indazole (293 mg, 0.976 mmol) in DMF (3 mL) was added NaH (120 mg, 3.00 mmol) in one portion. The reaction mixture was stirred at 0° C. for 1.5 h. MeI (75.0 μL, 1.21 mmol) was added and the mixture was brought back to RT and stirred for 1.5 h. Quenched with H₂O (10 mL), extracted with EtOAc (3×10 mL). The combined organic extracts were washed with brine (10 mL), dried over Na₂SO₄, filtered and concentrated. The crude mixture was purified by flash chromatography on a Biotage™ snap 25 g silica cartridge, using a gradient of EtOAc (0-40%) in Hex as eluent. The two regioisomers were separated, providing 5-butyl-7-iodo-1-methyl-1H-indazole (B6, 199 mg, 65% yield) and 5-butyl-7-iodo-2-methyl-2H-indazole (B7, 89 mg, 29% yield). Intermediate B6: ¹H NMR (400 MHz, CDCl₃) δ 7.83 (s, 1H), 7.71 (d, J=1.4 Hz, 1H), 7.46-7.42 (m, 1H), 4.39 (s, 3H), 2.67-2.59 (m, 2H), 1.67-1.55 (m, 2H), 1.36 (h, J=7.3 Hz, 2H), 0.93 (t, J=7.3 Hz, 3H). Intermediate B7: ¹H NMR (400 MHz, CDCl₃) δ 7.94 (s, 1H), 7.62 (d, J=1.3 Hz, 1H), 7.39-7.33 (m, 1H), 4.24 (s, 3H), 2.71-2.55 (m, 2H), 1.72-1.52 (m, 2H), 1.36 (h, J=7.3 Hz, 2H), 0.93 (t, J=7.3 Hz, 3H).

Preparation of Intermediates B8: 5-bromo-7-iodo-1H-indazole

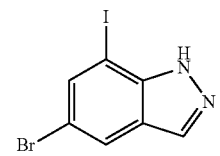

The title compound was prepared following the procedure described in WO 2007/117465.

Preparation of Intermediates B9 and B10: 5-bromo-7-iodo-2-(4-methoxybenzyl)-2H-indazole (B9) and 5-bromo-7-iodo-1-(4-methoxybenzyl)-1H-indazole (B10)

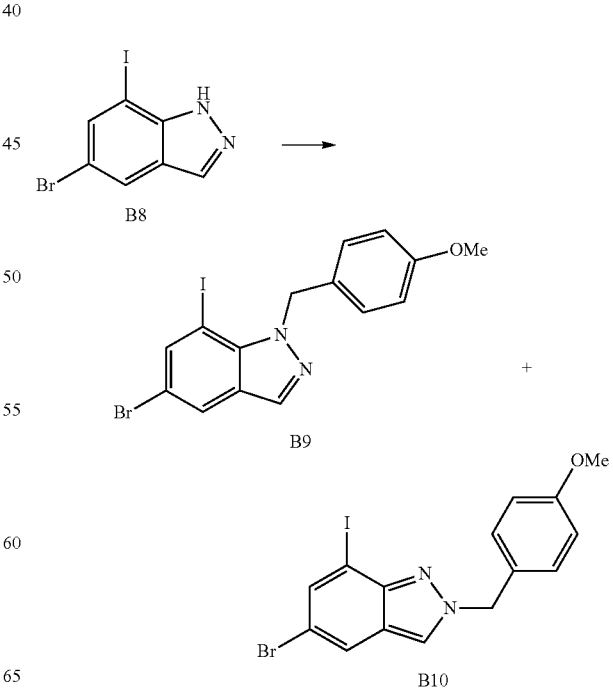

To a cold (0° C.) solution of Intermediate B8 (992 mg, 3.07 mmol) in DMF (5 mL) was added KOtBu (417 mg, 3.72 mmol). The reaction mixture was stirred for 40 min at 0° C. 1-(chloromethyl)-4-methoxy-benzene (500 μL, 3.69 mmol) was added and the reaction mixture was stirred overnight at RT, then quenched with aqueous saturated NH$_4$Cl solution (25 mL) and extracted with EtOAc (3×25 mL). The combined organic extracts were washed with brine (25 mL), dried over Na$_2$SO$_4$, filtered and concentrated. The crude mixture was purified by flash chromatography on a Biotage™ snap 50 g silica cartridge, using a gradient of EtOAc (0-30%) in Hex as eluent. The two regioisomers were separated, providing 5-bromo-7-iodo-1-(4-methoxybenzyl)-1H-indazole (B9, 328 mg, 24% yield) and 5-bromo-7-iodo-2-(4-methoxybenzyl)-2H-indazole (B10, 905 mg, 66% yield). Intermediate B9: $^1$H NMR (400 MHz, CDCl$_3$) δ 7.98-7.94 (m, 2H), 7.86 (d, J=1.7 Hz, 1H), 7.05 (d, J=8.4 Hz, 2H), 6.84-6.76 (m, 2H), 5.98 (s, 2H), 3.76 (s, 3H). Intermediate B10: $^1$H NMR (400 MHz, CDCl$_3$) δ7.83 (s, 1H), 7.82 (d, J=1.6 Hz, 1H), 7.71 (d, J=1.6 Hz, 1H), 7.31-7.25 (m, 2H), 6.95-6.87 (m, 2H), 5.57 (s, 2H), 3.82 (s, 3H).

Preparation of Intermediates B11: Methyl 7-iodo-1H-indazole-5-carboxylate

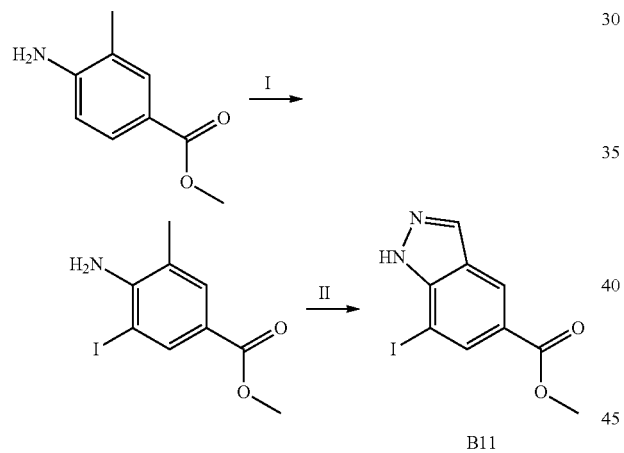

Step I: methyl 4-amino-3-iodo-5-methyl-benzoate

To a solution of methyl 4-amino-3-methyl-benzoate (12.17 g, 73.70 mmol) in DCM (135 mL) was added 1-pyridin-1-ium-1-yliodanuidylpyridin-1-ium (Boron Tetrafluoride Ion) (30.14 g, 81.00 mmol). The reaction mixture was stirred for 1.5 h, then 1-pyridin-1-ium-1-yliodanuidylpyridin-1-ium (Boron Tetrafluoride Ion) (2.740 g, 7.367 mmol) was added and the mixture was stirred for another 2 h, then quenched with aqueous saturated NaHCO$_3$ (100 mL). The layers were separated. The aqueous layer was extracted with DCM (2×100 mL) The combined organic extracts were washed with aqueous 1M Na$_2$S$_2$O$_3$ (100 mL) and dried over Na$_2$SO$_4$, filtered and concentrated. The crude residue was co-evaporated with heptane (2×) and purified by flash chromatography on a Biotage™ snap 340 g silica cartridge, using a gradient of EtOAc (0-25%) in Hex as eluent. The fractions were combined and concentrated to provide the title compound (18.0 g, 84% yield). $^1$H NMR (400 MHz, CDCl$_3$) δ 8.23 (s, 1H), 7.71 (s, 1H), 4.51 (s, 2H), 3.85 (s, 3H), 2.25 (s, 3H).

Step II: methyl 7-iodo-1H-indazole-5-carboxylate

To a stirred solution of methyl 4-amino-3-iodo-5-methyl-benzoate (9.00 g, 30.9 mmol) in AcOH (99 mL) was added a solution of NaNO$_2$ (2.347 g, 34.00 mmol) in H$_2$O (6.25 mL), rinsed with H$_2$O (2.7 mL), added to the reaction. The reaction mixture was stirred for 2 h then quenched with H$_2$O (150 mL) and extracted with CHCl$_3$-iPrOH mixture (4:1, 150 mL, 2×100 mL) The combined organic extracts were washed with brine (100 mL) dried over MgSO$_4$, filtered and concentrated, then co-evaporated with heptane (2×). The crude residue was purified by flash chromatography on a Biotage™ snap 340 g silica cartridge, using a gradient of EtOAc (0-20%) in DCM as eluent. The fractions were combined and concentrated to provide the title compound (5.37 g, 57% yield). $^1$H NMR (400 MHz, DMSO) δ 13.63 (s, 1H), 8.50-8.46 (m, 1H), 8.43 (d, J=1.4 Hz, 1H), 8.24 (d, J=1.4 Hz, 1H), 3.86 (s, 3H).

Preparation of Intermediates M1, M2 and M3

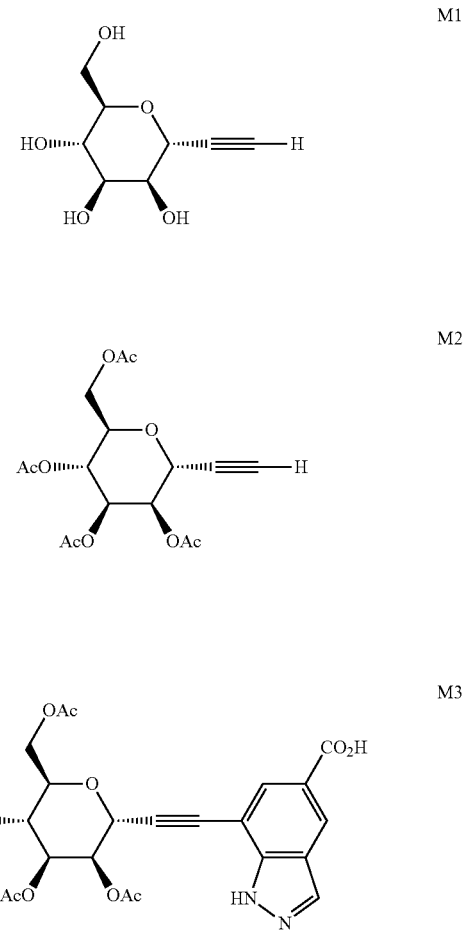

Preparation of Intermediates M1 and M2: (2R,3S,4R,5S,6R)-2-ethynyl-6-(hydroxymethyl)tetrahydropyran-3,4,5-triol (M1) and [(2R,3R,4R,5R,6R)-3,4,5-triacetoxy-6-ethynyl-tetrahydropyran-2-yl]methyl acetate (M2)

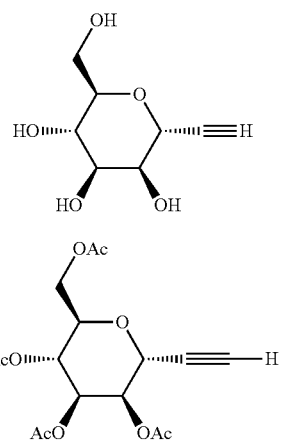

Intermediate M1 was prepared according to the procedure described in Jurgen Stichler-Bonaparte et. al. *Helvetica Chimica Acta*, 2001, 84(8), 2355-2367.

Intermediate M2 was obtained from acetylation of intermediate M1: To a solution of Intermediate M1 (290 mg, 1.54 mmol) in pyridine (2.9 mL) was added DMAP (17 mg, 0.14 mmol). The reaction mixture was cooled in an ice bath, then acetic anhydride (1.7 mL, 18.0 mmol) is added dropwise. The reaction mixture was left to warm to RT and stirred overnight. After concentrating under vacuum, the crude residue was diluted with DCM (10 mL) and H$_2$O (10 mL) is added, followed by 1N HCl (10 mL). The layers were separated, the aqueous layer was back extracted with DCM (2×10 mL). The combined organic extracts were concentrated and purified by flash chromatography on a Biotage™ snap 25 g silica cartridge, using a gradient of EtOAc (0-50%) in Hex as eluent. The fractions were combined and concentrated, affording Intermediate M2 (398 mg, 73% yield). $^1$H NMR (400 MHz, CDCl$_3$) δ 5.48 (dd, J=10.0, 3.4 Hz, 1H), 5.35 (dd, J=3.3, 2.1 Hz, 1H), 5.32-5.23 (m, 1H), 4.78 (t, J=2.2 Hz, 1H), 4.31 (dd, J=12.2, 5.0 Hz, 1H), 4.19 (ddd, J=9.9, 4.9, 2.2 Hz, 1H), 4.14 (dd, J=12.2, 2.2 Hz, 1H), 2.76 (d, J=2.4 Hz, 1H), 2.18 (s, 3H), 2.12 (s, 3H), 2.06 (s, 3H), 2.01 (s, 3H).

Preparation of Intermediates M3: 7-[2-[(2R,3R,4R,5R,6R)-3,4,5-triacetoxy-6-(acetoxymethyl)tetrahydropyran-2-yl]ethynyl]1H-indazole-5-carboxylic acid

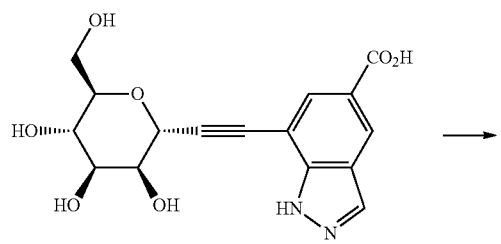

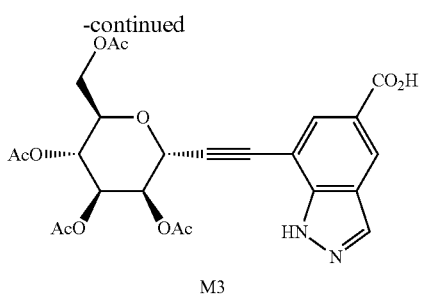

To a solution of Compound 58 (538 mg, 1.44 mmol) in pyridine (3.12 mL, 38.6 mmol) was added Ac$_2$O (1.750 mL, 18.55 mmol) and the reaction mixture was stirred at RT overnight. After concentrating to dryness, the crude residue was purified by flash chromatography on a Biotage™ snap 50 g silica cartridge, using a gradient of MeOH (2-20%) in DCM as eluent. The fractions were combined and concentrated and the penta-acetate/tetra-acetate mixture that was obtained was stirred in MeOH over 4 days, then concentrated to dryness and dried in vacuo, resulting in the title compound (379 mg, 51% yield) which still contained 7% penta-acetate by LCMS. $^1$H NMR (400 MHz, DMSO) δ 13.06 (br s, 1H), 8.54 (d, J=1.4 Hz, 1H), 8.38 (s, 1H), 8.07 (d, J=1.3 Hz, 1H), 5.52 (dd, J=3.4, 2.0 Hz, 1H), 5.48 (dd, J=10.0, 3.4 Hz, 1H), 5.26 (d, J=1.9 Hz, 1H), 5.18 (t, J=10.0 Hz, 1H), 4.36 (ddd, J=10.0, 4.4, 2.4 Hz, 1H), 4.24 (dd, J=12.4, 4.6 Hz, 1H), 4.10 (dd, J=12.4, 2.3 Hz, 1H), 2.16 (s, 3H), 2.03 (s, 3H), 2.02 (s, 3H), 1.96 (s, 4H).

Preparation of Compound 1 (Method A)

(2R,3S,4R,5S,6R)-2-(hydroxymethyl)-6-[2-(1H-indazol-7-yl)ethynyl]tetrahydropyran-3,4,5-triol

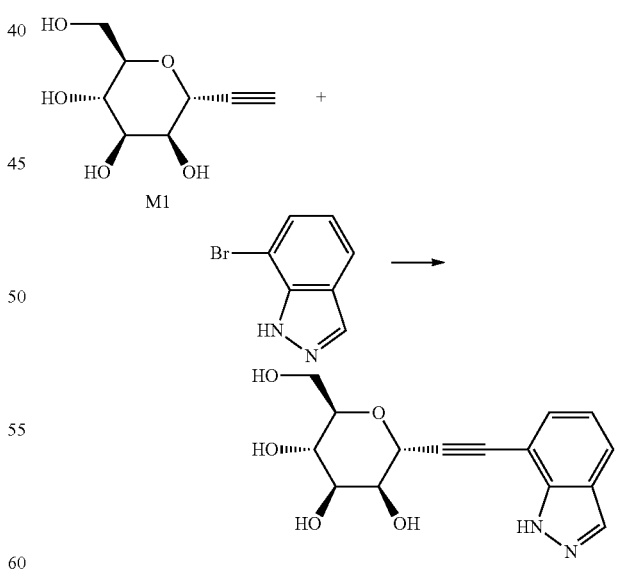

To a degassed (vacuum followed by nitrogen flush) stirred solution of commercially available 7-bromo-1H-indazole (41.0 mg, 0.208 mmol), Intermediate M1 (393 µL of 0.53 M in DMF, 0.208 mmol) was added DMF (100 µL), DIPEA (500 µL) and Pd(PPh$_3$)$_4$ (24 mg, 0.0211 mmol). The reaction tube was degassed once and heated at 80° C. for 20 h. The reaction mixture was concentrated, dissolved in DMSO (1 mL), and purified by reverse phase flash chromatography on a Biotage™ snap 30 g C18 silica gel cartridge using a gradient of MeCN (0-30%) in H$_2$O as eluent. The combined fractions were freeze-dried to provide the title compound (16.6 mg, 26% yield). $^1$H NMR (400 MHz, CD$_3$OD) δ 8.09 (s, 1H), 7.80 (dd, J=8.2, 0.9 Hz, 1H), 7.50 (dd, J=7.2, 0.8 Hz, 1H), 7.13 (dd, J=8.1, 7.2 Hz, 1H), 4.99 (d, J=2.1 Hz, 1H), 4.11 (dd, J=3.2, 2.2 Hz, 1H), 3.98 (dd, J=9.4, 3.3 Hz, 1H), 3.94-3.85 (m, 2H), 3.77-3.69 (m, 1H), 3.66-3.59 (m, 1H). ESI-MS m/z calc. 304.10593, found 305.38 (M+1)$^+$.

Compounds 2 to 14 were prepared as described for Compound 1 under Method A using the appropriate commercially available halogenated heterocycle.

TABLE 1

| Compound | IUPAC name | $^1$H-NMR | LC-MS m/z (M + H$^+$) |
|---|---|---|---|
| 2 | (2R,3S,4R,5S,6R)-2-(hydroxymethyl)-6-[2-(5-methyl-1H-indazol-7-yl)ethynyl]tetrahydropyran-3,4,5-triol | (400 MHz, CD3OD) δ 7.98 (s, 1H), 7.57 (s, 1H), 7.37 (s, 1H), 4.98 (d, J = 2.0 Hz, 1H), 4.12-4.06 (m, 1H), 4.02-3.85 (m, 3H), 3.81-3.70 (m, 1H), 3.63 (t, J = 9.6 Hz, 1H), 2.41 (s, 3H) | 319.34 |
| 3 | (2R,3S,4R,5S,6R)-2-(hydroxymethyl)-6-[2-(1H-indazol-4-yl)ethynyl]tetrahydropyran-3,4,5-triol | (400 MHz, CD3OD) δ 8.12 (d, J = 1.1 Hz, 1H), 7.56 (dt, J = 8.4, 1.0 Hz, 1H), 7.35 (dd, J = 8.4, 7.1 Hz, 1H), 7.27 (dd, J = 7.1, 0.8 Hz, 1H), 4.96 (d, J = 2.1 Hz, 1H), 4.08 (dd, J = 3.3, 2.1 Hz, 1H), 4.00 (dd, J = 9.4, 3.3 Hz, 1H), 3.94-3.84 (m, 2H), 3.80-3.69 (m, 1H), 3.65 (t, J = 9.4 Hz, 1H) | |
| 4 | (2R,3S,4R,5S,6R)-2-(hydroxymethyl)-6-[2-(5-methyl-1H-indol-7-yl)ethynyl]tetrahydropyran-3,4,5-triol | (400 MHz, CD3OD) δ 7.38 (dd, J = 1.3, 0.7 Hz, 1H), 7.23 (d, J = 3.2 Hz, 1H), 7.08 (d, J = 1.2 Hz, 1H), 6.40 (d, J = 3.1 Hz, 1H), 4.98 (d, J = 2.1 Hz, 1H), 4.10 (dd, J = 3.2, 2.2 Hz, 1H), 4.02 (dd, J = 9.4, 3.3 Hz, 1H), 3.96-3.87 (m, 2H), 3.75 (dd, J = 12.1, 6.6 Hz, 1H), 3.65 (t, J = 9.5 Hz, 1H), 2.39 (s, 3H) | 318.36 |
| 5 | 7-[2-[(2R,3S,4R,5S,6R)-3,4,5-trihydroxy-6-(hydroxymethyl)tetrahydropyran-2-yl]ethynyl]-3H-benzimidazole-5-carbonitrile | (400 MHz, CD3OD) δ 8.48 (s, 1H), 8.10 (broad s, 1H), 7.76 (s, 1H), 5.01 (d, J = 2.1 Hz, 1H), 4.20-4.08 (m, 1H), 4.07-3.85 (m, 3H), 3.77 (dd, J = 11.7, 6.1 Hz, 1H), 3.66 (t, J = 9.5 Hz, 1H) | 330.31 |
| 6 | (2R,3S,4R,5S,6R)-2-[2-(5-chloro-1H-indazol-7-yl)ethynyl]-6-(hydroxymethyl)tetrahydropyran-3,4,5-triol | (400 MHz, CD3OD) δ 8.09 (s, 1H), 7.84 (d, J = 1.8 Hz, 1H), 7.51 (d, J = 1.8 Hz, 1H), 5.01 (d, J = 2.1 Hz, 1H), 4.12 (dd, J = 3.2, 2.2 Hz, 1H), 3.97 (dd, J = 9.3, 3.3 Hz, 1H), 3.93 (dd, J = 11.5, 2.2 Hz, 1H), 3.91-3.85 (m, 1H), 3.75 (dd, J = 11.5, 6.2 Hz, 1H), 3.64 (t, J = 9.5 Hz, 1H) | 339.32 |
| 7 | (2R,3S,4R,5S,6R)-2-(hydroxymethyl)-6-[2-(6-methyl-1H-indazol-4-yl)ethynyl]tetrahydropyran-3,4,5-triol | (400 MHz, CD3OD) δ 8.04 (s, 1H), 7.34 (s, 1H), 7.14 (s, 1H), 4.95 (d, J = 2.1 Hz, 1H), 4.08-4.05 (m, 1H), 4.00 (dd, J = 9.3, 3.2 Hz, 1H), 3.93-3.84 (m, 2H), 3.74 (dd, J = 11.3, 5.5 Hz, 1H), 3.65 (t, J = 9.5 Hz, 1H), 2.44 (s, 3H) | 319.44 |
| 8 | (2R,3S,4R,5S,6R)-2-[2-(3H-benzotriazol-4-yl)ethynyl]-6-(hydroxymethyl)tetrahydropyran-3,4,5-triol | (400 MHz, CD3OD) δ 7.91 (d, J = 8.3 Hz, 1H), 7.60 (d, J = 6.9 Hz, 1H), 7.47 (dd, J = 8.3, 7.3 Hz, 1H), 5.02 (d, J = 2.1 Hz, 1H), 4.14 (dd, J = 3.2, 2.2 Hz, 1H), 4.03 (dd, J = 9.4, 3.3 Hz, 1H), 3.97-3.86 (m, 2H), 3.77 (dd, J = 12.2, 6.5 Hz, 1H), 3.67 (t, J = 9.4 Hz, 1H) | 306.31 |
| 9 | (2R,3S,4R,5S,6R)-2-(hydroxymethyl)-6-(2-indolin-7-ylethynyl)tetrahydropyran-3,4,5-triol | (400 MHz, CD3OD) δ 7.06 (d, J = 7.2 Hz, 1H), 7.00 (d, J = 7.8 Hz, 1H), 6.59 (t, J = 7.6 Hz, 1H), 4.94-4.83 (m, 1H), 4.05-4.00 (m, 1H), 3.96 (dd, J = 9.3, 3.3 Hz, 1H), 3.91-3.80 (m, 2H), 3.73 (dd, J = 11.4, 5.7 Hz, 1H), 3.62 (t, J = 9.4 Hz, 1H), 3.55 (t, J = 8.5 Hz, 2H), 3.02 (t, J = 8.5 Hz, 2H) | 306.36 |
| 10 | (2R,3S,4R,5S,6R)-2-[2-(1,3-benzoxazol-7-yl)ethynyl]-6-(hydroxymethyl)tetrahydropyran-3,4,5-triol | (400 MHz, CD3OD) δ 8.29 (s, 1H), 7.89 (dd, J = 8.1, 1.5 Hz, 1H), 7.15 (dd, J = 7.8, 1.5 Hz, 1H), 6.83 (t, J = 7.9 Hz, 1H), 4.91 (d, J = 2.0 Hz, | 306.31 |

TABLE 1-continued

| Compound | IUPAC name | ¹H-NMR | LC-MS m/z (M + H⁺) |
|---|---|---|---|
| 11 | 7-[2-[(2R,3S,4R,5S,6R)-3,4,5-trihydroxy-6-(hydroxymethyl)tetrahydropyran-2-yl]ethynyl]indolin-2-one | 1H), 4.07-4.03 (m, 1H), 3.97 (dd, J = 9.3, 3.3 Hz, 1H), 3.92-3.81 (m, 2H), 3.73 (dd, J = 11.3, 5.9 Hz, 1H), 3.63 (t, J = 9.4 Hz, 1H) (400 MHz, CD3OD) δ 7.31-7.21 (m, 2H), 6.98 (t, J = 7.7 Hz, 1H), 4.93 (d, J = 2.1 Hz, 1H), 4.06 (dd, J = 3.1, 2.3 Hz, 1H), 3.97-3.87 (m, 2H), 3.86-3.78 (m, 1H), 3.73 (dd, J = 11.5, 6.3 Hz, 1H), 3.61 (t, J = 9.5 Hz, 1H), 3.57 (s, 2H) | 320.37 |
| 12 | 6-chloro-4-[2-[(2R,3S,4R,5S,6R)-3,4,5-trihydroxy-6-(hydroxymethyl)tetrahydropyran-2-yl]ethynyl]-1,3-dihydrobenzimidazol-2-one | (400 MHz, CD3OD) δ 7.12 (d, J = 1.9 Hz, 1H), 7.05 (d, J = 1.9 Hz, 1H), 4.94 (d, J = 2.1 Hz, 1H), 4.07 (dd, J = 3.1, 2.3 Hz, 1H), 3.97-3.88 (m, 2H), 3.86-3.80 (m, 1H), 3.73 (dd, J = 11.6, 6.3 Hz, 1H), 3.62 (t, J = 9.5 Hz, 1H) | 355.25 |
| 13 | (2R,3S,4R,5S,6R)-2-(hydroxymethyl)-6-[2-(1-methylindazol-7-yl)ethynyl]tetrahydropyran-3,4,5-triol | (400 MHz, CD3OD) δ 8.04 (s, 1H), 7.80 (dd, J = 8.1, 0.9 Hz, 1H), 7.56 (dd, J = 7.2, 0.8 Hz, 1H), 7.13 (dd, J = 8.1, 7.2 Hz, 1H), 5.00 (d, J = 2.1 Hz, 1H), 4.39 (s, 3H), 4.09 (dd, J = 3.2, 2.1 Hz, 1H), 3.94 (dd, J = 9.3, 3.3 Hz, 1H), 3.90 (dd, J = 11.6, 2.1 Hz, 1H), 3.84 (ddd, J = 9.5, 6.0, 2.1 Hz, 1H), 3.74 (dd, J = 11.6, 6.1 Hz, 1H), 3.65 (t, J = 9.5 Hz, 1H) | 319.34 |
| 14 | (2R,3S,4R,5S,6R)-2-(hydroxymethyl)-6-[2-(1H-pyrazolo[3,4-c]pyridin-7-yl)ethynyl]tetrahydropyran-3,4,5-triol | (400 MHz, CD3OD) δ 8.27 (s, 1H), 8.21 (d, J = 5.6 Hz, 1H), 7.85 (d, J = 5.6 Hz, 1H), 5.07 (d, J = 2.1 Hz, 1H), 4.17 (dd, J = 3.1, 2.3 Hz, 1H), 4.00 (dd, J = 9.4, 3.3 Hz, 1H), 3.97-3.89 (m, 2H), 3.76 (dd, J = 11.7, 6.3 Hz, 1H), 3.66 (t, J = 9.6 Hz, 1H) | 306.31 |

Preparation of Compound 15 (Method B)

6-butyl-4-[2-[(2R,3S,4R,5S,6R)-3,4,5-trihydroxy-6-(hydroxymethyl)tetrahydropyran-2-yl]ethynyl]-1,3-dihydrobenzimidazol-2-one

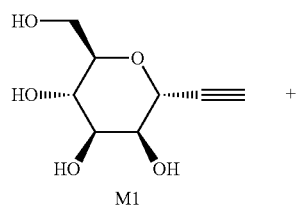

M1

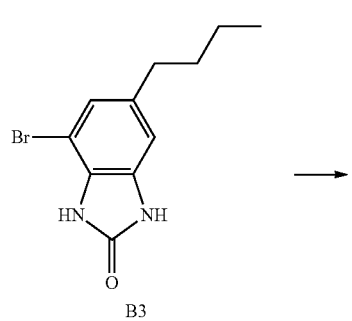

B3

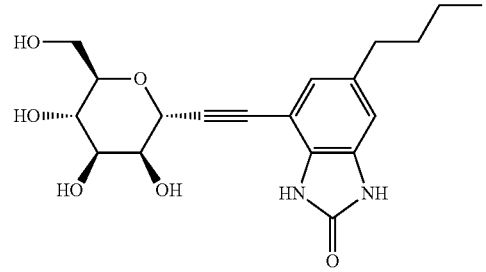

-continued

Intermediate B3 (78 mg, 0.290 mmol), CuI (10 mg, 0.053 mmol) and Pd(dppf)Cl₂.DCM (10 mg, 0.014 mmol) were loaded in a pressure vial, capped and degassed (vacuum then nitrogen flush, 3×). A solution of Intermediate M1 (500 μL of 0.53 M, 0.265 mmol) in DMF was added, followed by DIPEA (0.4 mL). The vial was degassed again and transferred to a preheated (80° C.) oil bath and stirred overnight (20 h). The crude reaction mixture was passed through a 200 mg Si-DMT cartridge, and rinsed with portions of DMSO to produce a 1 mL sample, which was purified by reverse phase HPLC. The fractions were combined and freeze-dried to provide the title compound (32 mg, 51% yield). ¹H NMR (400 MHz, CD₃OD) δ 6.94 (d, J=1.4 Hz, 1H), 6.88 (d, J=1.4 Hz, 1H), 4.94 (d, J=2.1 Hz, 1H), 4.08 (dd, J=3.2, 2.2 Hz, 1H), 3.97 (dd, J=9.4, 3.3 Hz, 1H), 3.92 (dd, J=11.5, 2.2 Hz, 1H), 3.89-3.83 (m, 1H), 3.74 (dd, J=11.5, 6.2 Hz, 1H), 3.63 (t, J=9.5 Hz, 1H), 2.67-2.51 (m, 2H), 1.66-1.50 (m, 2H), 1.35 (h, J=7.3 Hz, 2H), 0.94 (t, J=7.3 Hz, 3H). ESI-MS m/z calc. 376.16342, found 377.38 (M+1)⁺.

Preparation of Compound 16 (Method B)

(2R,3S,4R,5S,6R)-2-[2-(5-bromo-1H-indazol-7-yl)ethynyl]-6-(hydroxymethyl)tetrahydropyran-3,4,5-triol

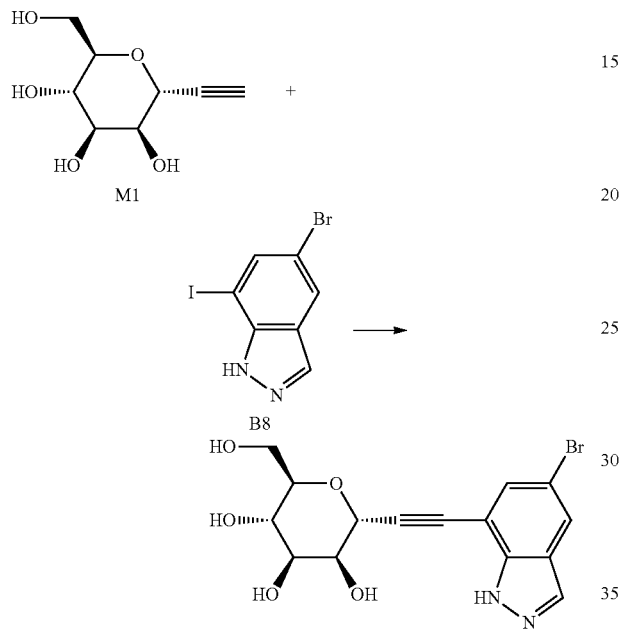

The title compound was prepared following the procedure used for Compound 15, using Intermediate B8 as starting material. The reaction mixture was stirred at RT for 24 h then at 50° C. for 24 h. After purification by reverse-phase flash chromatography on a Biotage™ 30 g C18 silica cartridge using a gradient of MeCN in H₂O (10 to 90%) as eluent and freeze-drying of the combined fractions, the title compound (47 mg, 14% yield) was obtained. ¹H NMR (400 MHz, CD₃OD) δ 8.08 (s, 1H), 8.00 (s, 1H), 7.63 (s, 1H), 5.01 (d, J=2.1 Hz, 1H), 4.14-4.09 (m, 1H), 3.97 (dd, J=9.4, 3.3 Hz, 1H), 3.93 (dd, J=11.5, 2.1 Hz, 1H), 3.91-3.85 (m, 1H), 3.75 (dd, J=11.5, 6.2 Hz, 1H), 3.64 (t, J=9.5 Hz, 1H). ESI-MS m/z calc. 382.01645, found 383.26 (M+1)⁺.

Alternative Preparation for Compound 16

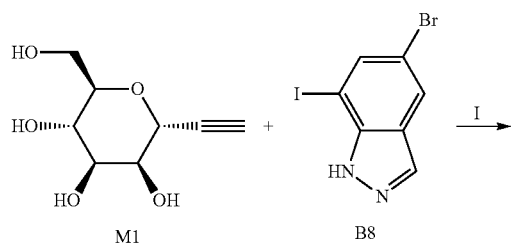

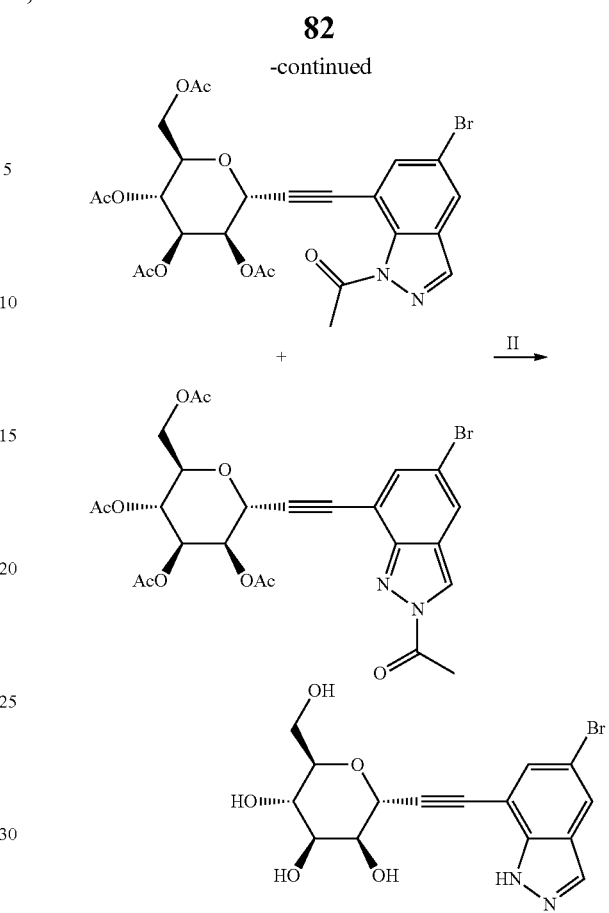

Step I: [(2R,3R,4R,5R,6R)-3,4,5-triacetoxy-6-[2-(1-acetyl-5-bromo-indazol-7-yl)ethynyl]tetrahydropyran-2-yl]methyl acetate and (2R,3R,4R,5R,6R)-2-(acetoxymethyl)-6-((2-acetyl-5-bromo-2H-indazol-7-yl)ethynyl)tetrahydro-2H-pyran-3,4,5-triyl triacetate In a pressure vessel charged with Intermediate B8 (2.33 g, 7.22 mmol), CuI (273 mg, 1.43 mmol) and Pd(dppf)Cl₂.DCM (266 mg, 0.364 mmol), capped and degassed (placed under vacuum and flushed with N₂, 3×) was added Intermediate M1 (15 mL of 0.53 M, 7.95 mmol) solution in DMF followed by DIPEA (12 mL) The pressure vessel was degassed again, sealed and transferred to a preheated (50° C.) oil bath and stirred overnight. After cooling down to RT, pyridine (15 mL, 186 mmol) was added, followed by acetic anhydride (15 mL, 159 mmol) and the resulting mixture was stirred overnight, then passed through a silica pad and rinsed with 200 mL EtOAc. The filtrate was transferred to a separatory funnel and washed with H₂O (2×100 mL) and aqueous saturated NH₄Cl solution (2×100 mL), dried over Na₂SO₄, filtered and concentrated, then co-evaporated with heptane (2×). The crude residue was purified by flash chromatography on a Biotage™ snap 100 g silica cartridge, using a gradient of EtOAc (10-60%) in Hex, as eluent. The fractions were combined and concentrated to provide the title compounds (as a mixture of regioisomers which were not separated) (3.03 g, 71% yield).

Step II: Compound 16

To a stirred suspension of the regioisomers from Step I (3.00 g, 5.06 mmol) in MeOH (20 mL) was added a solution of NaOMe (20.0 mL of 0.5 M, 10.1 mmol) in MeOH. After stirring for 30 min, the reaction mixture was diluted with MeOH (25 mL) and treated with a minimal amount of prewashed Dowex 50WX4-400 resin (until pH is slightly acidic), diluted with THF (20 mL), filtered and washed with 5 portions of MeOH/THF (1:1, 4×10 mL). The combined filtrates were concentrated to provide the title compound (1.85 g, 96% yield).

Preparation of Compound 17 (Method B)

(2R,3S,4R,5S,6R)-2-[2-[5-bromo-2-[(4-methoxyphenyl)methyl]indazol-7-yl]ethynyl]-6-(hydroxymethyl)tetrahydropyran-3,4,5-triol

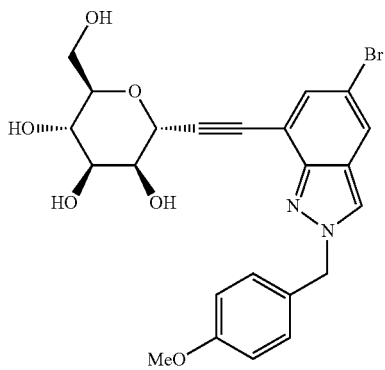 [SMILES: COc1ccc(Cn2cc3cc(Br)cc(C#C[C@H]4O[C@H](CO)[C@@H](O)[C@H](O)[C@@H]4O)c3n2)cc1]

The title compound was prepared following the procedure used for Compound 15, using Intermediate B10 as starting material. The reaction mixture was stirred at 65° C. for 18 h. gradient of MeOH (0-40%) in DCM as eluent and concentration of the combined fractions, the title compound (183 mg, 68% yield) was obtained. $^1$H NMR (400 MHz, CD$_3$OD) δ 8.26 (s, 1H), 7.91 (d, J=1.8 Hz, 1H), 7.54 (d, J=1.7 Hz, 1H), 7.38-7.25 (m, 2H), 6.98-6.83 (m, 2H), 5.57 (s, 2H), 4.97 (d, J=2.1 Hz, 1H), 4.12 (dd, J=3.2, 2.2 Hz, 1H), 4.04 (dd, J=9.4, 3.3 Hz, 1H), 3.98-3.86 (m, 2H), 3.84-3.73 (m, 4H), 3.68 (t, J=9.6 Hz, 1H). ESI-MS m/z calc. 502.07394, found 503.35 (M+1)$^+$.

Preparation of Compound 18 (Method B)

(2R,3S,4R,5S,6R)-2-[2-[5-bromo-1-[(4-methoxyphenyl)methyl]indazol-7-yl]ethynyl]-6-(hydroxymethyl)tetrahydropyran-3,4,5-triol

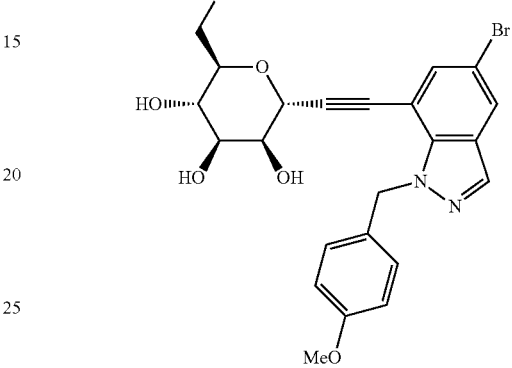

The title compound was prepared following the procedure used for Compound 17, using Intermediate B9 as starting material. The title compound (170 mg, 64% yield) was obtained. $^1$H NMR (400 MHz, CD$_3$OD) δ 8.10 (s, 1H), 8.01 (d, J=1.8 Hz, 1H), 7.68 (d, J=1.8 Hz, 1H), 7.14-6.98 (m, 2H), 6.93-6.68 (m, 2H), 6.07-5.78 (m, 2H), 4.91 (d, J=2.1 Hz, 1H), 3.95 (dd, J=3.2, 2.2 Hz, 1H), 3.86 (dd, J=9.2, 3.3 Hz, 1H), 3.84-3.68 (m, 7H), 3.65 (t, J=9.3 Hz, 1H). ESI-MS m/z calc. 502.07394, found 503.35 (M+1)$^+$.

Compounds 19 to 23 were prepared as described for Compound 1 under Method A using Intermediates B1, B2, B4, B6 and B7 respectively.

TABLE 2

| Compound | IUPAC name | $^1$H-NMR | LC-MS m/z (M + H$^+$) |
|---|---|---|---|
| 19 | (2R,3S,4R,5S,6R)-2-[2-(6-butyl-3H-benzotriazol-4-yl)ethynyl]-6-(hydroxymethyl)tetrahydropyran-3,4,5-triol | (400 MHz, CD$_3$OD) δ 7.66 (s, 1H), 7.47 (d, J = 0.9 Hz, 1H), 5.01 (d, J = 2.1 Hz, 1H), 4.13 (dd, J = 3.2, 2.2 Hz, 1H), 4.04 (dd, J = 9.4, 3.3 Hz, 1H), 3.97-3.89 (m, 2H), 3.77 (dd, J = 12.2, 6.5 Hz, 1H), 3.66 (t, J = 9.5 Hz, 1H), 2.86-2.73 (m, 2H), 1.78-1.60 (m, 2H), 1.39 (h, J = 7.3 Hz, 2H), 0.97 (t, J = 7.4 Hz, 3H). | 362.44 |
| 20 | (2R,3S,4R,5S,6R)-2-[2-(6-butyl-3H-benzimidazol-4-yl)ethynyl]-6-(hydroxymethyl)tetrahydropyran-3,4,5-triol | (400 MHz, DMSO) δ 12.51 (broad s, 1H), 8.19 (broad s, 1H), 7.36 ( broad s, 1H), 7.12 (s, 1H), 4.96 (broad s, 1H), 4.80 (s, 2H), 4.71 (broad s, 1H), 4.49 (broad s, 1H), 4.01-3.58 (m, 4H), 3.45 (dt, J = 17.0, 8.9 Hz, 2H), 2.66 (t, J = 7.4 Hz, 2H), 1.68-1.50 (m, 2H), 1.30 (h, J = 7.3 Hz, 2H), 0.89 (t, J = 7.3 Hz, 3H). | 361.36 |
| 21 | (2R,3S,4R,5S,6R)-2-[2-(1-butylindazol-4-yl)ethynyl]-6-(hydroxymethyl)tetrahydropyran-3,4,5-triol | (400 MHz, CD$_3$OD) δ 8.10 (d, J = 0.9 Hz, 1H), 7.62 (d, J = 8.5 Hz, 1H), 7.39 (dd, J = 8.5, 7.1 Hz, 1H), 7.29 (d, J = 7.1 Hz, 1H), 4.98 (d, J = 2.1 Hz, 1H), 4.44 (t, J = 7.0 Hz, 2H), 4.09 (dd, J = 3.2, 2.2 Hz, 1H), 4.01 (dd, J = 9.4, 3.3 Hz, 1H), 3.96-3.84 (m, 2H), 3.76 (dd, J = 12.0, 6.2 Hz, 1H), 3.67 | 361.41 |

TABLE 2-continued

| Compound | IUPAC name | $^1$H-NMR | LC-MS m/z (M + H$^+$) |
|---|---|---|---|
| | | (t, J = 9.5 Hz, 1H), 1.97-1.79 (m, 2H), 1.38-1.19 (m, 2H), 0.93 (t, J = 7.4 Hz, 3H). | |
| 22 | (2R,3S,4R,5S,6R)-2-[2-(5-butyl-1-methyl-indazol-7-yl)ethynyl]-6-(hydroxymethyl)tetrahydropyran-3,4,5-triol | (400 MHz, CD$_3$OD) δ 7.95 (s, 1H), 7.57 (s, 1H), 7.43 (d, J = 1.3 Hz, 1H), 5.00 (d, J = 2.0 Hz, 1H), 4.35 (s, 3H), 4.09 (dd, J = 3.1, 2.3 Hz, 1H), 3.95 (dd, J = 9.3, 3.3 Hz, 1H), 3.91 (dd, J = 11.6, 2.1 Hz, 1H), 3.88-3.79 (m, 1H), 3.75 (dd, J = 11.6, 6.1 Hz, 1H), 3.65 (t, J = 9.5 Hz, 1H), 2.77-2.61 (m, 2H), 1.73-1.56 (m, 2H), 1.45-1.29 (m, 2H), 0.95 (t, J = 7.4 Hz, 3H). | 375.42 |
| 23 | (2R,3S,4R,5S,6R)-2-[2-(5-butyl-2-methyl-indazol-7-yl)ethynyl]-6-(hydroxymethyl)tetrahydropyran-3,4,5-triol | (400 MHz, CD$_3$OD) δ 8.15 (s, 1H), 7.49 (s, 1H), 7.35 (d, J = 1.0 Hz, 1H), 4.97 (d, J = 2.0 Hz, 1H), 4.21 (s, 3H), 4.16-4.10 (m, 1H), 4.06 (dd, J = 9.4, 3.3 Hz, 1H), 3.97-3.85 (m, 2H), 3.77 (dd, J = 12.0, 5.9 Hz, 1H), 3.67 (t, J = 9.6 Hz, 1H), 2.73-2.61 (m, 2H), 1.70-1.56 (m, 2H), 1.45-1.29 (m, 2H), 0.95 (t, J = 7.4 Hz, 3H). | 375.42 |

Preparation of Compound 24 (Method B)

(2R,3S,4R,5S,6R)-2-[2-(5-butyl-1H-indazol-7-yl)ethynyl]-6-(hydroxymethyl)tetrahydropyran-3,4,5-triol

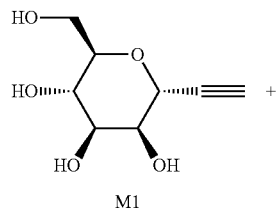

M1

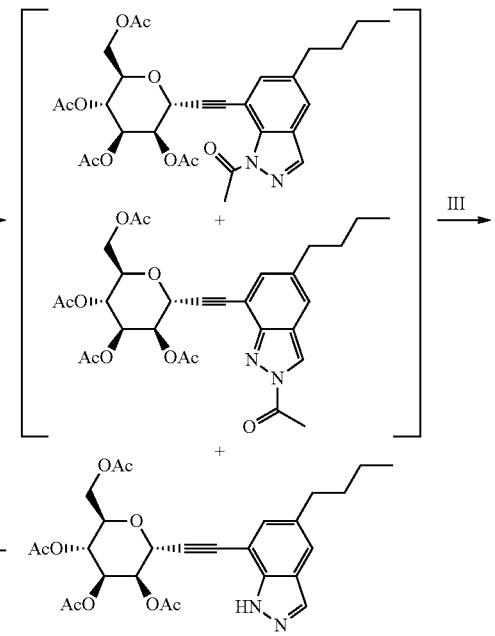

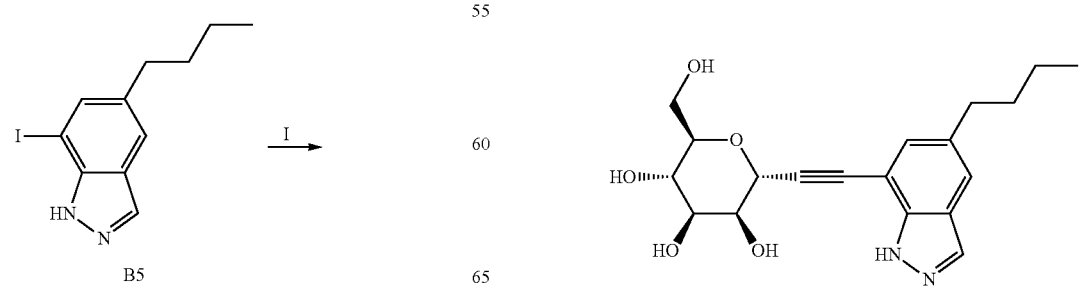

B5

Step I: (2R,3R,4R,5R,6R)-2-(acetoxymethyl)-6-(1-acetyl-5-butyl-1H-indazol-7-yl)ethynyl)tetrahydro-2H-pyran-3,4,5-triyl triacetate, (2R,3R,4R,5R,6R)-2-(acetoxymethyl)-6-((2-acetyl-5-butyl-2H-indazol-7-yl)ethynyl)tetrahydro-2H-pyran-3,4,5-triyl triacetate and (2R,3R,4R,5R,6R)-2-(acetoxymethyl)-6-((5-butyl-1H-indazol-7-yl)ethynyl)tetrahydro-2H-pyran-3,4,5-triyl triacetate A mixture of Intermediate M1 (7.68 g, 40.8 mmol), Intermediate B5 (9.8 g, 32.7 mmol), CuI (1.24 g, 6.53 mmol) and DMF (98.00 mL) was degassed (by bubbling $N_2$ for 2 minutes) then DIPEA (23.0 mL, 131 mmol) was added followed by Pd(dppf)Cl$_2$.DCM (1.19 g, 1.63 mmol). The reaction mixture was degassed again then stirred at 50° C. (internal temperature) for 90 min. The reaction mixture was then left to cool down to RT overnight and treated with pyridine (68 mL, 839 mmol) followed by acetic anhydride (69 mL, 719 mmol) added dropwise while maintaining the internal temperature at 30° C. The resulting mixture was stirred overnight at RT. The reaction mixture was passed through a 60 g silica pad, rinsed with 3×100 mL EtOAc. The filtrate was diluted with $H_2O$ (200 mL) and stirred for 20-30 min. Some brine was added and the layers were separated. The organic layer was washed sequentially with $H_2O$ (100 mL), aqueous saturated NH$_4$Cl solution (2×100 mL), aqueous saturated NaHCO$_3$ solution (100 mL), dried over Na$_2$SO$_4$, filtered, concentrated and coevaporated with heptane (2×). The crude residue was purified by flash chromatography on a Biotage™ snap 340 g silica cartridge, using a gradient of EtOAc (5-50%) in Hex as eluent. The fractions were combined and concentrated to provide the pentaacetylated compound (9.8 g, 53% yield) as a mixture of indazole regioisomers; (2R,3R,4R,5R,6R)-2-(acetoxymethyl)-6-((1-acetyl-5-butyl-1H-indazol-7-yl)ethynyl)tetrahydro-2H-pyran-3,4,5-triyl triacetate; (2R,3R,4R,5R,6R)-2-(acetoxymethyl)-6-((2-acetyl-5-butyl-2H-indazol-7-yl)ethynyl)tetrahydro-2H-pyran-3,4,5-triyl triacetate; (2R,3R,4R,5R,6R)-2-(acetoxymethyl)-6(5-butyl-1H-indazol-7-yl)ethynyl)tetrahydro-2H-pyran-3,4,5-triyl triacetate is also obtained (7.78 g, 45% yield).

Step II: (2R,3R,4R,5R,6R)-2-(acetoxymethyl)-6-((1-acetyl-5-butyl-1M-indazol-7-yl)ethynyl)tetrahydro-2H-pyran-3,4,5-triyl triacetate, (2R,3R,4R,5R,6R)-2-(acetoxymethyl)-6-((2-acetyl-5-butyl-2H-indazol-7-yl)ethynyl)tetrahydro-2H-pyran-3,4,5-triyl triacetate A solution of (2R,3R,4R,5R,6R)-2-(acetoxymethyl)-6-((5-butyl-1H-indazol-7-yl)ethynyl)tetrahydro-2H-pyran-3,4,5-triyl triacetate (7.70 g, 14.6 mmol) in pyridine (31 mL) was treated with acetic anhydride (3.1 mL, 32.8 mmol), added dropwise while maintaining the internal temperature below 30° C. The reaction mixture was stirred at RT for 3 h. The reaction mixture was diluted with DCM (75 mL) and $H_2O$ (50 mL) and stirred for 20-30 min. A 2N aqueous HCl solution was added until pH 4-5 was obtained (about 100 mL) and the layers were separated and the aqueous layer was extracted with DCM (2×75 mL). The combined organic extracts were washed with $H_2O$ (100 mL), dried over MgSO$_4$, filtered and concentrated under reduced pressure. The crude residue was purified by flash chromatography on a Biotage™ snap Ultra 100 g silica cartridge, using a gradient of EtOAc in Hex, 10-50%, as eluent. The fractions were combined and concentrated to provide the title compound (6.05 g, 73% yield) (mixture of regioisomers).

Step III: Compound 24

A mixture of (2R,3R,4R,5R,6R)-2-(acetoxymethyl)-6-((1-acetyl-5-butyl-1H-indazol-7-yl)ethynyl)tetrahydro-2H-pyran-3,4,5-triyl triacetate, (2R,3R,4R,5R,6R)-2-(acetoxymethyl)-6-((2-acetyl-5-butyl-2H-indazol-7-yl)ethynyl)tetrahydro-2H-pyran-3,4,5-triyl triacetate (23.15 g, 40.6 mmol) in EtOAc (230 mL) was treated with activated charcoal (12 g) and stirred under $N_2$ atmosphere for 4 h. The suspension was filtered on a Celite™ pad and washed with portions of EtOAc (6×115 mL) The filtrate was treated with SiliaMetS-Thiol (1.32 mmol/g, 3.6 g, 4.75 mmol) and stirred under $N_2$ atmosphere overnight (18 h), then filtered on Celite™ pad and rinsed with portions of EtOAc. The combined filtrates were concentrated and coevaporated with MeOH (2×), then dried under vacuum. The resulting material (21.8 g) was stirred in MeOH (436 mL) and treated with a solution of MeO Na in MeOH (9.10 mL of 25% w/v, 42.0 mmol) and stirred for 2 h. The reaction mixture was neutralized with AcOH (2.5 mL, 43.9 mmol) and stirred for 15 min then $H_2O$ (760 ml) was added dropwise via an addition funnel over 60 minutes and the mixture was stirred overnight. The resulting material was collected by filtration and washed with $H_2O$ (4×50 mL) and air-dried, providing the title compound (12.75 g, 92% yield). $^1$H NMR (400 MHz, DMSO) δ 13.31 (s, 1H), 8.07 (d, J=1.4 Hz, 1H), 7.66-7.54 (m, 1H), 7.32 (d, J=1.4 Hz, 1H), 5.00 (d, J=4.4 Hz, 1H), 4.84 (d, J=2.1 Hz, 1H), 4.76 (d, J=6.0 Hz, 1H), 4.69 (d, J=6.0 Hz, 1H), 4.48 (t, J=5.9 Hz, 1H), 3.98 (ddd, J=4.4, 3.2, 2.1 Hz, 1H), 3.78 (ddd, J=9.3, 6.0, 3.2 Hz, 1H), 3.72 (ddd, J=11.6, 5.8, 2.1 Hz, 1H), 3.64 (ddd, J=9.3, 6.1, 2.1 Hz, 1H), 3.50 (dt, J=11.9, 6.2 Hz, 1H), 3.42 (td, J=9.4, 6.0 Hz, 1H), 2.66 (t, J=7.6 Hz, 2H), 1.65-1.50 (m, 2H), 1.30 (h, J=7.3 Hz, 2H), 0.90 (t, J=7.3 Hz, 3H). ESI-MS m/z calc. 360.16852, found 361.36 (M+1)$^+$.

Preparation of Compound 25 (Method C)

(2R,3S,4R,5S,6R)-2-(hydroxymethyl)-6-[2-(5-phenyl-1H-indazol-7-yl)ethynyl]tetrahydropyran-3,4,5-triol

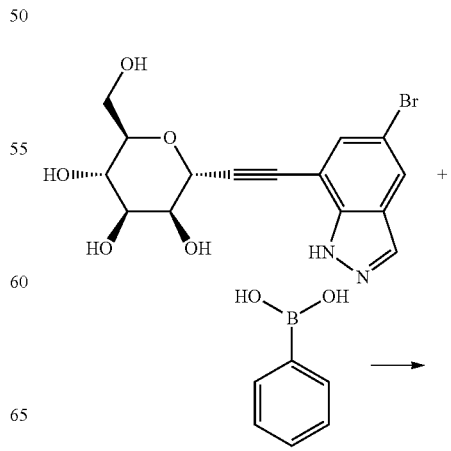

-continued

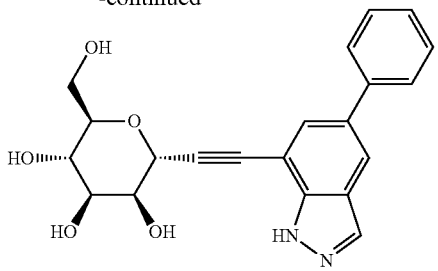

To a pressure vial loaded with Compound 16 (30.5 mg, 0.0796 mmol), DMF (600 μL), phenylboronic acid (200 μL of 0.5 M, 0.100 mmol) solution in NMP and aqueous Na$_2$CO$_3$ solution (165 μL of 1 M, 0.165 mmol) and degassed (placed under vacuum and flushed with N$_2$, 3×) was added Pd(dppf)Cl$_2$.DCM (8.0 mg, 0.00980 mmol). The reaction vial was capped and degassed again then transferred to a preheated (80° C.) oil bath and stirred overnight. The reaction mixture was filtered and rinsed with DMSO to provide a 1 mL size sample which was purified by reverse phase HPLC. The fractions were combined and freeze-dried to provide the title compound (7.2 mg, 22% yield). $^1$H NMR (400 MHz, CD$_3$OD) δ 8.18 (s, 1H), 8.04 (d, J=1.5 Hz, 1H), 7.81 (d, J=1.5 Hz, 1H), 7.68-7.62 (m, 2H), 7.51-7.42 (m, 2H), 7.35 (t, J=7.4 Hz, 1H), 5.03 (d, J=2.1 Hz, 1H), 4.15 (dd, J=2.9, 2.4 Hz, 1H), 4.03 (dd, J=9.4, 3.3 Hz, 1H), 3.98-3.89 (m, 2H), 3.76 (dd, J=12.2, 6.8 Hz, 1H), 3.66 (t, J=9.4 Hz, 1H). ESI-MS m/z calc. 380.1372, found 381.35 (M+1)$^+$.

Compounds 26 to 39 were prepared as described for Compound 25 under Method C using the appropriate commercially available boronic acid.

TABLE 3

| Compound | IUPAC name | $^1$H-NMR | LC-MS m/z (M + H$^+$) |
|---|---|---|---|
| 26 | (2R,3S,4R,5S,6R)-2-(hydroxymethyl)-6-[2-[5-(o-tolye-1H-indazol-7-yl]ethynyl]tetrahydropyran-3,4,5-triol | (400 MHz, CD$_3$OD) δ 8.15 (s, 1H), 7.72 (d, J = 1.4 Hz, 1H), 7.47 (d, J = 1.4 Hz, 1H), 7.34-7.18 (m, 4H), 5.02 (d, J = 2.1 Hz, 1H), 4.13 (dd, J = 3.1, 2.3 Hz, 1H), 4.00 (dd, J = 9.4, 3.3 Hz, 1H), 3.96-3.87 (m, 2H), 3.75 (dd, J = 11.9, 6.6 Hz, 1H), 3.64 (t, J = 9.5 Hz, 1H), 2.25 (s, 3H). | 395.4 |
| 27 | (2R,3S,4R,5S,6R)-2-(hydroxymethyl)-6-[2-[5-(3-pyridyl)-1H-indazol-7-yl]ethynyl]tetrahydropyran-3,4,5-triol | (400 MHz, CD$_3$OD) δ 8.89 (broad s, 1H), 8.57 (broad s, 1H), 8.22 (s, 1H), 8.17 (d, J = 8.0 Hz, 2H), 8.14 (d, J = 1.5 Hz, 2H), 7.86 (d, J = 1.5 Hz, 1H), 7.57 (broad s, 1H), 5.04 (d, J = 2.1 Hz, 1H), 4.15 (dd, J = 3.2, 2.2 Hz, 1H), 4.02 (dd, J = 9.3, 3.3 Hz, 1H), 3.98-3.88 (m, 2H), 3.76 (dd, J = 12.1, 6.8 Hz, 2H), 3.66 (t, J = 9.4 Hz, 1H). | 382.42 |
| 28 | (2R,3S,4R,5S,6R)-2-(hydroxymethyl)-6-[2-[5-(4-nitrophenyl)-1H-indazol-7-yl]ethynyl]tetrahydropyran-3,4,5-triol | (400 MHz, CD$_3$OD) δ 8.34 (d, J = 8.9 Hz, 2H), 8.23 (s, 1H), 8.21 (d, J = 1.6 Hz, 1H), 7.97-7.93 (m, 1H), 7.92 (d, J = 1.5 Hz, 1H), 5.04 (d, J = 2.1 Hz, 1H), 4.20-4.13 (m, 1H), 4.02 (dd, J = 9.3, 3.3 Hz, 1H), 3.98-3.88 (m, 1H), 3.77 (dd, J = 12.0, 6.7 Hz, 1H), 3.66 (t, J = 9.4 Hz, 1H). | 426.36 |
| 29 | (2R,3S,4R,5S,6R)-2-[2-[5-[4-(dimethylamino)phenyl]-1H-indazol-7-yl]ethynyl]-6-(hydroxymethyl)tetrahydropyran-3,4,5-triol | (400 MHz, CD$_3$OD) δ 8.12 (s, 1H), 7.95 (d, J = 1.6 Hz, 1H), 7.76 (d, J = 1.5 Hz, 1H), 7.57-7.46 (m, 2H), 6.99-6.81 (m, 2H), 5.03 (d, J = 2.1 Hz, 1H), 4.14 (dd, J = 3.2, 2.2 Hz, 1H), 4.03 (dd, J = 9.4, 3.3 Hz, 1H), 3.98-3.88 (m, 2H), 3.76 (dd, J = 12.1, 6.8 Hz, 1H), 3.66 (t, J = 9.4 Hz, 1H), 2.98 (s, 6H). | 424.44 |
| 30 | (2R,3S,4R,5S,6R)-2-(hydroxymethyl)-6-[2-[5-(4-methoxyphenyl)-1H-indazol-7-yl]ethynyl]tetrahydropyran-3,4,5-triol | (400 MHz, CD$_3$OD) δ 8.15 (s, 1H), 7.98 (d, J = 1.5 Hz, 1H), 7.76 (d, J = 1.5 Hz, 1H), 7.64-7.53 (m, 2H), 7.09-6.96 (m, 2H), 5.03 (d, J = 2.1 Hz, 1H), 4.14 (dd, J = 3.1, 2.3 Hz, 1H), 4.03 (dd, J = 9.3, 3.3 Hz, 1H), 3.97-3.89 (m, 2H), 3.84 (s, 3H), 3.76 (dd, J = 12.2, 6.8 Hz, 1H), 3.66 (t, J = 9.4 Hz, 1H). | 411.42 |
| 31 | 3-[7-[2-[(2R,3S,4R,5S,6R)-3,4,5-trihydroxy-6-(hydroxymethyl)tetrahydropyran-2-yl]ethynyl]-1H-indazol-5-yl]benzamide | (400 MHz, CD$_3$OD) δ 8.24-8.17 (m, 2H), 8.13 (d, J = 1.6 Hz, 1H), 7.94-7.83 (m, 3H), 7.64-7.50 (m, 1H), 5.04 (d, J = 2.1 Hz, 1H), 4.15 (dd, J = 3.2, 2.2 Hz, 1H), 4.03 (dd, J = 9.4, 3.3 Hz, 1H), 3.99-3.89 (m, 2H), 3.77 (dd, J = 12.2, 6.8 Hz, 1H), 3.66 (t, J = 9.4 Hz, 1H). | 424.4 |
| 32 | (2R,3S,4R,5S,6R)-2-(hydroxymethyl)-6-[2-(5-imidazo[1,2-a]pyridin-6-yl-1H-indazol-7-yl)ethynyl]tetrahydropyran-3,4,5-triol | (400 MHz, CD$_3$OD) δ 8.82 (s, 1H), 8.21 (s, 1H), 8.12 (d, J = 1.5 Hz, 1H), 7.95 (s, 1H), 7.86 (d, J = 1.5 Hz, 1H), 7.76 (dd, J = 9.4, 1.6 Hz, 1H), 7.72-7.62 (m, 2H), 5.03 (d, J = 2.1 Hz, 1H), 4.14 (dd, J = 3.0, 2.4 Hz, 1H), 4.02 (dd, J = 9.3, 3.3 Hz, 1H), 3.98-3.87 (m, 2H), 3.77 (dd, J = 12.1, 6.8 Hz, 1H), 3.66 (t, J = 9.4 Hz, 1H). | 421.41 |
| 33 | (2R,3S,4R,5S,6R)-2-(hydroxymethyl)-6-[2-[5-(3- | (400 MHz, CD$_3$OD) δ 8.19 (s, 1H), 8.13 (d, J = 1.4 Hz, 1H), 7.92 (d, J = 1.4 Hz, | 435.42 |

TABLE 3-continued

| Compound | IUPAC name | ¹H-NMR | LC-MS m/z (M + H⁺) |
|---|---|---|---|
|  | methylbenzimidazol-5-yl)-1H-indazol-7-yl]ethynyl]tetrahydropyran-3,4,5-triol | 1H), 7.87 (s, 1H), 7.76 (d, J = 9.2 Hz, 1H), 7.62 (d, J = 7.2 Hz, 1H), 5.04 (d, J = 2.1 Hz, 1H), 4.24-4.12 (m, 1H), 4.04 (dd, J = 9.3, 3.3 Hz, 1H), 4.01-3.90 (m, 5H), 3.77 (dd, J = 12.1, 6.7 Hz, 1H), 3.67 (t, J = 9.4 Hz, 1H). |  |
| 34 | (2R,3S,4R,5S,6R)-2-(hydroxymethyl)-6-[2-[5-(3-methyl-4-pyridyl)-1H-indazol-7-yl]ethynyl]tetrahydropyran-3,4,5-triol | (400 MHz, CD$_3$OD) δ 8.47 (2s, 2H), 8.21 (s, 1H), 7.86 (d, J = 1.5 Hz, 1H), 7.56 (d, J = 1.4 Hz, 1H), 7.37 (d, J = 3.0 Hz, 1H), 5.02 (d, J = 2.1 Hz, 1H), 4.13 (dd, J = 3.2, 2.2 Hz, 1H), 3.99 (dd, J = 9.3, 3.3 Hz, 1H), 3.95-3.86 (m, 2H), 3.75 (dd, J = 11.6, 6.3 Hz, 1H), 3.65 (t, J = 9.5 Hz, 1H), 2.33 (s, 3H). | 396.43 |
| 35 | (2R,3S,4R,5S,6R)-2-(hydroxymethyl)-6-[2-[5-(4-methylsulfonylphenyl)-1H-indazol-7-yl]ethynyl]tetrahydropyran-3,4,5-triol | (400 MHz, CD$_3$OD + DMSO) δ 8.23 (s, 1H), 8.19 (d, J = 1.6 Hz, 1H), 8.08-8.02 (m, 2H), 7.98-7.93 (m, 2H), 7.90 (d, J = 1.6 Hz, 1H), 5.04 (d, J = 2.1 Hz, 1H), 4.15 (dd, J = 3.2, 2.2 Hz, 1H), 4.02 (dd, J = 9.3, 3.3 Hz, 1H), 3.98-3.88 (m, 2H), 3.76 (dd, J = 12.0, 6.7 Hz, 1H), 3.66 (t, J = 9.5 Hz, 1H), 3.18 (s, 3H). | 459.32 |
| 36 | N-[3-[7-[2-[(2R,3S,4R,5S,6R)-3,4,5-trihydroxy-6-(hydroxymethyl)tetrahydropyran-2-yl]ethynyl]-1H-indazol-5-yl]phenyl]acetamide | (400 MHz, CD$_3$OD + DMSO) δ 8.19 (s, 1H), 8.05 (d, J = 1.5 Hz, 1H), 7.91 (s, 1H), 7.80 (d, J = 1.5 Hz, 1H), 7.57-7.47 (m, 1H), 7.45-7.35 (m, 2H), 5.04 (d, J = 2.1 Hz, 1H), 4.15 (dd, J = 3.1, 2.3 Hz, 1H), 4.03 (dd, J = 9.3, 3.3 Hz, 1H), 3.97-3.88 (m, 2H), 3.76 (dd, J = 12.0, 6.6 Hz, 1H), 3.66 (t, J = 9.5 Hz, 1H), 2.17 (s, 3H). | 438.36 |
| 37 | (2R,3S,4R,5S,6R)-2-[2-[5-(1,3-benzodioxol-5-yl)-1H-indazol-7-yl]ethynyl]-6-(hydroxymethyl)tetrahydropyran-3,4,5-triol | (400 MHz, CD$_3$OD + DMSO) δ 8.17 (s, 1H), 7.99 (d, J = 1.6 Hz, 1H), 7.76 (d, J = 1.6 Hz, 1H), 7.19 (d, J = 1.8 Hz, 1H), 7.15 (dd, J = 8.1, 1.9 Hz, 1H), 6.94 (d, J = 8.0 Hz, 1H), 6.02 (s, 2H), 5.03 (d, J = 2.1 Hz, 1H), 4.14 (dd, J = 3.1, 2.3 Hz, 1H), 4.02 (dd, J = 9.4, 3.3 Hz, 1H), 3.97-3.85 (m, 2H), 3.76 (dd, J = 12.0, 6.6 Hz, 1H), 3.65 (t, J = 9.5 Hz, 1H). | 425.38 |
| 38 | (2R,3S,4R,5S,6R)-2-(hydroxymethyl)-6-[2-[5-(3-methoxyphenyl)-1H-indazol-7-yl]ethynyl]tetrahydropyran-3,4,5-triol | (400 MHz, CD$_3$OD = DMSO) δ 8.19 (s, 1H), 8.06 (d, J = 1.6 Hz, 1H), 7.81 (d, J = 1.6 Hz, 1H), 7.39 (t, J = 7.9 Hz, 1H), 7.24 (ddd, J = 7.7, 1.6, 0.9 Hz, 1H), 7.22-7.19 (m, 1H), 6.94 (ddd, J = 8.2, 2.5, 0.8 Hz, 1H), 5.04 (d, J = 2.1 Hz, 1H), 4.15 (dd, J = 3.2, 2.3 Hz, 1H), 4.03 (dd, J = 9.3, 3.3 Hz, 1H), 3.93 (td, J = 7.3, 2.1 Hz, 2H), 3.88 (s, 3H), 3.76 (dd, J = 12.1, 6.7 Hz, 1H), 3.65 (t, J = 9.4 Hz, 1H). | 411.37 |
| 39 | (2R,3S,4R,5S,6R)-2-(hydroxymethyl)-6-[2-[5-[4-(5-methyl-1,3,4-oxadiazol-2-yl)phenyl]-1H-indazol-7-yl]ethynyl]tetrahydropyran-3,4,5-triol | (400 MHz, CD$_3$OD) δ 8.21 (s, 1H), 8.17 (d, J = 1.6 Hz, 1H), 8.15-8.09 (m, 2H), 7.92-7.85 (m, 3H), 5.04 (d, J = 2.1 Hz, 1H), 4.15 (dd, J = 3.2, 2.2 Hz, 1H), 4.03 (dd, J = 9.3, 3.3 Hz, 1H), 3.98-3.88 (m, 2H), 3.77 (dd, J = 12.2, 6.8 Hz, 1H), 3.66 (t, J = 9.4 Hz, 1H), 2.65 (s, 3H). | 463.43 |

Preparation of Compound 40 (Method C)

(2R,3S,4R,5S,6R)-2-(hydroxymethyl)-6-[2-[5-(1H-indol-6-yl)-1H-indazol-7-yl]ethynyl]tetrahydropyran-3,4,5-triol

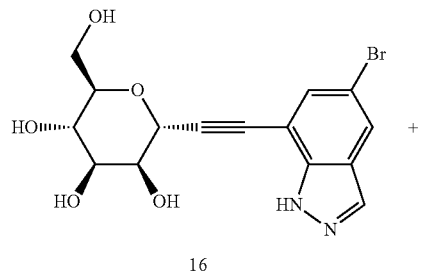

The title compound was prepared using the same protocol than Compound 25 but using commercially available 6-(4,4,5,5-tetramethyl-1,3,2-dioxaborolan-2-yl)-1H-indole as the starting material. Purification of the crude product by reverse phase HPLC and freeze-drying of the combined fractions provided the title compound (13.9 mg, 23% yield). $^1$H NMR (400 MHz, CD$_3$OD+DMSO) δ 8.19 (s, 1H), 8.08 (d, J=1.5 Hz, 1H), 7.88 (d, J=1.5 Hz, 1H), 7.68 (s, 1H), 7.65 (d, J=8.3 Hz, 1H), 7.36 (dd, J=8.2, 1.6 Hz, 1H), 7.31 (d, J=3.1 Hz, 1H), 6.49 (dd, J=3.1, 0.7 Hz, 1H), 5.05 (d, J=2.1 Hz, 1H), 4.21-4.13 (m, 1H), 4.04 (dd, J=9.3, 3.3 Hz, 1H), 3.98-3.88 (m, 2H), 3.76 (dd, J=12.1, 6.7 Hz, 1H), 3.66 (t, J=9.4 Hz, 1H). ESI-MS m/z calc. 419.14813, found 420.38 (M+1)$^+$.

Compounds 41 to 42 were prepared as described for Compound 40 under Method C using the appropriate commercially available pinacole boronate.

TABLE 4

| Compound | IUPAC name | $^1$H-NMR | LC-MS m/z (M + H$^+$) |
|---|---|---|---|
| 41 | 3-[7-[2-[(2R,3S,4R,5S,6R)-3,4,5-trihydroxy-6-(hydroxymethyl)tetrahydropyran-2-yl]ethynyl]-1H-indazol-5-yl]benzenesulfonamide | (400 MHz, CD$_3$OD) δ 8.21 (s, 1H), 8.20 (t, J = 1.7 Hz, 1H), 8.13 (d, J = 1.6 Hz, 1H), 7.95-7.87 (m, 2H), 7.86 (d, J = 1.6 Hz, 1H), 7.65 (t, J = 7.8 Hz, 1H), 5.04 (d, J = 2.1 Hz, 1H), 4.15 (dd, J = 3.2, 2.2 Hz, 1H), 4.02 (dd, J = 9.4, 3.3 Hz, 1H), 3.99-3.89 (m, 2H), 3.76 (dd, J = 12.1, 6.8 Hz, 1H), 3.66 (t, J = 9.4 Hz, 1H). | 460.4 |
| 42 | N-methyl-5-[7-[2-[(2R,3S,4R,5S,6R)-3,4,5-trihydroxy-6-(hydroxymethyl)tetrahydropyran-2-yl]ethynyl]-1H-indazol-5-yl]pyridine-3-carboxamide | (400 MHz, CD$_3$OD) δ? 9.02 (s, 1H), 8.95 (s, 1H), 8.52 (s, 1H), 8.24 (s, 1H), 8.21 (s, 1H), 7.92 (s, 1H), 5.04 (d, J = 2.0 Hz, 1H), 4.21-4.11 (m, 1H), 4.02 (dd, J = 9.3, 3.2 Hz, 1H), 3.98-3.87 (m, 2H), 3.77 (dd, J = 12.2, 6.8 Hz, 1H), 3.66 (t, J = 9.4 Hz, 1H), 2.98 (s, 3H). | 439.43 |

Preparation of Compound 43 (Method D)

(2R,3S,4R,5S,6R)-2-[2-[5-(2-cyclopropylethynyl)-1H-indazol-7-yl]ethynyl]-6-(hydroxymethyl)tetrahydropyran-3,4,5-triol

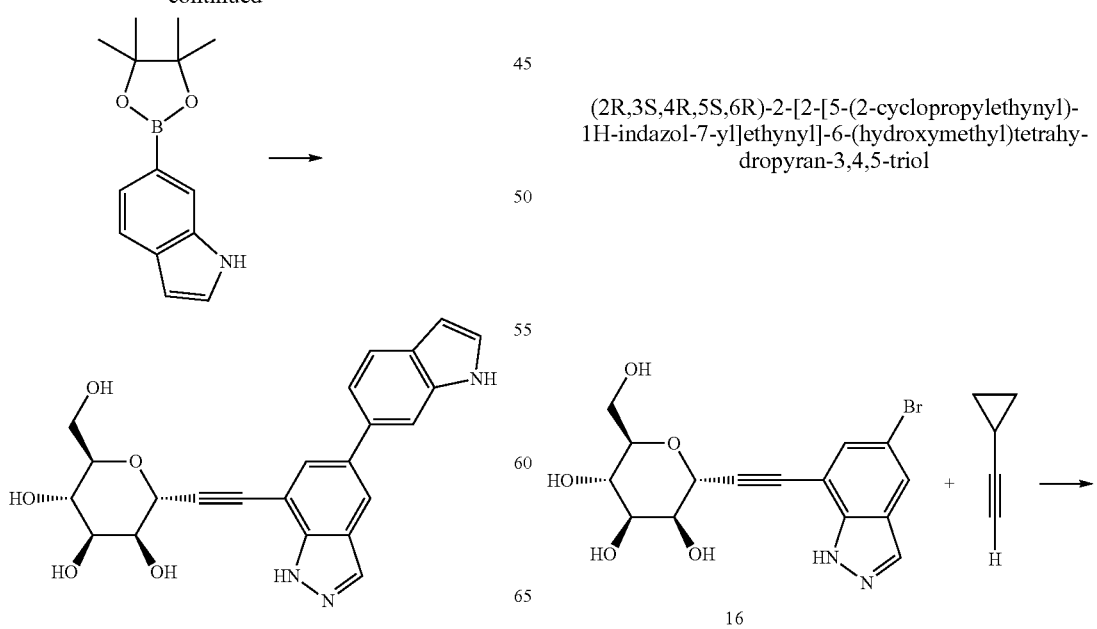

-continued

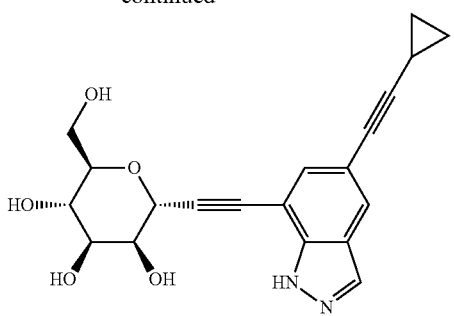

To a pressure vial loaded with Compound 16 (40 mg, 0.102 mmol), CuI (5.0 mg, 0.026 mmol) and Pd(dppf Cl$_2$.DCM (5.0 mg, 0.0068 mmol), capped and degassed (placed under vacuum and flushed with N$_2$, 3×) was added DMF (400 µL), ethynylcyclopropane (11 µL, 0.13 mmol), NMP (250 µL) and DIPEA (300 µL). The reaction vial was transferred to a preheated (80° C.) oil bath and stirred overnight. The reaction mixture was passed through a 200 mg Si-DMT cartridge, rinsed with portions of DMF to provide a 1 mL size sample which is purified by reverse phase HPLC. The fractions were combined and freeze-dried to provide the title compound (14.9 mg, 38% yield). $^1$H NMR (400 MHz, CD$_3$OD) δ 8.07 (s, 1H), 7.81 (d, J=1.2 Hz, 1H), 7.47 (d, J=1.1 Hz, 1H), 4.99 (d, J=2.0 Hz, 1H), 4.16-4.09 (m, 1H), 3.98 (dd, J=9.3, 3.2 Hz, 1H), 3.96-3.85 (m, 2H), 3.75 (dd, J=11.3, 6.0 Hz, 1H), 3.64 (t, J=9.4 Hz, 1H), 1.54-1.40 (m, 1H), 0.96-0.83 (m, 2H), 0.79-0.68 (m, 2H). ESI-MS m/z calc. 368.1372, found 369.35 (M+1)$^+$.

Compounds 44 to 53 were prepared as described for Compound 43 under Method D using the appropriate commercially available alkyne.

TABLE 5

| Compound | IUPAC name | $^1$H-NMR | LC-MS m/z (M + H$^+$) |
|---|---|---|---|
| 44 | (2R,3S,4R,5S,6R)-2-[2-[5-(3,3-dimethylbut-1-ynyl)-1H-indazol-7-yl]ethynyl]-6-(hydroxymethyl)tetrahydropyran-3,4,5-triol | (400 MHz, CD$_3$OD) δ 8.08 (s, 1H), 7.81 (d, J = 1.2 Hz, 1H), 7.47 (d, J = 1.2 Hz, 1H), 5.00 (d, J = 2.0 Hz, 1H), 4.12 (dd, J = 2.9, 2.3 Hz, 1H), 3.99 (dd, J = 9.3, 3.2 Hz, 1H), 3.96-3.86 (m, 2H), 3.75 (dd, J = 11.5, 6.1 Hz, 1H), 3.65 (t, J = 9.5 Hz, 1H), 1.33 (s, 9H). | 385.36 |
| 45 | (2R,3S,4R,5S,6R)-2-(hydroxymethyl)-6-[2-[5-(2-phenylethynyl)-1H-indazol-7-yl]ethynyl]tetrahydropyran-3,4,5-triol | 1H NMR (400 MHz, cd3od) ? 8.15 (s, 1H), 8.01 (d, J = 1.3 Hz, 1H), 7.66 (d, J = 1.2 Hz, 1H), 7.57-7.47 (m, 2H), 7.44-7.29 (m, 3H), 5.02 (d, J = 2.1 Hz, 1H), 4.13 (dd, J = 3.1, 2.3 Hz, 1H), 4.01 (dd, J = 9.4, 3.3 Hz, 1H), 3.97-3.87 (m, 2H), 3.76 (dd, J = 11.7, 6.3 Hz, 1H), 3.65 (t, J = 9.6 Hz, 1H). | 405.39 |
| 46 | (2R,3S,4R,5S,6R)-2-(hydroxymethyl)-6-[2-[5-[2-(3-pyridyl)ethynyl]-1H-indazol-7-yl]ethynyl]tetrahydropyran-3,4,5-triol | (400 MHz, CD$_3$OD) δ 8.72 (d, J = 1.4 Hz, 1H), 8.52 (dd, J = 5.0, 1.6 Hz, 1H), 8.18 (s, 1H), 8.08 (d, J = 1.3 Hz, 1H), 8.04-7.93 (m, 1H), 7.71 (d, J = 1.2 Hz, 1H), 7.48 (ddd, J = 7.9, 5.0, 0.7 Hz, 1H), 5.02 (d, J = 2.1 Hz, 1H), 4.13 (dd, J = 3.2, 2.2 Hz, 1H), 4.00 (dd, J = 9.3, 3.3 Hz, 1H), 3.97-3.86 (m, 2H), 3.76 (dd, J = 11.6, 6.3 Hz, 1H), 3.65 (t, J = 9.5 Hz, 1H). | 406.37 |
| 47 | (2R,3S,4R,5S,6R)-2-(hydroxymethyl)-6-[2-[5-[2-(3-hydroxyphenyl)ethynyl]-1H-indazol-7-yl]ethynyl]tetrahydropyran-3,4,5-triol | (400 MHz, CD$_3$OD) δ 8.15 (s, 1H), 8.00 (s, 1H), 7.65 (s, 1H), 7.19 (t, J = 7.9 Hz, 1H), 7.00 (d, J = 7.6 Hz, 1H), 6.94 (d, J = 1.8 Hz, 1H), 6.80 (dd, J = 8.2, 2.4 Hz, 1H), 5.02 (d, J = 2.0 Hz, 1H), 4.17-4.08 (m, 1H), 4.01 (dd, J = 9.3, 3.2 Hz, 1H), 3.97-3.85 (m, 2H), 3.76 (dd, J = 11.8, 6.4 Hz, 1H), 3.65 (t, J = 9.6 Hz, 1H). | 421.36 |
| 48 | (2R,3S,4R,5S,6R)-2-(hydroxymethyl)-6-[2-[5-(3-hydroxyprop-1-ynyl)-1H-indazol-7-yl]ethynyl]tetrahydropyran-3,4,5-triol | (400 MHz, CD$_3$OD) δ 8.12 (s, 1H), 7.92 (d, J = 1.3 Hz, 1H), 7.56 (d, J = 1.3 Hz, 1H), 5.00 (d, J = 2.1 Hz, 1H), 4.41 (s, 2H), 4.12 (dd, J = 3.2, 2.2 Hz, 1H), 3.98 (dd, J = 9.3, 3.3 Hz, 1H), 3.96-3.85 (m, 2H), 3.75 (dd, J = 11.4, 6.1 Hz, 1H), 3.64 (t, J = 9.4 Hz, 1H). | 359.36 |
| 49 | (2R,3S,4R,5S,6R)-2-[2-[5-[3-(1,1-dioxo-1,4-thiazinan-4-yl)prop-1-ynyl]-1H-indazol-7-yl]ethynyl]-6-(hydroxymethyl)tetrahydropyran-3,4,5-triol | (400 MHz, CD$_3$OD) δ 8.12 (s, 1H), 7.93 (d, J = 1.3 Hz, 1H), 7.56 (d, J = 1.3 Hz, 1H), 5.01 (d, J = 2.1 Hz, 1H), 4.62 (s, 2H), 4.12 (dd, J = 3.2, 2.2 Hz, 1H), 3.98 (dd, J = 9.4, 3.3 Hz, 1H), 3.96-3.83 (m, 2H), 3.79-3.70 (m, 3H), 3.65 (t, J = 9.4 Hz, 1H), 3.18 (s, 6H). | 476.41 |
| 50 | (2R,3S,4R,5S,6R)-2-[2-[5-[2-(1-aminocyclohexyl)ethynyl]-1H-indazol-7-yl]ethynyl]-6-(hydroxymethyl)tetrahydropyran-3,4,5-triol | (400 MHz, CD$_3$OD) δ 8.14 (s, 1H), 7.96 (d, J = 1.3 Hz, 1H), 7.57 (d, J = 1.3 Hz, 1H), 5.01 (d, J = 2.1 Hz, 1H), 4.12 (dd, J = 3.2, 2.2 Hz, 1H), 3.97 (dd, J = 9.3, 3.3 Hz, 1H), 3.95-3.85 (m, 2H), 3.75 (dd, J = 11.4, 6.1 Hz, 1H), 3.65 (t, J = 9.4 Hz, 1H), 2.10 (d, J = 12.0 Hz, 2H), 1.90- | 426.22 |

TABLE 5-continued

| Compound | IUPAC name | $^1$H-NMR | LC-MS m/z (M + H$^+$) |
|---|---|---|---|
| | | 1.69 (m, 5H), 1.61 (td, J = 12.0, 4.3 Hz, 2H), 1.37-1.17 (m, 1H). | |
| 51 | (2R,3S,4R,5S,6R)-2-[2-[5-[3-[benzyl(methyl)amino]prop-1-ynyl]-1H-indazol-7-yl]ethynyl]-6-(hydroxymethyl)tetrahydropyran-3,4,5-triol | (400 MHz, CD$_3$OD) δ 8.14 (s, 1H), 7.97 (d, J = 1.3 Hz, 1H), 7.59 (d, J = 1.3 Hz, 1H), 7.44-7.26 (m, 5H), 5.01 (d, J = 2.1 Hz, 1H), 4.13 (dd, J = 3.2, 2.2 Hz, 1H), 3.99 (dd, J = 9.3, 3.3 Hz, 1H), 3.96-3.86 (m, 2H), 3.80-3.71 (m, 3H), 3.65 (t, J = 9.5 Hz, 1H), 3.55 (s, 2H), 2.44 (s, 3H). | 462.45 |
| 52 | (2R,3S,4R,5S,6R)-2-(hydroxymethyl)-6-[2-[5-[3-(isobutylamino)prop-1-ynyl]-1H-indazol-7-yl]ethynyl]tetrahydropyran-3,4,5-triol | (400 MHz, CD$_3$OD) δ 8.15 (s, 1H), 7.99 (d, J = 1.3 Hz, 1H), 7.60 (d, J = 1.3 Hz, 1H), 5.01 (d, J = 2.1 Hz, 1H), 4.12 (dd, J = 3.2, 2.2 Hz, 1H), 4.02 (s, 2H), 3.99-3.84 (m, 3H), 3.75 (dd, J = 11.4, 6.2 Hz, 1H), 3.65 (t, J = 9.4 Hz, 1H), 2.89 (d, J = 7.1 Hz, 2H), 1.99 (hept, J = 6.8 Hz, 1H), 1.05 (d, J = 6.7 Hz, 6H). | 414.45 |
| 53 | (2R,3S,4R,5S,6R)-2-[2-[5-[3-(diethylamino)prop-1-ynyl]-1H-indazol-7-yl]ethynyl]-6-(hydroxymethyl)tetrahydropyran-3,4,5-triol | (400 MHz, CD$_3$OD) δ 8.15 (s, 1H), 8.00 (d, J = 1.2 Hz, 1H), 7.60 (d, J = 1.2 Hz, 1H), 5.01 (d, J = 2.1 Hz, 1H), 4.12 (dd, J = 3.1, 2.3 Hz, 1H), 4.10 (s, 2H), 3.97 (dd, J = 9.3, 3.3 Hz, 1H), 3.95-3.84 (m, 2H), 3.75 (dd, J = 11.4, 6.2 Hz, 1H), 3.65 (t, J = 9.4 Hz, 1H), 3.12 (q, J = 7.3 Hz, 4H), 1.31 (t, J = 7.3 Hz, 6H). | 414.45 |

Preparation of Compound 54 (Method C)

(2R,3S,4R,5S,6R)-2-[2-[5-(6-ethoxy-4-methyl-3-pyridyl)-1H-indazol-7-yl]ethynyl]-6-(hydroxymethyl)tetrahydropyran-3,4,5-triol

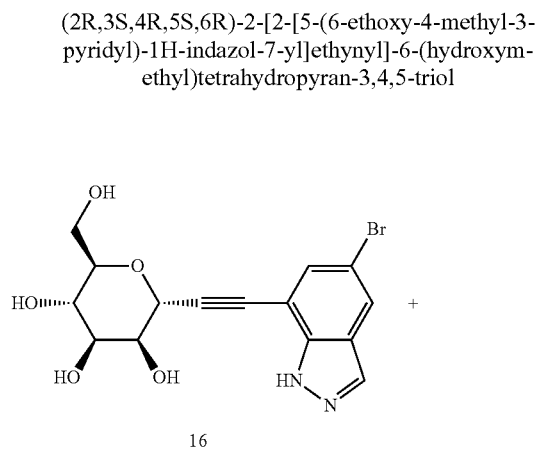

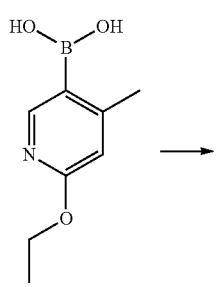

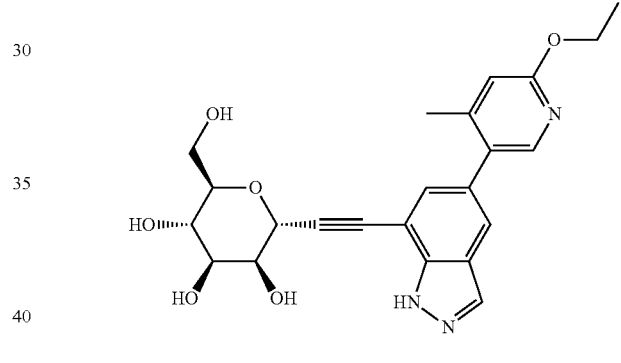

To a stirred solution of (6-ethoxy-4-methyl-3-pyridyl)boronic acid (35.4 mg, 0.196 mmol) and Compound 16 (50 mg, 0.131 mmol) in toluene (1.5 mL) and MeOH (300 µL) was added K$_3$PO$_4$ (83.1 mg, 0.392 mmol). The reaction tube was degassed (vacuum/nitrogen) and Pd(PPh$_3$)$_4$ (45.2 mg, 0.0392 mmol) was added and the tube was degassed again, sealed and heated at 95° C. overnight. After cooling down to RT, the reaction mixture was concentrated then redissolved in MeOH. H$_2$O was added, resulting in a precipitate which was collected by filtration and purified by reverse phase HPLC. The fractions were combined and freeze-dried to provide the title compound (3.4 mg, 5% yield). $^1$H NMR (400 MHz, CD$_3$OD) δ 8.14 (s, 1H), 7.92 (s, 1H), 7.73 (d, J=1.4 Hz, 1H), 7.46 (d, J=1.4 Hz, 1H), 6.73 (s, 1H), 5.00 (d, J=2.1 Hz, 1H), 4.31 (q, J=7.0 Hz, 2H), 4.11 (dd, J=3.1, 2.3 Hz, 1H), 3.98 (dd, J=9.4, 3.3 Hz, 1H), 3.94-3.84 (m, 2H), 3.73 (dd, J=11.5, 6.1 Hz, 1H), 3.62 (t, J=9.6 Hz, 1H), 2.23 (s, 3H), 1.38 (t, J=7.0 Hz, 3H). ESI-MS m/z calc. 439.17435, found 440.46 (M+1)$^+$.

Preparation of Compound 55 (Method C)

(2R,3S,4R,5S,6R)-2-[2-[5-(6-benzyloxy-4-methyl-3-pyridyl)-1H-indazol-7-yl]ethynyl]-6-(hydroxymethyl)tetrahydropyran-3,4,5-triol

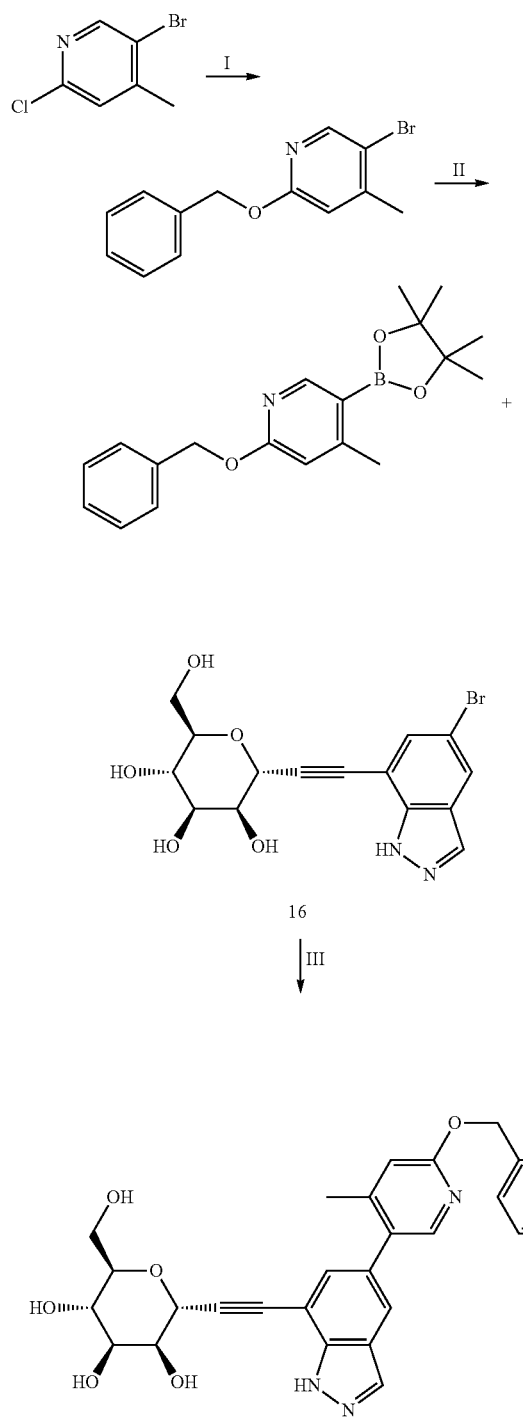

Step I: 2-benzyloxy-5-bromo-4-methyl-pyridine

To a suspension of sodium hydride (370 mg, 9.25 mmol, 60% w/w) in THF (20 mL), is added benzyl alcohol (957 µL 9.25 mmol) and the reaction mixture was stirred at RT for 15 minutes, after which 5-bromo-2-chloro-4-methyl-pyridine (1.91 g, 9.25 mmol) was added and the reaction mixture was stirred at reflux overnight. After cooling down to RT, the reaction mixture was diluted with 20% aqueous NH₄Cl solution and EtOAc. The layers were separated, the aqueous layer was back extracted with EtOAc and the combined organic extracts were washed with brine and dried over Na₂SO₄, filtered and concentrated. The crude product was purified by flash chromatography on a Biotage™ snap 100 g silica cartridge, using a gradient of EtOAc (5-60%) in Hex as eluent. The fractions were combined and concentrated to provide the title compound (1.65 g, 64% yield) which contained some starting material but was used directly in the next step.

Step II: 2-benzyloxy-4-methyl-5-(4,4,5,5-tetramethyl-1,3,2-dioxaborolan-2-yl)pyridine To a solution of 4,4,5,5-tetramethyl-2-(4,4,5,5-tetramethyl-1,3,2-dioxaborolan-2-yl)-1,3,2-dioxaborolane (2.67 g, 10.5 mmol), 2-benzyloxy-5-bromo-4-methyl-pyridine (1.17 g, 4.21 mmol) and Pd(dppf(Cl₂.DCM (344 mg, 0.420 mmol) in DMF (12 mL) degassed under nitrogen was added KOAc (1.24 g, 12.6 mmol). The mixture was stirred in a sealed tube under nitrogen atmosphere at 95° C. overnight. The reaction mixture was cooled down to RT, filtered over Celite™ and concentrated in vacuo. The crude residue was purified by flash chromatography on a Biotage™ snap silica cartridge, using a gradient of EtOAc in Hex, as eluent. The fractions were combined and concentrated to provide the title compound (932 mg, 68% yield).

Step III: Compound 55

To a degassed solution of Compound 16 (80.0 mg, 0.209 mmol), Pd(dppf(Cl₂.DCM (24.0 mg, 0.0297 mmol) and 2-benzyloxy-4-methyl-5-(4,4,5,5-tetramethyl-1,3,2-dioxaborolan-2-yl)pyridine from Step II (80.0 mg, 0.246 mmol) in DMF (1.45 mL) was added aqueous Na₂CO₃ solution (1.030 mL of 1 M, 1.03 mmol). The reaction vial was sealed and the resulting suspension is heated to 80° C. overnight. The reaction mixture was filtered on Celite™, the solvents were removed under reduced pressure. The residue was purified by reverse phase HPLC. The fractions were combined and freeze-dried to provide the title compound (10.5 mg, 10% yield). $^1$H NMR (400 MHz, CD3OD) δ 8.14 (s, 1H), 7.96 (s, 1H), 7.74 (d, J=1.5 Hz, 1H), 7.50-7.42 (m, J=12.2, 4.2 Hz, 3H), 7.40-7.26 (m, 3H), 6.81 (s, 1H), 5.35 (s, 2H), 4.99 (d, J=2.1 Hz, 1H), 4.13-4.08 (m, 1H), 3.98 (dd, J=9.4, 3.3 Hz, 1H), 3.94-3.85 (m, 2H), 3.73 (dd, J=11.8, 6.5 Hz, 1H), 3.62 (t, J=9.5 Hz, 1H), 2.24 (s, 3H). ESI-MS m/z calc. 501.18997, found 502.42 (M+1)⁺.

Alternatively, upon scale-up of the reaction, a larger amount of title compound (203 mg, 78% yield) was obtained after purification by reverse phase flash chromatography on a Biotage™ snap C18 cartridge, using a gradient of MeCN in H₂O, as eluent.

Preparation of Compound 56

4-methyl-5-[7-[2-[(2R,3S,4R,5S,6R)-3,4,5-trihydroxy-6-(hydroxymethyl)tetrahydropyran-2-yl]ethynyl]-1H-indazol-5-yl]-1H-pyridin-2-one

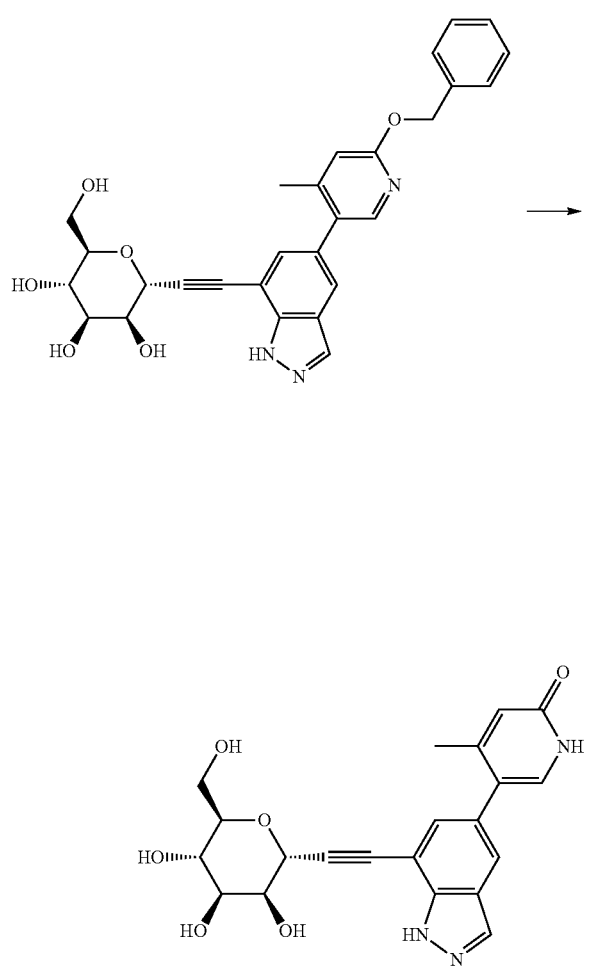

Compound 55 (96.0 mg, 0.191 mmol) was dissolved in DCM (3 mL) and treated with TFA (2.95 mL, 38.3 mmol) and the reaction mixture was stirred overnight. Another portion of TFA (2.95 mL, 38.3 mmol) was added and the stirring was continued for another 24 h. The reaction mixture was then cooled down to 0° C. and a solution of $NH_3$ in MeOH (11 mL of 7 M, 76.6 mmol) was added. The volatiles were removed under reduced pressure and the residue was purified by reverse phase flash chromatography on a Biotage™ snap C18 cartridge, using a gradient of MeCN in $H_2O$, as eluent. The fractions were combined and freeze-dried to provide the title compound (22.3 mg, 27% yield). $^1$H NMR (400 MHz, $CD_3OD$) δ 8.14 (s, 1H), 7.73 (d, J=1.5 Hz, 1H), 7.46 (d, J=1.5 Hz, 1H), 7.30 (s, 1H), 6.55-6.39 (m, 1H), 4.99 (d, J=2.1 Hz, 1H), 4.10 (dd, J=3.3, 2.2 Hz, 1H), 3.97 (dd, J=9.4, 3.3 Hz, 1H), 3.93-3.85 (m, 2H), 3.76-3.70 (m, 1H), 3.63 (t, J=9.6 Hz, 1H), 2.14 (d, J=1.0 Hz, 3H). ESI-MS m/z calc. 411.14304, found 412.35 (M+1)$^+$.

Preparation of Compound 57 (Method B)

Methyl 7-[2-[(2R,3S,4R,5S,6R)-3,4,5-trihydroxy-6-(hydroxymethyl)tetrahydropyran-2-yl]ethynyl]-1H-indazole-5-carboxylate

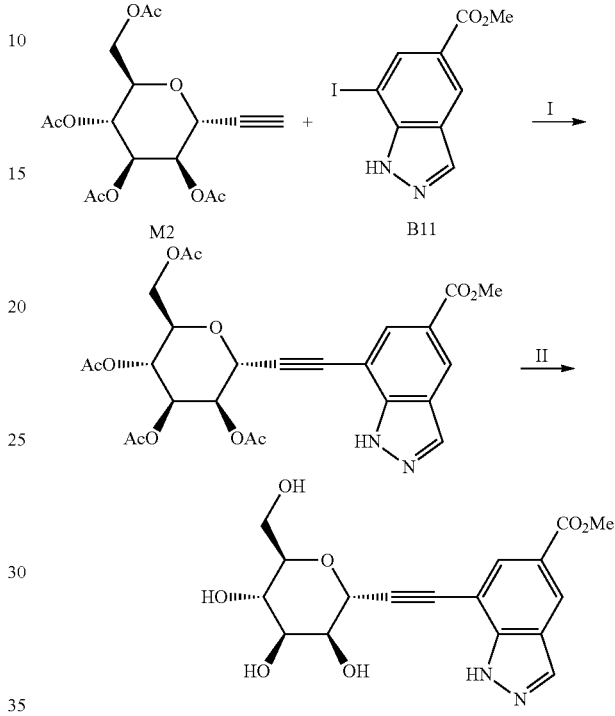

Step I: Methyl 7-[2-[(2R,3R,4R,5R,6R)-3,4,5-triacetoxy-6-(acetoxymethyl)tetrahydropyran-2-yl]ethynyl]-1H-indazole-5-carboxylate Intermediate M2 (3.10 g, 8.70 mmol), Intermediate B11 (2.63 g, 8.70 mmol), Pd(dppf(Cl$_2$.DCM (710.5 mg, 0.8700 mmol) and CuI (331 mg, 1.74 mmol) were dissolved in DMF (25 mL) The reaction mixture was degassed then DIPEA (7.58 mL, 43.5 mmol) was added and the mixture was heated to 50° C. and stirred overnight. After cooling down to RT, the reaction mixture was diluted with $H_2O$ (50 mL) and extracted with EtOAc (3×50 mL) The combined organic extracts were washed with $H_2O$ (3×25 mL) and brine (15 mL), dried over $Na_2SO_4$, filtered and concentrated. The crude residue was purified by flash chromatography on a Biotage™ snap 100 g silica cartridge, using a gradient of EtOAc (10-100%) in Hex as eluent. The fractions were combined and concentrated to provide the title compound (1.65 g, 36% yield).

Step II: Compound 57

Methyl 7-[2-[(2R,3R,4R,5R,6R)-3,4,5-triacetoxy-6-(acetoxymethyl)tetrahydropyran-2-yl]ethynyl]-1H-indazole-5-carboxylate from Step I (156 mg, 0.293 mmol) was dissolved in MeOH (1.6 mL) $H_2O$ (467 µL) was added followed by aqueous NaOH solution (293 µL of 2 M, 0.586 mmol) and the reaction mixture was stirred at RT for 5 h. The reaction mixture was then quenched by adding AcOH (33 µL, 0.586 mmol) and concentrated to dryness. Half of the crude residue was purified by reverse phase HPLC. The combined fractions were freeze-dried to provide the title compound (9.3 mg). ¹H NMR (400 MHz, CD₃OD) δ 8.54 (d, J=1.4 Hz, 1H), 8.24 (s, 1H), 8.10 (d, J=1.4 Hz, 1H), 5.00 (d, J=2.1 Hz, 1H), 4.12 (dd, J=3.3, 2.2 Hz, 1H), 3.92 (s, 3H), 3.91 (m, 2H), 3.73 (m, 1H), 3.63 (t, J=9.5 Hz, 1H). ESI-MS m/z calc. 362.1114, found 363.4 (M+1)⁺.

Preparation of Compound 58

7-[2-[(2R,3S,4R,5S,6R)-3,4,5-trihydroxy-6-(hydroxymethyl)tetrahydropyran-2-yl]ethynyl]-1H-indazole-5-carboxylic acid

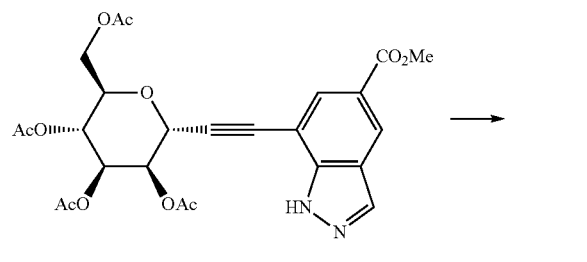

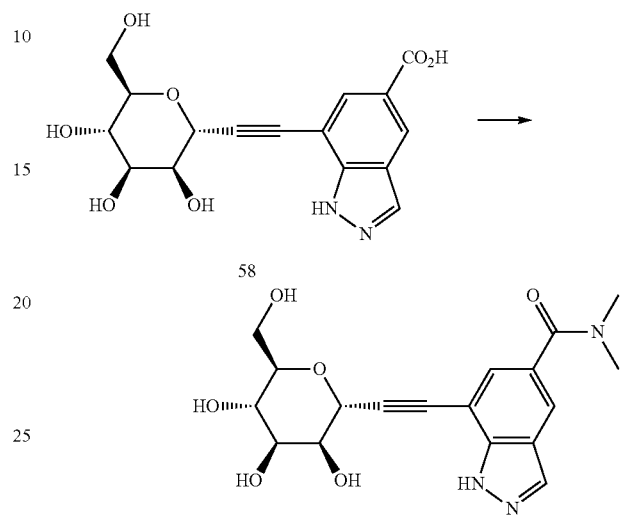

Methyl 7-[2-[(2R,3R,4R,5R,6R)-3,4,5-triacetoxy-6-(acetoxymethyl)tetrahydropyran-2-yl]ethynyl]-1H-indazole-5-carboxylate from Compound 57, Step I (858 mg, 1.62 mmol) was dissolved in dioxane (8.6 mL) and treated with aqueous NaOH solution (3.2 mL of 2 M, 6.47 mmol) and stirred overnight at RT. More NaOH solution (3.2 mL of 2 M, 6.47 mmol) was added and stirring was continued for another 24 h. The reaction mixture was then acidified with aqueous HCl (3.65 mL of 4 M), pH=1-2 and concentrated to dryness. The crude residue was purified by reverse phase flash chromatography on a Biotage™ snap 120 g C18 cartridge, using a gradient of MeCN (0-50%) in H₂O as eluent. The mixed fractions were combined and concentrated and 10 mg of the residue obtained was further purified by reverse phase HPLC. The combined fractions were freeze-dried to provide the title compound (4.6 mg). The rest of the material (538 mg, 89% yield) was used for further derivatisation. ¹H NMR (400 MHz, CD₃OD) δ 8.54 (t, J=1.8 Hz, 1H), 8.24 (d, J=2.1 Hz, 1H), 8.12 (t, J=1.9 Hz, 1H), 5.01 (t, J=2.2 Hz, 1H), 4.12 (dd, J=3.2, 2.2 Hz, 1H), 3.99 (dd, J=9.4, 3.2 Hz, 1H), 3.90 (m, 2H), 3.74 (m, 1H), 3.63 (t, J=9.6 Hz, 1H). ESI-MS m/z calc. 348.09576, found 349.3 (M+1)⁺.

Preparation of Compound 59 (Method E)

N,N-dimethyl-7-[2-[(2R,3S,4R,5S,6R)-3,4,5-trihydroxy-6-(hydroxymethyl)tetrahydropyran-2-yl]ethynyl]-1H-indazole-5-carboxamide Compound 58 (53.2 mg, 0.153 mmol) was dissolved in DMF (800 μL) and treated with DIPEA (40 μL, 0.229 mmol), dimethylamine in THF (229 μL of 2 M, 0.458 mmol) and HATU (64 mg, 0.168 mmol) and stirred overnight at RT. More dimethylamine in THF (1.0 mL of 2 M, 2.00 mmol) was added and the reaction mixture was stirred for another 5.5 h. H₂O (200 μL) was added and the reaction mixture was concentrated to half the initial volume and purified by reverse phase HPLC. The fraction was freeze-dried to provide the title compound (16.2 mg, 26% yield). ¹H NMR (400 MHz, CD₃OD) δ 8.19 (s, 1H), 7.92 (d, J=1.4 Hz, 1H), 7.59 (d, J=1.4 Hz, 1H), 5.00 (d, J=2.1 Hz, 1H), 4.10 (dd, J=3.3, 2.2 Hz, 1H), 3.96 (dd, J=9.4, 3.3 Hz, 1H), 3.89 (m, 2H), 3.74 (m, 1H), 3.63 (t, J=9.4 Hz, 1H), 3.11 (broad s, 3H), 3.04 (broad s, 3H). ESI-MS m/z calc. 375.14304, found 376.35 (M+1)⁺.

Preparation of Compound 60 (Method E)

N-cyclohexyl-N-methyl-7-[2-[(2R,3S,4R,5S,6R)-3,4,5-trihydroxy-6-(hydroxymethyl)tetrahydropyran-2-yl]ethynyl]-1H-indazole-5-carboxamide

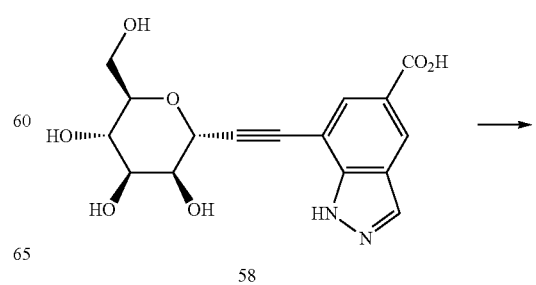

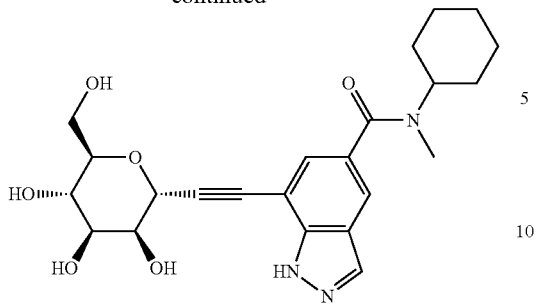

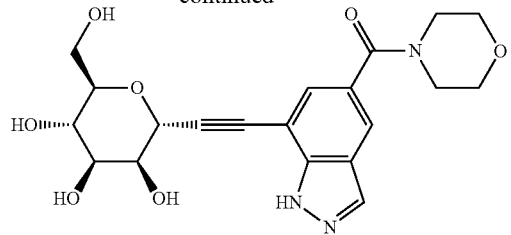

Compound 58 (50.4 mg, 0.145 mmol) was dissolved in DMF (756 μL) and treated with DIPEA (38 μL, 0.217 mmol), N-methylcyclohexanamine (57 μL, 0.434 mmol) and HATU (61 mg, 0.159 mmol) and stirred overnight at RT. H$_2$O (200 μL) was added and the reaction mixture was concentrated to half the initial volume, diluted with DMSO (0.5 mL) and purified by reverse phase HPLC. The fraction was freeze-dried to provide the title compound (35.9 mg, 49% yield). $^1$H NMR (400 MHz, CD$_3$OD) δ 8.20 (s, 1H), 7.85 (s, 1H), 7.53 (s, 1H), 5.00 (d, J=2.1 Hz, 1H), 4.41 (broad s, 0.5H), 4.11 (dd, J=3.3, 2.2 Hz, 1H), 3.96 (dd, J=9.3, 3.3 Hz, 1H), 3.89 (m, 2H), 3.73 (m, 1H), 3.63 (t, J=9.4 Hz, 1H), 3.47 (broad s, 0.5H), 2.91 (m, 3H), 1.68 (m, 8H), 1.09 (m, 2H). ESI-MS m/z calc. 443.20563, found 444.4 (M+1)$^+$.

Preparation of Compound 61 (Method E)

morpholino-[7-[2-[(2R,3S,4R,5S,6R)-3,4,5-trihydroxy-6-(hydroxymethyl)tetrahydropyran-2-yl]ethynyl]-1H-indazol-5-yl]methanone

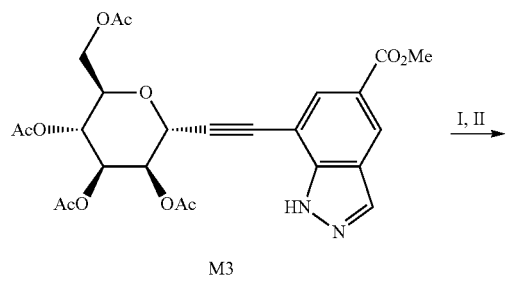

M3

Step I: [(2R,3R,4R,5R,6R)-3,4,5-triacetoxy-6-[2-[5-(morpholine-4-carbonyl)-1H-indazol-7-yl]ethynyl] tetrahydropyran-2-yl]methyl acetate To a solution of Intermediate M3 (97.8 mg, 0.189 mmol) in DMF (1.5 mL), was added DIPEA (49 μL, 0.284 mmol), morpholine (50 μL, 0.568 mmol) and HATU (79 mg, 0.208 mmol) and the resulting mixture was stirred overnight. The reaction mixture was diluted with H2O (4 mL) and extracted with EtOAc (3×5 mL). The combined organic extracts were washed with H$_2$O (3×2 mL) and brine (2 mL) and concentrated to dryness. The crude residue which was obtained (139 mg) was used directly for the next step.

Step II: Compound 61

[(2R,3R,4R,5R,6R)-3,4,5-triacetoxy-6-[2-[5-(morpholine-4-carbonyl)-1H-indazol-7-yl]ethynyl]tetrahydropyran-2-yl]methyl acetate (139 mg, 0.2374 mmol) was dissolved in MeOH (2 mL) and treated with a solution of MeO Na in MeOH (475 μL of 0.5 M, 0.237 mmol) and the mixture was stirred overnight at RT, then neutralized by adding AcOH (13.5 μL, 0.2374 mmol) and concentrated to dryness then purified by reverse phase HPLC. The fractions were combined and freeze-dried to provide the title compound (44.5 mg, 44% yield). $^1$H NMR (400 MHz, CD$_3$OD) δ 8.19 (s, 1H), 7.92 (d, J=1.4 Hz, 1H), 7.58 (d, J=1.4 Hz, 1H), 5.00 (d, J=2.1 Hz, 1H), 4.10 (dd, J=3.3, 2.1 Hz, 1H), 3.96 (m, 1H), 3.89 (d, J=2.2 Hz, 1H), 3.86 (m, 1H), 3.78-3.55 (m, 10H). ESI-MS m/z calc. 417.1536, found 418.42 (M+1)$^+$.

Compounds 62 to 65 were prepared as described for Compound 61 under Method E using the appropriate commercially amine.

TABLE 6

| Compound | IUPAC name | $^1$H-NMR | LC-MS m/z (M + H$^+$) |
|---|---|---|---|
| 62 | N-methyl-7-[2-[(2R,3S,4R,5S,6R)-3,4,5-trihydroxy-6-(hydroxymethyl)tetrahydropyran-2-yl]ethynyl]-1H-indazole-5-carboxamide | (400 MHz, CD$_3$OD) δ 8.31 (d, J = 1.5 Hz, 1H), 8.21 (s, 1H), 7.98 (d, J = 1.5 Hz, 1H), 5.00 (d, J = 2.1 Hz, 1H), 4.11 (dd, J = 3.3, 2.1 Hz, 1H), 3.97 (dd, J = 9.4, 3.3 Hz, 1H), 3.88 (m, 2H), 3.74 (m, 1H), 3.64 (t, J = 9.6 Hz, 1H), 2.93 (s, 3H). | 362.4 |
| 63 | N-cyclohexyl-7-[2-[(2R,3S,4R,5S,6R)-3,4,5-trihydroxy-6-(hydroxymethyl)tetrahydropyran-2-yl]ethynyl]-1H-indazole-5-carboxamide | (400 MHz, CD$_3$OD) δ 13.64 (broad s, 1H), 8.31 (m, 4H), 7.92 (d, J = 1.5 Hz, 1H), 4.83 (d, J = 2.1 Hz, 1H), 3.97 (t, J = 2.7 Hz, 1H), 3.73 (m, 3H), 3.62 (m, 1H), 3.48 (m,1H), 3.40 (t, J = 9.4 Hz, 1H), 1.76 (m, 4H), 1.58 (m, 1H), 1.28 (m, 4H), 1.10 (m, 1H). | 430.42 |
| 64 | N-cyclopentyl-7-[2-[(2R,3S,4R,5S,6R)-3,4,5-trihydroxy-6-(hydroxymethyl)tetrahydropyran- | (400 MHz, CD$_3$OD) δ 8.39 (d, J = 7.3 Hz, 1H), 8.31 (d, J = 1.5 Hz, 1H), 8.21 (s, 1H), 7.98 (d, J = 1.5 Hz, 1H), 5.00 (d, J = 2.1 | 416.37 |

TABLE 6-continued

| Compound | IUPAC name | ¹H-NMR | LC-MS m/z (M + H⁺) |
|---|---|---|---|
| | 2-yl]ethynyl]-1H-indazole-5-carboxamide | Hz, 1H), 4.33 (m, 1H), 4.11 (dd, J = 3.3, 2.1 Hz, 1H), 3.98 (dd, J = 9.4, 3.3 Hz, 1H), 3.89 (m, 2H), 3.74 (dd, J = 11.8, 6.4 Hz, 1H), 3.64 (t, J = 9.6 Hz, 1H), 2.02 (m, 2H), 1.79 (m, 2H), 1.62 (m, 4H). | |
| 65 | N-methyl-N-propyl-7-[2-[(2R,3S,4R,5S,6R)-3,4,5-trihydroxy-6-(hydroxymethyl)tetrahydropyran-2-yl]ethynyl]-1H-indazole-5-carboxamide | 1H NMR (400 MHz, DMSO-d6) ? 13.62 (s, 1H), 8.21 (s, 1H), 7.84 (s, 1H), 7.42 (s, 1H), 4.81 (d, J = 2.1 Hz, 1H), 3.95 (d, J = 2.7 Hz, 1H), 3.75 (dd, J = 9.3, 3.2 Hz, 1H), 3.69 (dd, J = 11.7, 2.0 Hz, 1H), 3.61 (m, 1H), 3.46 (dd, J = 11.6, 6.2 Hz, 1H), 3.39 (t, J = 9.4 Hz, 2H), 3.19 (broad s, 1H), 2.91 (s, 3H), 1.55 (broad s, 2H), 0.77 (broad d, 3H). | 404.4 |

Preparation of Compound 66

(2R,3S,4R,5S,6R)-2-(hydroxymethyl)-6-[2-[5-(4-phenyltriazol-1-yl)-1H-indazol-7-yl]ethynyl]tetrahydropyran-3,4,5-triol

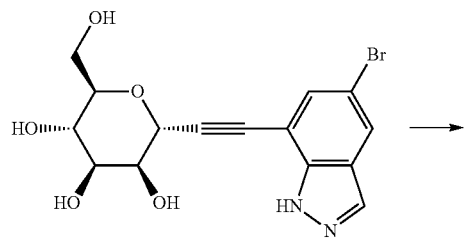

A reaction tube was charged with Compound 16 (100 mg, 0.245 mmol), NaN₃ (34.0 mg, 0.523 mmol), CuI (5.0 mg, 0.026 mmol), (1R,2R)—N,N'-dimethylcyclohexane-1,2-diamine (5.8 mg, 0.041 mmol) and sodium ascorbate (6.0 mg, 0.030 mmol) followed by EtOH (700 μL) and H₂O (300 μL). After degassing (vacuum followed by nitrogen flush), the reaction tube was sealed and the reaction mixture was stirred at 100° C. for 100 min then cooled-down to RT. Ethynylbenzene (60.0 μL, 0.545 mmol) was added to the reaction tube and the reaction mixture was stirred overnight at RT. The volatiles were removed under vacuum and the crude residue was dissolved in DMSO, filtered and purified by reverse phase HPLC. The fractions were combined and freeze-dried to provide the title compound (21.4 mg, 19% yield). ¹H NMR (400 MHz, CD₃OD) δ 8.97 (s, 1H), 8.36 (d, J=1.9 Hz, 1H), 8.29 (s, 1H), 8.12 (d, J=1.9 Hz, 1H), 8.00-7.89 (m, 2H), 7.56-7.44 (m, 2H), 7.43-7.34 (m, 1H), 5.05 (d, J=2.1 Hz, 1H), 4.16 (dd, J=3.2, 2.3 Hz, 1H), 4.02 (dd, J=9.3, 3.3 Hz, 1H), 3.98-3.90 (m, 2H), 3.77 (dd, J=11.8, 6.5 Hz, 1H), 3.67 (t, J=9.6 Hz, 1H). ESI-MS m/z calc. 447.15427, found 448.4 (M+1)⁺.

Compounds 67 to 94 were prepared as described for Compound 25 under Method C using the appropriate commercially available pinacol boronate or boronic acid. The preparation of 1,4-dimethyl-5-(4,4,5,5-tetramethyl-1,3,2-dioxaborolan-2-yl)pyridin-2(1H)-one for the synthesis of Compound 76 is shown below. 1,4-dimethyl-5-(4,4,5,5-tetramethyl-1,3,2-dioxaborolan-2-yl)pyridin-2(1H)-one was further employed to prepare Compound 76 in a similar manner as that for Compound 25 under Method C.

Preparation of 1,4-dimethyl-5-(4,4,5,5-tetramethyl-1,3,2-dioxaborolan-2-yl)pyridin-2(1H)-one

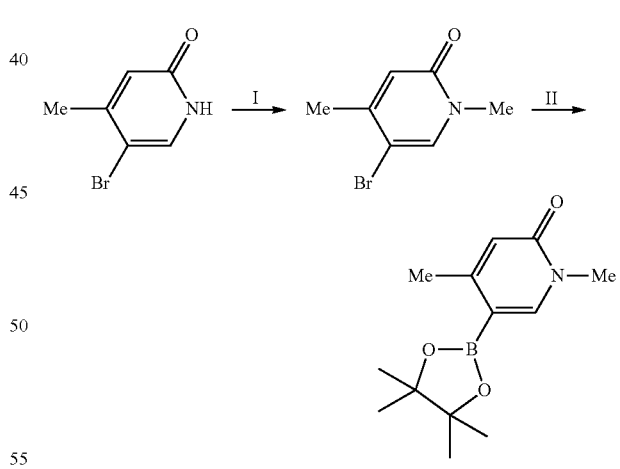

Step I: 5-bromo-1,4-dimethylpyridin-2(1H)-one

To a suspension of 5-bromo-4-methyl-pyridin-2-ol (1.00 g, 5.32 mmol) in acetone (35.0 mL) is added K₂CO₃ (3.47 g, 25.1 mmol) then MeI (1.50 mL, 24.1 mmol). The resulting mixture was stirred for 6 h, filtered and the resulting precipitate washed with three portions of acetone. The combined filtrates were concentrated and the residue purified by flash chromatography on a Biotage™ snap 50 g silica cartridge, using a gradient of MeOH in CH₂Cl₂ (0-20%) as eluent. The fractions were combined and concentrated, providing the title compound (950 mg, 88% yield). ¹H NMR (400 MHz, CDCl₃) δ 7.43 (s, 1H), 6.49 (s, 1H), 3.51 (s, 3H), 2.23 (s, 3H). ESI-MS m/z 204.04 (M+1)⁺.

Step II: 1,4-dimethyl-5-(4,4,5,5-tetramethyl-1,3,2-dioxaborolan-2-yl)pyridin-2(1H)-one Potassium acetate (666 mg, 6.79 mmol), 4,4,5,5-tetramethyl-2-(4,4,5,5-tetramethyl-1,3,2-dioxaborolan-2-yl)-1,3,2-dioxaborolane (1.47 g, 5.79 mmol), 5-bromo-1,4-dimethyl-pyridin-2-one from Step I (454 mg, 2.25 mmol) and PdCl₂(dppf).DCM (177 mg, 0.217 mmol) were charged in a pressure vessel. Degassed (house-vacuum then N₂, 3×). DMF (5.5 mL) was added and the resulting mixture was degassed again, capped and transferred to a preheated (90° C.) oil bath and stirred overnight. The resulting reaction mixture was cooled down to room temperature, diluted with EtOAc (10 mL), filtered through a celite pad, rinsed with EtOAc (15 mL). The organic phase was washed with saturated NH₄Cl (2×25 mL), H₂O (25 mL), brine (25 mL), dried over Na₂SO₄ and concentrated. The residue was purified on Biotage™ snap 25 g, using EtOAc as the eluent. Fractions were combined and concentrated to provide 610 mg (72% yield) of the title compound. ¹H NMR (400 MHz, CDCl₃) δ 7.71 (s, 1H), 6.33 (s, 1H), 3.52 (s, 3H), 2.31 (d, J=0.9 Hz, 3H), 1.30 (s, 12H). ESI-MS m/z 249.29 (M+1)⁺.

TABLE 7

| Compound | IUPAC name | ¹H-NMR | LC-MS m/z (M + H⁺) |
|---|---|---|---|
| 67 | (2R,3S,4R,5S,6R)-2-(hydroxymethyl)-6-[2-[5-(1-methyl-3,6-dihydro-2H-pyridin-4-yl)-1H-indazol-7-yl]ethynyl]tetrahydropyran-3,4,5-triol | (400 MHz, CD₃OD) δ 8.11 (s, 1H), 7.89 (d, J = 1.6 Hz, 1H), 7.69 (d, J = 1.6 Hz, 1H), 6.22-6.12 (m, 1H), 4.99 (d, J = 2.1 Hz, 1H), 4.10 (dd, J = 3.3, 2.2 Hz, 1H), 3.96 (dd, J = 9.3, 3.3 Hz, 1H), 3.93-3.85 (m, 2H), 3.80 (d, J = 3.1 Hz, 2H), 3.78-3.71 (m, 1H), 3.63 (t, J = 9.5 Hz, 1H), 3.42 (t, J = 6.0 Hz, 2H), 2.91 (s, 5H). | 400.44 |
| 68 | (2R,3S,4R,5S,6R)-2-[2-[5-(3,6-dihydro-2H-pyran-4-yl)-1H-indazol-7-yl]ethynyl]-6-(hydroxymethyl)tetrahydropyran-3,4,5-triol | (400 MHz, CD₃OD) δ 8.08 (s, 1H), 7.82 (d, J = 1.5 Hz, 1H), 7.66 (d, J = 1.6 Hz, 1H), 6.20 (td, J = 2.9, 1.4 Hz, 1H), 4.99 (d, J = 2.1 Hz, 1H), 4.30 (q, J = 2.7 Hz, 2H), 4.11 (dd, J = 3.3, 2.1 Hz, 1H), 3.98 (dd, J = 9.3, 3.2 Hz, 1H), 3.93 (t, J = 5.5 Hz, 3H), 3.91-3.86 (m, 1H), 3.74 (dd, J = 11.6, 6.3 Hz, 1H), 3.63 (t, J = 9.6 Hz, 1H), 2.57 (tdd, J = 5.1, 4.4, 3.5, 2.0 Hz, 2H). | 387.37 |
| 69 | (2R,3S,4R,5S,6R)-2-[2-[5-[(E)-2-(4-ethylphenyl)vinyl]-1H-indazol-7-yl]ethynyl]-6-(hydroxymethyl)tetrahydropyran-3,4,5-triol | (400 MHz, CD₃OD) δ 8.09 (s, 1H), 7.89 (d, J = 1.5 Hz, 1H), 7.82 (d, J = 1.5 Hz, 1H), 7.47 (d, J = 8.0 Hz, 2H), 7.25-7.10 (m, 4H), 5.01 (d, J = 2.1 Hz, 1H), 4.13 (t, J = 2.7 Hz, 1H), 4.01 (dd, J = 9.3, 3.3 Hz, 1H), 3.97-3.87 (m, 2H), 3.75 (dd, J = 12.2, 6.8 Hz, 1H), 3.64 (t, J = 9.4 Hz, 1H), 2.63 (q, J = 7.7 Hz, 2H), 1.22 (t, J = 7.6 Hz, 3H). | 435.42 |
| 70 | (2R,3S,4R,5S,6R)-2-[2-[5-(cyclopenten-1-yl)-1H-indazol-7-yl]ethynyl]-6-(hydroxymethyl)tetrahydropyran-3,4,5-triol | (400 MHz, CD₃OD) δ 8.06 (s, 1H), 7.75 (d, J = 6.0 Hz, 2H), 6.22 (s, 1H), 4.99 (d, J = 2.0 Hz, 1H), 4.11 (t, J = 2.7 Hz, 1H), 3.99 (dd, J = 9.3, 3.3 Hz, 1H), 3.96-3.84 (m, 2H), 3.74 (dd, J = 11.7, 6.4 Hz, 1H), 3.63 (t, J = 9.7 Hz, 1H), 2.76 (t, J = 7.7 Hz, 2H), 2.60-2.49 (m, 2H), 2.12-1.98 (m, 3H). | 371.36 |
| 71 | ethyl 4-[7-[2-[(2R,3S,4R,5S,6R)-3,4,5-trihydroxy-6-(hydroxymethyl)tetrahydropyran-2-yl]ethynyl]-1H-indazol-5-yl]cyclohex-3-ene-1-carboxylate | (400 MHz, CD₃OD) δ 8.06 (s, 1H), 7.77 (d, J = 1.6 Hz, 1H), 7.61 (d, J = 1.6 Hz, 1H), 6.12 (dt, J = 4.8, 2.4 Hz, 1H), 4.98 (d, J = 2.1 Hz, 1H), 4.15 (q, J = 7.1 Hz, 2H), 4.10 (dd, J = 3.3, 2.1 Hz, 1H), 3.99 (dd, J = 9.4, 3.3 Hz, 1H), 3.94-3.86 (m, 2H), 3.73 (dd, J = 11.7, 6.3 Hz, 1H), 3.63 (t, J = 9.6 Hz, 1H), 2.70-2.37 (m, 6H), 2.23-2.14 (m, 1H), 1.85 (dddd, J = 12.9, 11.0, 9.0, 6.4 Hz, 1H), 1.26 (t, J = 7.1 Hz, 3H). | 457.45 |
| 72 | tert-butyl 3-[7-[2-[(2R,3S,4R,5S,6R)-3,4,5-trihydroxy-6-(hydroxymethyl)tetrahydropyran-2-yl]ethynyl]-1H-indazol-5-yl]pyrrole-1-carboxylate | (400 MHz, CD₃OD) δ 8.08 (s, 1H), 7.98 (s, 1H), 7.76 (s, 1H), 7.58 (d, J = 2.1 Hz, 1H), 7.29 (t, J = 2.7 Hz, 1H), 6.69-6.63 (m, 1H), 4.16-4.09 (m, 1H), 4.01 (dd, J = 9.4, 3.2 Hz, 1H), 3.96-3.88 (m, 2H), 3.74 (dd, J = 11.9, 6.6 Hz, 1H), 3.64 (t, J = 9.6 Hz, 1H), 1.62 (s, 9H). | 470.43 |
| 73 | (2R,3S,4R,5S,6R)-2-(hydroxymethyl)-6-[2-[5-(6-methoxy-3-pyridyl)-1H-indazol-7-yl]ethynyl]tetrahydropyran-3,4,5-triol | (400 MHz, CD₃OD) δ 8.44 (dd, J = 2.6, 0.6 Hz, 1H), 8.19 (s, 1H), 8.04 (d, J = 1.6 Hz, 1H), 8.01 (dd, J = 8.6, 2.6 Hz, 1H), 7.79 (d, J = 1.6 Hz, 1H), 6.92 (dd, J = 8.6, 0.6 Hz, 1H), 5.04 (d, J = 2.1 Hz, 1H), 4.15 (dd, J = 3.1, 2.3 Hz, 1H), 4.02 (dd, J = 9.3, 3.3 Hz, 1H), 3.97 (s, 3H), 3.96-3.89 (m, 2H), 3.76 (dd, J = 11.9, 6.5 Hz, 1H), 3.65 (t, J = 9.5 Hz, 1H). | 412.3 |
| 74 | 5-[7-[2-[(2R,3S,4R,5S,6R)-3,4,5-trihydroxy-6-(hydroxymethyl)tetrahydropyran-2-yl]ethynyl]-1H-indazol-5-yl]-1H-pyridin-2-one | (400 MHz, CD₃OD) δ 8.16 (s, 1H), 8.01 (dd, J = 9.5, 2.7 Hz, 1H), 7.97 (d, J = 1.6 Hz, 1H), 7.74 (d, J = 2.7 Hz, 1H), 7.72 (d, J = 1.6 Hz, 1H), 6.67 (d, J = 9.5 Hz, 1H), 5.02 (d, J = 2.1 Hz, 1H), 4.14 (dd, J = 3.2, 2.3 Hz, 1H), 4.01 (dd, J = 9.3, 3.3 Hz, 1H), 3.97-3.88 (m, 2H), | 398.3 |

TABLE 7-continued

| Compound | IUPAC name | ¹H-NMR | LC-MS m/z (M + H⁺) |
|---|---|---|---|
| | | 3.76 (dd, J = 11.8, 6.4 Hz, 1H), 3.66 (t, J = 9.5 Hz, 1H). | |
| 75 | (2R,3S,4R,5S,6R)-2-[2-[5-(6-benzyloxy-3-pyridyl)-indazol-7-yl]ethynyl]-6-(hydroxymethyl)tetrahydropyran-3,4,5-triol | (400 MHz, CD₃OD) δ 8.43 (d, J = 2.5 Hz, 1H), 1H-8.17 (s, 1H), 8.03 (d, J = 1.5 Hz, 1H), 8.01 (dd, J = 8.6, 2.6 Hz, 1H), 7.78 (d, J = 1.5 Hz, 1H), 7.47 (d, J = 7.1 Hz, 2H), 7.37 (t, J = 7.3 Hz, 2H), 7.31 (t, J = 6.7 Hz, 1H), 6.96 (d, J = 8.6 Hz, 1H), 5.41 (s, 2H), 5.03 (d, J = 2.1 Hz, 1H), 4.14 (dd, J = 3.1, 2.3 Hz, 1H), 4.02 (dd, J = 9.3, 3.3 Hz, 1H), 3.97-3.88 (m, 2H), 3.76 (dd, J = 12.1, 6.7 Hz, 1H), 3.66 (t, J = 9.4 Hz, 1H). | 488.41 |
| 76 | 1,4-dimethyl-5-[7-[2-[(2R,3S,4R,5S,6R)-3,4,5-trihydroxy-6-(hydroxymethyl)tetrahydropyran-2-yl]ethynyl]-1H-indazol-5-yl]pyridin-2-one | (400 MHz, CD₃OD) δ 8.16 (s, 1H), 7.77 (s, 1H), 7.59 (s, 1H), 7.50 (s, 1H), 6.52 (s, 1H), 5.01 (d, J = 1.4 Hz, 1H), 4.12 (s, 1H), 3.99 (dd, J = 9.3, 3.2 Hz, 1H), 3.96-3.86 (m, 2H), 3.75 (dd, J = 11.8, 6.4 Hz, 1H), 3.65 (t, J = 9.7 Hz, 1H), 3.59 (s, 3H), 2.15 (s, 3H). | 426.36 |
| 77 | (2R,3S,4R,5S,6R)-2-(hydroxymethyl)-6-[2-[5-(4-methyl-3-pyridyl)-1H-indazol-7-yl]ethynyl]tetrahydropyran-3,4,5-triol | (400 MHz, CD₃OD) δ 8.40 (d, J = 5.1 Hz, 1H), 8.38 (s, 1H), 8.20 (s, 1H), 7.82 (d, J = 1.5 Hz, 1H), 7.53 (d, J = 1.5 Hz, 1H), 7.41 (d, J = 5.1 Hz, 1H), 5.02 (d, J = 2.1 Hz, 1H), 4.13 (dd, J = 3.2, 2.2 Hz, 1H), 4.00 (dd, J = 9.4, 3.3 Hz, 1H), 3.96-3.87 (m, 2H), 3.75 (dd, J = 11.9, 6.6 Hz, 1H), 3.65 (t, J = 9.6 Hz, 1H), 2.34 (s, 3H). | 396.38 |
| 78 | (2R,3S,4R,5S,6R)-2-(hydroxymethyl)-6-[2-[5-(2-methoxy-5-methyl-3-pyridyl)-1H-indazol-7-yl]ethynyl]tetrahydropyran-3,4,5-triol | (400 MHz, CD₃OD) δ 8.15 (s, 1H), 7.96 (s, 2H), 7.69 (s, 1H), 7.60 (s, 1H), 5.02 (d, J = 1.7 Hz, 1H), 4.14 (d, J = 2.4 Hz, 1H), 4.01 (dd, J = 9.3, 3.1 Hz, 1H), 3.98-3.86 (m, 5H), 3.76 (dd, J = 11.5, 6.2 Hz, 1H), 3.65 (t, J = 9.6 Hz, 1H), 2.32 (s, 3H). | 426.36 |
| 79 | 3-methyl-5-[7-[2-[(2R,3S,4R,5S,6R)-3,4,5-trihydroxy-6-(hydroxymethyl)tetrahydropyran-2-yl]ethynyl]-1H-indazol-5-yl]-1H-pyridin-2-one | (400 MHz, CD₃OD) δ 8.15 (s, 1H), 7.95 (d, J = 1.6 Hz, 1H), 7.86 (dd, J = 2.6, 1.1 Hz, 1H), 7.70 (d, J = 1.6 Hz, 1H), 7.58 (dd, J = 2.7, 0.6 Hz, 1H), 5.02 (d, J = 2.1 Hz, 1H), 4.14 (dd, J = 3.2, 2.2 Hz, 1H), 4.01 (dd, J = 9.3, 3.3 Hz, 1H), 3.97-3.88 (m, 2H), 3.76 (dd, J = 11.9, 6.6 Hz, 1H), 3.66 (t, J = 9.5 Hz, 1H), 2.21 (s, 3H). | 412.35 |
| 80 | (2R,3S,4R,5S,6R)-2-(hydroxymethyl)-6-[2-[5-(6-hydroxy-2-methyl-3-pyridyl)-1H-indazol-7-yl]ethynyl]tetrahydropyran-3,4,5-triol | (400 MHz, CD₃OD) δ 8.15 (s, 1H), 7.75 (d, J = 1.5 Hz, 1H), 7.57 (d, J = 9.2 Hz, 1H), 7.48 (d, J = 1.5 Hz, 1H), 6.47 (d, J = 9.2 Hz, 1H), 5.01 (d, J = 2.1 Hz, 1H), 4.12 (dd, J = 3.2, 2.2 Hz, 1H), 3.99 (dd, J = 9.3, 3.3 Hz, 1H), 3.96-3.84 (m, 2H), 3.75 (dd, J = 11.6, 6.3 Hz, 1H), 3.65 (t, J = 9.6 Hz, 1H), 2.28 (s, 3H). | 412.35 |
| 81 | (2R,3S,4R,5S,6R)-2-[2-[5-(2,4-difluorophenyl)-1H-indazol-7-yl]ethynyl]-6-(hydroxymethyl)tetrahydropyran-3,4,5-triol | (400 MHz, CD₃OD) δ 8.18 (s, 1H), 7.95 (s, 1H), 7.67 (s, 1H), 7.61-7.47 (m, 1H), 7.17-6.98 (m, 2H), 5.03 (d, J = 1.4 Hz, 1H), 4.18-4.09 (m, 1H), 4.01 (dd, J = 9.3, 3.1 Hz, 1H), 3.98-3.86 (m, 2H), 3.76 (dd, J = 11.6, 6.3 Hz, 1H), 3.65 (t, J = 9.6 Hz, 1H). | 417.3 |
| 82 | (2R,3S,4R,5S,6R)-2-[2-[5-(2,5-dimethylphenyl)-1H-indazol-7-yl]ethynyl]-6-(hydroxymethyl)tetrahydropyran-3,4,5-triol | (400 MHz, CD₃OD) δ 8.14 (s, 1H), 7.70 (d, J = 1.2 Hz, 1H), 7.46 (d, J = 1.2 Hz, 1H), 7.16 (d, J = 7.7 Hz, 1H), 7.08 (d, J = 7.9 Hz, 1H), 7.04 (s, 1H), 5.02 (d, J = 2.0 Hz, 1H), 4.19-4.08 (m, 1H), 4.01 (dd, J = 9.4, 3.2 Hz, 1H), 3.97-3.86 (m, 2H), 3.75 (dd, J = 11.9, 6.5 Hz, 1H), 3.65 (t, J = 9.5 Hz, 1H), 2.33 (s, 3H), 2.19 (s, 3H). | 409.36 |
| 83 | (2R,3S,4R,5S,6R)-2-[2-[5-(2,6-dimethyl-4-pyridyl)-1H-indazol-7-yl]ethynyl]-6-(hydroxymethyl)tetrahydropyran-3,4,5-triol | (400 MHz, CD₃OD) δ 8.50 (d, J = 1.6 Hz, 1H), 8.31 (s, 1H), 8.12 (s, 3H), 5.04 (d, J = 2.1 Hz, 1H), 4.15 (dd, J = 3.2, 2.2 Hz, 1H), 3.99 (dd, J = 9.3, 3.3 Hz, 1H), 3.97-3.87 (m, 2H), 3.77 (dd, J = 11.5, 6.2 Hz, 1H), 3.67 (t, J = 9.5 Hz, 1H), 2.80 (s, 6H). | 410.39 |
| 84 | (2R,3S,4R,5S,6R)-2-(hydroxymethyl)-6-[2-[5-(2-methyl-4-pyridyl)-1H-indazol-7-yl]ethynyl]tetrahydropyran-3,4,5-triol | (400 MHz, CD₃OD) δ 8.65 (d, J = 6.3 Hz, 1H), 8.51 (d, J = 1.6 Hz, 1H), 8.32 (s, 1H), 8.27 (d, J = 1.4 Hz, 1H), 8.19 (dd, J = 6.3, 1.8 Hz, 1H), 8.12 (d, J = 1.6 Hz, 1H), 5.05 (d, J = 2.1 Hz, 1H), 4.15 (dd, J = 3.1, 2.3 Hz, 1H), 4.00 (dd, J = 9.3, 3.3 Hz, 1H), 3.97-3.87 (m, 2H), 3.77 (dd, J = 11.8, 6.5 Hz, 1H), 3.67 (t, J = 9.5 Hz, 1H), 2.82 (s, 3H). | 396.34 |
| 85 | 4-[7-[2-[(2R,3S,4R,5S,6R)-3,4,5-trihydroxy-6-(hydroxymethyl)tetrahydropyran-2-yl]ethynyl]-1H-indazol-5-yl]- | (400 MHz, CD₃OD + DMSO) δ 8.24 (s, 1H), 8.20 (d, J = 1.6 Hz, 1H), 7.86 (d, J = 1.6 Hz, 1H), 7.57-7.49 (m, 1H), 6.87-6.76 (m, 2H), 5.04 (d, J = 2.1 Hz, 1H), 4.15 (dd, J = 3.2, 2.2 | 398.3 |

TABLE 7-continued

| Compound | IUPAC name | ¹H-NMR | LC-MS m/z (M + H⁺) |
|---|---|---|---|
| | 1H-pyridin-2-one | Hz, 1H), 4.01 (dd, J = 9.3, 3.3 Hz, 1H), 3.98-3.86 (m, 2H), 3.76 (dd, J = 11.9, 6.6 Hz, 1H), 3.65 (t, J = 9.5 Hz, 1H). | |
| 86 | (2R,3S,4R,5S,6R)-2-[2-[5-(2,5-difluorophenyl)-1H-indazol-7-yl]ethynyl]-6-(hydroxymethyl)tetrahydropyran-3,4,5-triol | (400 MHz, CD₃OD) δ 8.19 (s, 1H), 8.00 (t, J = 1.3 Hz, 1H), 7.70 (t, J = 1.5 Hz, 1H), 7.31 (ddd, J = 9.2, 6.1, 3.2 Hz, 1H), 7.27-7.19 (m, 1H), 7.16-7.07 (m, 1H), 5.03 (d, J = 2.1 Hz, 1H), 4.14 (dd, J = 3.1, 2.3 Hz, 1H), 4.02 (dd, J = 9.3, 3.3 Hz, 1H), 3.97-3.87 (m, 2H), 3.76 (dd, J = 11.9, 6.5 Hz, 1H), 3.66 (t, J = 9.5 Hz, 1H). | 417.3 |
| 87 | (2R,3S,4R,5S,6R)-2-[2-[5-(2-ethylphenye-1H-indazol-7-yl]ethynyl]-6-(hydroxymethyl)tetrahydropyran-3,4,5-triol | (400 MHz, CD₃OD) δ 8.15 (s, 1H), 7.71 (d, J = 1.4 Hz, 1H), 7.45 (d, J = 1.4 Hz, 1H), 7.34-7.27 (m, 2H), 7.26-7.16 (m, 2H), 5.02 (d, J = 2.1 Hz, 1H), 4.13 (dd, J = 3.2, 2.2 Hz, 1H), 4.00 (dd, J = 9.4, 3.3 Hz, 1H), 3.96-3.87 (m, 2H), 3.75 (dd, J = 12.0, 6.6 Hz, 1H), 3.64 (t, J = 9.5 Hz, 1H), 2.59 (q, J = 7.5 Hz, 2H), 1.05 (t, J = 7.5 Hz, 3H). | 409.36 |
| 88 | (2R,3S,4R,5S,6R)-2-[2-[5-(2,4-dimethylphenyl)-1H-indazol-7-yl]ethynyl]-6-(hydroxymethyl)tetrahydropyran-3,4,5-triol | 1HNMR(400 MHz, cd3od) ? 8.13 (s, 1H), 7.70 (d, J = 1.5 Hz, 1H), 7.45 (d, J = 1.4 Hz, 1H), 7.12-7.08 (m, 2H), 7.05 (d, J = 7.7 Hz, 1H), 5.01 (d, J = 2.1 Hz, 1H), 4.12 (dd, J = 3.2, 2.2 Hz, 1H), 4.00 (dd, J = 9.4, 3.3 Hz, 1H), 3.97-3.86 (m, 2H), 3.75 (dd, J = 12.0, 6.6 Hz, 1H), 3.64 (t, J = 9.5 Hz, 1H), 2.35 (s, 3H), 2.21 (s, 3H). | 409.36 |
| 89 | 4-methyl-3-[7-[2-[(2R,3S,4R,5S,6R)-3,4,5-trihydroxy-6-(hydroxymethyl)tetrahydropyran-2-yl]ethynyl]-1H-indazol-5-yl]benzonitrile | (400 MHz, CD₃OD) δ 8.18 (s, 1H), 7.78 (d, J = 1.5 Hz, 1H), 7.64 (dd, J = 7.9, 1.8 Hz, 1H), 7.61 (d, J = 1.7 Hz, 1H), 7.53-7.46 (m, 2H), 5.02 (d, J = 2.1 Hz, 1H), 4.13 (dd, J = 3.2, 2.2 Hz, 1H), 3.99 (dd, J = 9.3, 3.3 Hz, 1H), 3.96-3.85 (m, 2H), 3.75 (dd, J = 11.9, 6.5 Hz, 1H), 3.65 (t, J = 9.5 Hz, 1H), 2.34 (s, 3H). | 420.34 |
| 90 | 4-fluoro-N-methyl-3-[7-[2-[(2R,3S,4R,5S,6R)-3,4,5-trihydroxy-6-(hydroxymethyl)tetrahydropyran-2-yl]ethynyl]-1H-indazol-5-yl]benzamide | (400 MHz, CD₃OD) δ 8.20 (s, 1H), 8.05 (t, J = 1.3 Hz, 1H), 8.03 (d, J = 7.5, 2.3 Hz, 1H), 7.86 (ddd, J = 8.5, 4.6, 2.4 Hz, 1H), 7.76 (t, J = 1.4 Hz, 1H), 7.32 (dd, J = 10.3, 8.6 Hz, 1H), 5.03 (d, J = 2.1 Hz, 1H), 4.14 (dd, J = 3.1, 2.3 Hz, 1H), 4.02 (dd, J = 9.3, 3.3 Hz, 1H), 3.97-3.88 (m, 2H), 3.76 (dd, J = 11.9, 6.5 Hz, 1H), 3.66 (t, J = 9.5 Hz, 1H), 2.94 (s, 3H). | 456.38 |
| 91 | (2R,3S,4R,5S,6R)-2-(hydroxymethyl)-6-[2-[5-(4-hydroxy-2-methyl-phenyl)-1H-indazol-7-yl]ethynyl]tetrahydropyran-3,4,5-triol | (400 MHz, CD₃OD) δ 8.12 (s, 1H), 7.67 (d, J = 1.4 Hz, 1H), 7.44 (d, J = 1.4 Hz, 1H), 7.05 (d, J = 8.2 Hz, 1H), 6.73 (d, J = 2.5 Hz, 1H), 6.67 (dd, J = 8.2, 2.6 Hz, 1H), 5.01 (d, J = 2.1 Hz, 1H), 4.13 (dd, J = 3.2, 2.2 Hz, 1H), 4.01 (dd, J = 9.4, 3.3 Hz, 1H), 3.96-3.87 (m, 2H), 3.75 (dd, J = 12.0, 6.6 Hz, 1H), 3.65 (t, J = 9.5 Hz, 1H), 2.18 (s, 3H). | 411.37 |
| 92 | N-methyl-4-[7-[2-[(2R,3S,4R,5S,6R)-3,4,5-trihydroxy-6-(hydroxymethyl)tetrahydropyran-2-yl]ethynyl]-1H-indazol-5-yl]pyridine-2-carboxamide | (400 MHz, CD₃OD) δ 8.67 (d, J = 5.1 Hz, 1H), 8.40 (d, J = 1.3 Hz, 1H), 8.29 (d, J = 1.6 Hz, 1H), 8.25 (s, 1H), 7.95 (d, J = 1.5 Hz, 1H), 7.88 (dd, J = 5.1, 1.9 Hz, 1H), 5.04 (d, J = 2.1 Hz, 1H), 4.16 (dd, J = 3.2, 2.2 Hz, 1H), 4.03 (dd, J = 9.3, 3.3 Hz, 1H), 3.98-3.87 (m, 2H), 3.77 (dd, J = 12.1, 6.7 Hz, 1H), 3.66 (t, J = 9.4 Hz, 1H), 3.01 (s, 3H). | 439.34 |
| 93 | N,N-diethyl-4-methyl-3-[7-[2-[(2R,3S,4R,5S,6R)-3,4,5-trihydroxy-6-(hydroxymethyl)tetrahydropyran-2-yl]ethynyl]-1H-indazol-5-yl]benzenesulfonamide | (400 MHz, CD₃OD) δ 8.18 (s, 1H), 7.78 (d, J = 1.4 Hz, 1H), 7.72 (dd, J = 8.0, 2.0 Hz, 1H), 7.64 (d, J = 2.0 Hz, 1H), 7.52 (d, J = 8.1 Hz, 1H), 7.49 (d, J = 1.4 Hz, 1H), 5.02 (d, J = 2.1 Hz, 1H), 4.13 (dd, J = 3.1, 2.3 Hz, 1H), 4.00 (dd, J = 9.3, 3.3 Hz, 1H), 3.97-3.85 (m, 2H), 3.75 (dd, J = 11.8, 6.5 Hz, 1H), 3.64 (t, J = 9.6 Hz, 1H), 3.26 (q, J = 7.1 Hz, 4H), 2.34 (s, 3H), 1.14 (t, J = 7.1 Hz, 6H). | 530.38 |
| 94 | (2R,3S,4R,5S,6R)-2-[2-[5-(4-fluoro-2-methyl-phenyl)-1H-indazol-7-yl]ethynyl]-6-(hydroxymethyl)tetrahydropyran-3,4,5-triol | (400 MHz, CD₃OD) δ 8.15 (s, 1H), 7.71 (d, J = 1.4 Hz, 1H), 7.45 (d, J = 1.5 Hz, 1H), 7.24 (dd, J = 8.4, 5.9 Hz, 1H), 7.05 (dd, J = 9.9, 2.7 Hz, 1H), 6.98 (td, J = 8.5, 2.7 Hz, 1H), 5.01 (d, J = 2.1 Hz, 1H), 4.12 (dd, J = 3.2, 2.2 Hz, 1H), 4.00 (dd, J = 9.3, 3.3 Hz, 1H), 3.96-3.84 (m, 2H), 3.75 (dd, J = 11.9, 6.5 Hz, 1H), 3.64 (t, J = 9.5 Hz, 1H), 2.25 (s, 3H). | 413.38 |

Bacterial Binding Assay

The purpose of the Bacterial Binding Assay (BBA) is to determine the inhibition activity of selective FimH antagonists on the bacterial strain LF82 binding to the glycoprotein BSA-(Mannose)$_3$.

Below is a list of the Materials used to run the BBA are described below.
1. LB broth: Supplier: Gibco, #10855
2. D-PBS: Supplier: Wisent, #311-425-CL
3. LB agar plates
4. 96-well black plate (high binding): Supplier: Costar, #3925
5. TopSeal™-A adhesive sealing films; Supplier PerkinElmer, #6005185
6. Carbonate-bicarbonate buffer pH 9.6 tablets, Supplier: Medicago, #09-8922-24
7. Water, Supplier: Gibco, #15230-162
8. Bovine serum albumin (BSA): Supplier: Sigma, #A-7888
9. (Man)3-BSA (α1-3, α1-6 Mannotriose-BSA, 1 mg), V-Labs, #NGP1336, lot# HGDX37-169-1
10. Tween 20: Supplier: Sigma, #P9416
11. Bright-Glo Luciferase Assay System: Supplier: Promega, #E2610
12. LF82/Luciferase strain: Invasive ability of an *Escherichia coli* strain isolated from the ileal mucosa of a patient with Crohn's disease. Boudeau J, Glasser A L, Masseret E, Joly B, Darfeuille-Michaud A, *Infect Immun.* 1999, 67(9), 4499-509

Solutions and buffers used to run the BBA are described below.
1. 0.04M carbonate-bicarbonate buffer (coating buffer)
2. 40 μg/mL BSA-(Man)$_3$: Dissolve 1 mg of (Man)3-BSA in 25 mL of water.
3. 4000 μg/mL BSA
4. 40 μg/mL BSA
5. 1 μg/mL BSA-(Man)$_3$: 150 μL of 40 μg/mL BSA-(Man)$_3$+5.85 mL of 40 μg/mL BSA
6. 0.5 μg/mL BSA-(Man)$_3$ in 0.02M carbonate-bicarbonate buffer.
7. 20 μg/mL BSA in 0.02M carbonate-bicarbonate buffer
8. Blocking buffer (2% BSA/DPBS): 1 g of BSA in 50 mL D-PBS
9. 2× binding buffer (0.2% BSA/D-PBS): 5 mL of blocking buffer+45 mL D-PBS.
10. Washing buffer (D-PBS/0.01% Tween 20): 10 μL of Tween 20 in 100 mL D-PBS.
11. 1× Bright-Glo Luciferase substrate: Dilute 1:1 the Bright-Glo Luciferase Assay System with D-PBS The experimental protocol used in this example to run the BBA is described below.

Overnight culture of LF82/Luciferase strain: Into two Falcon 50 mL tubes, add 20 mL of LB+20 μL of 50 mg/mL Kanamycin and inoculate with a loop from glycerol stock of the LF82/Luciferase strain. Incubate overnight at 37° C. with no shaking.

Glycoprotein coating of 96-well plates: Add 100 μL/well of 0.5-2 μg/mL BSA-(Man)$_3$. 20 μg/mL BSA is used as the control background. Seal plate using an adhesive sealing film and incubate overnight at room temperature. Wash the 96-well plate three times with 150 μL/well of D-PBS, add 170 μL/well of blocking solution and incubate 45 min (minimum) at room temperature.

Preparation of bacterial suspension: Mix the two cultures tubes (40 mL) and perform a 1:10 dilution in LB (900 μl LB+100 μl culture. Measure optical density (OD) of the bacterial cultures. OD1 ~5×10$^8$ cells/mL. Centrifuge LF82 culture for 20 min at 3500 rpm at room temperature. Re-suspend bacterial pellet in D-PBS and centrifuge again for 20 min at 3500 rpm. Re-suspend bacterial pellet in D-PBS to obtain a bacterial concentration of 2×10$^9$ bacteria/mL. Dilute ¹/₁₀ in D-PBS to obtain a final bacterial concentration of 2×10$^8$ bacteria/mL (=107 bacteria/50 μL). Perform ¹/₁₀ serial dilutions in LB of each bacterial suspension, plate 10 μL of dilutions on LB agar plates (final dilutions of 10$^{-7}$) and incubate overnight at 37° C. and count CFUs to determine the actual bacteria density in the assay.

Bacterial binding assay: Add 147 μL 2× binding buffer to compound plate (containing 3 μL of compound). After blocking step is performed (at least 45 min), wash plates three times with 200 μL/well of D-PBS. With a 100 μL multichannel manual pipettor, add 50 μL/well of compound diluted in 2× binding buffer. With a 100 μL multichannel manual pipettor, add 50 μL/well of bacterial suspension. Agitate at slow speed for 1 min and incubate 40-75 min at room temperature. Wash 5 times with 150 μL/well of washing buffer and then once with D-PBS. Add 100 μL/well of 1× Bright-Glo Luciferase substrate. Read luminescence by using the Analyst HT plate reader or the Trilux 1450 microbeta plate reader. Table 8 below provides IC50 data for compounds 1-94 in the bacterial binding assay.

TABLE 8

| Compound | Bacterial Binding Assay *IC$_{50}$ ± SEM (μM) |
|---|---|
| 1 | 0.098 ± 0.022 (2) |
| 2 | 0.014 ± 0.002 (3) |
| 3 | 0.11 ± 0.01 (2) |
| 4 | 0.046 ± 0.012 (2) |
| 5 | 0.02 ± 0.002 (2) |
| 6 | 0.024 ± 0.005 (2) |
| 7 | 0.076 ± 0.026 (3) |
| 8 | 0.18 ± 0.04 (3) |
| 9 | 0.725 ± 0.155 (2) |
| 10 | 0.217 ± 0.133 (2) |
| 11 | 0.19 ± 0.075 (3) |
| 12 | 0.016 ± 0.006 (3) |
| 13 | 0.48 ± 0.15 (2) |
| 14 | 0.35 ± 0.08 (2) |
| 15 | 0.0007 ± 0.0002 (4) |
| 16 | 0.008 ± 0.001 (2) |
| 17 | 0.046 ± 0.014 (2) |
| 18 | 0.067 ± 0.026 (2) |
| 19 | 0.002 ± 0.0006 (2) |
| 20 | 0.002 ± 0.0002 (2) |
| 21 | 0.022 ± 0.0005 (2) |
| 22 | 0.053 ± 0.004 (2) |
| 23 | 0.009 ± 0.0 (2) |
| 24 | 0.001 ± 0.0002 (10) |
| 25 | 0.0004 ± 0.00004 (5) |
| 26 | 0.0007 ± 0.0003 (3) |
| 27 | 0.0002 ± 0.00003 (4) |
| 28 | 0.0006 ± 0.0004 (3) |
| 29 | 0.001 ± 0.0007 (3) |
| 30 | 0.0005 ± 0.0002 (2) |
| 31 | 0.0007 ± 0.00001 (2) |
| 32 | 0.0006 ± 0.000005 (2) |
| 33 | 0.0004 ± 0.00005 (2) |
| 34 | 0.0004 ± 0.00009 (2) |
| 35 | 0.0005 ± 0.0001 (2) |
| 36 | 0.002 ± 0.0002 (2) |
| 37 | 0.0007 ± 0.00002 (2) |
| 38 | 0.0008 ± 0.0005 (3) |
| 39 | 0.0002 ± 0.00005 (2) |
| 40 | 0.001 ± 0.0003 (2) |
| 41 | 0.0004 ± 0.00004 (2) |
| 42 | 0.0006 ± 0.0002 (3) |
| 43 | 0.002 ± 0.001 (2) |
| 44 | 0.005 ± 0.0005 (2) |
| 45 | 0.015 ± 0.003 (2) |
| 46 | 0.003 ± 0.001 (3) |
| 47 | 0.012 ± 0.006 (3) |

TABLE 8-continued

| Compound | Bacterial Binding Assay *IC$_{50}$ ± SEM (μM) |
| --- | --- |
| 48 | 0.009 ± 0.0007 (2) |
| 49 | 0.026 ± 0.0005 (2) |
| 50 | 0.009 ± 0.001 (2) |
| 51 | 0.003 ± 0.0004 (2) |
| 52 | 0.022 ± 0.01 (2) |
| 53 | 0.004 ± 0.0005 (2) |
| 54 | 0.0004 ± 0.0001 (2) |
| 55 | 0.002 ± 0.00005 (2) |
| 56 | 0.0002 ± 0.00002 (9) |
| 57 | 0.002 ± 0.0006 (2) |
| 58 | 0.074 ± 0.015 (2) |
| 59 | 0.0004 ± 0.0002 (3) |
| 60 | 0.003 ± 0.002 (3) |
| 61 | 0.0006 ± 0.0001 (2) |
| 62 | 0.034 ± 0.02 (3) |
| 63 | 0.026 ± 0.001 (2) |
| 64 | 0.05 ± 0.007 (2) |
| 65 | 0.0008 ± 0.0001 (3) |
| 66 | 0.002 ± 0 (2) |
| 67 | 0.002 ± 0.0009 (2) |
| 68 | 0.001 ± 0.0004 (2) |
| 69 | 0.013 ± 0.009 (2) |
| 70 | 0.0002 ± 0.00004 (2) |
| 71 | 0.0006 ± 0.0002 (4) |
| 72 | 0.007 ± 0.004 (4) |
| 73 | 0.0005 ± 0.00009 (3) |
| 74 | 0.0003 ± 0.00005 (3) |
| 75 | 0.002 ± 0.0007 (3) |
| 76 | 0.0003 ± 0.00009 (3) |
| 77 | 0.0001 ± 0.00002 (3) |
| 78 | 0.002 ± 0.0006 (3) |
| 79 | 0.0004 ± 0.0001 (5) |
| 80 | 0.0002 ± 0.00008 (2) |
| 81 | 0.0004 ± 0.0002 (2) |
| 82 | 0.001 (1) |
| 83 | 0.0007 ± 0.0005 (2) |
| 84 | 0.0005 ± 0.0002 (2) |
| 85 | 0.0004 ± 0.0002 (2) |
| 86 | 0.001 ± 0.0002 (2) |
| 87 | 0.001 (1) |
| 88 | 0.002 (1) |
| 89 | 0.0005 ± 0.00004 (2) |
| 90 | 0.003 (1) |
| 91 | 0.0003 ± 0.00003 (2) |
| 92 | 0.001 (1) |
| 93 | 0.001 (1) |
| 94 | 0.0006 ± 0.0003 (2) |

*SEM: Standard Error of the Mean.
Number in parenthesis indicate n values.

Mouse Model of Inflammatory Bowel Disease (IBD)

Transgenic humanized-CEACAM6 mouse model may be used to test the compounds of the invention (Carvalho F A et al. (2009) J Exp Med. September 28; 206(10):2179-89). The Transgenic humanized-CEACAM6 5 mice are infected as described in Carvalho et al. The infected mice can then treated with compounds of the present invention.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997.

Adhesion Assays of AIEC LF82 Strain on T84 Intestinal Epithelial Cells

Compound 56 was evaluated for its ability to inhibit the adhesion of bacteria AIEC LF82 strain on T84 intestinal cells, in order to assess the therapeutic potential of the tested compounds in Crohn's Disease (CD) in particular. The following post-incubation test was used (also described in Brument et al. *J. Med. Chem.* 2013, 56, 5395-5406), wherein the tested compound is added after the bacteria are brought into contact with the cells. This test thus mimics a use of the compounds in curative treatment of pathologies associated with AIECs, in particular Crohn's disease.

Materials and Methods

*E. coli* strain LF82 isolated from an ileal biopsy of a CD patient was used as the AIEC reference strain. Bacteria were grown overnight in Luria-Bertani (LB) broth, and a bacterial suspension was prepared at a concentration of 6×10$^6$ bacteria/mL in DMEM/F12/SVF dec 10% medium for adhesion assays. The human intestinal cell line T84, purchased from American Type Culture Collection (ATCC, CCL-248), was maintained in an atmosphere containing 5% CO$_2$ in the culture medium recommended by ATCC. T84 cells were seeded in 48-wells tissue culture plates at a density of 1.5×10$^5$ cells/well and incubated at 37° C. for 48 h.

Cells were washed twice with PBS and infected by addition of 250 μL per well of the bacteria suspension, then incubated for 3 h at 37° C. with the AIEC reference strain LF82 at a multiplicity of infection (MOI) of 10 bacteria per cell (1.5×10$^6$ bacteria/well).

The cells were washed 5 time with PBS, then incubated 3 h at 37° C. with 250 μL/well of HM (heptylmannose) or compound 56 at the final concentrations of 1 nM, 10 nM, 100 nM, 1 μM and 10 μM in DMEM/F12/SVF dec 10% medium. Effects of compound 56 treatment were compared with HM. Monolayers were washed five times with PBS and lysed with 1% Triton X-100 (Sigma) in deionized water at room temperature (250 μL/well, incubation 5 minutes). Samples were diluted and plated onto LB agar plates to determine the number of colony-forming units (CFU) after overnight incubation at 37° C.

Results

The results are depicted in FIG. 1, which shows residual adhesion (colonization/decolonization of AIEC measured on cells), expressed in percentage. Compound 56 displays a potent activity for the decolonization of the LF82 Adherent and Invasive *E. coli* (AIEC bacteria) from T84 cells from a concentration of 100 nM. At 10 nM, it enables a decolonization of about 50% of adherent bacteria.

What is claimed is:

1. A compound represented by the following structural formula or a pharmaceutically acceptable salt thereof:

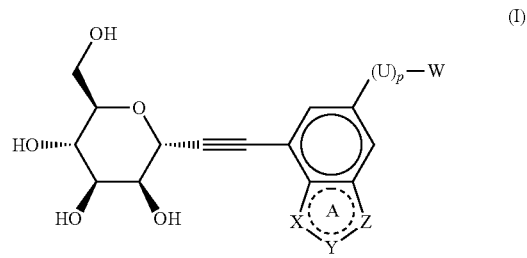

(I)

or a pharmaceutically acceptable salt thereof, wherein:
X—Y—Z is —NR—N═CH—, ═N—NR—CH—, —CH═N—NR—, —NH—CH═CH—, —NH—

CH=N—, —NH—N=N—, —NH—CH₂—CH₂—, —O—CH=N—, —NH—C(=O)—CH₂—, or —NH—C(=O)—NH—;

R is —H, $C_{1-4}$alkyl, $C_{1-4}$haloalkyl or —($C_{1-4}$alkyl)-Ph, wherein Ph is phenyl optionally substituted with 1-3 occurrences of $J^{Ph}$;

U is —CH=CH—, —C≡C—, or phenylene;

p is 0 or 1;

W is —H; halogen; —CN; —C(=O)NR¹R²; —C(=O)OR³; $C_{1-6}$alkyl; a 3-8 membered partially unsaturated, or aromatic monocyclic ring having 0-4 heteroatoms selected from oxygen, nitrogen, or sulfur; or an 8-10 membered partially unsaturated, or aromatic bicyclic ring having 0-4 heteroatoms selected from oxygen, nitrogen, or sulfur; wherein said $C_{1-6}$alkyl is optionally substituted with 1-4 occurrences of $J^{W1}$, and wherein each of said monocyclic and bicyclic rings independently and optionally is substituted with 1-4 occurrences of $J^{W2}$;

$J^{W1}$ is halogen, —CN, —OR⁶, —NR⁴R⁵, —NR⁴COR⁵, —C(=O)NR⁴R⁵, —C(=O)OR⁶, —S(O)₂NR⁴R⁵—, S(O)₂R⁶—, or Ph, wherein said Ph is phenyl optionally substituted with 1-3 occurrences of $J^{Ph}$;

$J^{W2}$ is oxo, —NO₂, halogen, —CN, —OR⁶, —O(CH₂)O—, —O(CH₂)₂O—, —NR⁴R⁵, —NR⁴COR⁵, —C(=O)NR⁴R⁵, —C(=O)OR⁶, —S(O)₂NR⁴R⁵—, S(O)₂R⁶—, —$C_{1-6}$alkyl, Ph, —($C_{1-4}$alkyl)Ph, or —O($C_{1-4}$alkyl)Ph, wherein said —$C_{1-6}$alkyl is optionally substituted with 1-3 occurrences of $J^A$, and wherein said Ph is phenyl optionally substituted with 1-3 occurrences of $J^{Ph}$;

each of R¹, R³, R⁴, R⁵, and R⁶ independently is —H; $C_{1-6}$alkyl optionally substituted with 1-3 occurrences of $J^A$; $C_{3-6}$cycloalkyl optionally substituted with 1-3 occurrences of $J^B$; or —($C_{1-4}$alkyl)-Ph wherein Ph is phenyl optionally substituted with 1-3 occurrences of $J^{Ph}$;

R² is $C_{1-6}$alkyl optionally substituted with 1-3 occurrences of $J^A$; $C_{3-6}$cycloalkyl optionally substituted with 1-3 occurrences of $J^B$; or —($C_{1-4}$alkyl)-Ph wherein Ph is phenyl optionally substituted with 1-3 occurrences of $J^{Ph}$; or optionally R¹ and R² together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)₂; or optionally R⁴ and R⁵ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)₂; and each $J^A$ independently is halogen, CN, —OH, —O($C_{1-4}$alkyl), or —O($C_{1-4}$haloalkyl);

each $J^B$ independently is halogen, —CN, —OH, —O($C_{1-4}$haloalkyl), —O($C_{1-4}$haloalkyl), $C_{1-4}$alkyl, or $C_{1-4}$haloalkyl; and each $J^{Ph}$ independently is halogen, —CN, —OH, —O($C_{1-4}$alkyl), —O($C_{1-4}$haloalkyl), $C_{1-4}$alkyl, or $C_{1-4}$haloalkyl.

2. The compound of claim 1, wherein R is H, $C_{1-4}$alkyl, or —($C_{1-4}$alkyl)-Ph, wherein Ph of —($C_{1-4}$alkyl)-Ph for R is phenyl optionally substituted with 1-2 occurrences of halogen, CN, —OH, —O($C_{1-4}$alkyl), —O($C_{1-4}$haloalkyl), $C_{1-4}$alkyl, or $C_{1-4}$haloalkyl.

3. The compound of claim 1, wherein:

each of R¹, R³, R⁴, R⁵, and R⁶ independently is —H, $C_{1-4}$alkyl, $C_{1-4}$haloalkyl, or $C_{3-6}$cycloalkyl;

R² is $C_{1-4}$alkyl, $C_{1-4}$haloalkyl, or $C_{3-6}$cycloalkyl; or optionally R¹ and R² together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)₂; or optionally R⁴ and R⁵ together with the nitrogen atom to which they are attached form a 4-6 membered, non-aromatic, monocyclic ring wherein up to one methylene unit of the ring is optionally replaced with O, NH, N($C_{1-4}$alkyl), S, C(O), S(O), or S(O)₂.

4. The compound of claim 1, wherein p is 0.

5. The compound of claim 1, represented by any one of the following structural formulae or a pharmaceutically acceptable salt thereof:

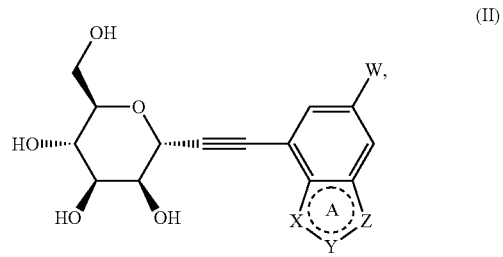

(II)

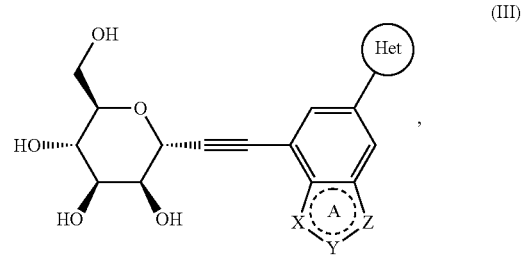

(III)

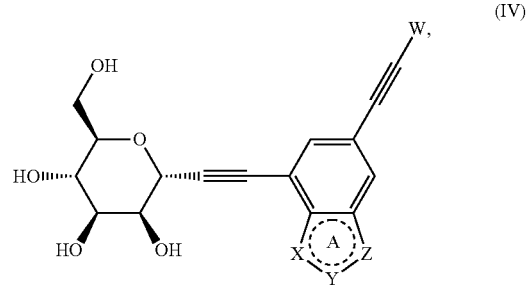

(IV)

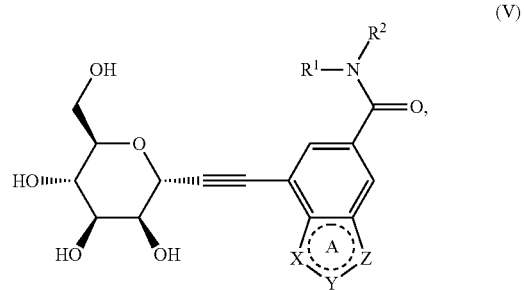

(V)

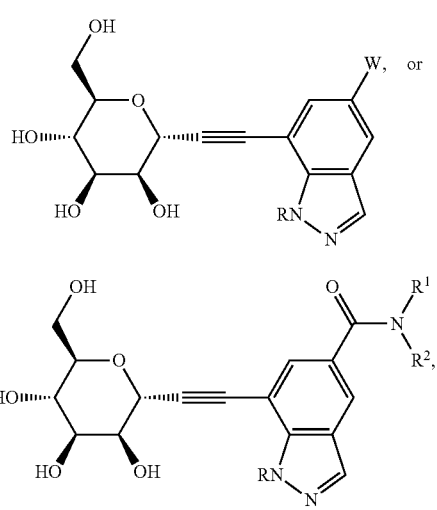

(VI)

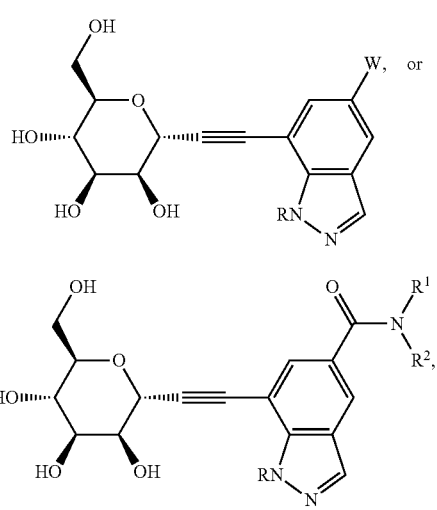

(VII)

wherein Het of Formula (III) is a 3-8 membered partially unsaturated, or aromatic monocyclic ring having 1-4 heteroatoms selected from oxygen, nitrogen, or sulfur; or an 8-10 membered partially unsaturated, or aromatic bicyclic ring having 1-4 heteroatoms selected from oxygen, nitrogen, or sulfur; wherein each of said monocyclic and bicyclic rings independently and optionally is substituted with 1-4 occurrences of $J^{W2}$.

6. The compound of claim 1, represented by the following structural formula or a pharmaceutically acceptable salt thereof:

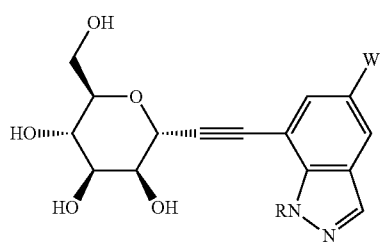

(VI)

wherein R is —H or —CH₃.

7. The compound of claim 6, wherein W is —C(=O)NR¹R²; $C_{1-6}$alkyl optionally substituted with 1-4 occurrences of $J^{W1}$; a 3-8 membered partially unsaturated, or aromatic monocyclic ring having 0-4 heteroatoms selected from oxygen, nitrogen, or sulfur; or an 8-10 membered partially unsaturated, or aromatic bicyclic ring having 0-4 heteroatoms selected from oxygen, nitrogen, or sulfur; wherein each of said monocyclic and bicyclic rings independently and optionally is substituted with 1-4 occurrences of $J^{W2}$.

8. The compound of claim 6, wherein:
$J^{W1}$ is selected from the group consisting of halogen, CN, —OH, —O($C_{1-4}$alkyl), —O($C_{1-4}$haloalkyl), —O($C_{1-4}$alkyl)-Ph, —NH₂, —NH($C_{1-4}$alkyl), and —N($C_{1-4}$alkyl)₂; and
$J^{W2}$ is selected from the group consisting of halogen, CN, oxo, NO₂, $C_{1-4}$alkyl, $C_{1-4}$haloalkyl, —NH₂, —NH($C_{1-4}$ alkyl), —N($C_{1-4}$alkyl)₂, —C(=O)OH, —C(=O)O($C_{1-4}$alkyl), —OH, —O($C_{1-4}$alkyl), —O($C_{1-4}$haloalkyl), —O($C_{1-4}$alkyl)-Ph, —O(CH₂)O—, —O(CH₂)₂O—, —C(=O)NH₂, —C(=O)NH($C_{1-4}$ alkyl), —C(=O)N($C_{1-4}$alkyl)₂, —SO₂($C_{1-4}$alkyl), —NHCO($C_{1-4}$alkyl), —SO₂NH₂, —SO₂NH($C_{1-4}$ alkyl), and —SO₂N($C_{1-4}$alkyl)₂.

9. The compound of claim 6, wherein W is

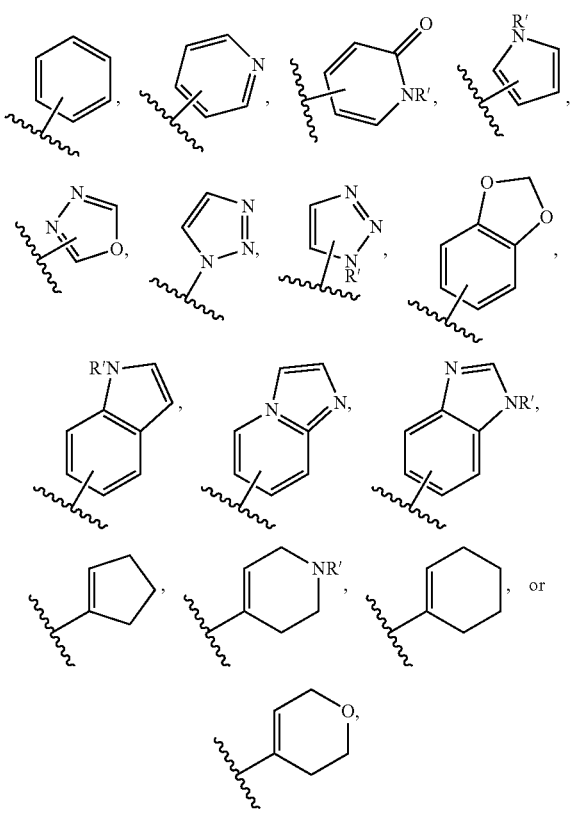

wherein each W is independently and optionally substituted, and each R' independently —H or —$C_{1-4}$alkyl.

10. The compound of claim 6, wherein W is optionally substituted $C_{1-6}$alkyl, or a benzene, pyridine, pyridine-2-one, imidazo[1,2-a]pyridine, benzoimidazole, benzo[d][1,3]dioxole, indole, 1,3,4-oxadiazole, pyrrole, or triazole, each of which independently and optionally is substituted.

11. The compound of claim 1, represented by anyone of the following structural formulae or a pharmaceutically acceptable salt thereof:

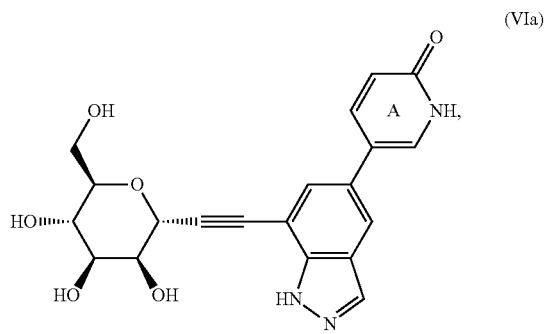

(VIa)

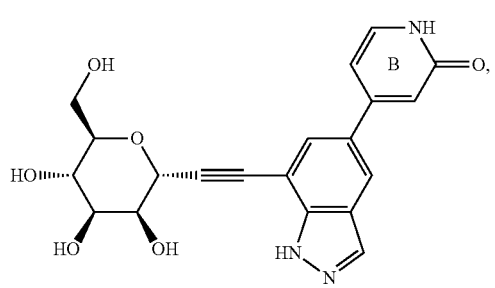 (VIb)
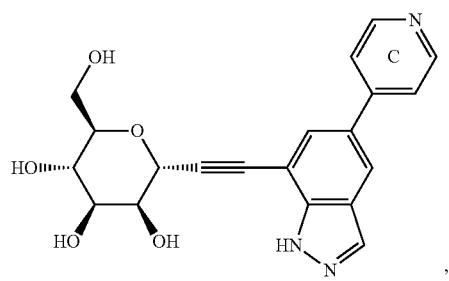 (VIc)
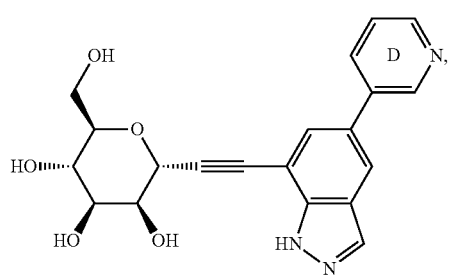 (VId)
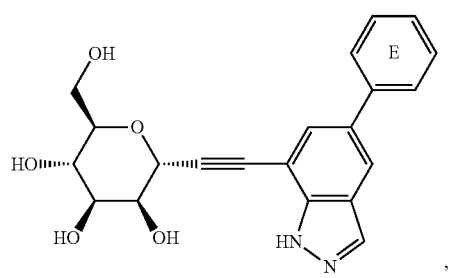 (VIe)
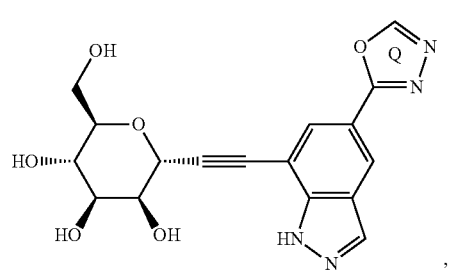 (VIf)
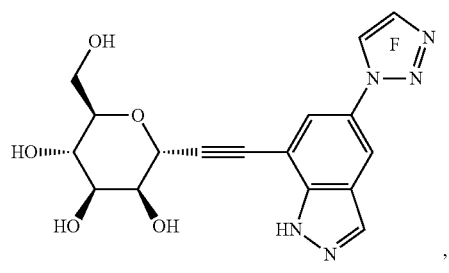 (VIg)
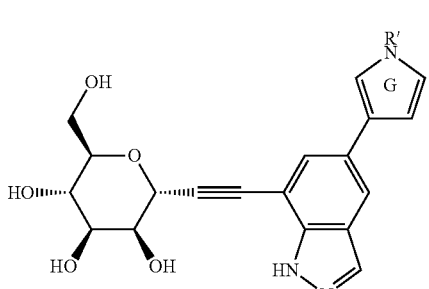 (VIh)
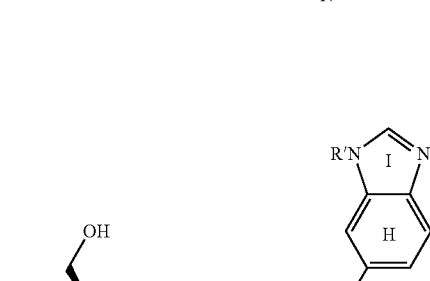 (VIi)
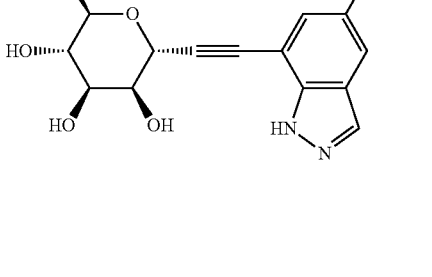 (VIj)
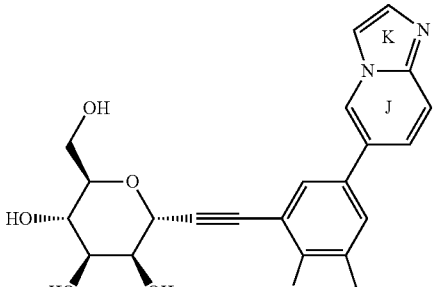 
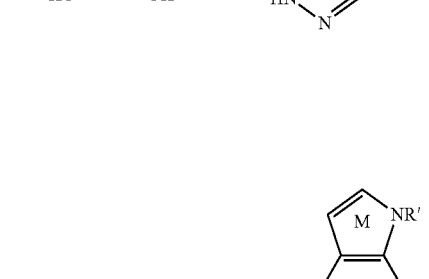 (VIk)
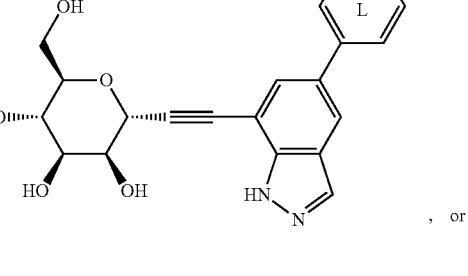 , or -continued

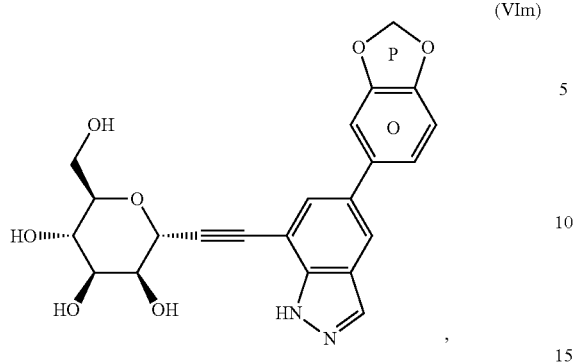
(VIm)

wherein each of rings A-Q independently and optionally is substituted, and each R' is —H or methyl.

12. The compound of claim 11, wherein each of rings A-Q is independently and optionally substituted with 1-3 occurrences of $J^{W2}$ selected from —F, —Cl, —CN, NO$_2$, C$_{1-2}$alkyl, C$_{1-2}$haloalkyl, —NH$_2$, —NH(C$_{1-2}$alkyl), —N(C$_{1-2}$ alkyl)$_2$, —C(=O)O(C$_{1-2}$alkyl), —OH, —O(C$_{1-2}$ alkyl), —O(C$_{1-2}$haloalkyl), —O(C$_{1-2}$alkyl)-Ph, —C(=O)NH$_2$, —C(=O)NH(C$_{1-2}$alkyl), —C(=O)N(C$_{1-2}$alkyl)$_2$, —SO$_2$(C$_{1-2}$alkyl), —NHCO(C$_{1-2}$alkyl), —SO$_2$NH$_2$, —SO$_2$NH(C$_{1-2}$alkyl), or —SO$_2$N(C$_{1-2}$alkyl)$_2$.

13. The compound of claim 1, represented by the following structural formula or a pharmaceutically acceptable salt thereof:

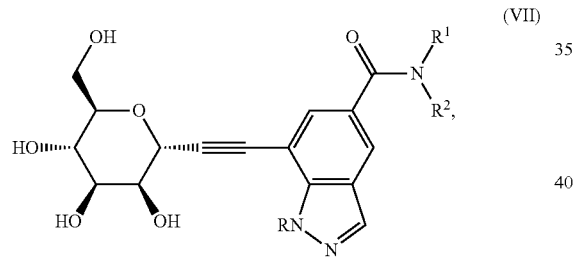
(VII)

wherein R is —H or —CH$_3$.

14. The compound of claim 13, wherein R is —H and each of R$^1$ and R$^2$ independently is an optionally substituted, C$_{1-4}$alkyl or C$_{3-6}$cycloalkyl group; or optionally R$^1$ and R$^2$ together with the nitrogen atom to which they are attached form a 5-6 membered, non-aromatic, monocyclic ring wherein up to one methylene unit of the ring is optionally replaced with O, NH, N(C$_{1-4}$alkyl), S, C(O), S(O), or S(O)$_2$.

15. The compound of claim 1, selected from any one of the following structural formulae or a pharmaceutically acceptable salt thereof:

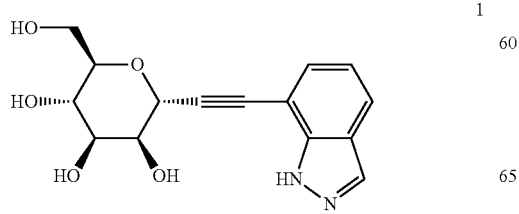
1

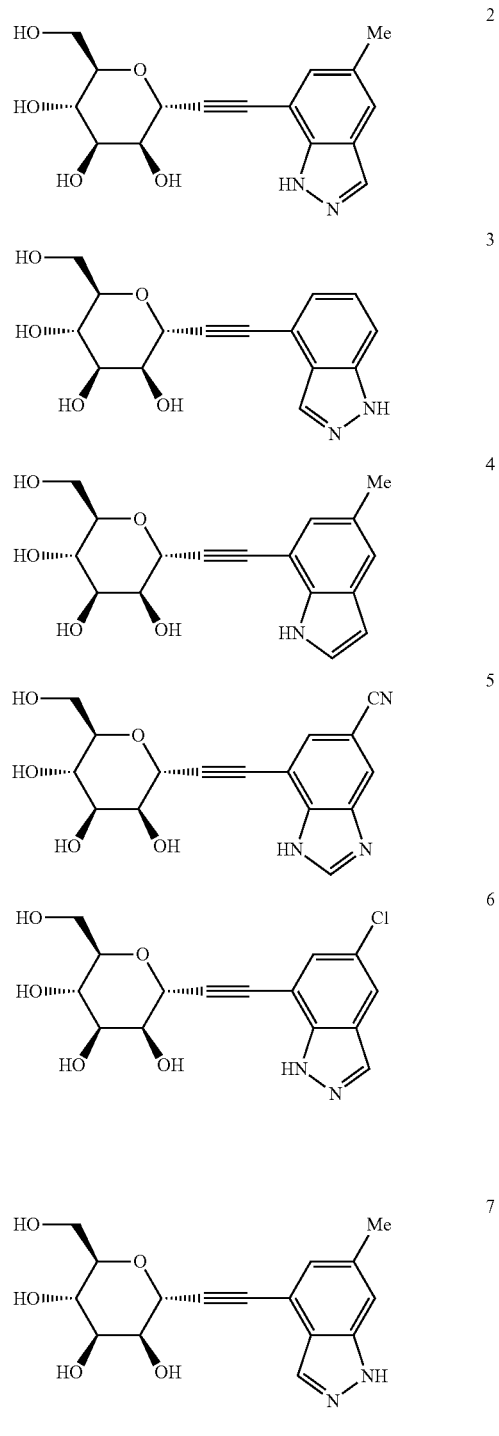

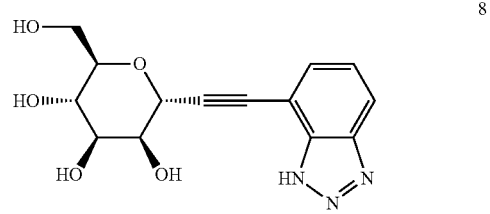
8

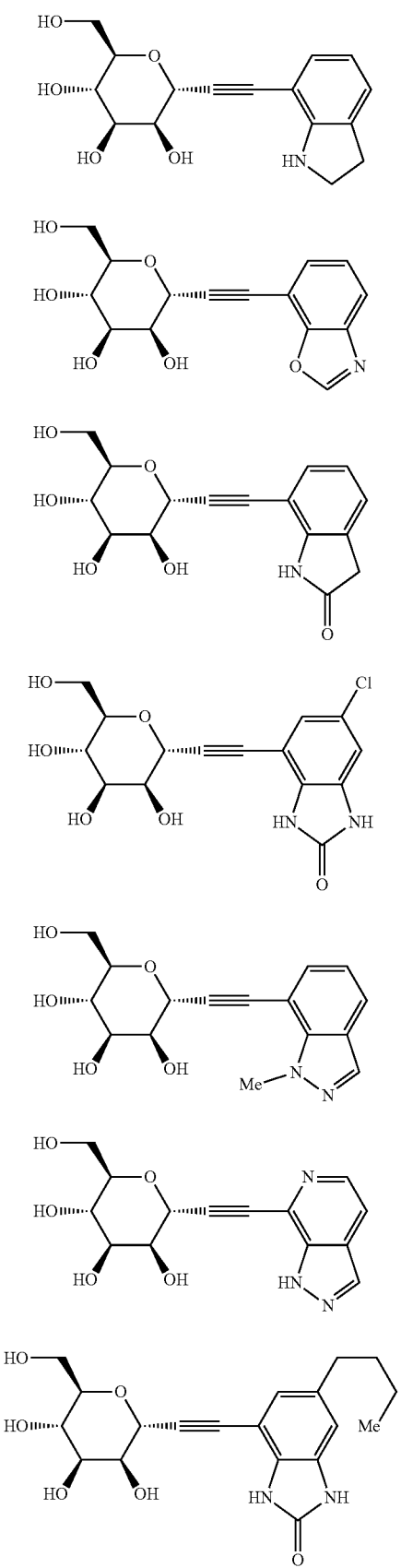
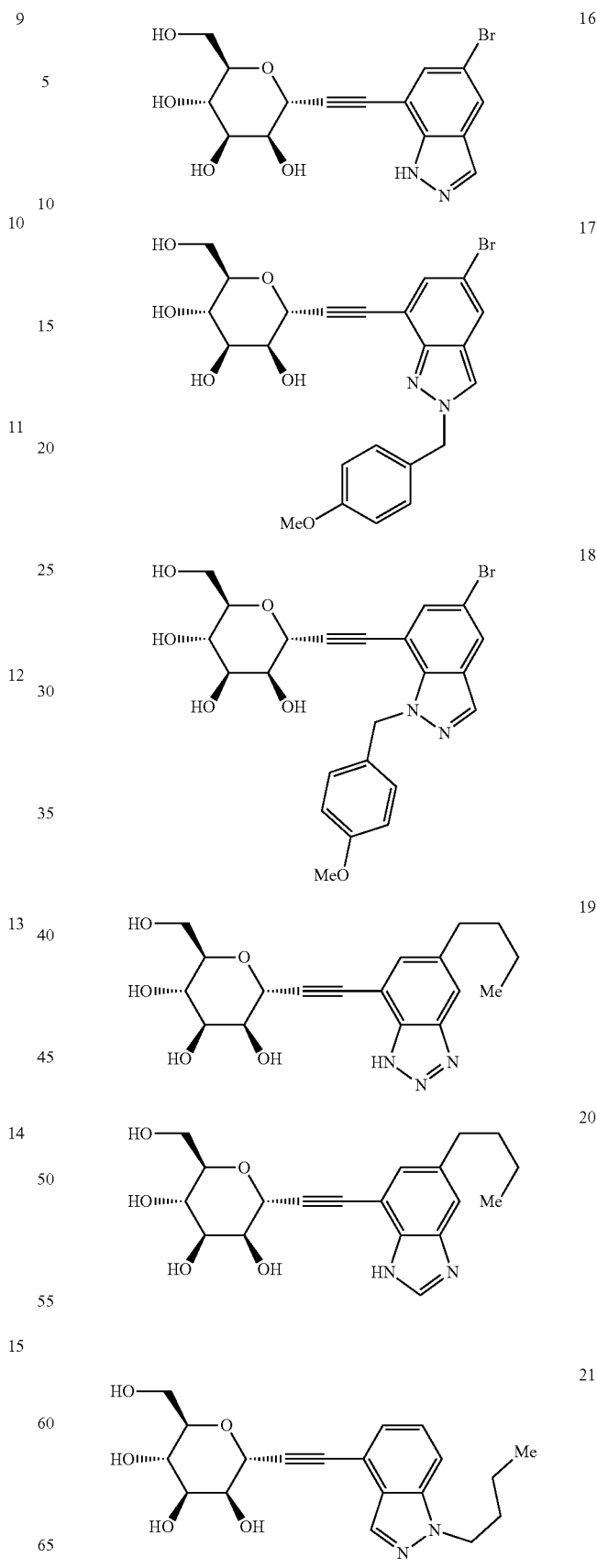

129
-continued
22
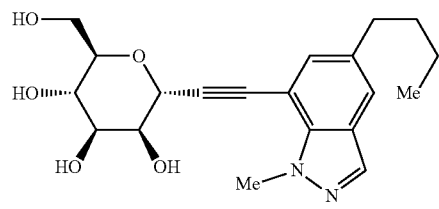
23
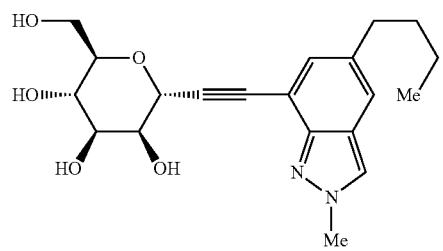
24
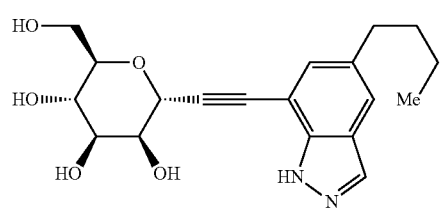
25
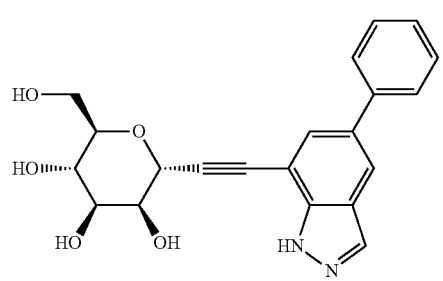
26
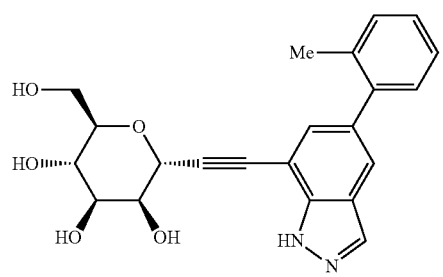
27
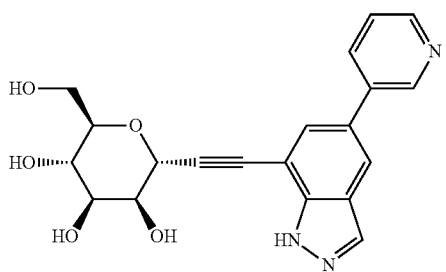
130
-continued
28
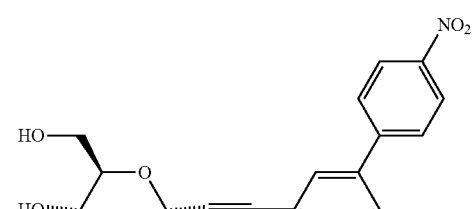
29
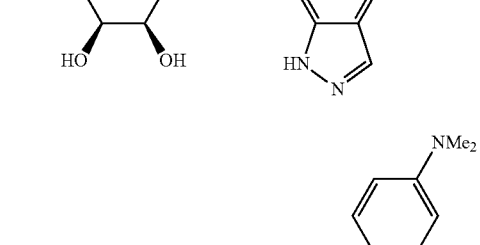
30
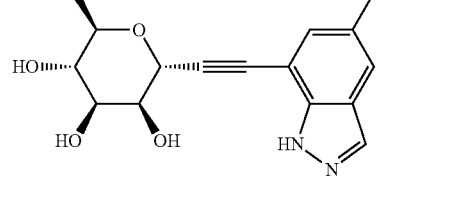
31
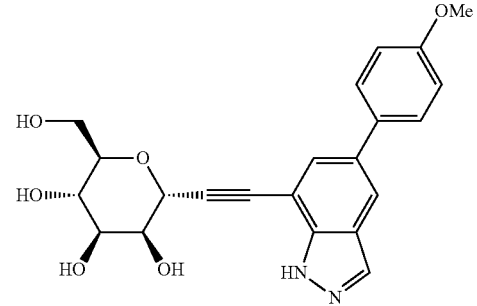
32
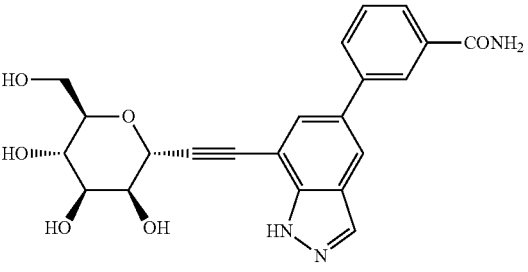
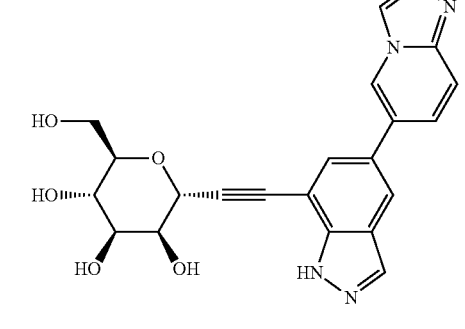

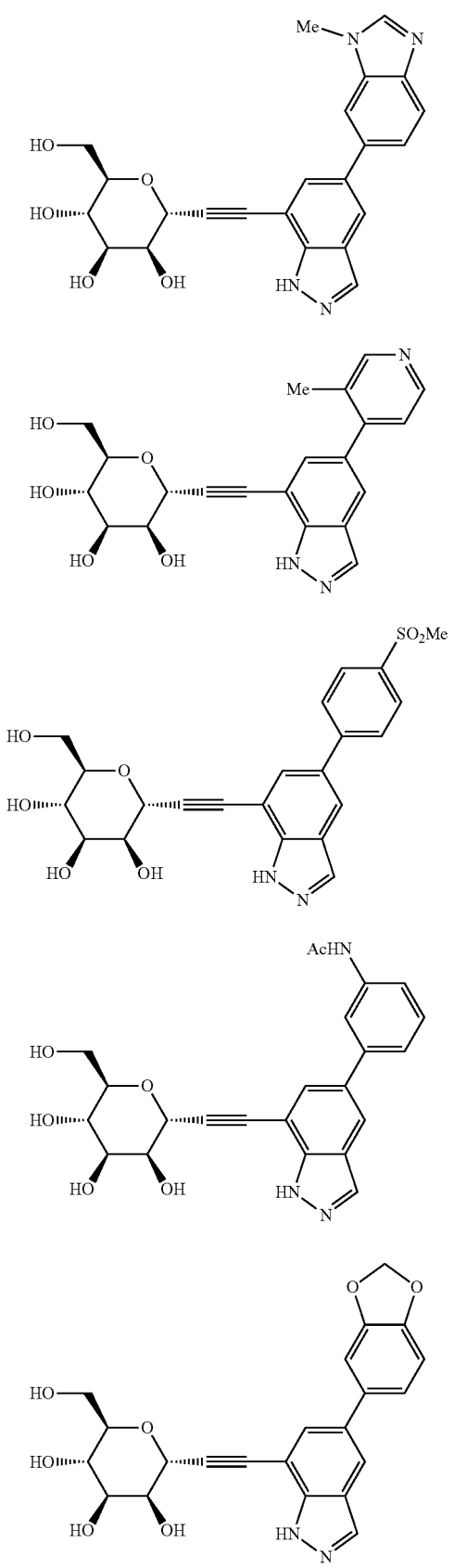
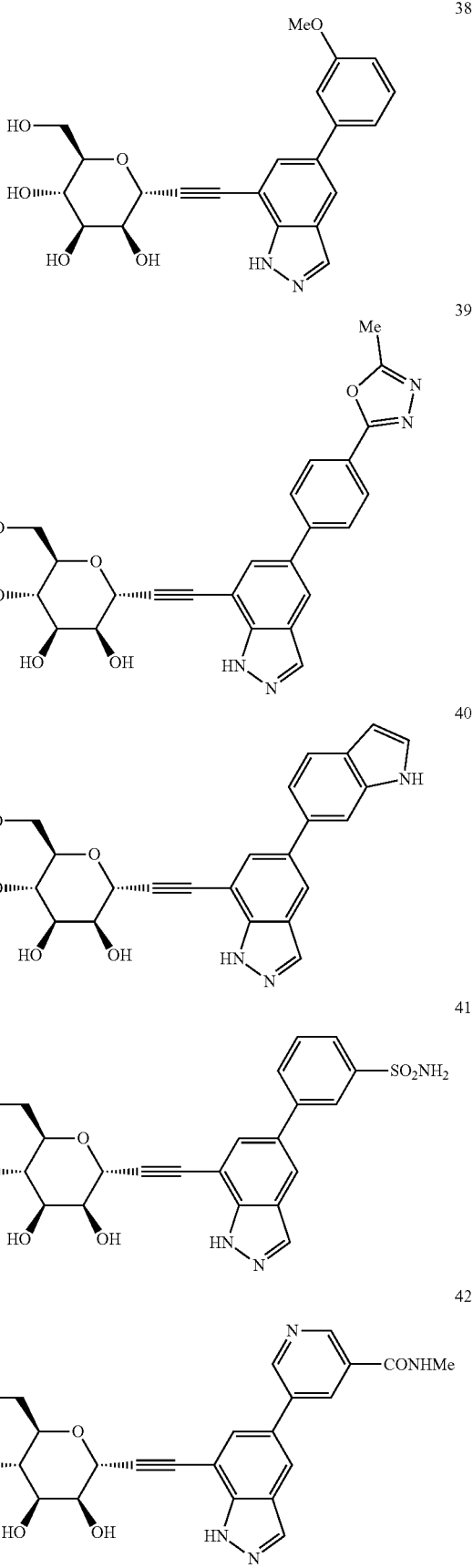

133
-continued
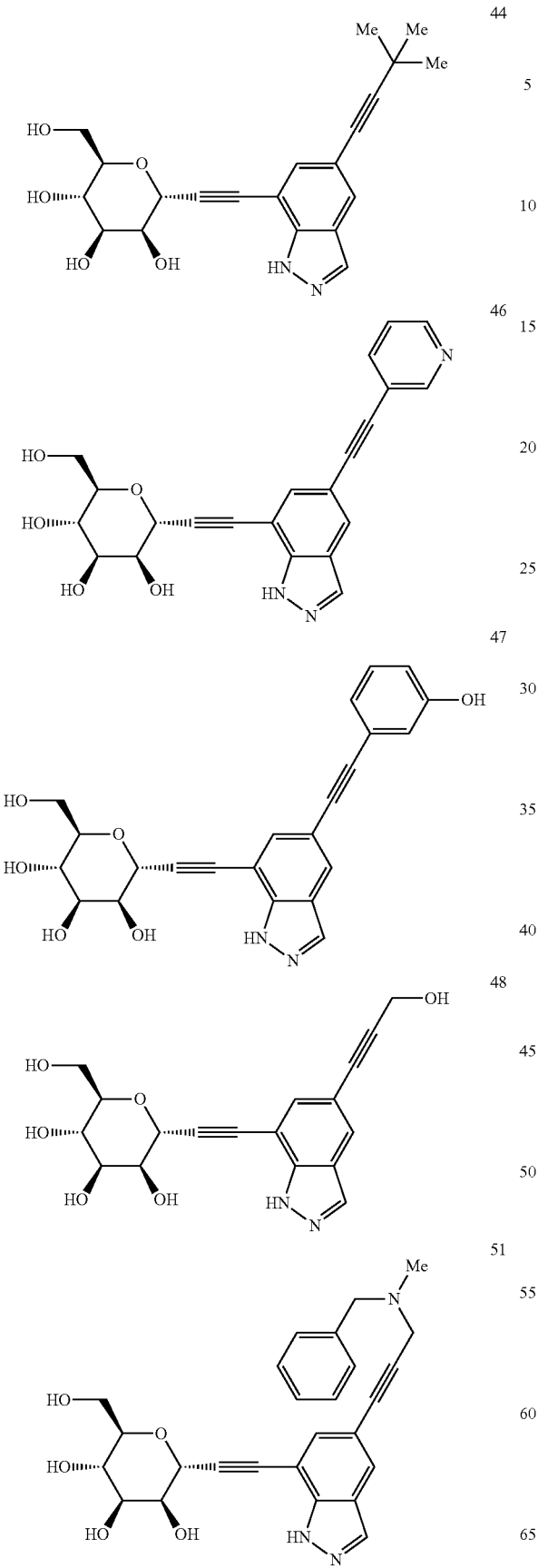
134
-continued
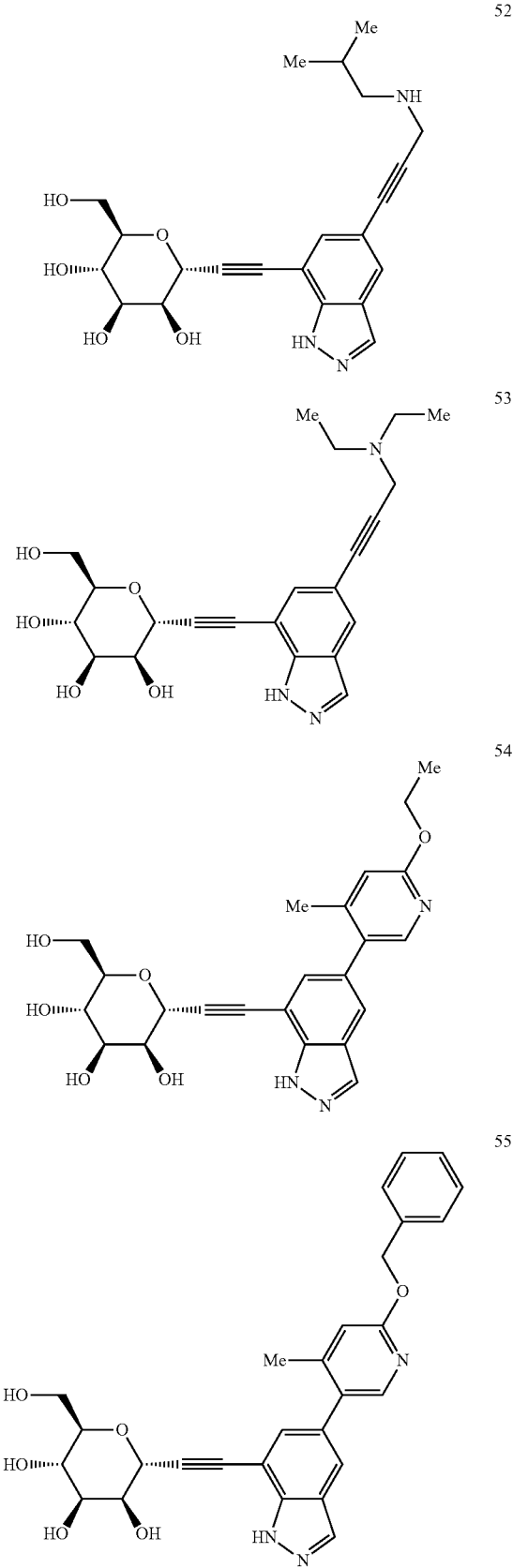

135
56
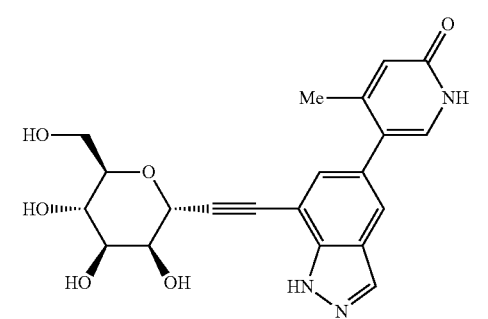
57
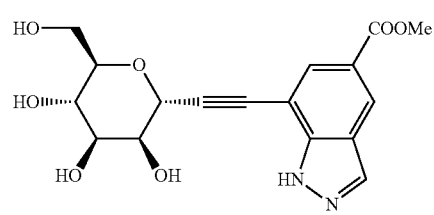
58
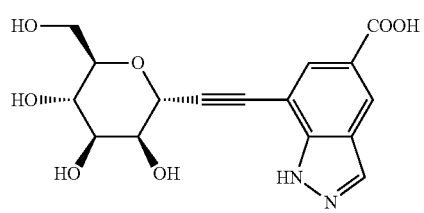
59
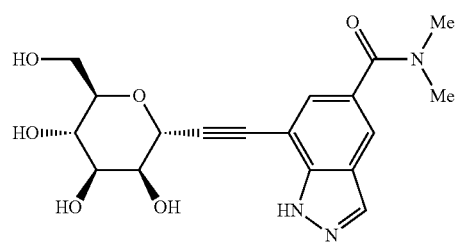
60
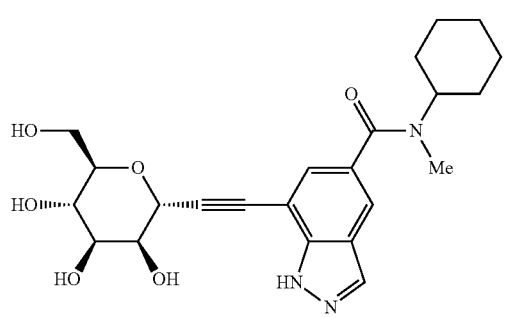
61
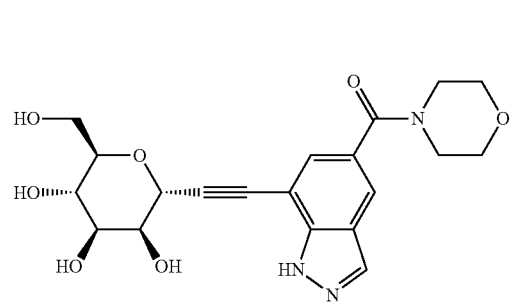
136
62
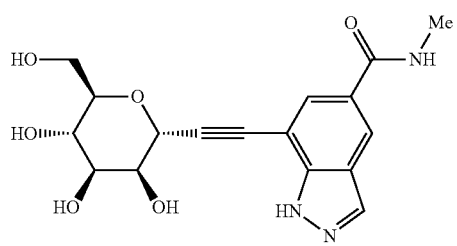
63
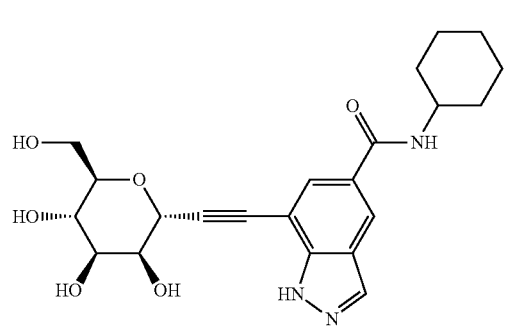
64
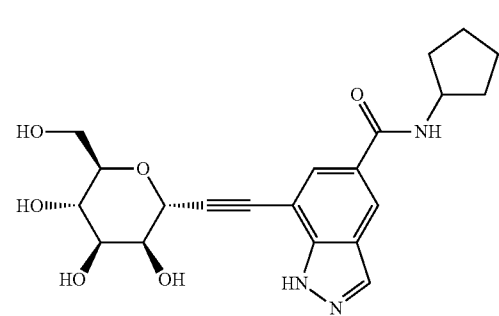
65
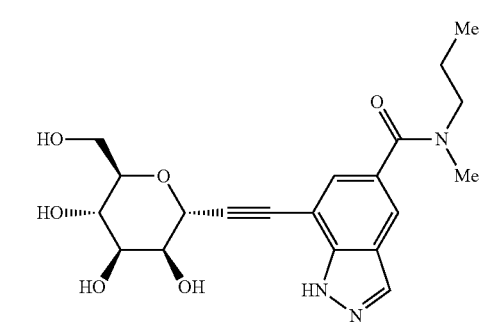
66
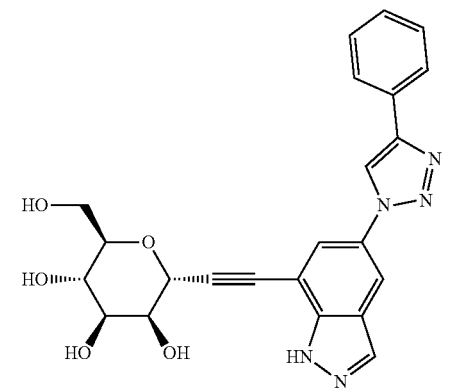

-continued
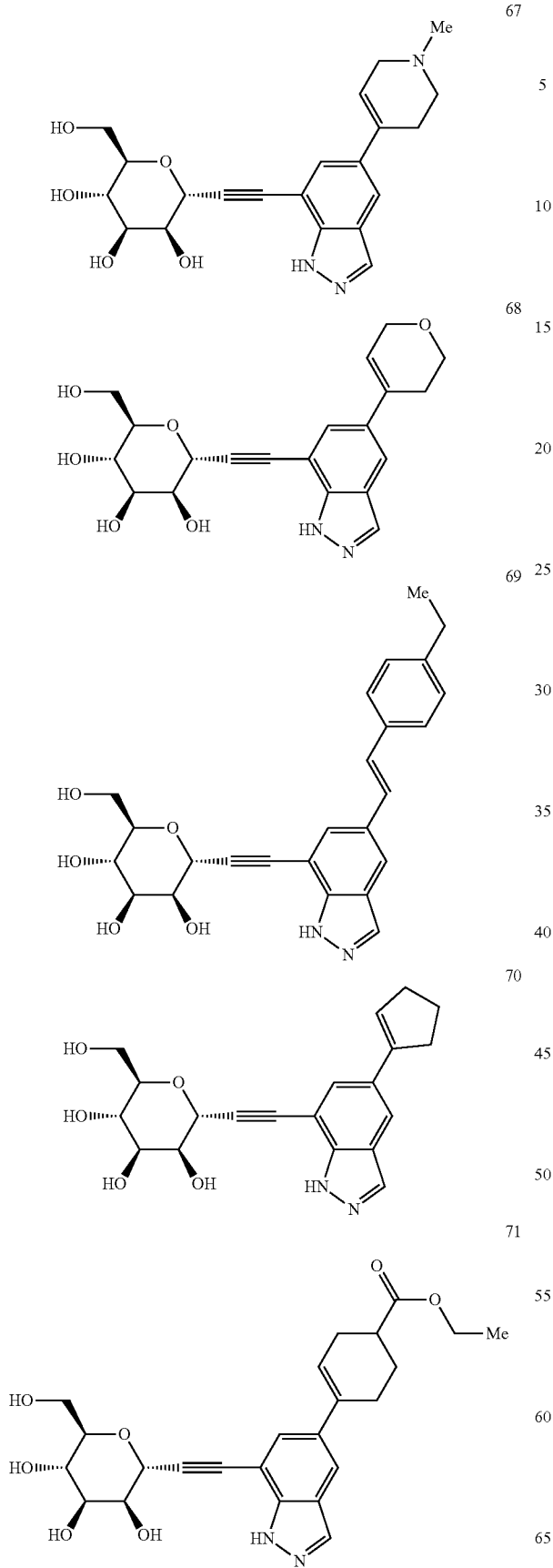
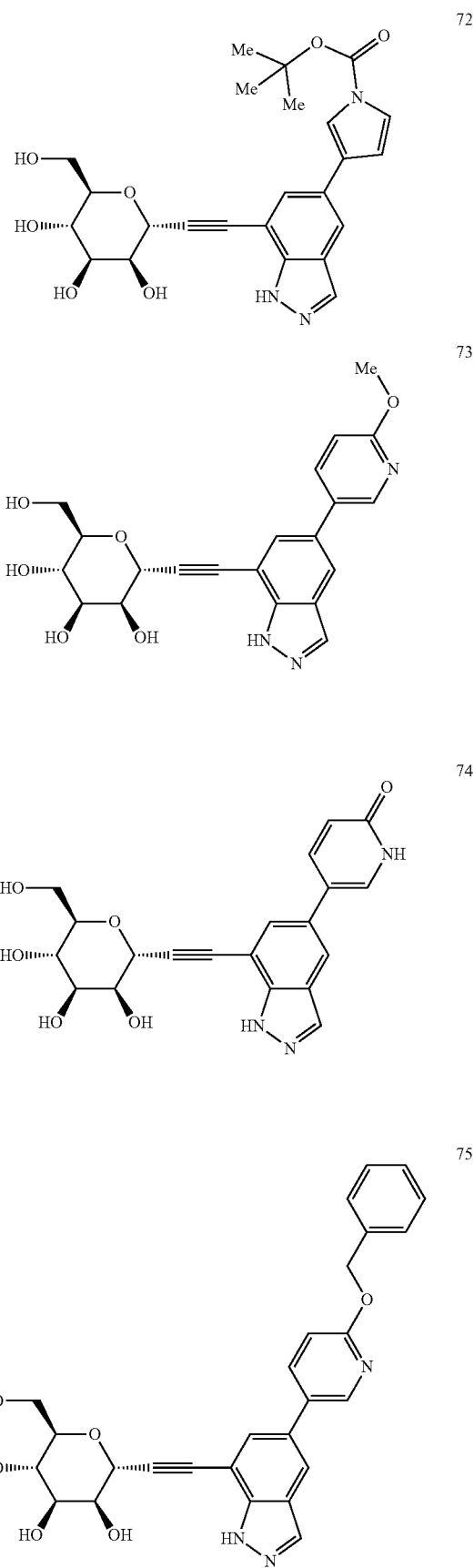

76
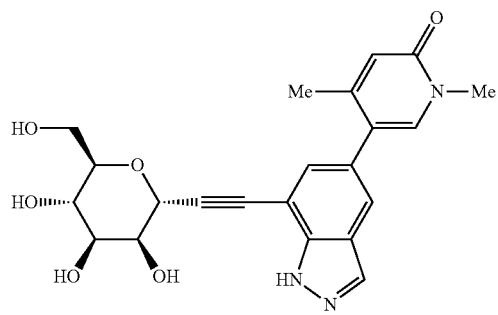
77
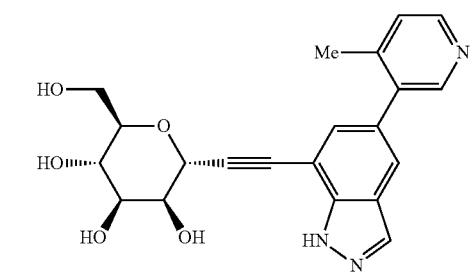
78
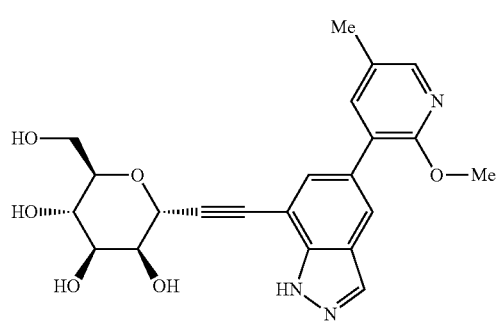
79
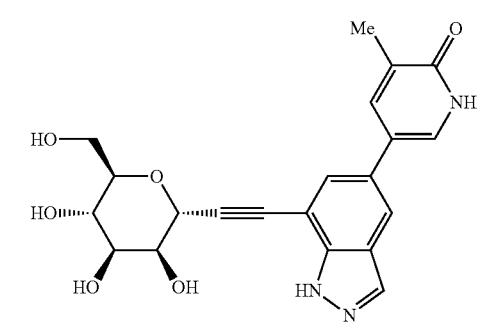
80
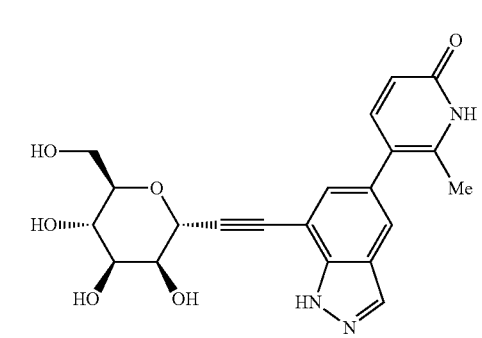
81
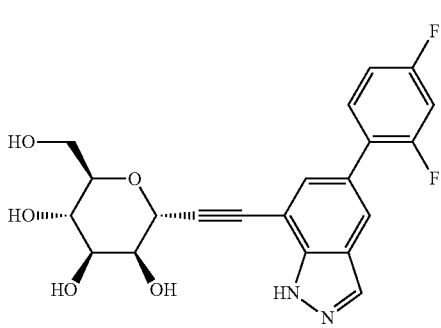
82
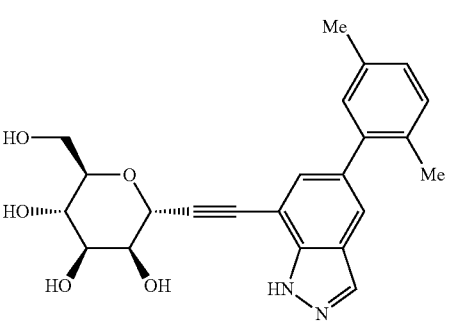
83
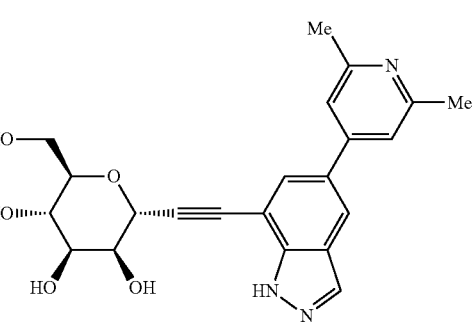
84
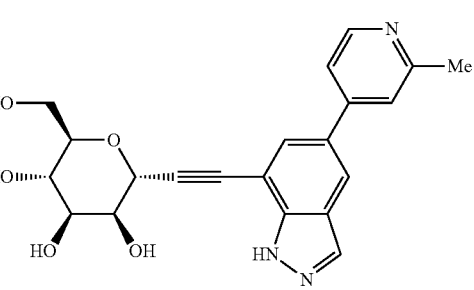
85
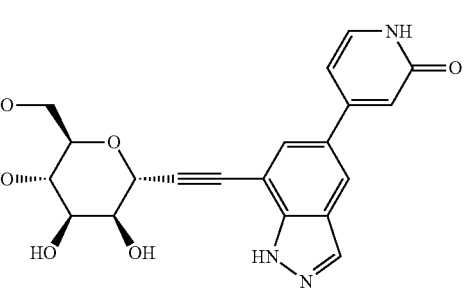

-continued
86
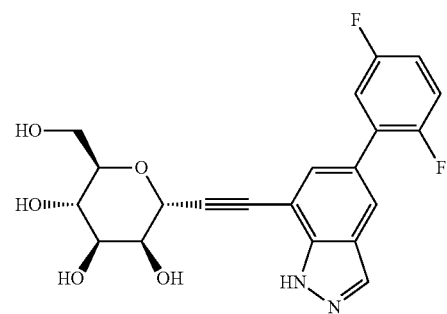
87
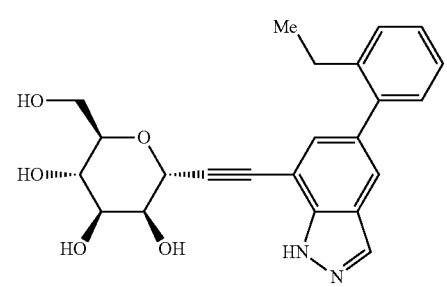
88
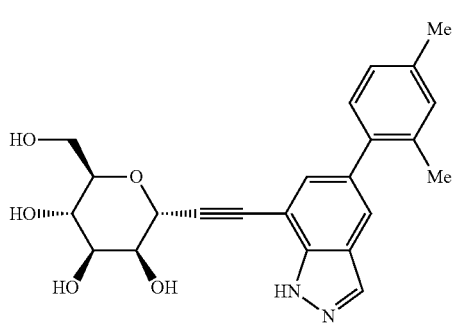
89
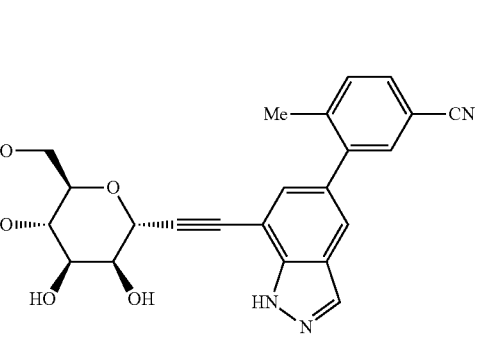
90
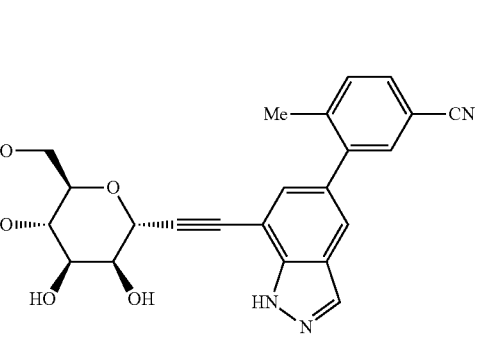
-continued
91
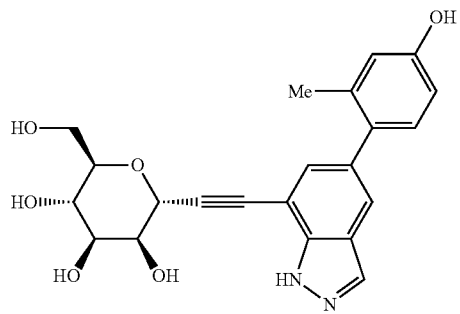
92
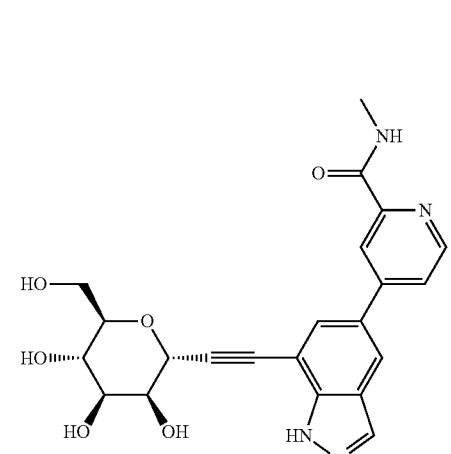
93
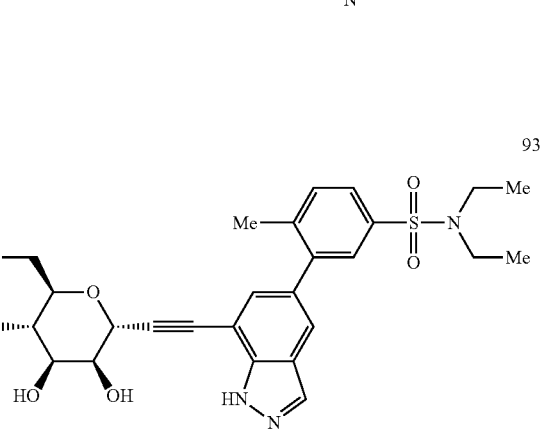
94
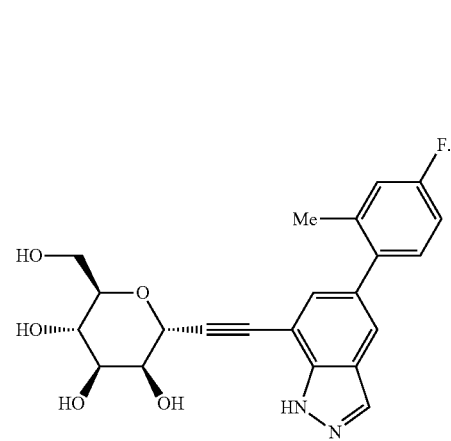

16. The compound of claim 1, having the following structural formula:

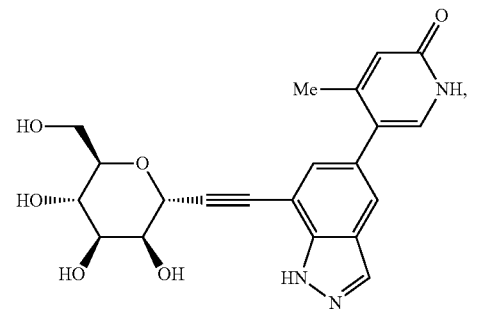

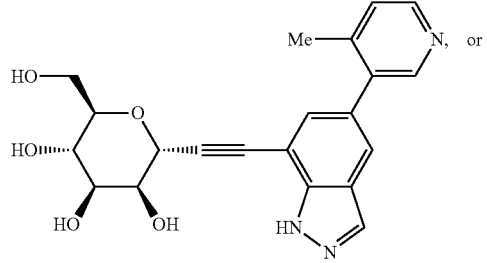

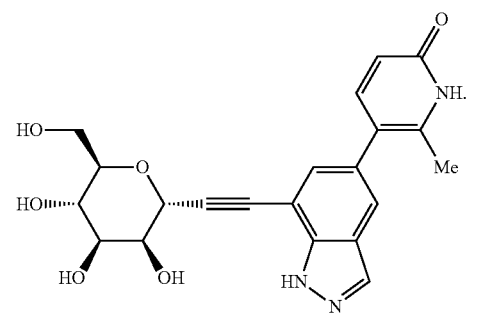

17. A composition comprising the compound of claim 1 or a pharmaceutically acceptable salt thereof, and a pharmaceutically acceptable carrier, adjuvant, or vehicle.

18. A method of treating or preventing a bacteria infection in a subject, comprising administering to the subject an effective amount of the compound of claim 1 or a pharmaceutically acceptable salt thereof, wherein the bacteria infection is urinary tract infection or inflammatory bowel disease.

19. A method of preparing a compound represented by formula (I) or a pharmaceutically acceptable salt thereof, said method comprising:

a)

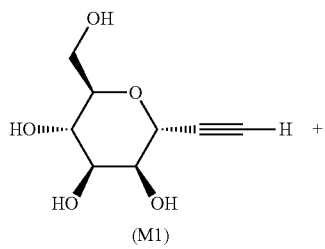

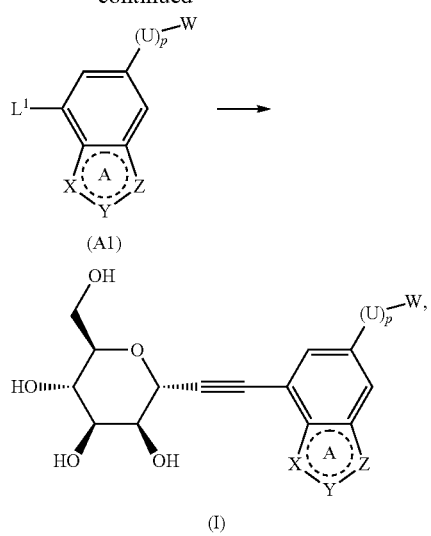

comprising reacting Compound (A1) with Compound (M1) in the presence of a Pd or Pd/Cu catalyst, wherein U, X, Y, Z, and p of Compound (A1) and Formula (I) are each independently as defined in claim 1; W of Compound (A1) and Formula (I) are each independently —H, halogen, —CN, —C(=O)OR$^3$ or C$_{1-6}$alkyl, wherein R$^3$ is as defined in claim 1; and L$^1$ of Compound (A1) is —Cl or —Br; or b)

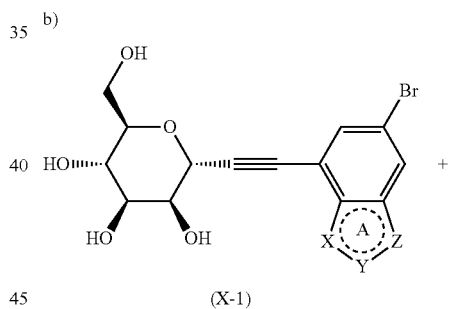

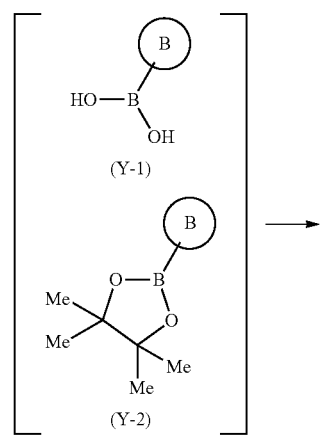

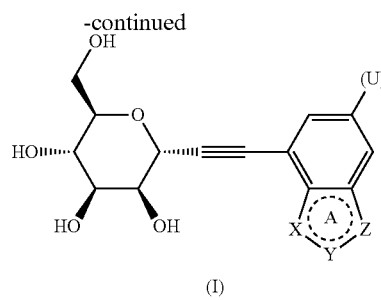

(I)

comprising reacting Compound (X-1) with Compound (Y-1) or (Y-2) in the presence of a Pd catalyst, wherein X, Y, and Z of Compound (X-1) and Formula (I) are each and independently as defined in claim 1; p of Formula (I) is 0; W of Formula (I) is Ring B; and Ring B of Compounds (Y-1) and (Y-2) are each independently a 3-8 membered partially unsaturated, or aromatic monocyclic ring having 0-4 heteroatoms selected from oxygen, nitrogen, or sulfur; or an 8-10 membered partially unsaturated, or aromatic bicyclic ring having 0-4 heteroatoms selected from oxygen, nitrogen, or sulfur; wherein said $C_{1-6}$alkyl is optionally substituted with 1-4 occurrences of $J^{W1}$, and wherein each of said monocyclic and bicyclic rings independently and optionally is substituted with 1-4 occurrences of $J^{W2}$; or c)

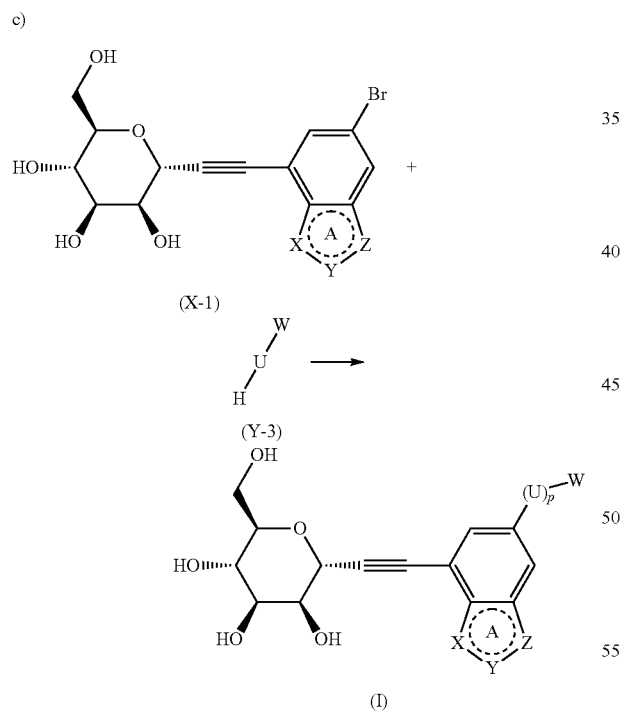

comprising reacting Compound (X-1) with Compound (Y-3) in the presence of a Pd or Pd/Cu catalyst, wherein p of Formula (I) is 1; and the other variables of Formula (I) and the variables of Compounds (X-1) and (Y-3) are each and independently as defined in claim 1; or d)

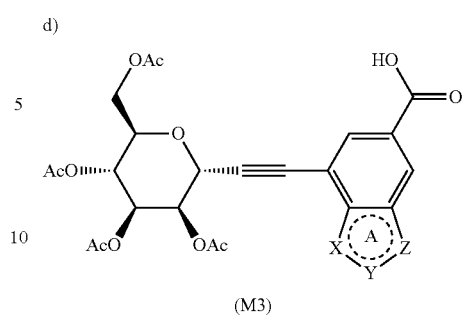

(M3)

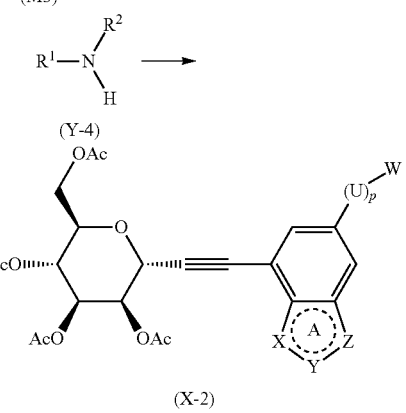

(X-2)

comprising:
  coupling between Compound (M3) and Compound (Y-4) to generate Compound (X-2); and
  deprotecting -OAc groups of Compound (X-2) to generate a compound of Formula (I)

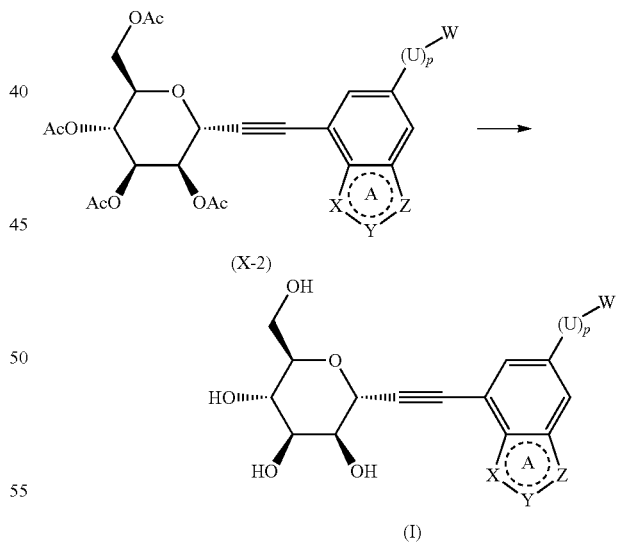

wherein the variables of Compounds (M3), (Y-4), and (X-2), and Formula (I) are each independently as defined in claim 1; and OAc of Compound (X-2) is acetate.

* * * * *